US012600711B2

(12) United States Patent
Johnson

(10) Patent No.: US 12,600,711 B2
(45) **Date of Patent: *Apr. 14, 2026**

(54) TRIAZACYCLODODECANSULFONAMIDE (TCD)-BASED PROTEIN SECRETION INHIBITORS

(71) Applicant: KEZAR LIFE SCIENCES, INC., South San Francisco, CA (US)

(72) Inventor: Henry Johnson, San Bruno, CA (US)

(73) Assignee: KEZAR LIFE SCIENCES, INC., South San Francisco, CA (US)

( * ) Notice: Subject to any disclaimer, the term of this patent is extended or adjusted under 35 U.S.C. 154(b) by 743 days.

This patent is subject to a terminal disclaimer.

(21) Appl. No.: 17/741,989

(22) Filed: May 11, 2022

(65) Prior Publication Data

US 2022/0402891 A1 Dec. 22, 2022

Related U.S. Application Data

(63) Continuation of application No. 16/979,457, filed as application No. PCT/US2019/022533 on Mar. 15, 2019, now Pat. No. 11,578,055.

(60) Provisional application No. 62/803,704, filed on Feb. 11, 2019, provisional application No. 62/643,931, filed on Mar. 16, 2018.

(51) Int. Cl.

| | |
|---|---|
| ***A61K 31/395*** | (2006.01) |
| ***A61K 31/4523*** | (2006.01) |
| ***A61P 19/02*** | (2006.01) |
| ***A61P 29/00*** | (2006.01) |
| ***A61P 35/00*** | (2006.01) |
| ***A61P 37/00*** | (2006.01) |
| ***A61P 37/02*** | (2006.01) |
| ***C07D 255/02*** | (2006.01) |
| ***C07D 401/12*** | (2006.01) |
| ***C07D 401/14*** | (2006.01) |
| ***C07D 403/12*** | (2006.01) |
| ***C07D 413/14*** | (2006.01) |

(52) U.S. Cl.

CPC ............ *C07D 401/14* (2013.01); *A61P 35/00* (2018.01); *C07D 255/02* (2013.01); *C07D 401/12* (2013.01); *C07D 403/12* (2013.01); *C07D 413/14* (2013.01)

(58) Field of Classification Search

None

See application file for complete search history.

(56) References Cited

U.S. PATENT DOCUMENTS 5,663,161 A 9/1997 Bell

FOREIGN PATENT DOCUMENTS

| | | | | |
|---|---|---|---|---|
| WO | 96/25167 A1 | | 8/1996 | |
| WO | 02/80856 A2 | | 10/2002 | |
| WO | WO-02080856 A2 | * | 10/2002 | ........... A61K 31/395 |

OTHER PUBLICATIONS

Puyenbroeck et al., A Proteomic Survey Indicates Sortilin as a Secondary Substrate of the ER Translocation Inhibitor Cyclotriazadisulfonamide (CADA), vol. 16, Issue 2, Feb. 2017, pp. 157-167 (Year: 2017).*

Chawla (Chawla et al., Tuning Side Arm Electronics in Unsymmetrical Cyclotriazadisulfonamide (CADA) Endoplasmic Reticulum (ER) Translocation Inhibitors to Improve their Human Cluster of Differentiation 4 (CD4) Receptor Down-Modulating Potencies, J. Med Chem. 2016, 59, 2633-2647 (Year: 2016).*

Chawla Supporting Information (SI) (Year: 2016).*

Bell et al., Syntheses, Conformations, and Basicities of Bicyclic Triamines, J. Am. Chem. Soc., 125:12196-12210 (2003).

Bell et al., Synthesis and Structure-Activity Relationship Studies of CD4 Down-Modulating Cyclotriazadisulfonamide (CADA) Analogues, J. Med. Chem., 49:1291-1312 (2006).

Beaudoin et al., Preparation of unsymmetrical sulfonylureas from N,N'-sulfuryldiimidazoles, J. Org. Chem., 68:115-119 (2002).

Berge et al., Pharmaceutical salts, J. Pharm. Sci., 66:1-19 (1977).

Chawla et al., Tuning side Arm electronics in unsymmetrical cyclotriazadisulfonamide (CADA) endoplasmic reticulum (ER) translocation inhibitors to improve their human cluster of differentiation 4 (CD4) receptor down-modulating potencies, J. Med. Chem., 59:2633-2647 (2016).

Chernichenk et al., Synthesis of Dansyl-Substituted Cryptands Containing Triaza-cycloalkane Moieties and their Evaluation as Fluorescent Chemosensors, Synlett, 28(20):2800-2806 (2017).

(Continued)

*Primary Examiner* — Kortney L. Klinkel
*Assistant Examiner* — Alison Azar Salamatian
(74) *Attorney, Agent, or Firm* — MARSHALL, GERSTEIN & BORUN LLP

(57) ABSTRACT

Provided herein are triazacyclododecansulfonamide ("TCD")-based protein secretion inhibitors, such as inhibitors of Sec61, methods for their preparation, related pharmaceutical compositions, and methods for using the same. For example, provided herein are compounds of Formula (I) and pharmaceutically acceptable salts and compositions including the same. The compounds disclosed herein may be used, for example, in the treatment of diseases including inflammation and/or cancer.

(I)

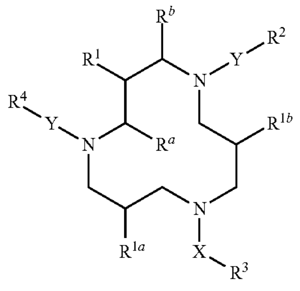

12 Claims, 1 Drawing Sheet

Specification includes a Sequence Listing.

(56) References Cited

OTHER PUBLICATIONS

Demillo et al., Unsymmetrical Cyclotriazadisulfonamide (CADA) Compounds as Human CD4 Receptor Down-Modulating Agents—Journal of Medicinal Chemistry (ACS Publications), 54(16):5712-5721 (2011).

Garrison et al., A substrate-specific inhibitor of protein translocation into the endoplasmic reticulum, Nat., 436:285-289 (2005).

Golub et al., Molecular classification of cancer: class discovery and class prediction by gene expression monitoring, Science, 286:531-537 (1999).

International Application No. PCT/US2019/022533, International Preliminary Report on Patentability, mailed Oct. 1, 2020.

International Application No. PCT/US2019/022533, International Search Report and Written Opinion, mailed May 20, 2019.

Kalies et al., Inhibitors of protein translocation across the ER membrane, Traffic, 16:1027-1038 (2015).

Lowe et al., Blocking protein secretion and degradation is a novel treatment strategy for malignant cells with high protein load, Blood, 122(21):4439 (2013).

Maifeld et al., Secretory protein profiling reveals TNF-(Alpha) inactivation by selective and promiscuous Sec61 modulators, Chem. Biol., 18:1082-1088, (2011).

Puyenbroeck et al., A Proteomic Survey Indicates Sortilin as a Secondary Substrate of the ER Translocation Inhibitor Cyclotriazadisulfonamide (CADA), Mol. Cell. Prot., 16(2):157-167 (2016).

Riiz-Saenz et al., Targeting HER3 by interfering with its Sec61-mediated cotranslational insertion into the endoplasmic reticulum, Oncogene., 1-7 (2015).

* cited by examiner

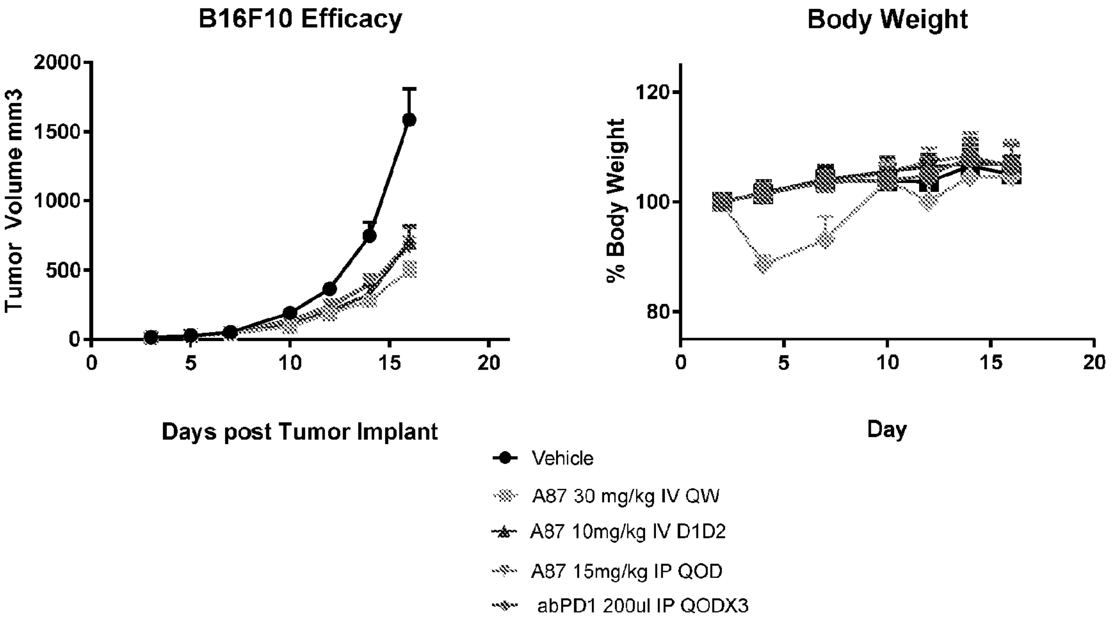
B16F10 Efficacy
Tumor Volume mm3
2000
1500
1000
500
0
0
5
10
15
20
Days post Tumor Implant
Body Weight
% Body Weight
120
100
80
0
5
10
15
20
Day
Vehicle
A87 30 mg/kg IV QW
A87 10mg/kg IV D1D2
A87 15mg/kg IP QOD
abPD1 200ul IP QODX3

TRIAZACYCLODODECANSULFONAMIDE (TCD)-BASED PROTEIN SECRETION INHIBITORS

BACKGROUND

Field of the Invention

The present disclosure relates to triazacyclododecansulfonamide ("TCD")-based protein secretion inhibitors, including methods of making and using the same.

INCORPORATION BY REFERENCE OF MATERIAL SUBMITTED ELECTRONICALLY

This application contains, as a separate part of disclosure, a sequence listing in computer-readable form (filename 40056_Seqlisting.txt; 20,275 bytes; created Feb. 14, 2019) which is incorporated by reference in its entirety.

DESCRIPTION OF RELATED TECHNOLOGY

Protein translocation into the endoplasmic reticulum ("ER") constitutes the first step of protein secretion. ER protein import is essential in all eukaryotic cells and is particularly important in fast-growing tumour cells. Thus, the process of protein secretion can serve as a target both for potential cancer drugs and for bacterial virulence factors. See Kalies and Romisch, Traffic, 16(10):1027-1038 (2015).

Protein transport to the ER is initiated in the cytosol when N-terminal hydrophobic signal peptides protrude from the ribosome. Binding of signal recognition particle ("SRP") to the signal sequence allows targeting of the ribosome—nascent chain—SRP complex to the ER membrane where contact of SRP with its receptor triggers handing over of the signal peptide to Sec61. Sec61 is an ER membrane protein translocator (aka translocon) that is doughnut-shaped with 3 major subunits (heterotrimeric). It includes a "plug," which blocks transport into or out of the ER. The plug is displaced when the hydrophobic region of a nascent polypeptide interacts with the "seam" region of Sec61, allowing translocation of the polypeptide into the ER lumen. In mammals, only short proteins (<160 amino acids) can enter the ER posttranslationally, and proteins smaller than 120 amino acids are obliged to use this pathway. Some of the translocation competence is maintained by the binding of calmodulin to the signal sequence. Upon arrival at the Sec61 channel, the signal peptide or signal anchor intercalates between transmembrane domains ("TMDs") 2 and 7 of Sec61α, which form the lateral portion of the gate, allowing the channel to open for soluble secretory proteins. As the Sec61 channel consists of 10 TMDs (Sec61α) surrounded by a hydrophobic clamp formed by Sec61γ, channel opening is dependent on conformational changes that involve practically all TMDs.

Inhibition of protein transport across the ER membrane has the potential to treat or prevent diseases, such as the growth of cancer cells and inflammation. Known secretion inhibitors, which range from broad-spectrum to highly substrate-specific, can interfere with virtually any stage of this multistep process, and even with transport of endocytosed antigens into the cytosol for cross-presentation. These inhibitors interact with the signal peptide, chaperones, or the Sec61 channel to block substrate binding or to prevent the conformational changes needed for protein import into the ER. Examples of protein secretion inhibitors include, calmodulin inhibitors (e.g., E6 Berbamine and Ophiobolin A), Lanthanum, sterols, cyclodepsipeptides (e.g., HUN-7293, CAM741, NF1028, Cotrainsin, Apratoxin A, Decatransin, Valinomycin), CADA, Mycolactone, Eeyarestatin I ("ESI"), and Exotoxin A. However, the above secretion inhibitors suffer from one or more of the following: lack selectivity for the Sec61 channel, challenging manufacture due to structural complexity, and molecular weight limited administration, bio-availability and distribution.

Thus, a need exists for new small molecule inhibitors of protein secretion.

SUMMARY

In one aspect, provided herein is a compound of Formula (I), or a pharmaceutically acceptable salt thereof:

(I)

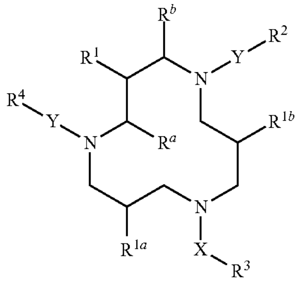

wherein: each of $R^a$ and $R^b$ is independently H or $C_{1-3}$alkyl; $R^1$ is H, OH, $C_{1-3}$alkyl, $OC_{1-3}$alkyl, $=CH_2$, or $=NOR^5$; or $R^1$ is $C_{3-6}$cycloalkyl or $C_{3-6}$heterocycloalkyl and forms a Spiro group with the ring carbon to which it is attached; each of $R^{1a}$ and $R^{1b}$ is independently H or $C_{1-3}$alkyl; $R^2$ is $C_{1-6}$alkyl, $N(R^5)_2$, $C_{3-8}$cycloalkyl, $C_{3-9}$heterocycloalkyl, $C_{3-9}$heterocycloalkenyl, or $C_{6-10}$aryl; $R^3$ is H, $C_{1-6}$alkyl, $C_{3-8}$cycloalkyl, $C_{3-8}$cycloalkenyl, $C_{3-7}$heterocycloalkyl, $C_{6-10}$aryl, or $C_{2-6}$heteroaryl; $R^4$ is $C_{3-8}$cycloalkyl, $C_{3-9}$heterocycloalkyl, $C_{6-10}$aryl, or $C_{2-9}$heteroaryl; each $R^5$ independently is H, $C_{1-3}$alkyl, or $C_{0-2}$alkylene-$C_{6-10}$aryl; X is absent, $C_{1-3}$alkylene, C═O, or (C═O)O; Y is SO or $SO_2$; each heterocycloalkyl, heterocycloalkenyl, and heteroaryl group independently has 1, 2, or 3 ring heteroatoms selected from N, O, and S.

In some embodiments, each Y is SO. In various embodiments, each Y is $SO_2$.

In various cases, $R^a$ is H. In some cases, $R^a$ is $C_{1-3}$alkyl. In some embodiments, $R^a$ is $CH_3$. In some embodiments, $R^b$ is H. In various embodiments, $R^b$ is $C_{1-3}$alkyl. In various cases, $R^b$ is $CH_3$. In various cases, each of $R^a$ and $R^b$ is H.

In some cases, $R^1$ is H, OH, or $=NOR^5$. In various cases, $R^5$ is each $R^5$ independently is H, $C_{1-3}$alkyl, or $C_{0-2}$alkylene-$C_{6-10}$aryl. In some cases, $R^5$ is H or $CH_3$. In some embodiments, $R^1$ is $C_{1-3}$alkyl or $OC_{1-3}$alkyl. In various embodiments, $R^1$ is $CH_3$ or $OCH_3$. In some cases, $R^1$ is $CH_3$ and exhibits S stereochemistry. In various embodiments, $R^1$ is $C_{3-6}$cycloalkyl or $C_{3-6}$heterocycloalkyl and forms a Spiro group with the ring carbon to which it is attached. In some cases, $R^1$ together with the ring atom to which it is attached forms

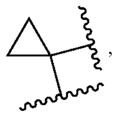,
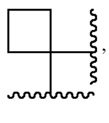,
or
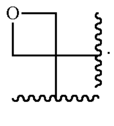.

In various cases, $R^1$ is $=CH_2$.

In some cases, each of $R^{1a}$ and $R^{1b}$ is H. In some cases, at least one of $R^{1a}$ and $R^{1b}$ is $C_{1-3}$alkyl. In some cases, each of $R^{1a}$ and $R^{1b}$ is $CH_3$.

In some embodiments, $R^2$ is $C_{1-6}$alkyl or $N(R^5)_2$. In various cases, each $R^5$ independently comprises H, $C_{1-3}$alkyl, or benzyl. In various embodiments, $R^2$ is Et, iPr,N $(CH_3)_2$,

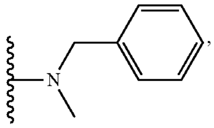 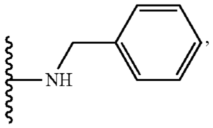

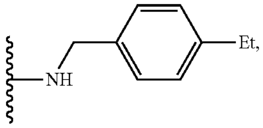 or

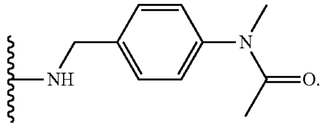

In some cases, $R^2$ comprises $C_{3-8}$cycloalkyl. In various cases, $R^2$ comprises cyclopentyl or cyclohexyl. In some embodiments, $R^2$ is $C_{3-9}$heterocycloalkyl or $C_{3-9}$heterocycloalkenyl. In various embodiments, $R^2$ comprises oxetanyl, azetidinyl, tetrahydrofuranyl, pyrrolidinyl, tetrahydropyranyl, pyranyl, piperidinyl, piperazinyl, azepanyl, morpholinyl, or tetrahydropyridinyl. In various embodiments, the $C_{3-9}$heterocycloalkyl or $C_{3-9}$heterocycloalkenyl comprises a bridge or a spiro group. In some cases, the $C_{3-9}$ heterocycloalkyl comprising a bridge or a spiro group is selected from the group consisting of

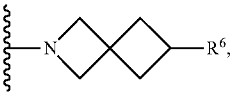 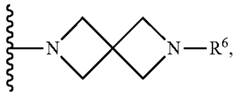

and

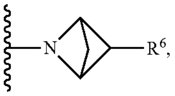

and $R^6$ is $C_{1-6}$alkyl, $C_{3-8}$cycloalkyl, or $C_{6-10}$aryl. In some cases, $R^6$ is phenyl optionally substituted with one to three groups independently selected from halo, $C_{1-3}$alkyl, $C_{1-3}$alkoxy, and CN. In various cases, $R^2$ is selected from the group consisting of

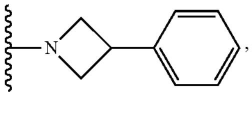 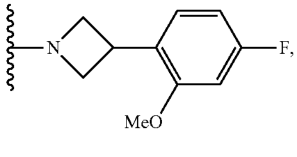

-continued

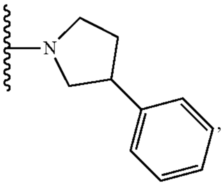 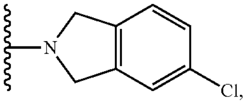

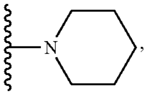 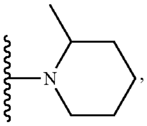 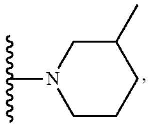

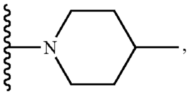 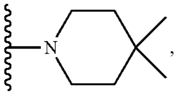

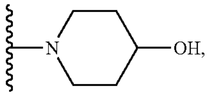 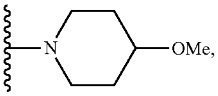

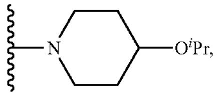 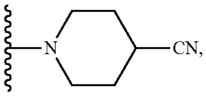

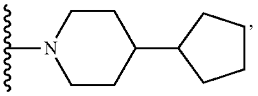 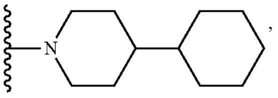

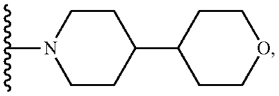 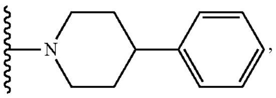

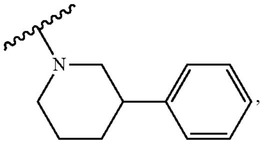

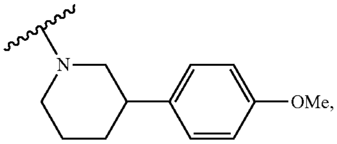

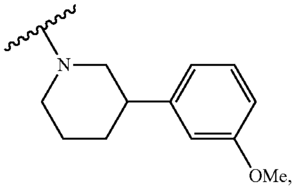 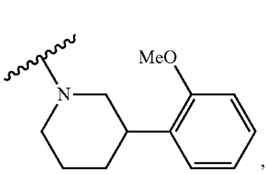

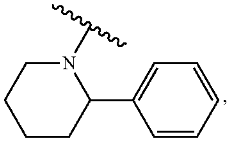 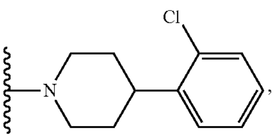

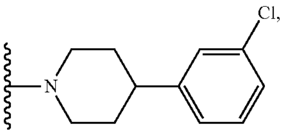

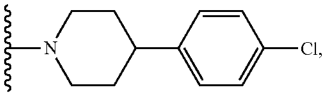

-continued
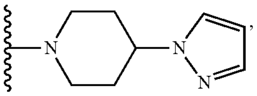
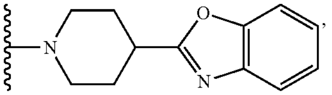
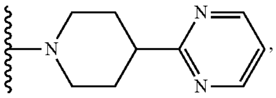
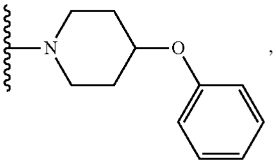
,
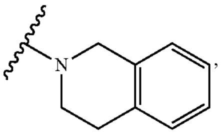
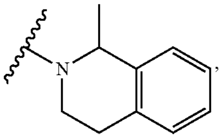
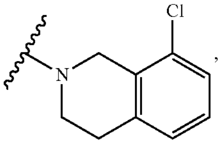
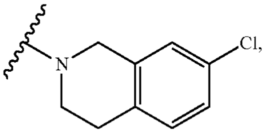
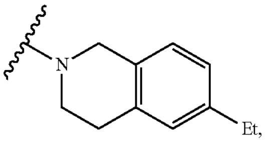
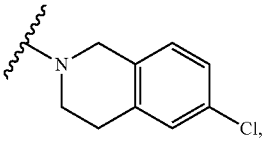
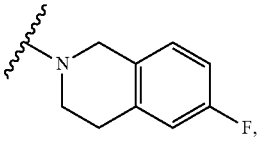
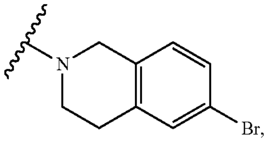
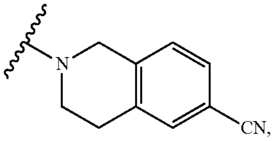
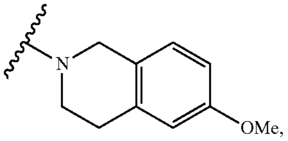
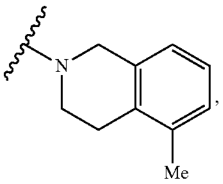
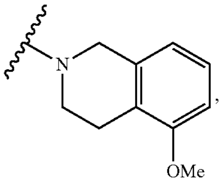
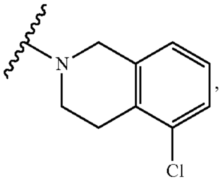
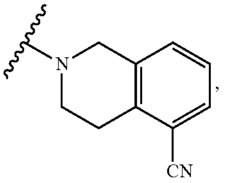
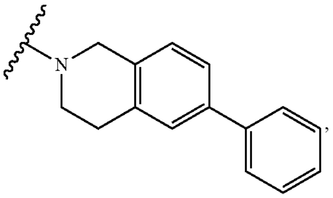
-continued
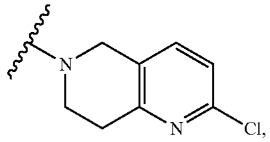
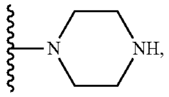
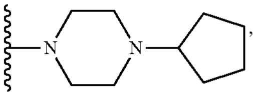
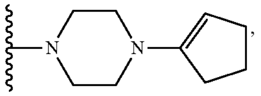
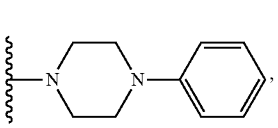
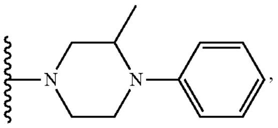
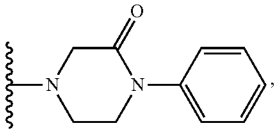
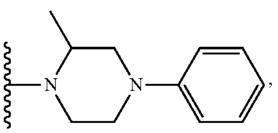
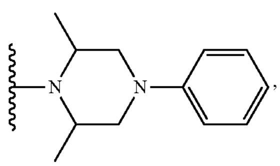
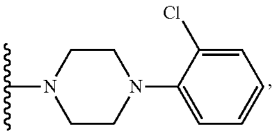
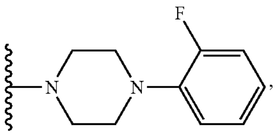
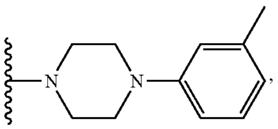
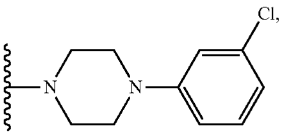
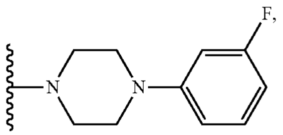
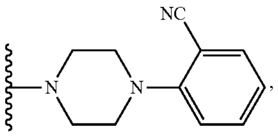
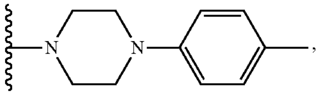
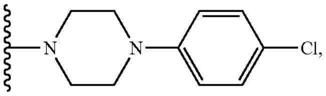
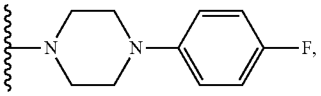
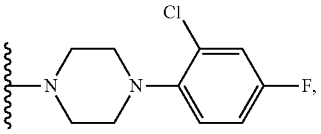
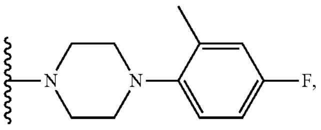

-continued
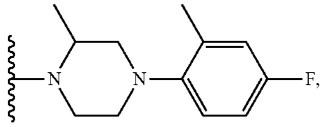
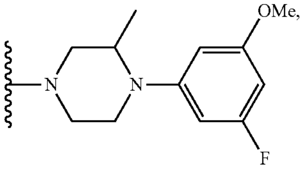
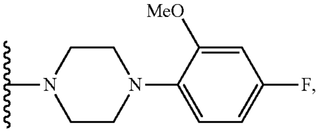
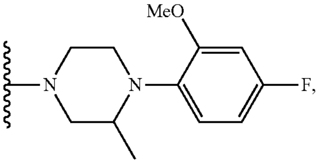
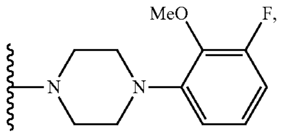
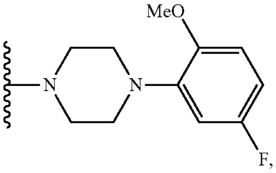
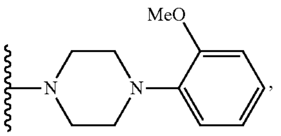
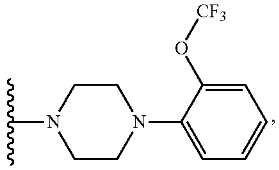
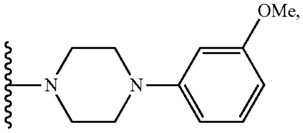
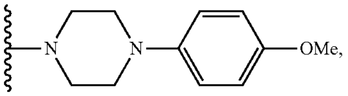
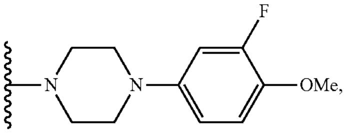
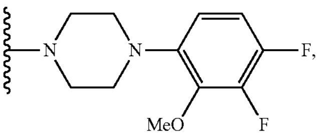
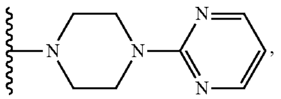
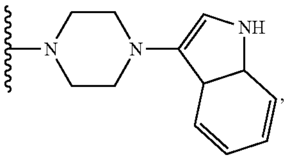
-continued
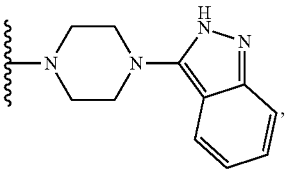
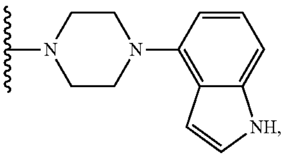
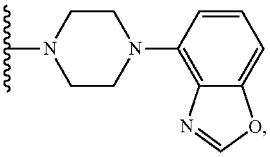
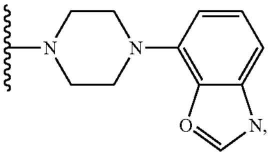
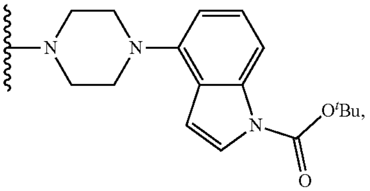
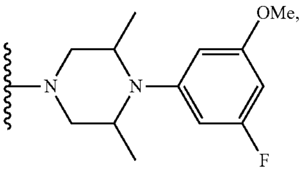
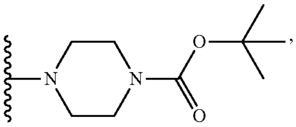
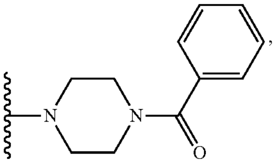
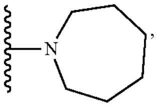
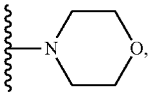
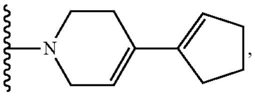
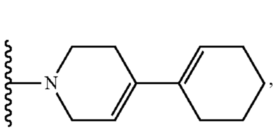
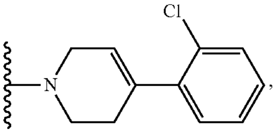
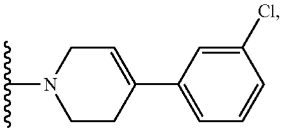
and
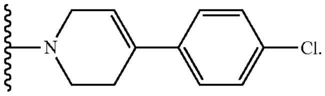

In some cases, $R^2$ is selected from the group consisting of

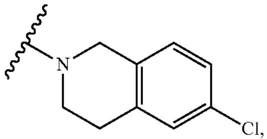
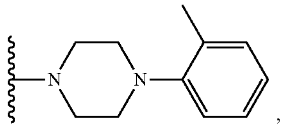
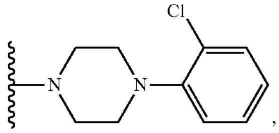
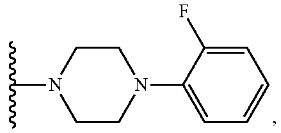
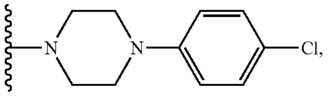
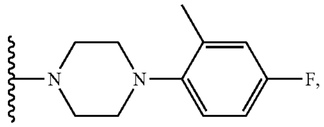
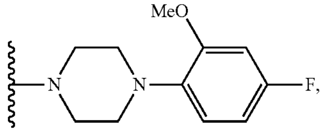
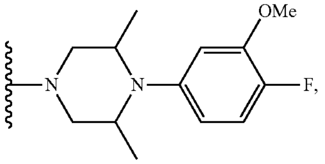
and
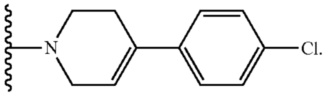

In various cases, $R^2$ is $C_{6-10}$aryl. In some embodiments, $R^2$ is

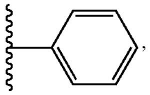
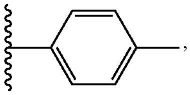
or
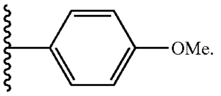

In various embodiments, X is absent. In some embodiments, $R^3$ comprises $C_{1-6}$alkyl or H. In some cases, $R^3$ is 2-methylbutyl, isopropyl, isopentyl, $CH_2CH_2OCH_3$, $CH_2C(CH_3)_2CN$, $CH_2CF_3$, or $CH_2CH_2CF_3$. In various cases, $R^3$ is isobutyl.

In some embodiments, X is $C_{1-3}$alkylene. In some cases, X is $CH_2$, $CH_2CH_2$, or $CH(CH_3)$. In various cases, $R^3$ comprises $C_{3-8}$cycloalkyl, $C_{3-8}$cycloalkenyl, $O_{3-7}$heterocycloalkyl, $C_{6-10}$aryl, or $C_{2-6}$heteroaryl. In some embodiments, $R^3$ comprises cyclopropyl, cyclobutyl, cyclopentyl, cyclohexyl, cyclopentenyl, cyclohexenyl, tetrahydropyranyl, phenyl, pyrrolyl, pyrazolyl, imidazolyl, tetrazolyl, furanyl, thiophenyl, thiazolyl, oxazolyl, isoxazolyl, oxadiazolyl, thiadiazolyl, pyridinyl, pyrazinyl, or pyrimidinyl. In various embodiments, X—$R^3$ is selected from the group consisting of

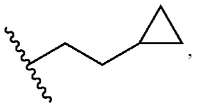
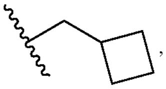
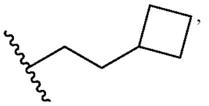
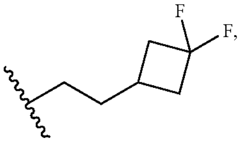
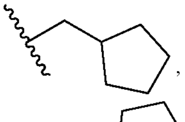
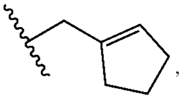
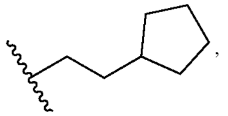
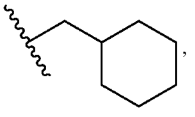
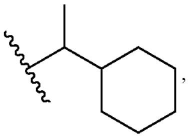
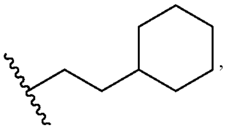
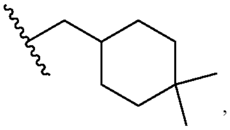
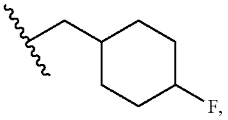
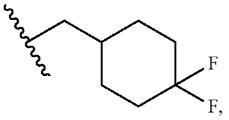
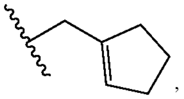
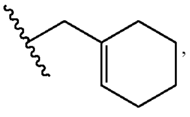
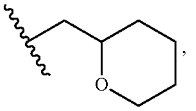
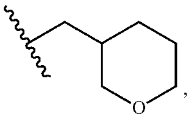
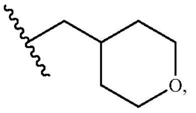
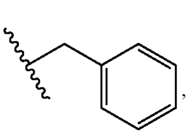
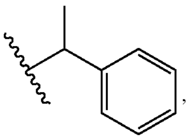
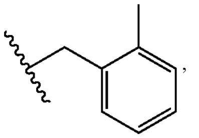
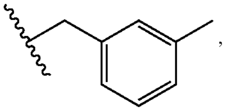
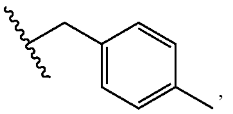
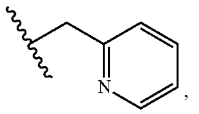
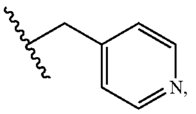
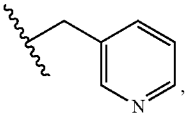
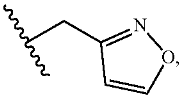
and
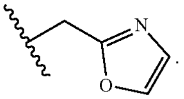

In some cases, X—$R^3$ is

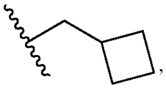,
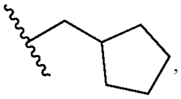,
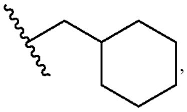, or

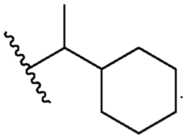.

In some cases, X—$R^3$ is

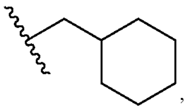, or
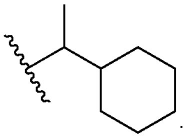.

In some embodiments, X is C═O or (C═O)O. In various embodiments, $R^3$ comprises $C_{1-6}$alkyl or $C_{6-10}$aryl. In some cases, X—$R^3$ is

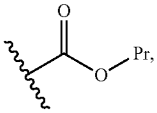,
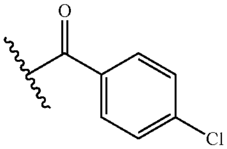, or
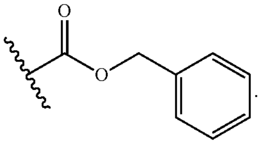.

In various cases, $R^4$ comprises $C_{3-8}$cycloalkyl or $C_{3-9}$heterocycloalkyl. In some embodiments, $R^4$ is

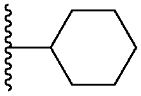 or
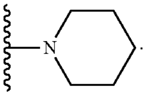.

In various embodiments, $R^4$ comprises $C_{6-10}$aryl or $C_{2-9}$heteroaryl, and $R^4$ is optionally substituted with one to three groups independently selected from halo, $C_{1-3}$alkyl, $C_{1-3}$alkoxy, $C(O)N(R^N)_2$, and $N(R^N)_2$, and each $R^N$ is independently H or $C_{1-3}$alkyl. In some embodiments, $R^4$ is selected from the group consisting of

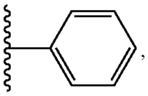,
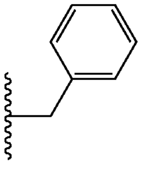,
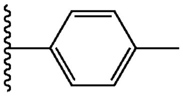,

-continued

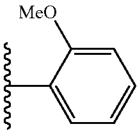,
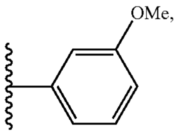,
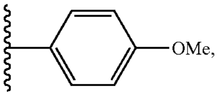,
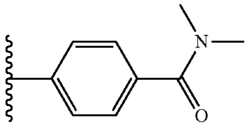,
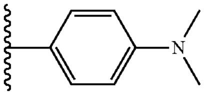,
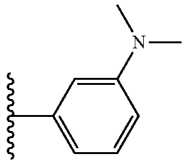,
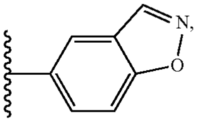,
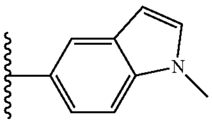,
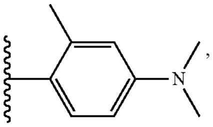,
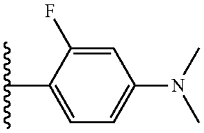, and
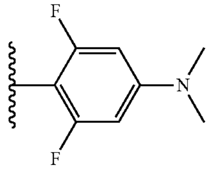.

In various embodiments, $R^4$ is

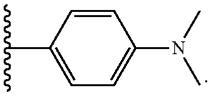 [SMILES: *c1ccc(N(C)C)cc1].

In some embodiments, $R^a$, $R^b$, $R^{1a}$, and $R^{1b}$ are each H; $R^1$ is ═CH, or $CH_3$; $R^2$ is

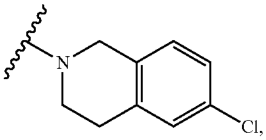,
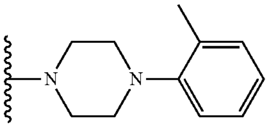,
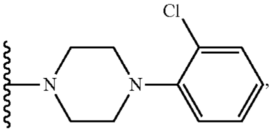,
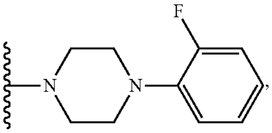,
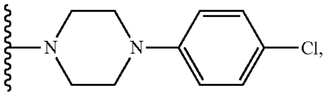,
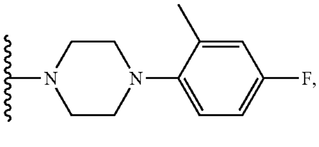,

-continued
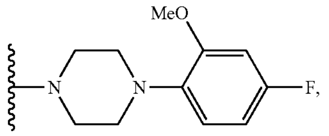
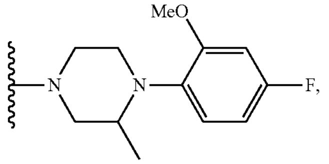
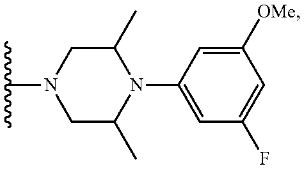 or
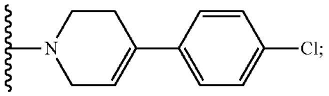
X—$R^3$ is isobutyl,
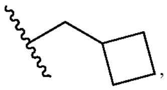, 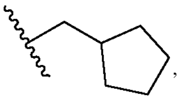, 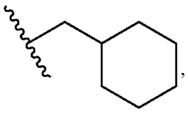, or
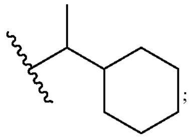;
$R^4$ is
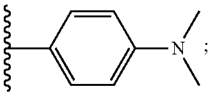;
and each Y is $SO_2$.
In some embodiments, $R^1$ is in a (S) configuration.
Also provided herein are compounds listed in Table A, Table B, and pharmaceutically acceptable salts thereof. In some embodiments, provided herein is a compound is selected from the group consisting of:
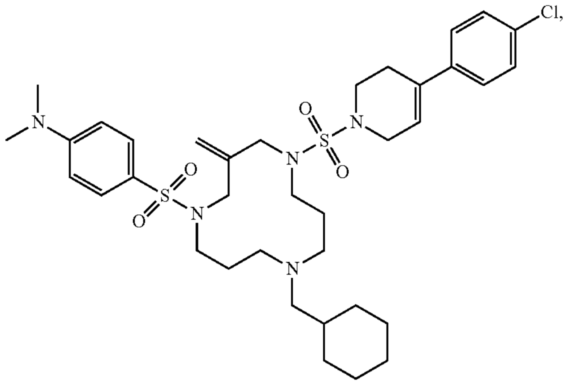
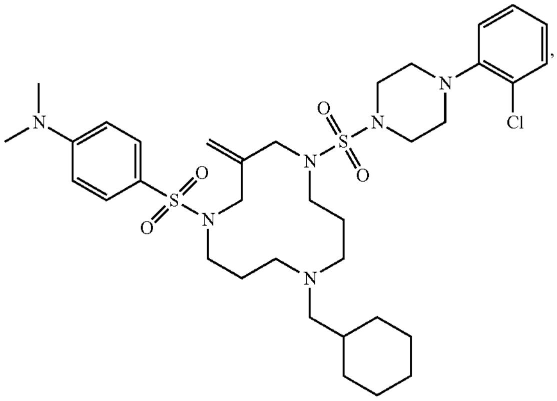
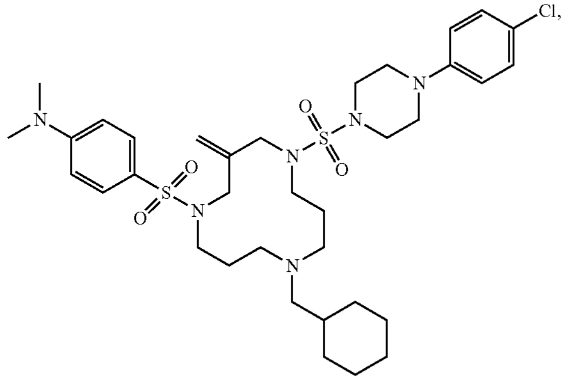
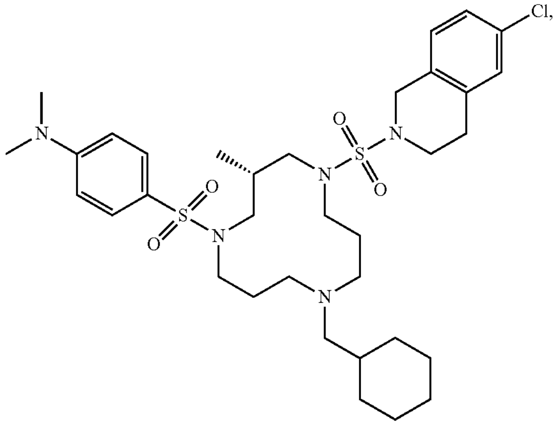

-continued

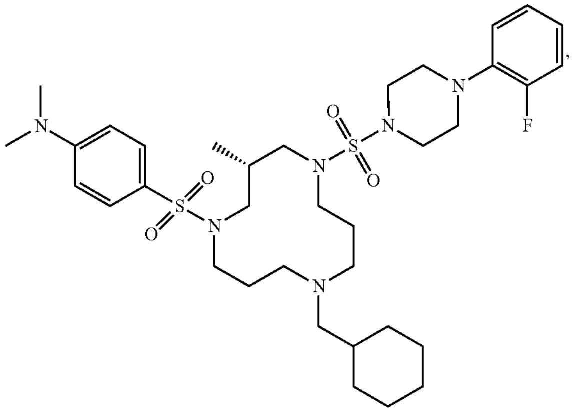

,

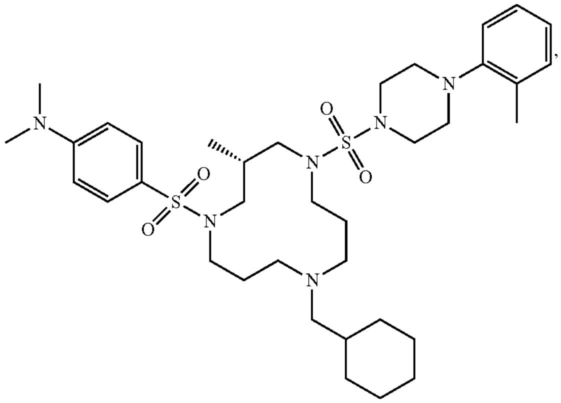

,

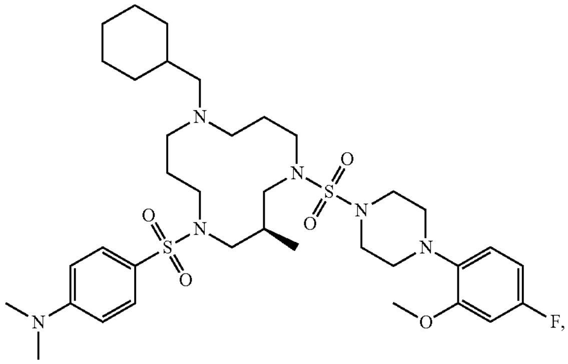

,

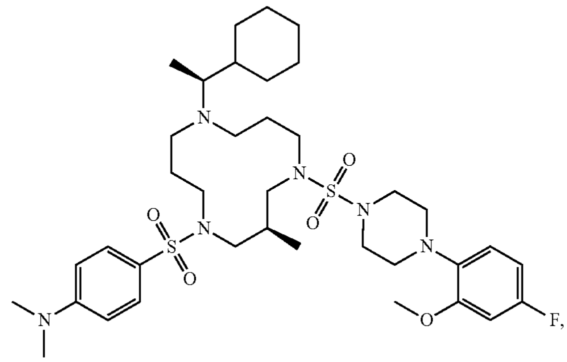

,

-continued

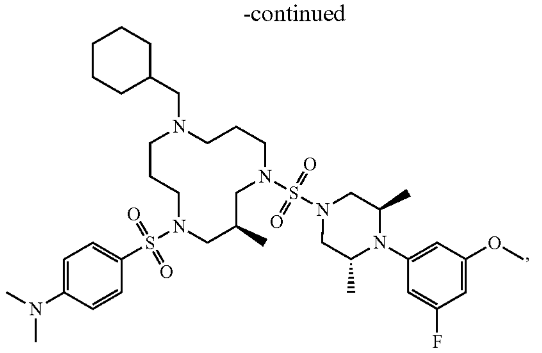

, and

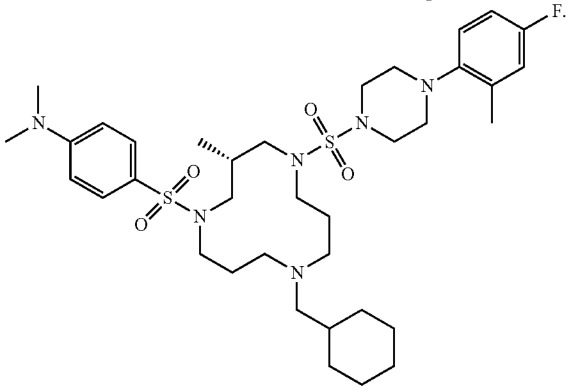

.

Further provided herein is a pharmaceutical composition comprising a compound of Formula (I), a compound listed in Table A, a compound listed in Table B, or a pharmaceutically acceptable salt thereof, and a pharmaceutically acceptable carrier.

Also provided herein is a method of inhibiting protein secretion in a cell comprising contacting the cell with the compound or salt of Formula (I), the compound listed in Table A or a pharmaceutically acceptable salt thereof, a compound listed in Table B or a pharmaceutically acceptable salt thereof, or the pharmaceutical composition described herein in an amount effective to inhibit secretion. In some cases, the contacting comprises administering the compound or the composition to a subject.

Further provided herein is a method for treating inflammation in a subject comprising administering to the subject a therapeutically effective amount of a compound or salt of Formula (I), a compound listed in Table A or a pharmaceutically acceptable salt thereof, a compound listed in Table B or a pharmaceutically acceptable salt thereof, or the pharmaceutical composition described herein.

Also provided herein is a method for treating or preventing cancer or precancerous conditions in a subject comprising administering to the subject a therapeutically effective amount of the compound or salt of Formula (I), a compound listed in Table A or a pharmaceutically acceptable salt thereof, a compound listed in Table B or a pharmaceutically acceptable salt thereof, or the pharmaceutical composition described herein.

Further aspects and advantages will be apparent to those of ordinary skill in the art from a review of the following detailed description, taken in conjunction with the drawings. The description hereafter includes specific embodiments with the understanding that the disclosure is illustrative, and is not intended to limit the invention to the specific embodiments described herein.

BRIEF DESCRIPTION OF THE DRAWINGS

FIG. 1 depicts B16F10 efficacy data for compound A87 compared to an anti-PD-1 therapy. Compound A87 exhibited superior efficacy with once-a-week dosing over the anti-PD-1 therapy in the refractory model with respect to tumor growth inhibition and percent body weight.

Further aspects and advantages will be apparent to those of ordinary skill in the art from a review of the following detailed description. While the compounds and methods disclosed herein are susceptible of embodiments in various forms, the description hereafter includes specific embodiments with the understanding that the disclosure is illustrative, and is not intended to limit the invention to the specific embodiments described herein.

DETAILED DESCRIPTION

Provided herein are compounds that inhibit protein secretion. The compounds described herein can be used to treat or prevent diseases associated with excessive protein secretion, such as inflammation and cancer, improving the quality of life for afflicted individuals.

The compounds described herein have a structure of Formula (I)

(I)

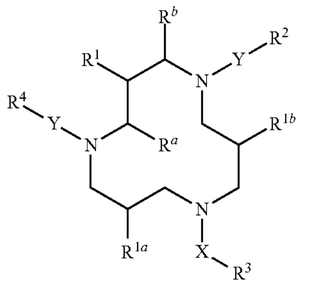

wherein the substituents are described in detail below.

Without being bound by any particular theory, the compounds described herein inhibit protein secretion by binding to and disabling components of the translocon, including but not limited to Sec61, and in some cases, disrupting in a sequence specific fashion interactions between the nascent signaling sequence of translated proteins with components of the translocon including but not limited to Sec61. The compounds described herein can bind specifically to the signal sequence with little to no interaction with the translocon itself.

The compounds described herein can advantageously inhibit the secretion of TNFα with an $IC_{50}$ of up to 5 μM, or up to 3 μM, or up to 1 μM. In various cases, the compounds disclosed herein can inhibit the secretion of IL-2 with an $IC_{50}$ of up to 5 μM, or up to 3 μM, or up to 1 μM. In some cases, the compounds disclosed herein can inhibit the secretion of PD-1 with an $IC_{50}$ of up to 5 μM, or up to 3 μM, or up to 1 μM.

The compounds described herein are efficacious in reducing tumor growth and body weight. For example, compound A87 showed superior efficacy in reducing tumor growth with once-a-week dosing in a refractory model compared to anti-PD-1 therapy. See the Examples section and FIG. 1.

Chemical Definitions

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_{1-7}$alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

As used herein, the term "alkylene" refers to a bivalent saturated aliphatic radical. The term $C_n$ means the alkylene group has "n" carbon atoms. For example, $C_{1-6}$alkylene refers to an alkylene group having a number of carbon atoms encompassing the entire range, as well as all subgroups, as previously described for "alkyl" groups.

As used herein, the term "alkenyl" is defined identically as "alkyl" except for containing at least one carbon-carbon double bond, and having two to thirty carbon atoms, for example, two to twenty carbon atoms, or two to ten carbon atoms. The term $C_n$ means the alkenyl group has "n" carbon atoms. For example, $C_4$ alkenyl refers to an alkenyl group that has 4 carbon atoms. $C_{2-7}$alkenyl refers to an alkenyl group having a number of carbon atoms encompassing the entire range (i.e., 2 to 7 carbon atoms), as well as all subgroups (e.g., 2-6, 2-5, 3-6, 2, 3, 4, 5, 6, and 7 carbon atoms). Specifically contemplated alkenyl groups include ethenyl, 1-propenyl, 2-propenyl, and butenyl. Unless otherwise indicated, an alkenyl group can be an unsubstituted alkenyl group or a substituted alkenyl group.

As used herein, the term "cycloalkyl" refers to an aliphatic cyclic hydrocarbon. The term $C_n$ means the cycloalkyl group has "n" carbon atoms. For example, $C_5$ cycloalkyl refers to a cycloalkyl group that has 5 carbon atoms in the ring. $C_{5-8}$ cycloalkyl refers to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group.

As used herein, the term "cycloalkenyl" is defined similarly to "cycloalkyl" except for containing at least one carbon-carbon double bond, but is not aromatic. The term $C_n$ means the cycloalkenyl group has "n" carbon atoms. For example, $C_5$ cycloalkenyl refers to a cycloalkenyl group that has 5 carbon atoms in the ring. $C_{5-8}$ cycloalkenyl refers to cycloalkenyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkenyl groups include cyclopropenyl, cyclobutenyl, cyclopentenyl, cyclohexenyl, cycloheptenyl, and cyclooctenyl. Unless otherwise indicated, a cycloalkenyl group can be an unsubstituted cycloalkenyl group or a substituted cycloalkenyl group.

As used herein, the term "heterocycloalkyl" is defined similarly as cycloalkyl, except the ring contains one to three heteroatoms independently selected from oxygen, nitrogen, or sulfur. Nonlimiting examples of heterocycloalkyl groups include piperdine, tetrahydrofuran, tetrahydropyran, dihydrofuran, morpholine, oxazepaneyl, and the like. Cycloalkyl and heterocycloalkyl groups can be saturated or partially unsaturated ring systems optionally substituted with, for example, one to three groups, independently selected alkyl, alkyleneOH, $C(O)NH_2$, $NH_2$, oxo (=O), aryl, haloalkyl, halo, and OH. Heterocycloalkyl groups optionally can be further N-substituted as described herein.

As used herein, the term "aryl" refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, fluorenyl, tetralinyl. Unless otherwise indicated, an aryl group can be an unsubstituted aryl group or a substituted aryl group.

As used herein, the term "heteroaryl" refers to monocyclic or polycyclic (e.g., fused bicyclic and fused tricyclic) aromatic ring systems, wherein one to four-ring atoms are selected from oxygen, nitrogen, or sulfur, and the remaining ring atoms are carbon, said ring system being joined to the remainder of the molecule by any of the ring atoms. Non-limiting examples of heteroaryl groups include, but are not limited to, pyridyl, pyridazinyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, thienyl, quinolinyl, isoquinolinyl, benzoxazolyl, benzimidazolyl, benzofuranyl, benzothiazolyl, triazinyl, triazolyl, purinyl, pyrazinyl, purinyl, indolinyl, phthalzinyl, indazolyl, quinolinyl, isoquinolinyl, cinnolinyl, quinazolinyl, naphthyridinyl, pyridopyridinyl, indolyl, 3H-indolyl, pteridinyl, and quinooxalinyl. Unless otherwise indicated, a heteroaryl group can be an unsubstituted heteroaryl group or a substituted heteroaryl group.

As used herein, the term "hydroxy" or "hydroxyl" as used herein refers to the "—OH" group.

As used herein, the term "alkoxy" or "alkoxyl" refers to a "—O-alkyl" group.

As used herein, the term "halo" is defined as fluoro, chloro, bromo, and iodo.

As used herein, the term "carboxy" or "carboxyl" refers to a "—COOH" group.

As used herein, the term "amino" refers to a $—NH_2$ or —NH— group, wherein any hydrogen can be replaced with an alkyl, cycloalkyl, aryl, heteroaryl, or heterocycloalkyl group.

As used herein, the term "sulfonyl" refers to a

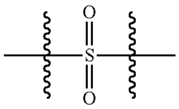 [SMILES: *S(*)(=O)=O]

group.

A "substituted" functional group (e.g., a substituted alkyl, alkyleneyl, cycloalkyl, aryl, or heteroaryl) is a functional group having at least one hydrogen radical that is substituted with a non-hydrogen radical (i.e., a substitutent). Examples of non-hydrogen radicals (or substituents) include, but are not limited to, alkyl, cycloalkyl, alkenyl, cycloalkenyl, alkynyl, ether, aryl, heteroaryl, heterocycloalkyl, hydroxyl, oxy (or oxo), alkoxyl, ester, thioester, acyl, carboxyl, cyano, nitro, amino, sulfhydryl, and halo. When a substituted alkyl group includes more than one non-hydrogen radical, the substituents can be bound to the same carbon or two or more different carbon atoms.

Protein Secretion Inhibitors

In one aspect, the compounds of the disclosure have a structure of Formula (I), or a pharmaceutically acceptable salt thereof:

(I)

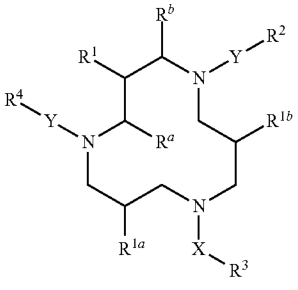

wherein:

each of $R^a$ and $R^b$ is independently H or $C_{1-3}$alkyl;

$R^1$ is H, OH, $C_{1-3}$alkyl, $OC_{1-3}$alkyl, $=CH_2$, or $=NOR^5$; or $R^1$ is $C_{3-6}$cycloalkyl or $C_{3-6}$heterocycloalkyl and forms a Spiro group with the ring carbon to which it is attached;

each of $R^{1a}$ and $R^{1b}$ is independently H or $C_{1-3}$alkyl;

$R^2$ is $C_{1-6}$alkyl, $N(R^5)_2$, $C_{3-8}$cycloalkyl, $C_{3-9}$heterocycloalkyl, $C_{3-9}$heterocycloalkenyl, or $C_{6-10}$aryl;

$R^3$ is H, $C_{1-6}$alkyl, $C_{3-8}$cycloalkyl, $C_{3-8}$cycloalkenyl, $C_{3-7}$heterocycloalkyl, $C_{6-10}$aryl, or $C_{2-6}$heteroaryl;

$R^4$ is $C_{3-8}$cycloalkyl, $C_{3-9}$heterocycloalkyl, $C_{6-10}$aryl, or $C_{2-9}$heteroaryl;

each $R^5$ independently is H, $C_{1-3}$alkyl, or $C_{0-2}$alkylene-$C_{6-10}$aryl;

X is absent, $C_{1-3}$alkylene, C=O, or (C=O)O;

Y is SO or $SO_2$;

each heterocycloalkyl, heterocycloalkenyl, and heteroaryl group independently has 1, 2, or 3 ring heteroatoms selected from N, O, and S.

In some embodiments, each Y is SO. In various embodiments, each Y is $SO_2$.

In various cases, $R^a$ is H. In some cases, $R^a$ is $C_{1-3}$alkyl. In some embodiments, $R^a$ is $CH_3$. In some embodiments, $R^b$ is H. In various embodiments, $R^b$ is $C_{1-3}$alkyl. In various cases, $R^b$ is $CH_3$. In some cases, both $R^a$ and $R^b$ are H.

In some cases, $R^1$ is H, OH, or $=NOR^5$. In various cases, $R^5$ is H or $CH_3$. Therefore, suitable $R^1$ groups can include H, OH, =NOH, and $=NORCH_3$. In some embodiments, $R^1$ is $C_{1-3}$alkyl or $OC_{1-3}$alkyl. For example, $R^1$ can be $CH_3$ or $OCH_3$. In some cases, $R^1$ is $CH_3$ and exhibits S stereochemistry. In various embodiments, $R^1$ is $C_{3-6}$cycloalkyl or $C_{3-6}$heterocycloalkyl and forms a Spiro group with the ring carbon to which it is attached. Suitable $R^1$ spiro groups can include

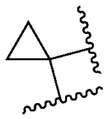,
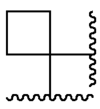,
and
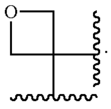.

In various cases, $R^1$ is $=CH_2$. In some embodiments, each of $R^{1a}$ and $R^{1b}$ is H. In some embodiments, at least one of $R^{1a}$ and $R^{1b}$ is $C_{1-3}$alkyl. In some embodiments, each of $R^{1a}$ and $R^{1b}$ is $CH_3$. In some embodiments, $R^a$ is H, $R^b$ is H, and $R^1$ is $CH_3$. In various embodiments, $R^a$ is $CH_3$, $R^b$ is H, and $R^1$ is H. In some cases, $R^a$ is H, $R^b$ is $CH_3$, and $R^1$ is H. In various cases, $R^a$ is $CH_3$, $R^b$ is H, and $R^1$ is $CH_3$. In some embodiments, $R^a$ is H, $R^b$ is $CH_3$, and $R^1$ is $CH_3$. In various embodiments, $R^a$ is $CH_3$, $R^b$ is $CH_3$, and $R^1$ is H.

In some embodiments, $R^2$ is $C_{1-6}$alkyl or $N(R^5)_2$. In some cases, each $R^5$ independently comprises H, $C_{1-3}$alkyl, or benzyl. Suitable $R^2$ groups can include Et, iPr, $N(CH_3)_2$,

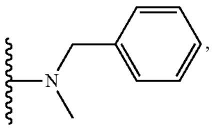
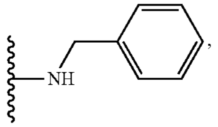
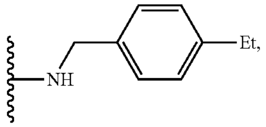
and
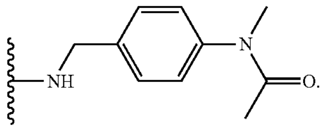

In some cases, $R^2$ comprises $C_{3-8}$cycloalkyl. In various cases, $R^2$ comprises cyclopentyl or cyclohexyl. In some embodiments, $R^2$ is $C_{3-9}$heterocycloalkyl or $C_{3-9}$heterocycloalkenyl. In various embodiments, $R^2$ comprises oxetanyl, azetidinyl, tetrahydrofuranyl, pyrrolidinyl, tetrahydropyranyl, pyranyl, piperidinyl, piperazinyl, azepanyl, morpholinyl, or tetrahydropyridinyl. In various embodiments, the $C_{3-9}$heterocycloalkyl or $C_{3-9}$heterocycloalkenyl comprises a bridge or a Spiro group. In some cases, the $C_{3-9}$heterocycloalkyl comprising a bridge or a Spiro group is selected from the group consisting of

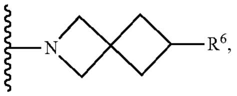
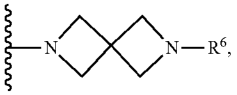
and
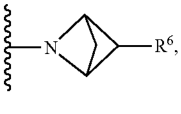

and $R^6$ is $C_{1-8}$alkyl, $C_{3-8}$cycloalkyl, or $C_{6-10}$aryl. In some cases, $R^6$ is phenyl optionally substituted with one to three groups independently selected from halo, $C_{1-3}$alkyl, $C_{1-3}$alkoxy, and CN. Examples of suitable $R^2$ groups include

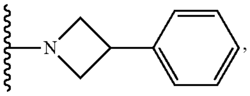
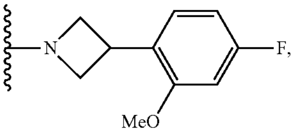
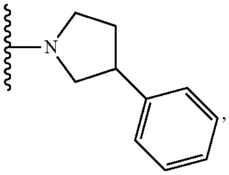
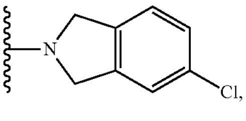

-continued

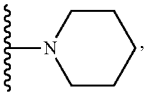
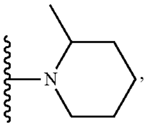
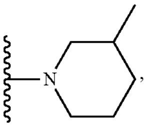
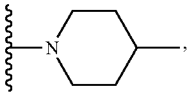
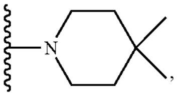
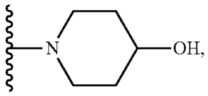
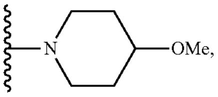
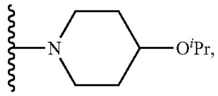
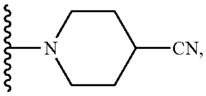
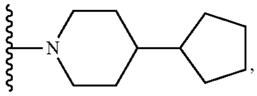
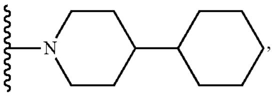
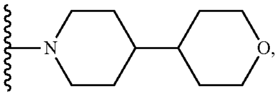
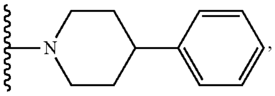
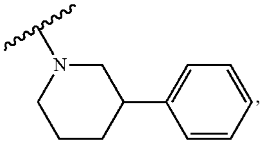
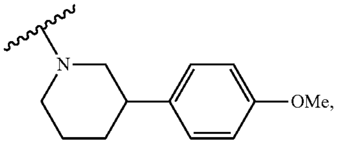
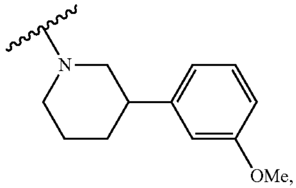
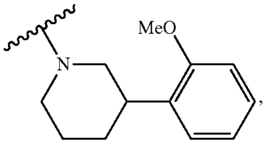
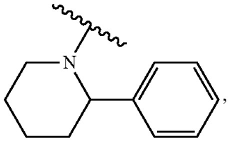
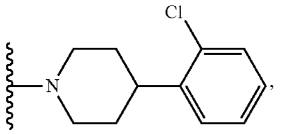
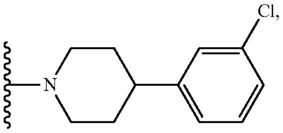
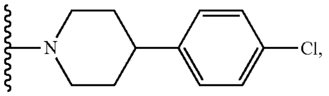
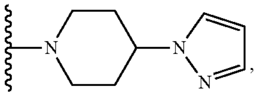

-continued
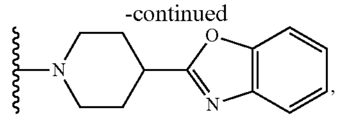,
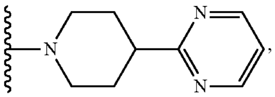, 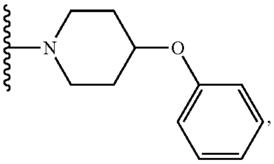,
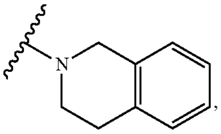, 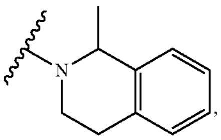,
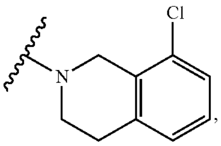, 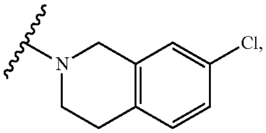,
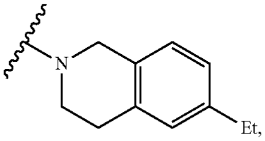, 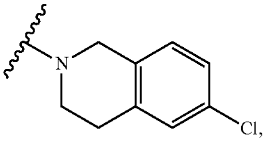,
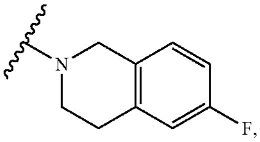, 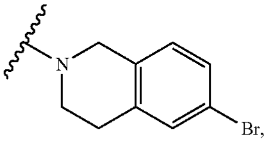,
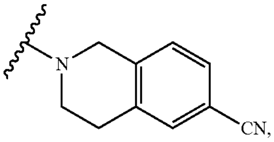, 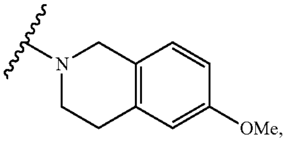,
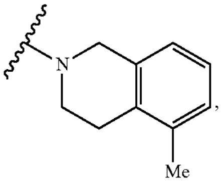, 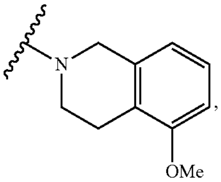,
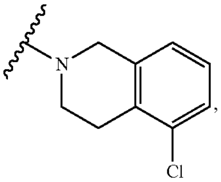, 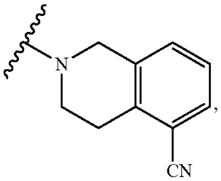,
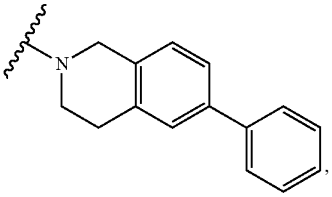,
-continued
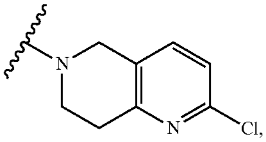, 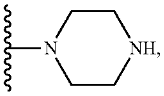,
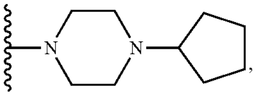, 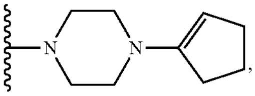,
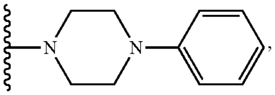, 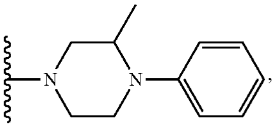,
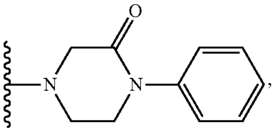, 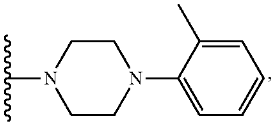,
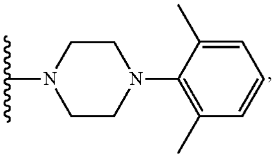, 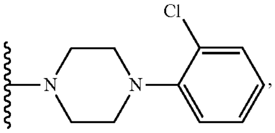,
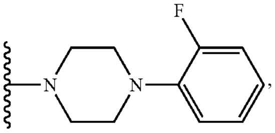, 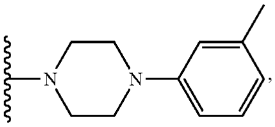,
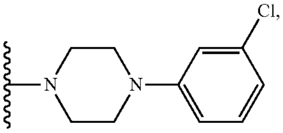, 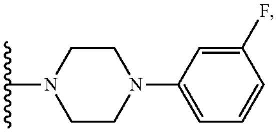,
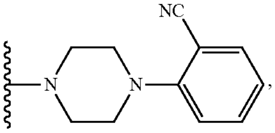,
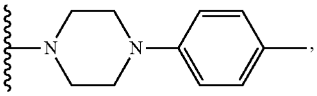,
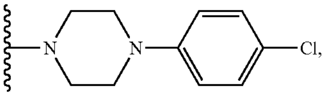,
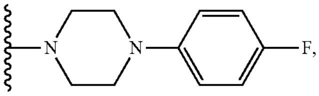,
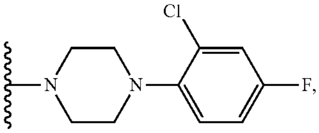,
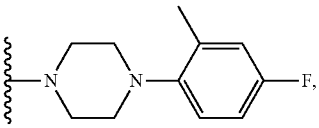,

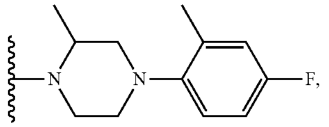
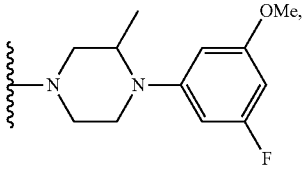
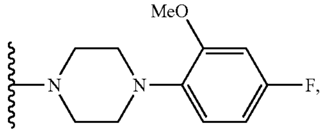
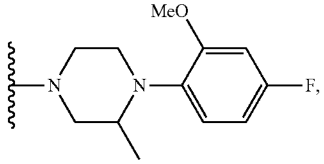
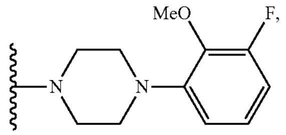
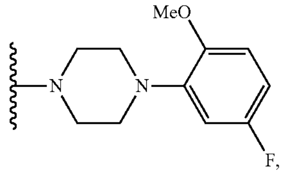
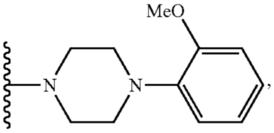
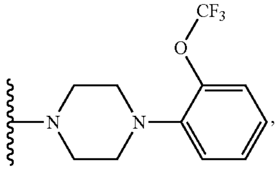
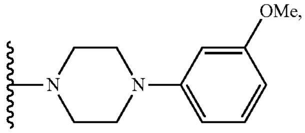
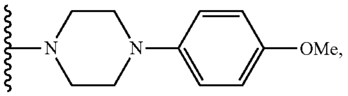
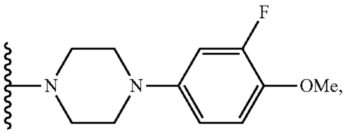
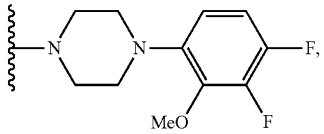
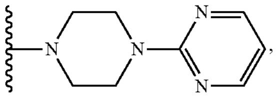
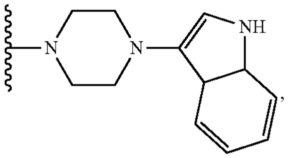
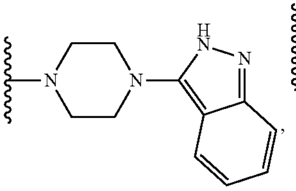
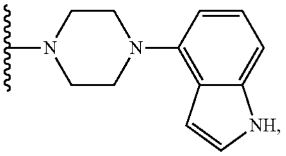
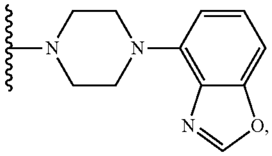
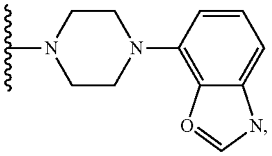
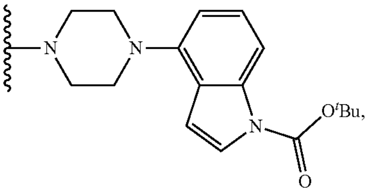
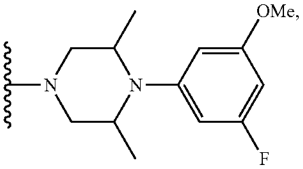
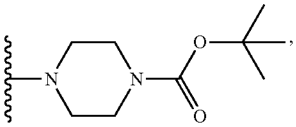
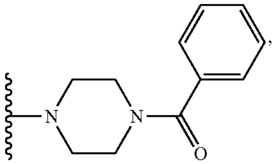
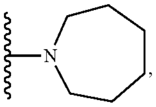
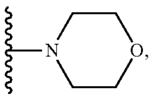
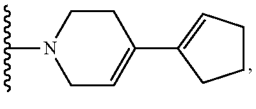
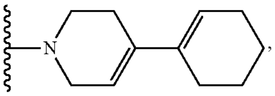
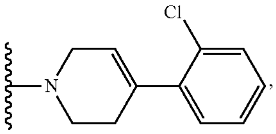
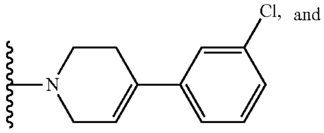
and
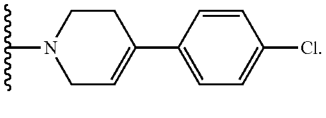

In some cases, $R^2$ is selected from the group consisting of

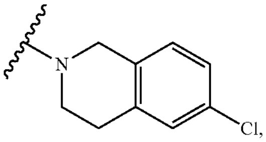
,
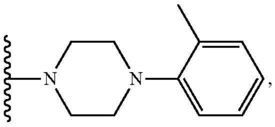
,
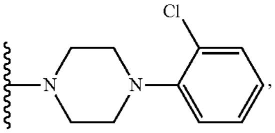
,
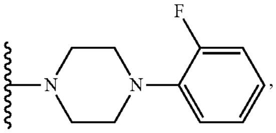
,
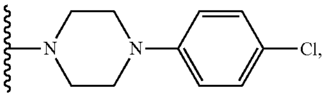
,
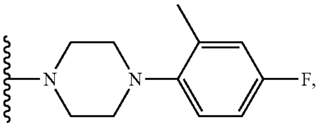
,
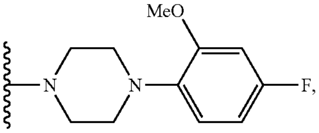
,
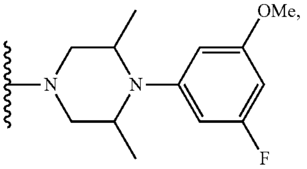
, and
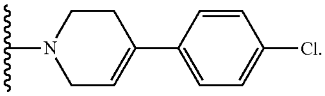
.

In various cases, $R^2$ is $C_{6-10}$aryl. In some embodiments, $R^2$ is

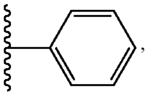
,
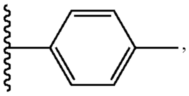
, or
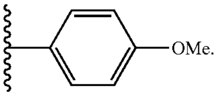
.

In various embodiments, X is absent. In some embodiments, $R^3$ comprises $C_{1-6}$alkyl or H. In some cases, $R^3$ is $C_{1-6}$alkyl, such as methyl, ethyl, propyl, butyl, pentyl, or hexyl. In some cases, $R^3$ is 2-methylbutyl, isopropyl, isopentyl, $CH_2CH_2OCH_3$, $CH_2C(CH_3)_2CN$, $CH_2CF_3$, or $CH_2CH_2CF_3$. In various cases, $R^3$ is isobutyl.

In some embodiments, X is $C_{1-3}$alkylene. In some cases, X is $CH_2$, $CH_2CH_2$, or $CH(CH_3)$. In various cases, $R^3$ comprises $C_{3-8}$cycloalkyl, $C_{3-8}$cycloalkenyl, $C_{3-7}$heterocycloalkyl, $C_{6-10}$aryl, or $C_{2-6}$heteroaryl. In some embodiments, $R^3$ comprises cyclopropyl, cyclobutyl, cyclopentyl, cyclohexyl, cyclopentenyl, cyclohexenyl, tetrahydropyranyl, phenyl, pyrrolyl, pyrazolyl, imidazolyl, tetrazolyl, furanyl, thiophenyl, thiazolyl, oxazolyl, isoxazolyl, oxadiazolyl, thiadiazolyl, pyridinyl, pyrazinyl, or pyrimidinyl. Examples of suitable X—$R^3$ include

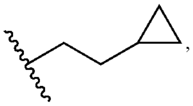
,
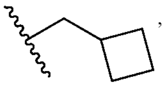
,
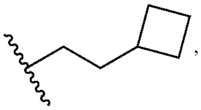
,
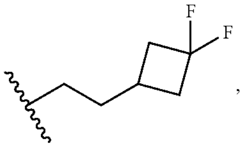
,
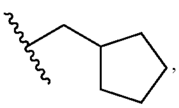
,
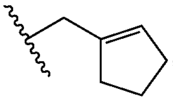
,
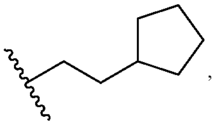
,
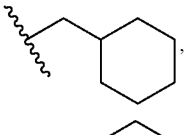
,
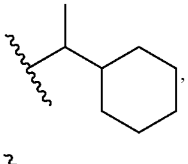
,
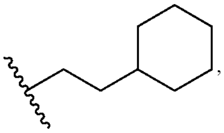
,
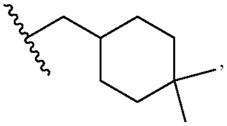
,
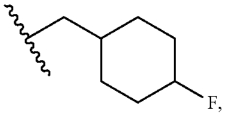
,
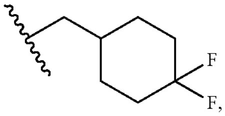
,
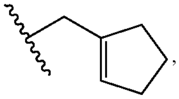
,
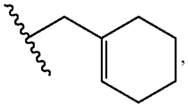
,
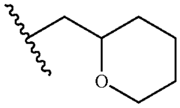
,
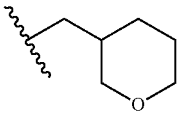
,
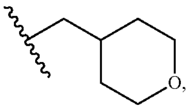
,
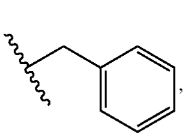
,
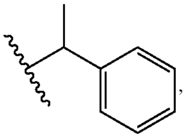
,
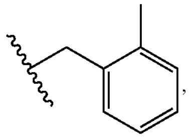
,
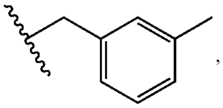
,
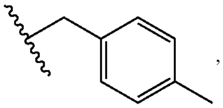
,
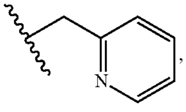
,
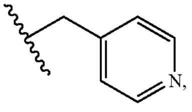
,
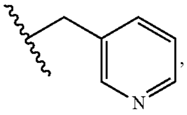
,
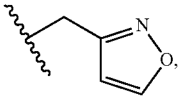
, and
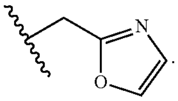 [SMILES: *Cc1ncco1]
.

In some cases, X—$R^3$ is

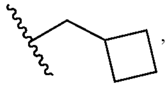, 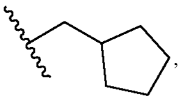,

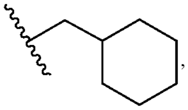, or 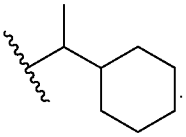.

In some cases, X—$R^3$ is

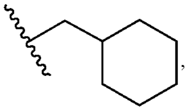, or 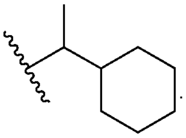.

In some embodiments, X is C═O or (C═O)O. In various embodiments, $R^3$ comprises $C_{1-6}$alkyl or $C_{6-10}$aryl. In some cases, X—$R^3$ is

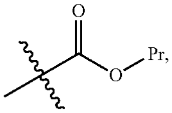 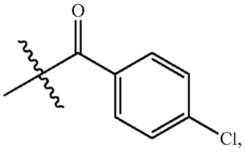 or

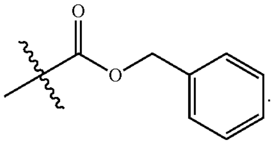.

In various cases, $R^4$ comprises $C_{3-8}$cycloalkyl or $C_{3-9}$heterocycloalkyl, such as

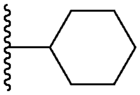 or 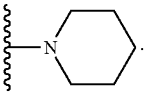.

In various embodiments, $R^4$ comprises $C_{6-10}$aryl or $C_{2-9}$heteroaryl, and $R^4$ is optionally substituted with one to three groups independently selected from halo, $C_{1-3}$alkyl, $C_{1-3}$alkoxy, $C(O)N(R^N)_2$, and $N(R^N)_2$, and each $R^N$ is independently H or $C_{1-3}$alkyl. In some embodiments, $R^4$ is selected from the group consisting of

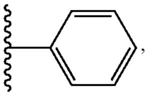, 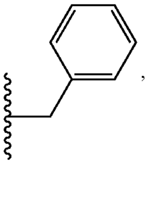, 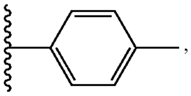,

-continued

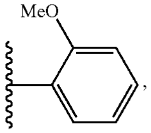, 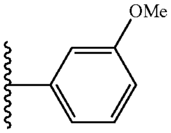, 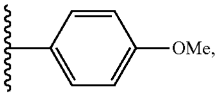

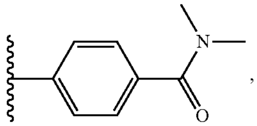, 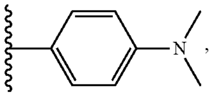 [SMILES: *c1ccc(N(C)C)cc1],

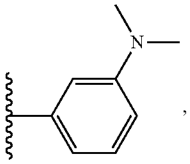, 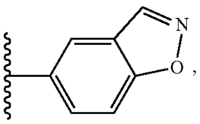,

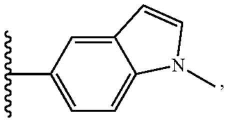, 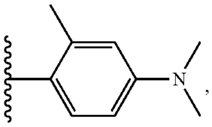,

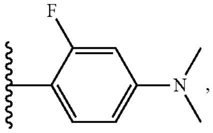, and 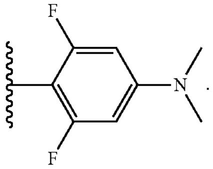.

In various embodiments, $R^4$ is

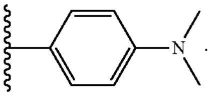.

In some embodiments, $R^a$, $R^b$, $R^{1a}$, and $R^{1b}$ are each H, $R^1$ is ═$CH_2$ or $CH_3$; $R^2$ is

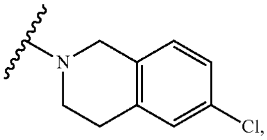 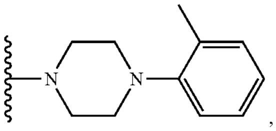,

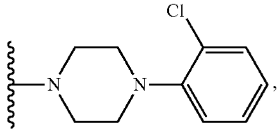, 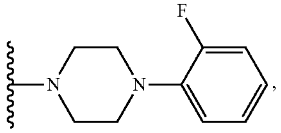,

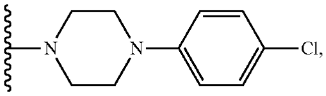

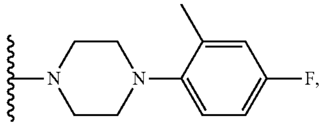

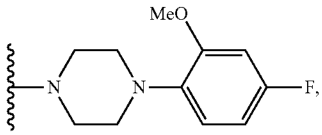

-continued

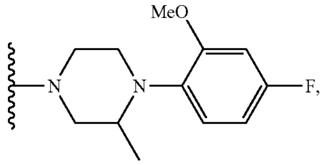

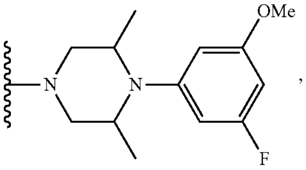

, or

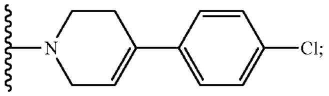

X—$R^3$ is isobutyl,

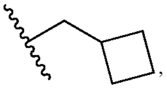

,

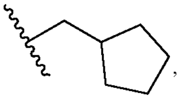

,

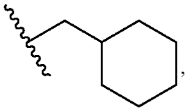

, or

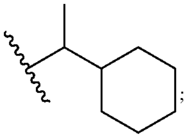

;

$R^4$ is

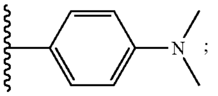

;

and each Y is $SO_2$. In some cases, $R^1$ is in a (S) configuration. In some cases, provided herein are compounds comprising a structure

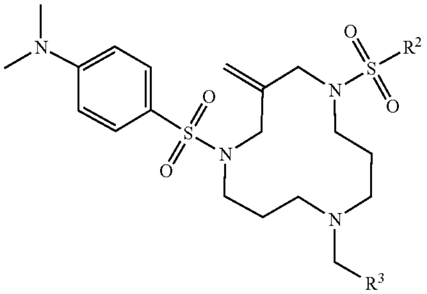

or

-continued

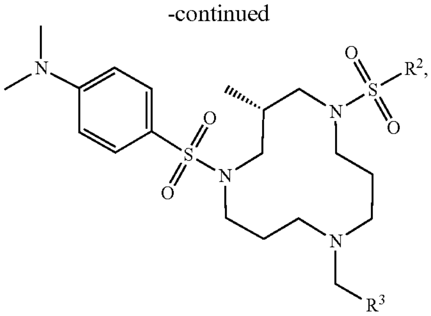

wherein $R^2$ is

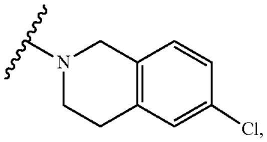

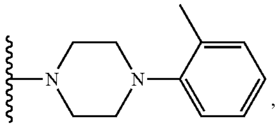

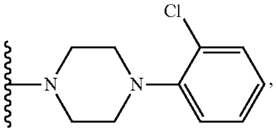

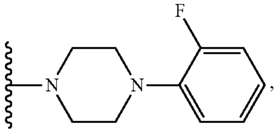

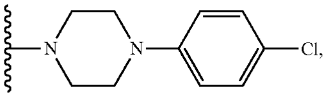

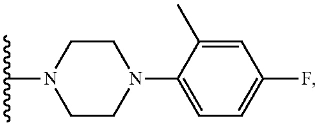

or

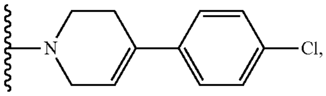

and $R^3$ is cyclobutyl, cyclopentyl, or cyclohexyl.

Examples of compounds of Formula (I) are shown in Table A, as compounds A1-A210, or a pharmaceutically acceptable salt thereof. In some cases, the compound is a compound of A1-A151, or pharmaceutically acceptable salt thereof.

TABLE A

| No. | Structure |
|---|---|
| A1 | 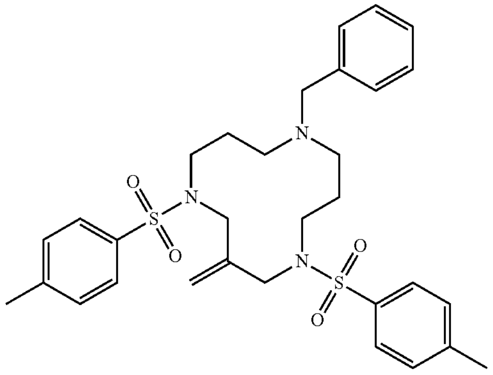 |

TABLE A-continued
| No. | Structure |
|---|---|
| A2 | 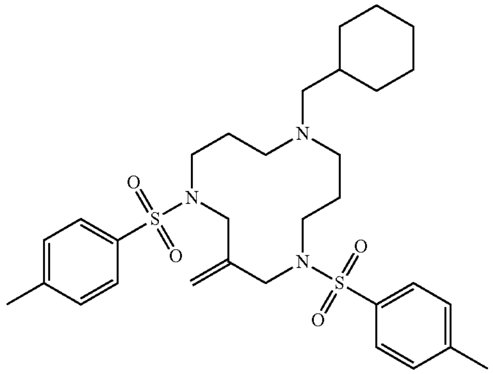 |
| A3 | 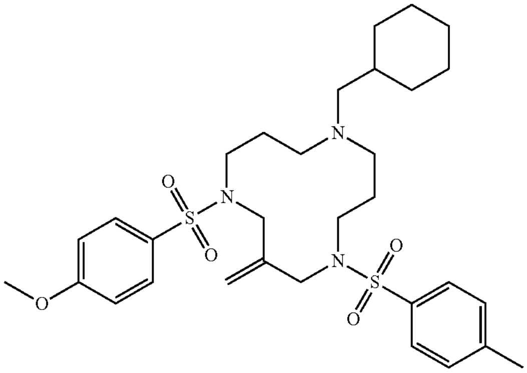 |
| A4 | 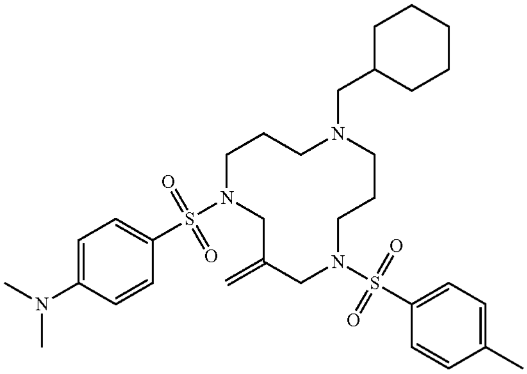 |
| A5 | 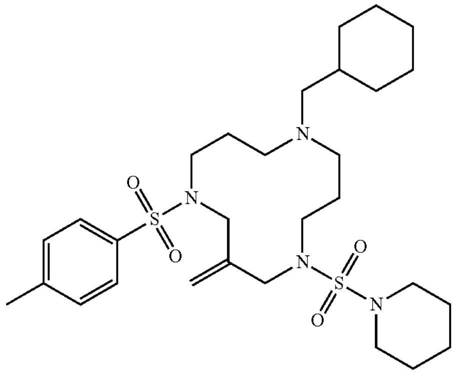 [SMILES: C=C1CN(S(=O)(=O)c2ccc(C)cc2)CCCN(CC2CCCCC2)CCCN(S(=O)(=O)N2CCCCC2)C1] |
TABLE A-continued
| No. | Structure |
|---|---|
| A6 | 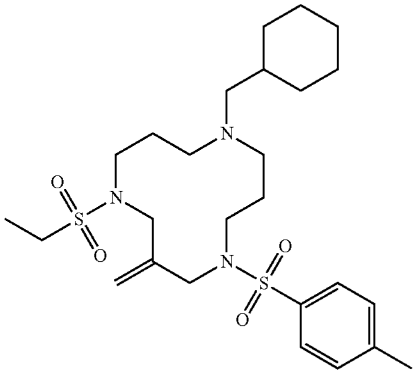 [SMILES: C=C1CN(S(=O)(=O)CC)CCCN(CC2CCCCC2)CCCN(S(=O)(=O)c2ccc(C)cc2)C1] |
| A7 | 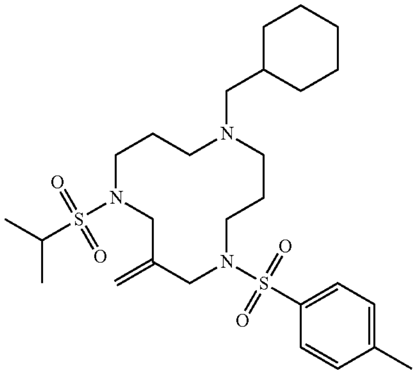 [SMILES: C=C1CN(S(=O)(=O)c2ccc(C)cc2)CCCN(CC2CCCCC2)CCCN(S(=O)(=O)C(C)C)C1] |
| A8 | 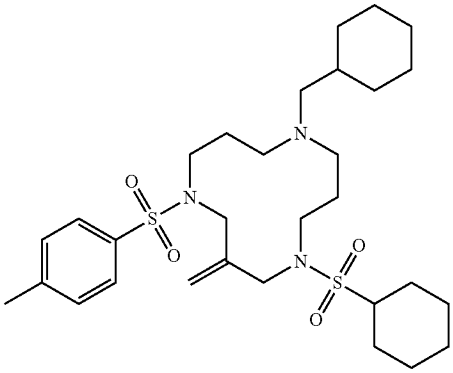 [SMILES: C=C1CN(S(=O)(=O)c2ccc(C)cc2)CCCN(CC2CCCCC2)CCCN(S(=O)(=O)C2CCCCC2)C1] |
| A9 | 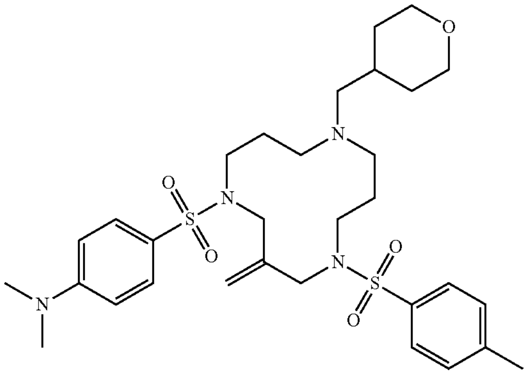 |

TABLE A-continued
| No. | Structure |
|---|---|
| A10 | 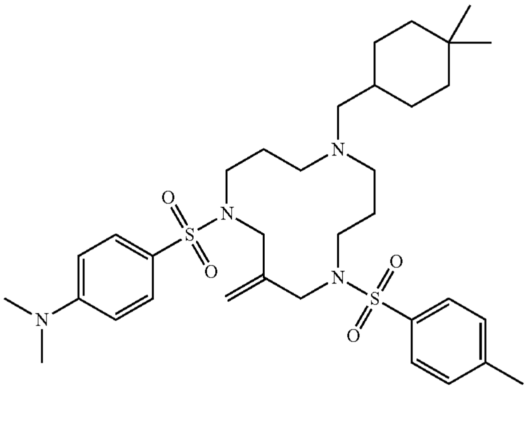 |
| A11 | 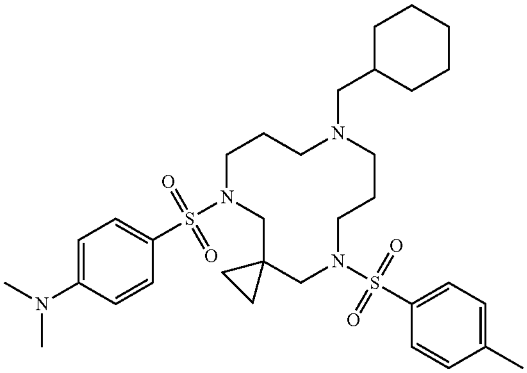 |
| A12 | 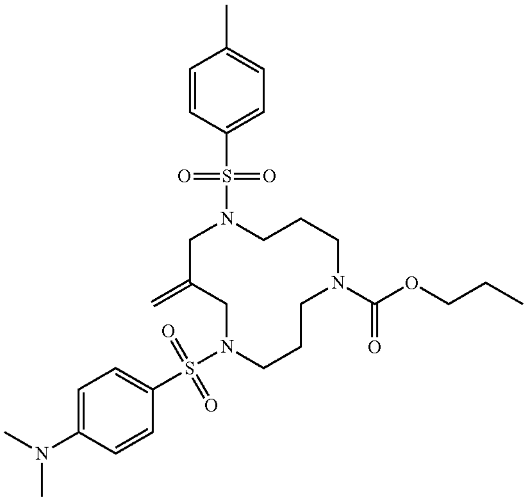 [SMILES: C=C1CN(S(=O)(=O)c2ccc(C)cc2)CCCN(C(=O)OCCC)CCCN(S(=O)(=O)c2ccc(N(C)C)cc2)C1] |
TABLE A-continued
| No. | Structure |
|---|---|
| A13 | 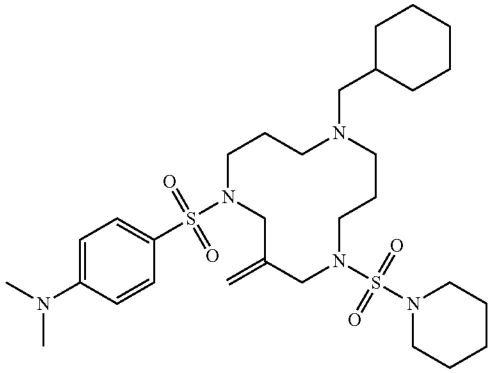 [SMILES: C=C1CN(S(=O)(=O)c2ccc(N(C)C)cc2)CCCN(CC2CCCCC2)CCCN(S(=O)(=O)N2CCCCC2)C1] |
| A14 | 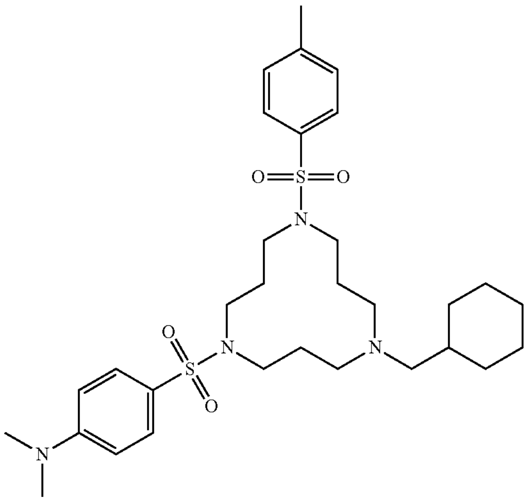 [SMILES: Cc1ccc(S(=O)(=O)N2CCCN(CC3CCCCC3)CCCN(S(=O)(=O)c3ccc(N(C)C)cc3)CCC2)cc1] |
| A15 | 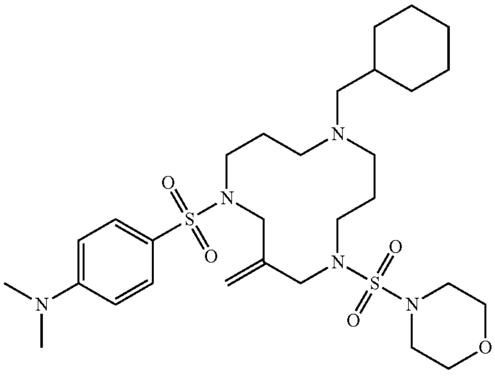 [SMILES: C=C1CN(S(=O)(=O)c2ccc(N(C)C)cc2)CCCN(CC2CCCCC2)CCCN(S(=O)(=O)N2CCOCC2)C1] |
| A16 | 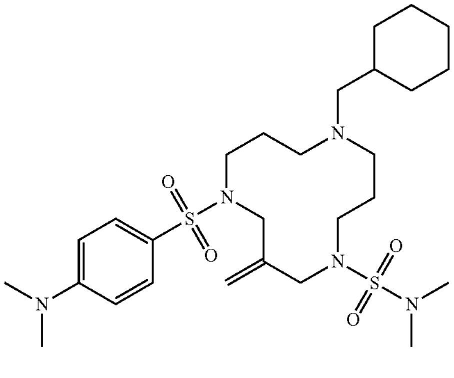 |

TABLE A-continued
| No. | Structure |
|---|---|
| A17 | 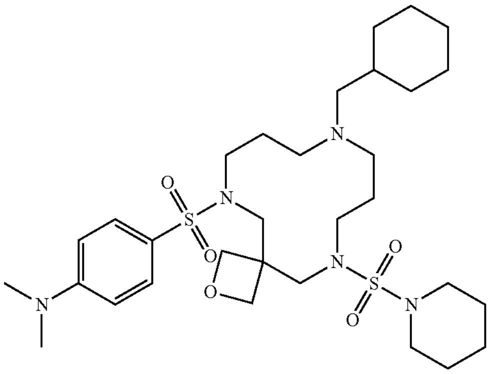 [SMILES: CN(C)c1ccc(S(=O)(=O)N2CCCN(CC3CCCCC3)CCCN(S(=O)(=O)N3CCCCC3)CC3(COC3)C2)cc1] |
| A18 | 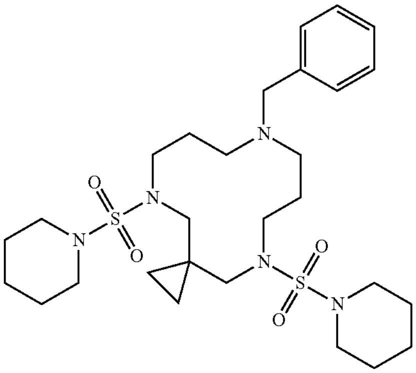 [SMILES: O=S(=O)(N1CCCCC1)N1CCCN(Cc2ccccc2)CCCN(S(=O)(=O)N2CCCCC2)CC2(CC2)C1] |
| A19 | 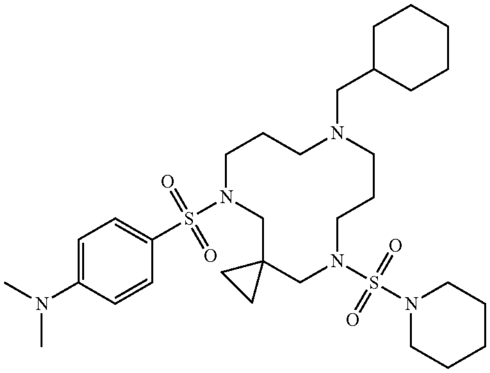 [SMILES: CN(C)c1ccc(S(=O)(=O)N2CCCN(CC3CCCCC3)CCCN(S(=O)(=O)N3CCCCC3)CC3(CC3)C2)cc1] |
| A20 | 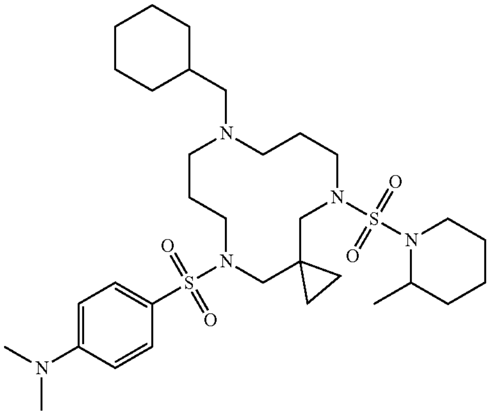 [SMILES: CC1CCCCN1S(=O)(=O)N1CCCN(CC2CCCCC2)CCCN(S(=O)(=O)c2ccc(N(C)C)cc2)CC2(CC2)C1] |
TABLE A-continued
| No. | Structure |
|---|---|
| A21 | 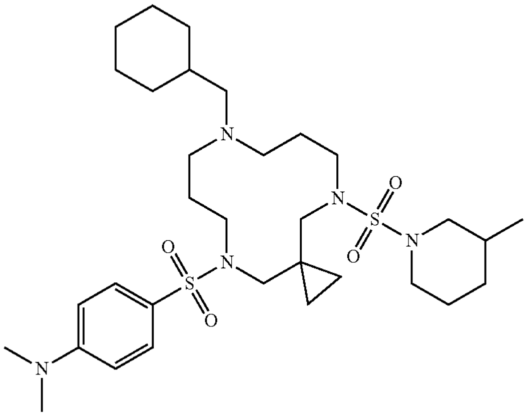 |
| A22 | 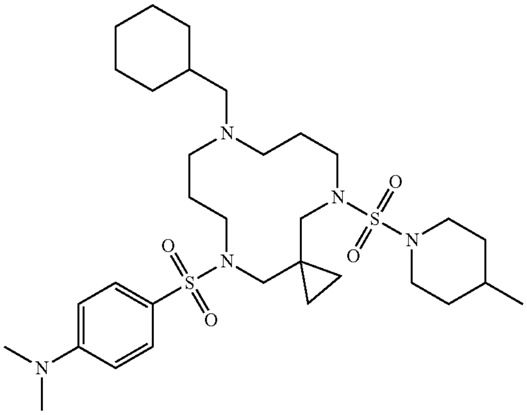 |
| A23 | 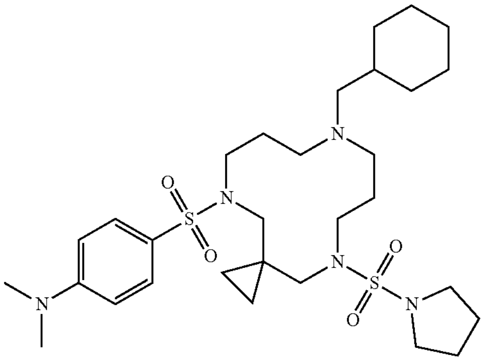 [SMILES: CN(C)c1ccc(S(=O)(=O)N2CCCN(CC3CCCCC3)CCCN(S(=O)(=O)N3CCCC3)CC3(CC3)C2)cc1] |
| A24 | 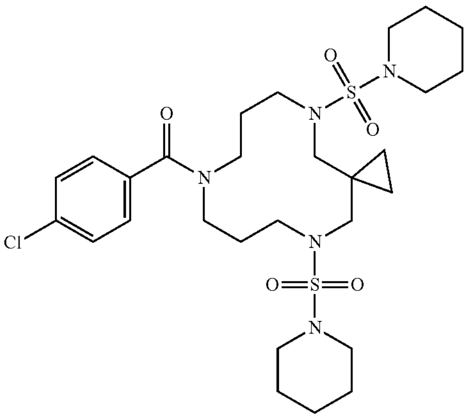 [SMILES: O=C(c1ccc(Cl)cc1)N1CCCN(S(=O)(=O)N2CCCCC2)CC2(CC2)CN(S(=O)(=O)N2CCCCC2)CCC1] |

TABLE A-continued
| No. | Structure |
|---|---|
| A25 | 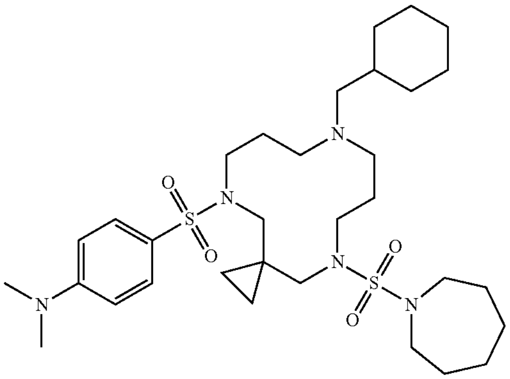 [SMILES: CN(C)c1ccc(S(=O)(=O)N2CCCN(CC3CCCCC3)CCCN(S(=O)(=O)N3CCCCCC3)CC3(CC3)C2)cc1] |
| A26 | 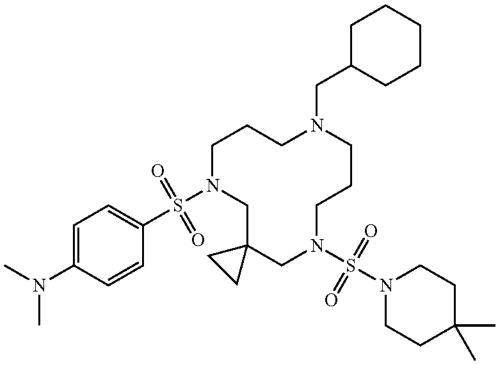 |
| A27 | 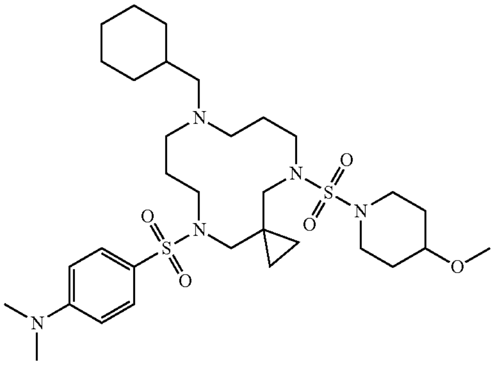 |
| A28 | 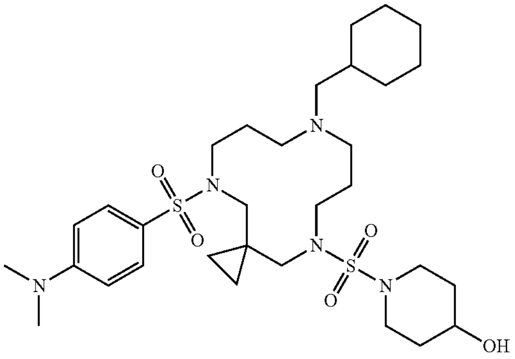 [SMILES: CN(C)c1ccc(S(=O)(=O)N2CCCN(CC3CCCCC3)CCCN(S(=O)(=O)N3CCC(O)CC3)CC3(CC3)C2)cc1] |
TABLE A-continued
| No. | Structure |
|---|---|
| A29 | 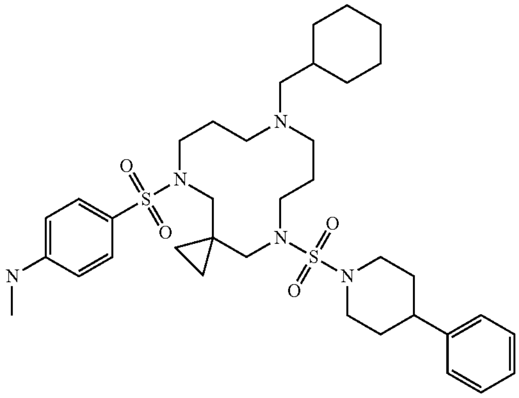 [SMILES: CNc1ccc(S(=O)(=O)N2CCCN(CC3CCCCC3)CCCN(S(=O)(=O)N3CCC(c4ccccc4)CC3)CC3(CC3)C2)cc1] |
| A30 | 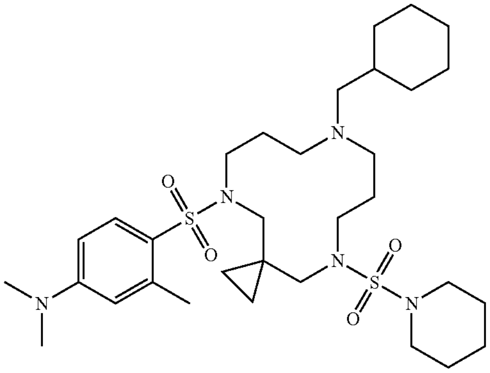 [SMILES: Cc1cc(N(C)C)ccc1S(=O)(=O)N1CCCN(CC2CCCCC2)CCCN(S(=O)(=O)N2CCCCC2)CC2(CC2)C1] |
| A31 | 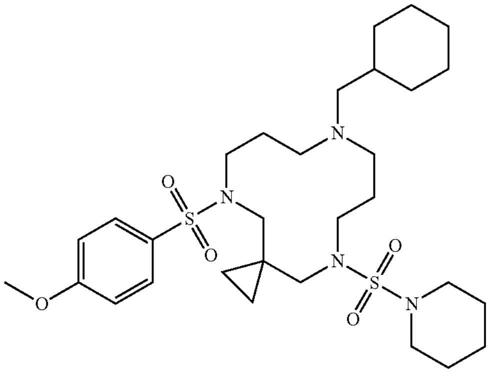 [SMILES: COc1ccc(S(=O)(=O)N2CCCN(CC3CCCCC3)CCCN(S(=O)(=O)N3CCCCC3)CC3(CC3)C2)cc1] |
| A32 | 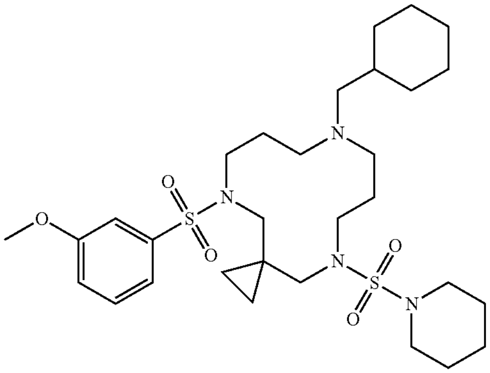 [SMILES: COc1cccc(S(=O)(=O)N2CCCN(CC3CCCCC3)CCCN(S(=O)(=O)N3CCCCC3)CC3(CC3)C2)c1] |

TABLE A-continued
| No. | Structure |
| --- | --- |
| A33 | 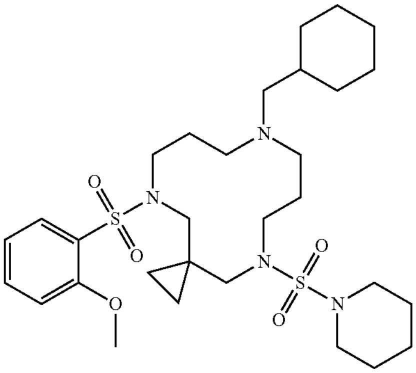 [SMILES: COc1ccccc1S(=O)(=O)N1CCCN(CC2CCCCC2)CCCN(S(=O)(=O)N2CCCCC2)CC2(CC2)C1] |
| A34 | 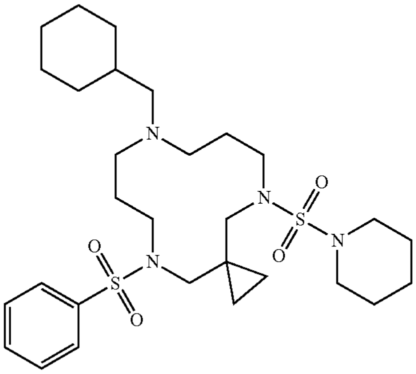 [SMILES: O=S(=O)(c1ccccc1)N1CCCN(CC2CCCCC2)CCCN(S(=O)(=O)N2CCCCC2)CC2(CC2)C1] |
| A35 | 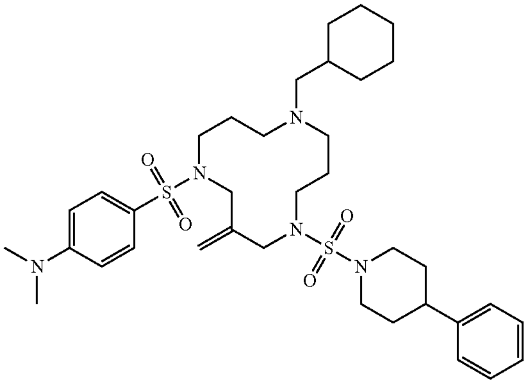 [SMILES: C=C1CN(S(=O)(=O)c2ccc(N(C)C)cc2)CCCN(CC2CCCCC2)CCCN(S(=O)(=O)N2CCC(c3ccccc3)CC2)C1] |
| A36 | 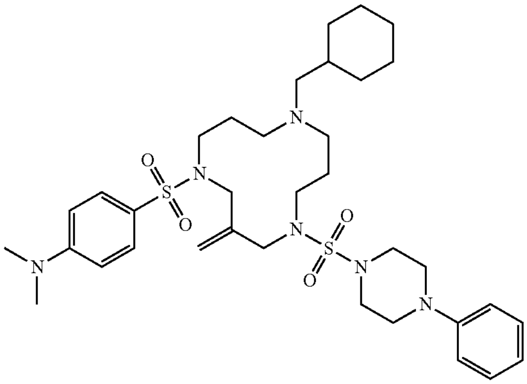 [SMILES: C=C1CN(S(=O)(=O)c2ccc(N(C)C)cc2)CCCN(CC2CCCCC2)CCCN(S(=O)(=O)N2CCN(c3ccccc3)CC2)C1] |
TABLE A-continued
| No. | Structure |
| --- | --- |
| A37 | 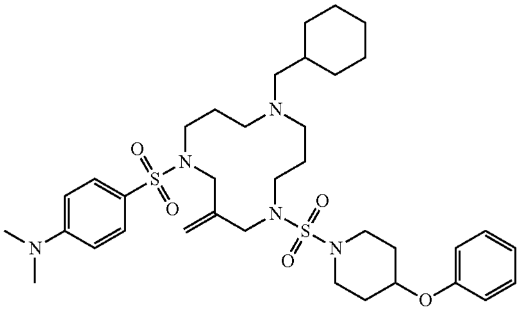 [SMILES: C=C1CN(S(=O)(=O)c2ccc(N(C)C)cc2)CCCN(CC2CCCCC2)CCCN(S(=O)(=O)N2CCC(Oc3ccccc3)CC2)C1] |
| A38 | 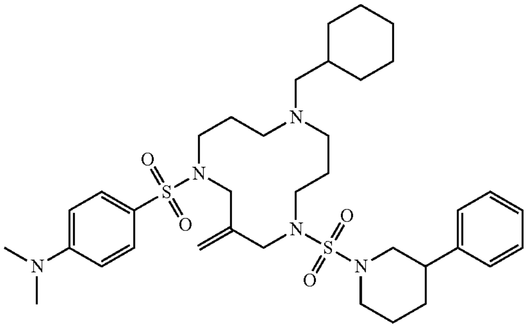 [SMILES: C=C1CN(S(=O)(=O)c2ccc(N(C)C)cc2)CCCN(CC2CCCCC2)CCCN(S(=O)(=O)N2CCCC(c3ccccc3)C2)C1] |
| A39 | 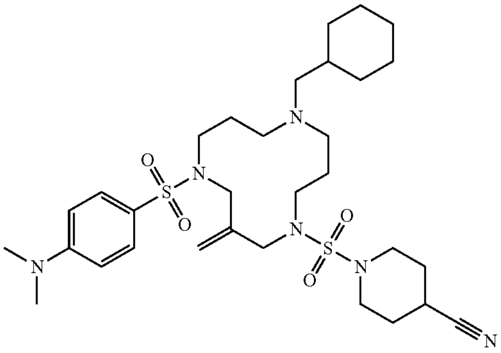 [SMILES: C=C1CN(S(=O)(=O)c2ccc(N(C)C)cc2)CCCN(CC2CCCCC2)CCCN(S(=O)(=O)N2CCC(C#N)CC2)C1] |
| A40 | 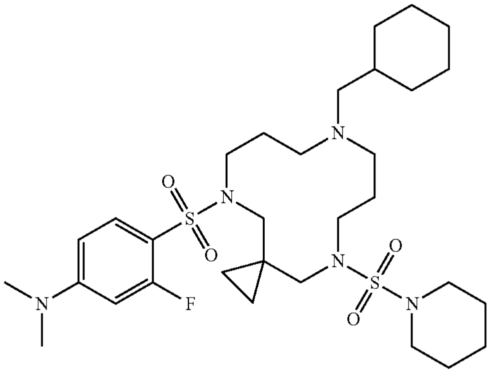 [SMILES: CN(C)c1ccc(S(=O)(=O)N2CCCN(CC3CCCCC3)CCCN(S(=O)(=O)N3CCCCC3)CC3(CC3)C2)c(F)c1] |

| No. | Structure |
|---|---|
| A41 | 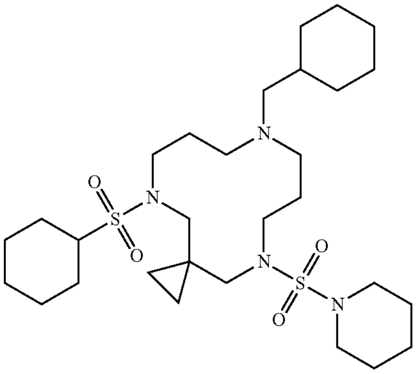 [SMILES: O=S(=O)(C1CCCCC1)N1CCCN(CC2CCCCC2)CCCN(S(=O)(=O)N2CCCCC2)CC2(CC2)C1] |
| A42 | 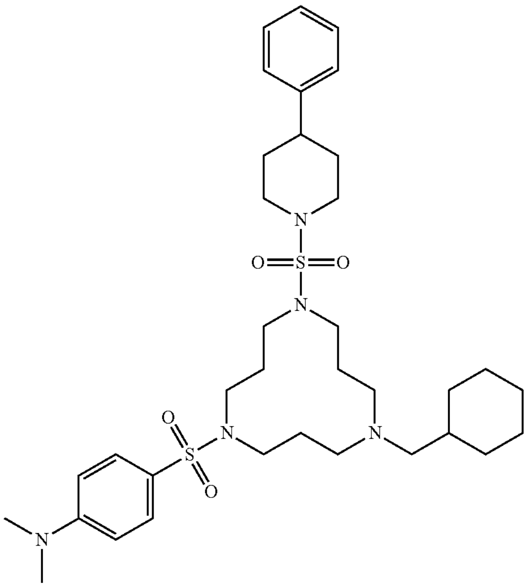 [SMILES: CN(C)c1ccc(S(=O)(=O)N2CCCN(CC3CCCCC3)CCCN(S(=O)(=O)N3CCC(c4ccccc4)CC3)CCC2)cc1] |
| A43 | 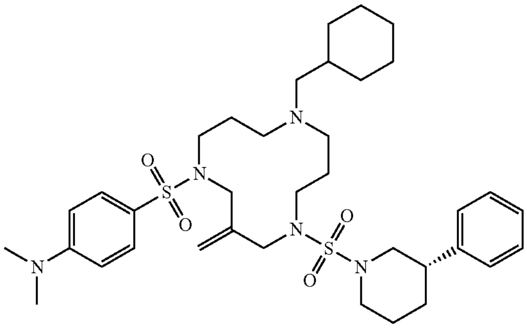 [SMILES: C=C1CN(S(=O)(=O)c2ccc(N(C)C)cc2)CCCN(CC2CCCCC2)CCCN(S(=O)(=O)N2CCC[C@@H](c3ccccc3)C2)C1] |
| No. | Structure |
|---|---|
| A44 | 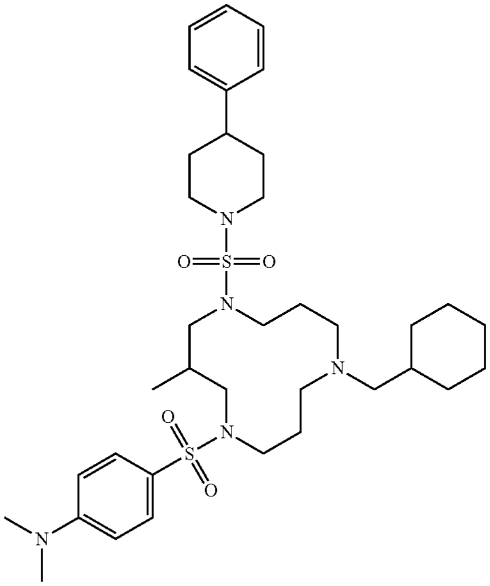 [SMILES: CC1CN(S(=O)(=O)c2ccc(N(C)C)cc2)CCCN(CC2CCCCC2)CCCN(S(=O)(=O)N2CCC(c3ccccc3)CC2)C1] |
| A46 | 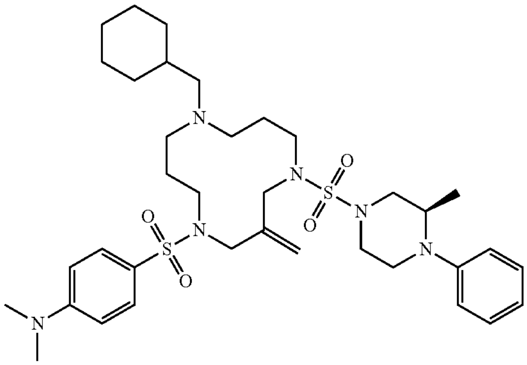 [SMILES: C=C1CN(S(=O)(=O)c2ccc(N(C)C)cc2)CCCN(CC2CCCCC2)CCCN(S(=O)(=O)N2CCN(c3ccccc3)[C@H](C)C2)C1] |
| A47 | 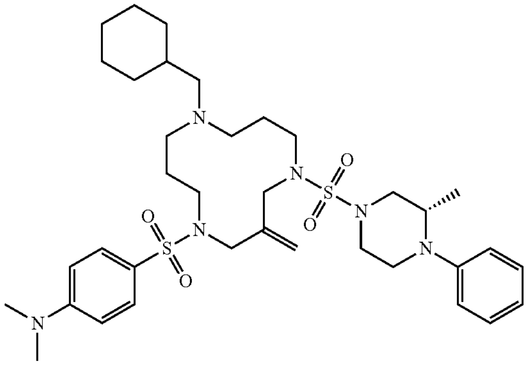 [SMILES: C=C1CN(S(=O)(=O)c2ccc(N(C)C)cc2)CCCN(CC2CCCCC2)CCCN(S(=O)(=O)N2CCN(c3ccccc3)[C@@H](C)C2)C1] |

TABLE A-continued
| No. | Structure |
|---|---|
| A48 | 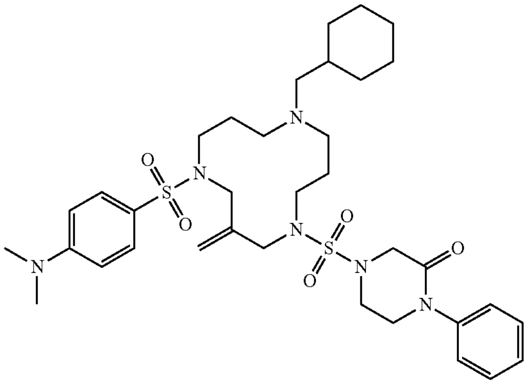 [SMILES: C=C1CN(S(=O)(=O)c2ccc(N(C)C)cc2)CCCN(CC2CCCCC2)CCCN(S(=O)(=O)N2CCN(c3ccccc3)C(=O)C2)C1] |
| A49 | 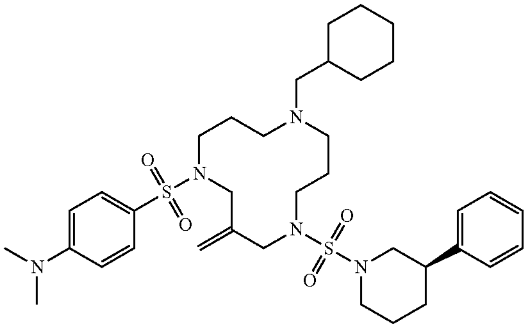 [SMILES: C=C1CN(S(=O)(=O)c2ccc(N(C)C)cc2)CCCN(CC2CCCCC2)CCCN(S(=O)(=O)N2CCC[C@H](c3ccccc3)C2)C1] |
| A50 | 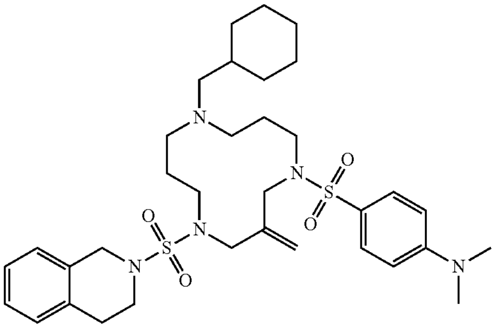 [SMILES: C=C1CN(S(=O)(=O)c2ccc(N(C)C)cc2)CCCN(CC2CCCCC2)CCCN(S(=O)(=O)N2CCc3ccccc3C2)C1] |
| A51 | 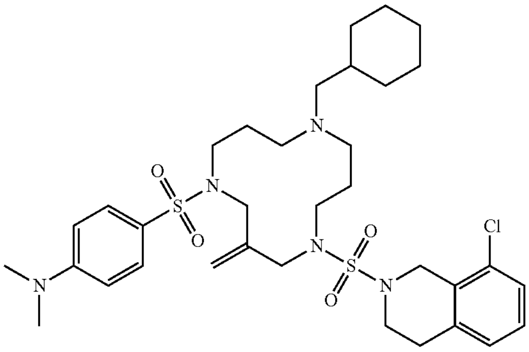 [SMILES: C=C1CN(S(=O)(=O)c2ccc(N(C)C)cc2)CCCN(CC2CCCCC2)CCCN(S(=O)(=O)N2CCc3cccc(Cl)c3C2)C1] |
TABLE A-continued
| No. | Structure |
|---|---|
| A52 | 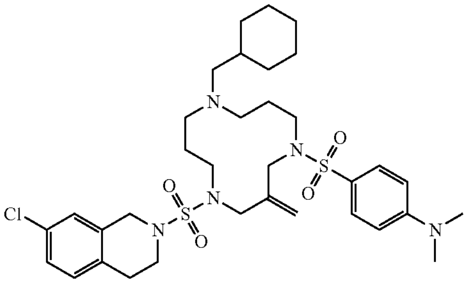 [SMILES: C=C1CN(S(=O)(=O)c2ccc(N(C)C)cc2)CCCN(CC2CCCCC2)CCCN(S(=O)(=O)N2CCc3ccc(Cl)cc3C2)C1] |
| A53 | 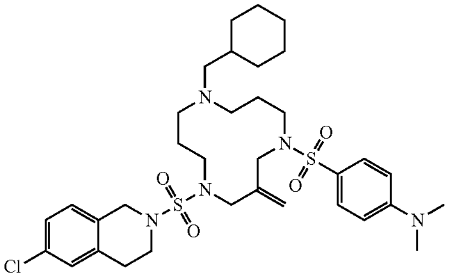 [SMILES: C=C1CN(S(=O)(=O)c2ccc(N(C)C)cc2)CCCN(CC2CCCCC2)CCCN(S(=O)(=O)N2CCc3cc(Cl)ccc3C2)C1] |
| A54 | 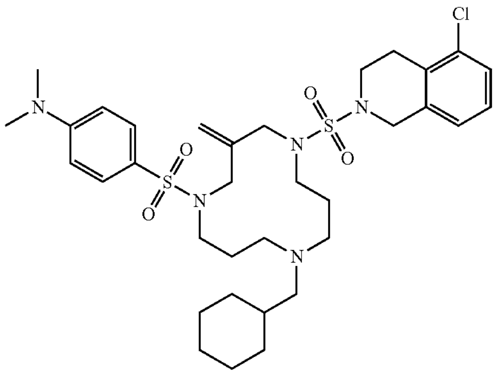 [SMILES: C=C1CN(S(=O)(=O)c2ccc(N(C)C)cc2)CCCN(CC2CCCCC2)CCCN(S(=O)(=O)N2CCc3c(Cl)cccc3C2)C1] |
| A55 | 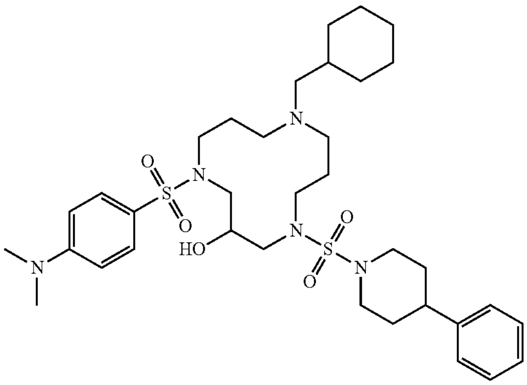 [SMILES: CN(C)c1ccc(S(=O)(=O)N2CCCN(CC3CCCCC3)CCCN(S(=O)(=O)N3CCC(c4ccccc4)CC3)CC(O)C2)cc1] |

TABLE A-continued
| No. | Structure |
|---|---|
| A56 | 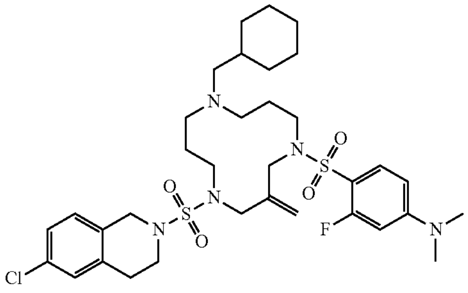 [SMILES: C=C1CN(S(=O)(=O)c2ccc(N(C)C)cc2F)CCCN(CC2CCCCC2)CCCN(S(=O)(=O)N2CCc3cc(Cl)ccc3C2)C1] |
| A57 | 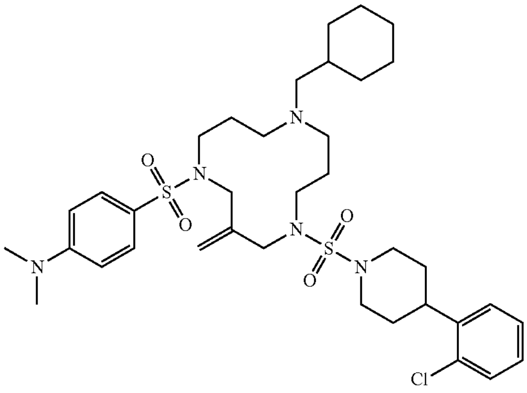 [SMILES: C=C1CN(S(=O)(=O)c2ccc(N(C)C)cc2)CCCN(CC2CCCCC2)CCCN(S(=O)(=O)N2CCC(c3ccccc3Cl)CC2)C1] |
| A58 | 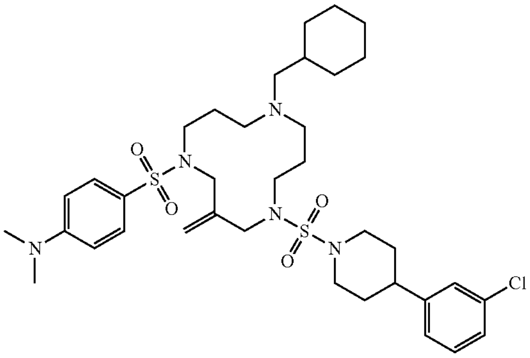 [SMILES: C=C1CN(S(=O)(=O)c2ccc(N(C)C)cc2)CCCN(CC2CCCCC2)CCCN(S(=O)(=O)N2CCC(c3cccc(Cl)c3)CC2)C1] |
| A59 | 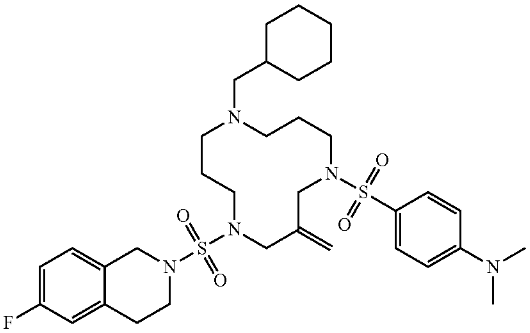 [SMILES: C=C1CN(S(=O)(=O)c2ccc(N(C)C)cc2)CCCN(CC2CCCCC2)CCCN(S(=O)(=O)N2CCc3cc(F)ccc3C2)C1] |
TABLE A-continued
| No. | Structure |
|---|---|
| A60 | 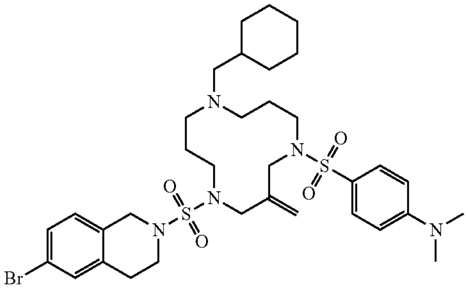 |
| A61 | 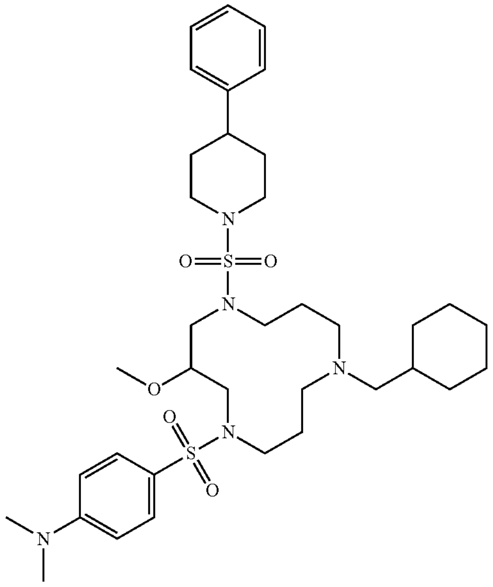 [SMILES: COC1CN(S(=O)(=O)c2ccc(N(C)C)cc2)CCCN(CC2CCCCC2)CCCN(S(=O)(=O)N2CCC(c3ccccc3)CC2)C1] |
| A63 | 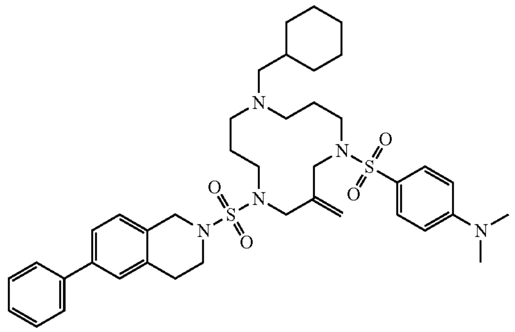 [SMILES: C=C1CN(S(=O)(=O)c2ccc(N(C)C)cc2)CCCN(CC2CCCCC2)CCCN(S(=O)(=O)N2CCc3cc(-c4ccccc4)ccc3C2)C1] |
| A64 | 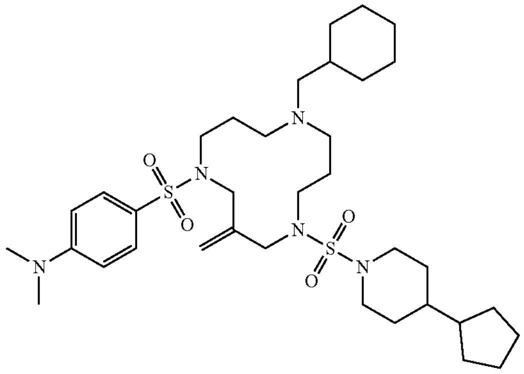 [SMILES: C=C1CN(S(=O)(=O)c2ccc(N(C)C)cc2)CCCN(CC2CCCCC2)CCCN(S(=O)(=O)N2CCC(C3CCCC3)CC2)C1] |

TABLE A-continued
| No. | Structure |
|---|---|
| A65 | 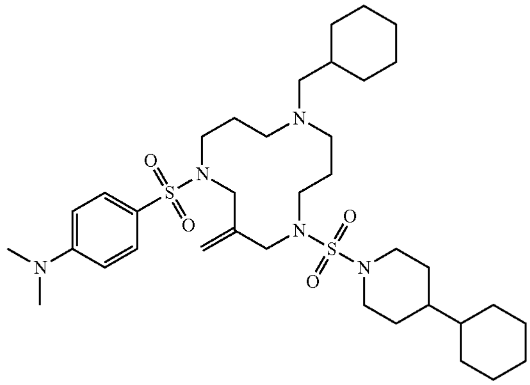 [SMILES: C=C1CN(S(=O)(=O)c2ccc(N(C)C)cc2)CCCN(CC2CCCCC2)CCCN(S(=O)(=O)N2CCC(C3CCCCC3)CC2)C1] |
| A66 | 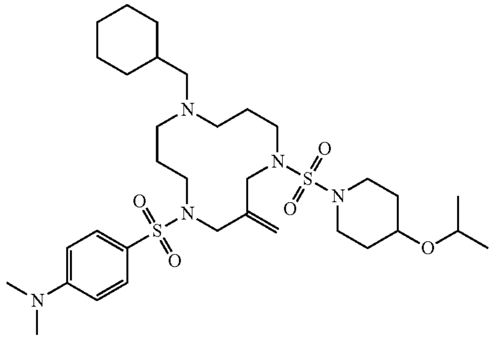 [SMILES: C=C1CN(S(=O)(=O)c2ccc(N(C)C)cc2)CCCN(CC2CCCCC2)CCCN(S(=O)(=O)N2CCC(OC(C)C)CC2)C1] |
| A67 | 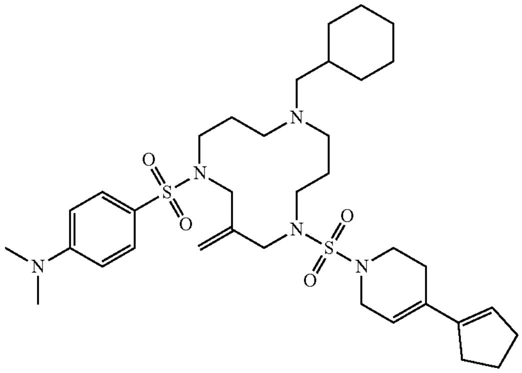 [SMILES: C=C1CN(S(=O)(=O)c2ccc(N(C)C)cc2)CCCN(CC2CCCCC2)CCCN(S(=O)(=O)N2CC=C(C3=CCCC3)CC2)C1] |
| A68 | 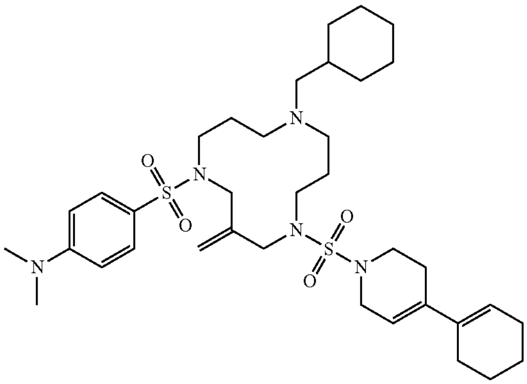 [SMILES: C=C1CN(S(=O)(=O)c2ccc(N(C)C)cc2)CCCN(CC2CCCCC2)CCCN(S(=O)(=O)N2CC=C(C3=CCCCC3)CC2)C1] |
TABLE A-continued
| No. | Structure |
|---|---|
| A69 | 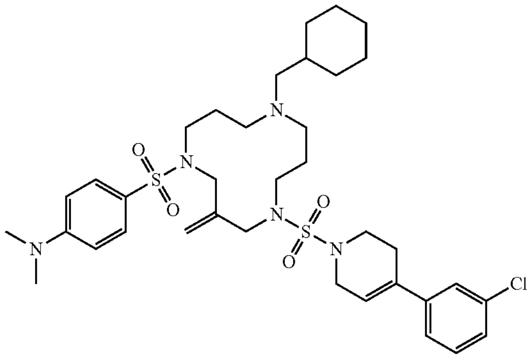 [SMILES: C=C1CN(S(=O)(=O)c2ccc(N(C)C)cc2)CCCN(CC2CCCCC2)CCCN(S(=O)(=O)N2CC=C(c3cccc(Cl)c3)CC2)C1] |
| A70 | 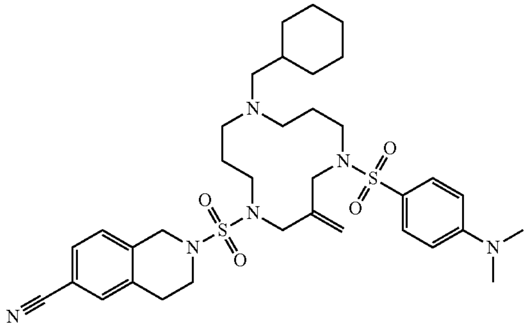 [SMILES: C=C1CN(S(=O)(=O)c2ccc(N(C)C)cc2)CCCN(CC2CCCCC2)CCCN(S(=O)(=O)N2CCc3cc(C#N)ccc3C2)C1] |
| A71 | 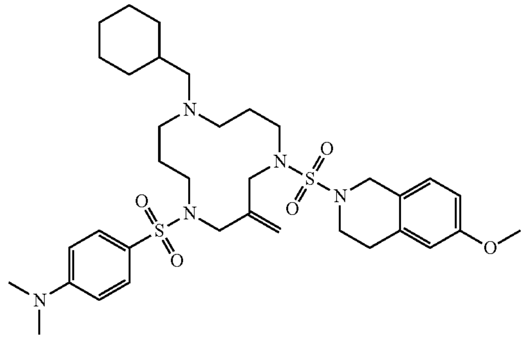 |
| A72 | 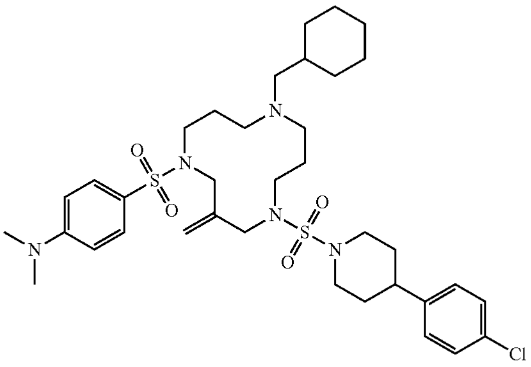 [SMILES: C=C1CN(S(=O)(=O)c2ccc(N(C)C)cc2)CCCN(CC2CCCCC2)CCCN(S(=O)(=O)N2CCC(c3ccc(Cl)cc3)CC2)C1] |

TABLE A-continued
| No. | Structure |
|---|---|
| A73 | 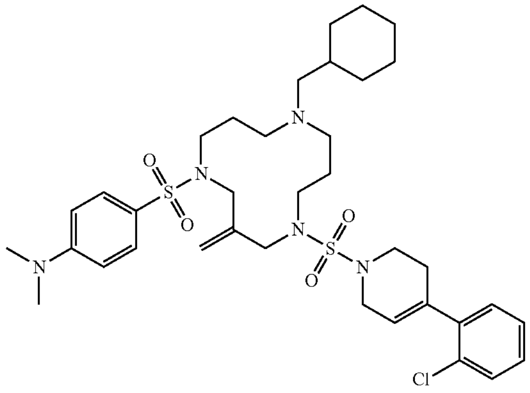 [SMILES: C=C1CN(S(=O)(=O)c2ccc(N(C)C)cc2)CCCN(CC2CCCCC2)CCCN(S(=O)(=O)N2CC=C(c3ccccc3Cl)CC2)C1] |
| A74 | 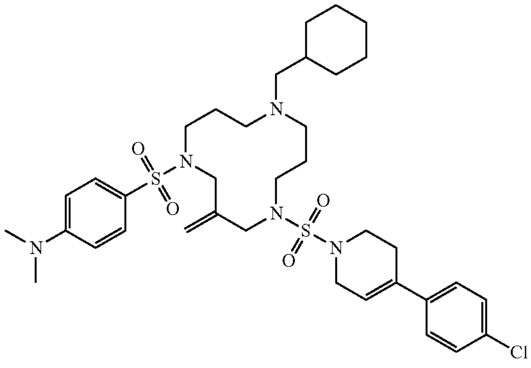 [SMILES: C=C1CN(S(=O)(=O)c2ccc(N(C)C)cc2)CCCN(CC2CCCCC2)CCCN(S(=O)(=O)N2CC=C(c3ccc(Cl)cc3)CC2)C1] |
| A75 | 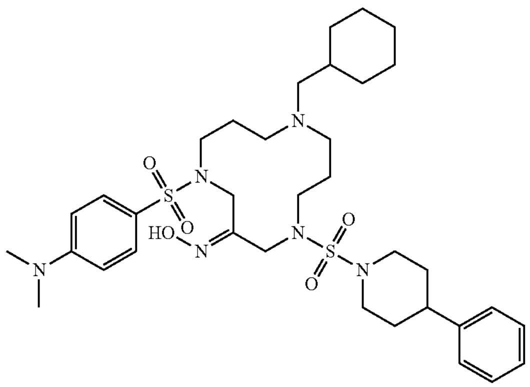 [SMILES: CN(C)c1ccc(S(=O)(=O)N2CCCN(CC3CCCCC3)CCCN(S(=O)(=O)N3CCC(c4ccccc4)CC3)C/C(=N/O)C2)cc1] |
TABLE A-continued
| No. | Structure |
|---|---|
| A76 | 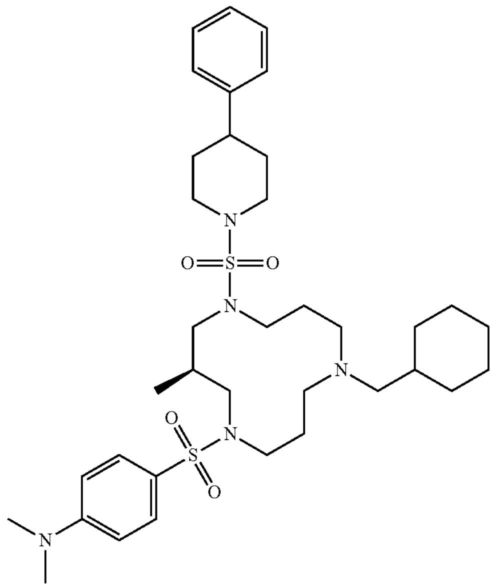 [SMILES: C[C@@H]1CN(S(=O)(=O)c2ccc(N(C)C)cc2)CCCN(CC2CCCCC2)CCCN(S(=O)(=O)N2CCC(c3ccccc3)CC2)C1] |
| A77 | 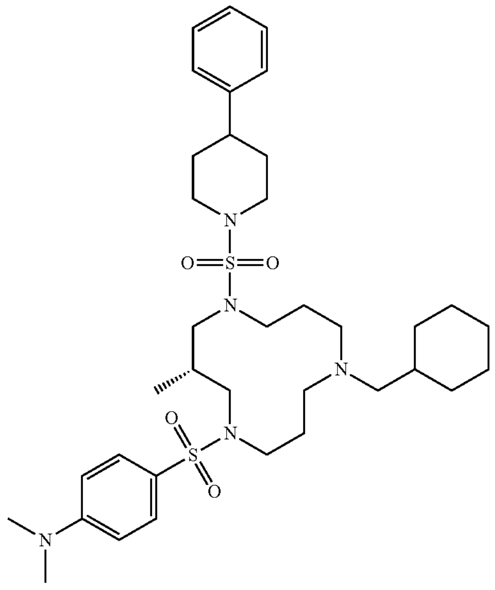 [SMILES: C[C@H]1CN(S(=O)(=O)c2ccc(N(C)C)cc2)CCCN(CC2CCCCC2)CCCN(S(=O)(=O)N2CCC(c3ccccc3)CC2)C1] |
| A78 | 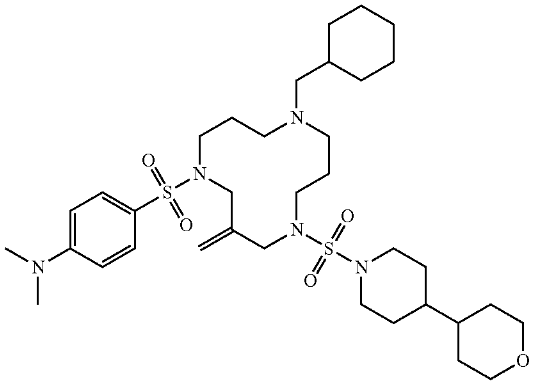 [SMILES: C=C1CN(S(=O)(=O)c2ccc(N(C)C)cc2)CCCN(CC2CCCCC2)CCCN(S(=O)(=O)N2CCC(C3CCOCC3)CC2)C1] |

TABLE A-continued
| No. | Structure |
|---|---|
| A79 | 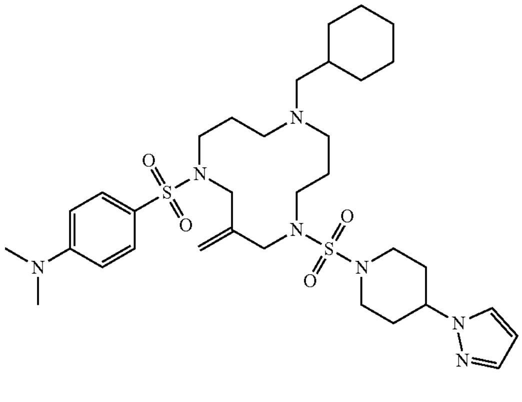 [SMILES: C=C1CN(S(=O)(=O)c2ccc(N(C)C)cc2)CCCN(CC2CCCCC2)CCCN(S(=O)(=O)N2CCC(n3cccn3)CC2)C1] |
| A80 | 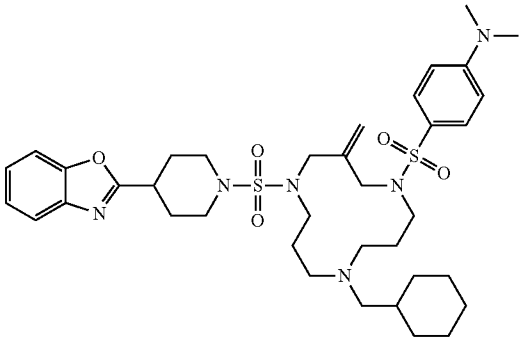 [SMILES: C=C1CN(S(=O)(=O)c2ccc(N(C)C)cc2)CCCN(CC2CCCCC2)CCCN(S(=O)(=O)N2CCC(c3nc4ccccc4o3)CC2)C1] |
| A81 | 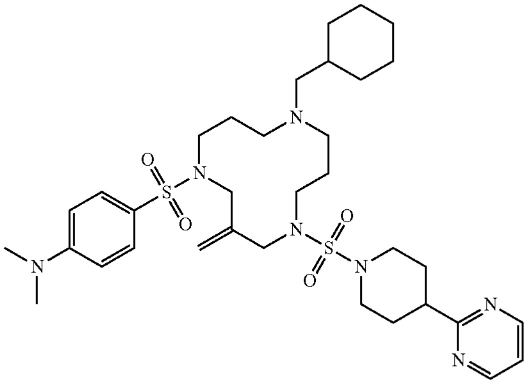 [SMILES: C=C1CN(S(=O)(=O)c2ccc(N(C)C)cc2)CCCN(CC2CCCCC2)CCCN(S(=O)(=O)N2CCC(c3ncccn3)CC2)C1] |
| A82 | 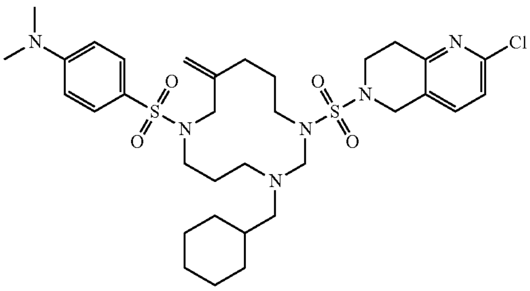 [SMILES: C=C1CCCN(S(=O)(=O)N2CCc3nc(Cl)ccc3C2)CN(CC2CCCCC2)CCCN(S(=O)(=O)c2ccc(N(C)C)cc2)C1] |
| A83 | 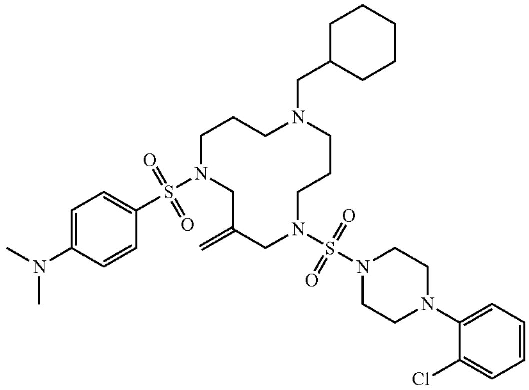 [SMILES: C=C1CN(S(=O)(=O)c2ccc(N(C)C)cc2)CCCN(CC2CCCCC2)CCCN(S(=O)(=O)N2CCN(c3ccccc3Cl)CC2)C1] |
| A84 | 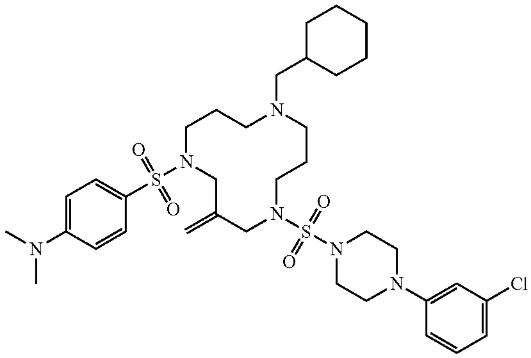 [SMILES: C=C1CN(S(=O)(=O)c2ccc(N(C)C)cc2)CCCN(CC2CCCCC2)CCCN(S(=O)(=O)N2CCN(c3cccc(Cl)c3)CC2)C1] |
| A85 | 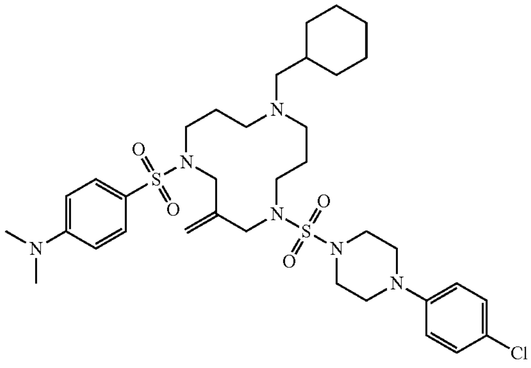 [SMILES: C=C1CN(S(=O)(=O)c2ccc(N(C)C)cc2)CCCN(CC2CCCCC2)CCCN(S(=O)(=O)N2CCN(c3ccc(Cl)cc3)CC2)C1] |
| A86 | 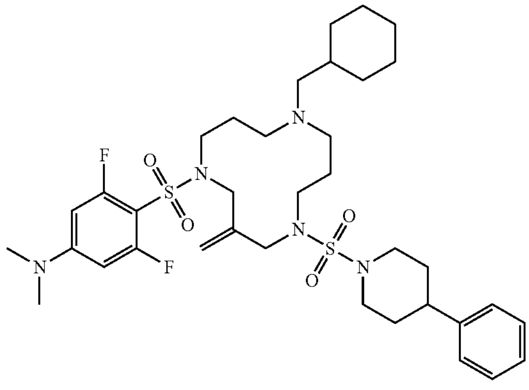 [SMILES: C=C1CN(S(=O)(=O)c2c(F)cc(N(C)C)cc2F)CCCN(CC2CCCCC2)CCCN(S(=O)(=O)N2CCC(c3ccccc3)CC2)C1] |

TABLE A-continued
| No. | Structure |
|---|---|
| A87 | 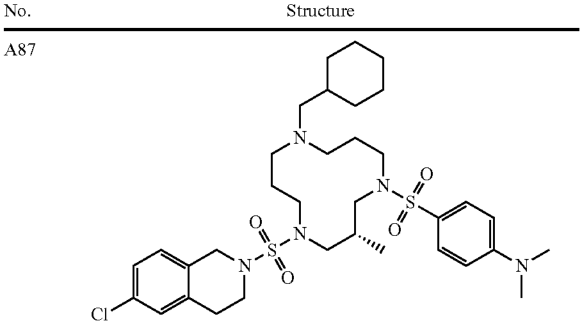 |
| A88 | 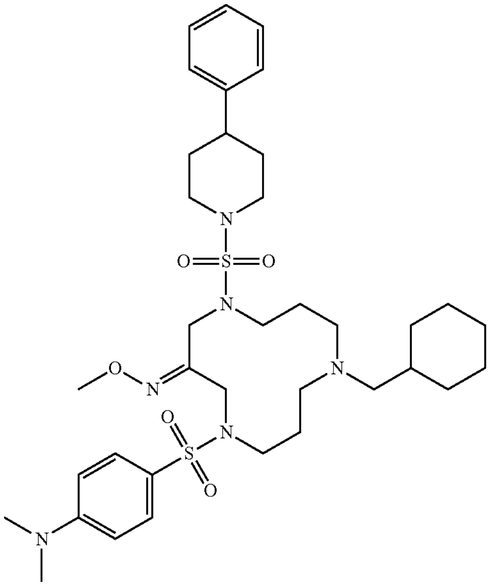 [SMILES: CO/N=C1/CN(S(=O)(=O)c2ccc(N(C)C)cc2)CCCN(CC2CCCCC2)CCCN(S(=O)(=O)N2CCC(c3ccccc3)CC2)C1] |
| A89 | 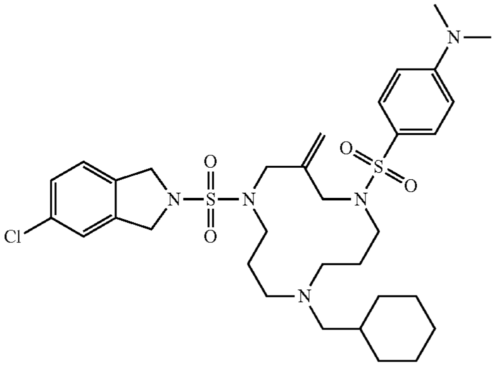 [SMILES: C=C1CN(S(=O)(=O)c2ccc(N(C)C)cc2)CCCN(CC2CCCCC2)CCCN(S(=O)(=O)N2Cc3ccc(Cl)cc3C2)C1] |
TABLE A-continued
| No. | Structure |
|---|---|
| A90 | 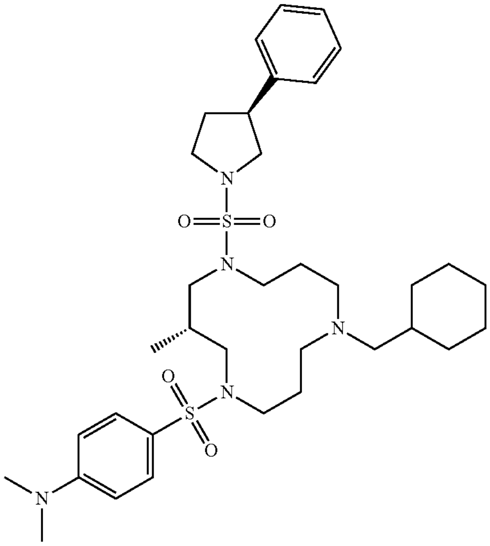 [SMILES: C[C@H]1CN(S(=O)(=O)c2ccc(N(C)C)cc2)CCCN(CC2CCCCC2)CCCN(S(=O)(=O)N2CC[C@@H](c3ccccc3)C2)C1] |
| A91 | 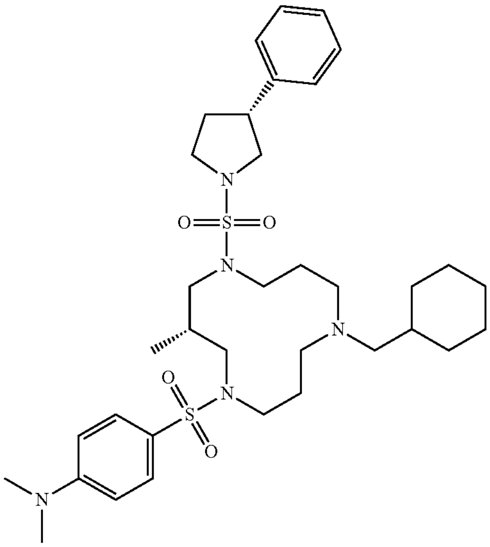 [SMILES: C[C@H]1CN(S(=O)(=O)c2ccc(N(C)C)cc2)CCCN(CC2CCCCC2)CCCN(S(=O)(=O)N2CC[C@H](c3ccccc3)C2)C1] |

TABLE A-continued
| No. | Structure |
|---|---|
| A92 | 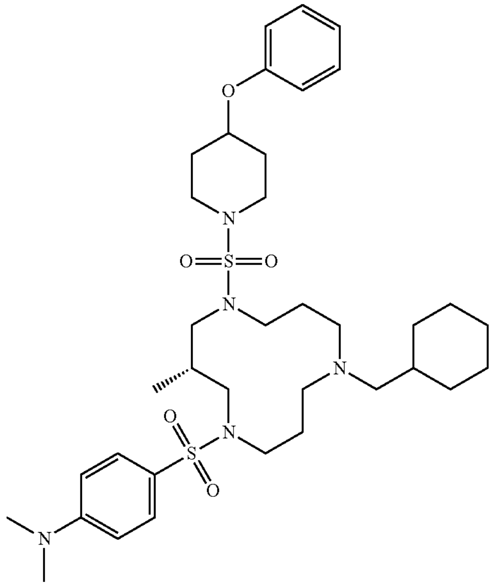 [SMILES: C[C@H]1CN(S(=O)(=O)c2ccc(N(C)C)cc2)CCCN(CC2CCCCC2)CCCN(S(=O)(=O)N2CCC(Oc3ccccc3)CC2)C1] |
| A93 | 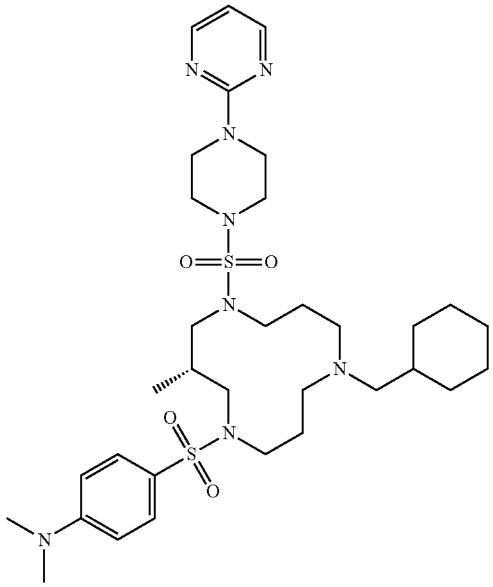 [SMILES: C[C@H]1CN(S(=O)(=O)c2ccc(N(C)C)cc2)CCCN(CC2CCCCC2)CCCN(S(=O)(=O)N2CCN(c3ncccn3)CC2)C1] |
TABLE A-continued
| No. | Structure |
|---|---|
| A94 | 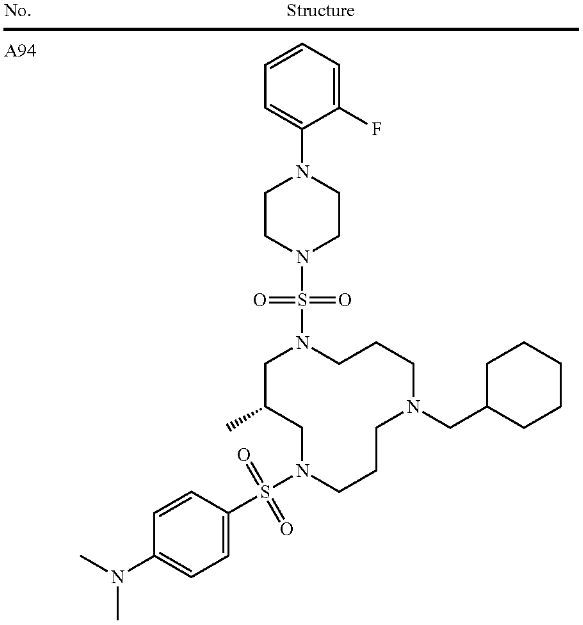 |
| A95 | 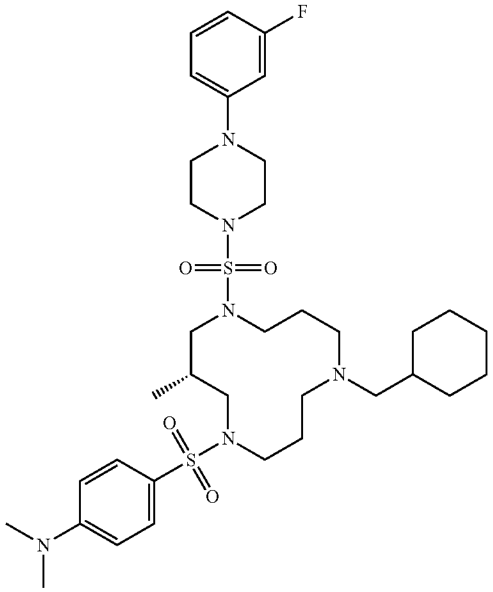 [SMILES: C[C@H]1CN(S(=O)(=O)c2ccc(N(C)C)cc2)CCCN(CC2CCCCC2)CCCN(S(=O)(=O)N2CCN(c3cccc(F)c3)CC2)C1] |

TABLE A-continued
| No. | Structure |
| --- | --- |
| A96 | 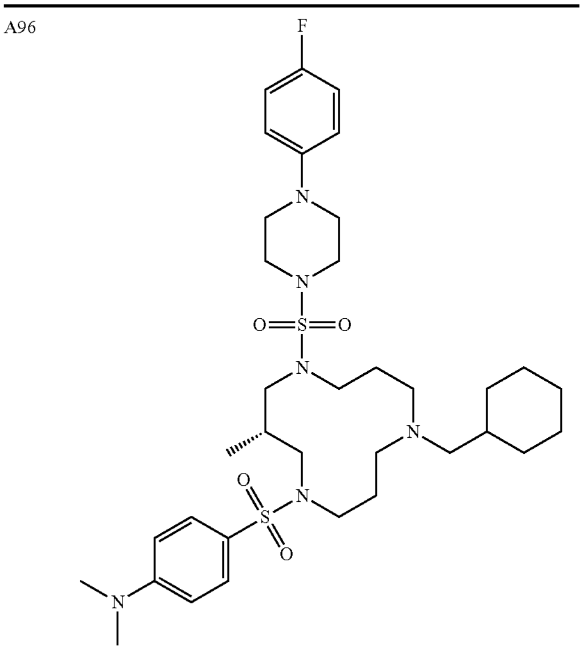 |
| A97 | 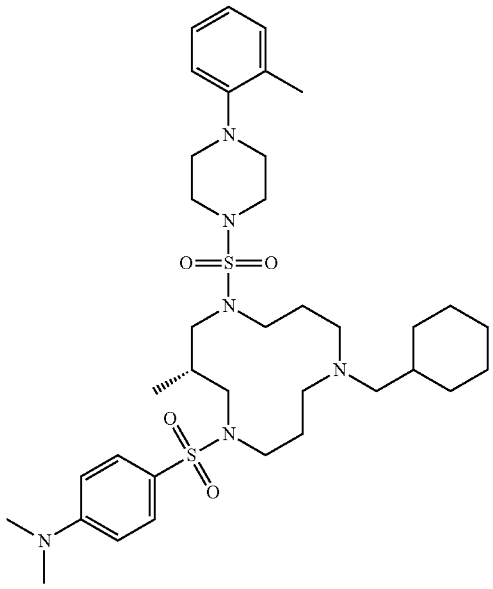 [SMILES: Cc1ccccc1N1CCN(S(=O)(=O)N2CCCN(CC3CCCCC3)CCCN(S(=O)(=O)c3ccc(N(C)C)cc3)C[C@H](C)C2)CC1] |
TABLE A-continued
| No. | Structure |
| --- | --- |
| A98 | 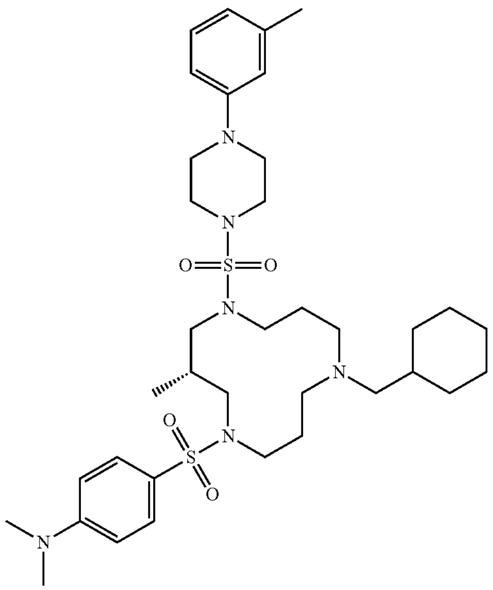 [SMILES: Cc1cccc(N2CCN(S(=O)(=O)N3CCCN(CC4CCCCC4)CCCN(S(=O)(=O)c4ccc(N(C)C)cc4)C[C@H](C)C3)CC2)c1] |
| A99 | 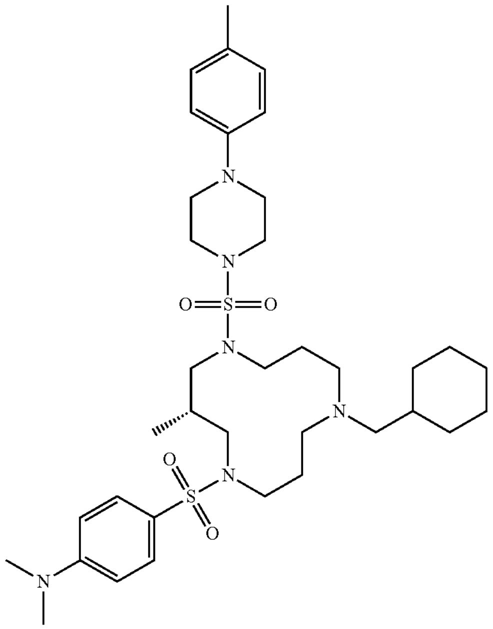 [SMILES: Cc1ccc(N2CCN(S(=O)(=O)N3CCCN(CC4CCCCC4)CCCN(S(=O)(=O)c4ccc(N(C)C)cc4)C[C@H](C)C3)CC2)cc1] |

TABLE A-continued
| No. | Structure |
|---|---|
| A100 | 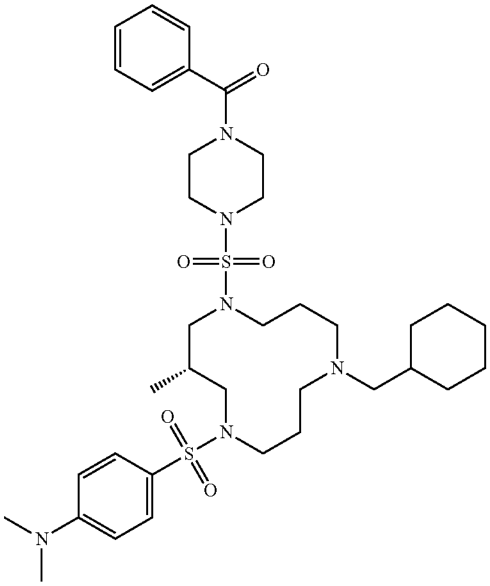 [SMILES: C[C@H]1CN(S(=O)(=O)c2ccc(N(C)C)cc2)CCCN(CC2CCCCC2)CCCN(S(=O)(=O)N2CCN(C(=O)c3ccccc3)CC2)C1] |
| A101 | 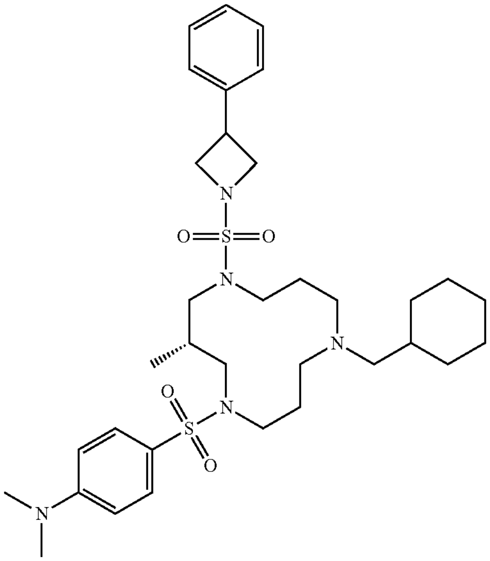 [SMILES: C[C@H]1CN(S(=O)(=O)c2ccc(N(C)C)cc2)CCCN(CC2CCCCC2)CCCN(S(=O)(=O)N2CC(c3ccccc3)C2)C1] |
| A102 | 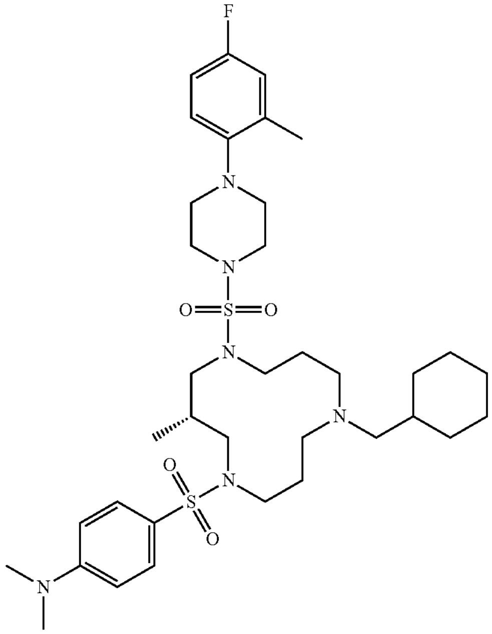 [SMILES: Cc1cc(F)ccc1N1CCN(S(=O)(=O)N2CCCN(CC3CCCCC3)CCCN(S(=O)(=O)c3ccc(N(C)C)cc3)C[C@H](C)C2)CC1] |
| A103 | 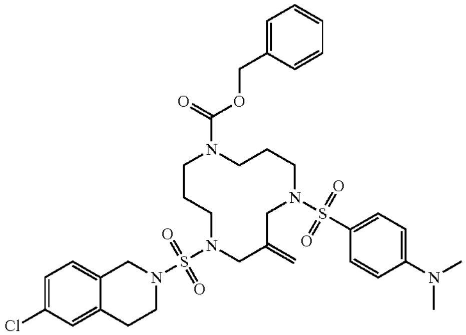 [SMILES: C=C1CN(S(=O)(=O)c2ccc(N(C)C)cc2)CCCN(C(=O)OCc2ccccc2)CCCN(S(=O)(=O)N2CCc3cc(Cl)ccc3C2)C1] |
| A104 | 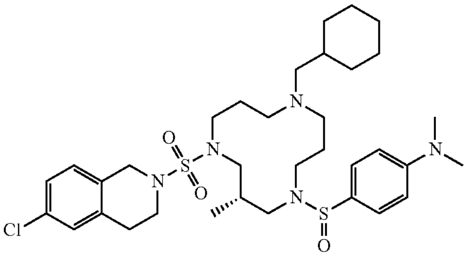 [SMILES: C[C@H]1CN(S(=O)c2ccc(N(C)C)cc2)CCCN(CC2CCCCC2)CCCN(S(=O)(=O)N2CCc3cc(Cl)ccc3C2)C1] |
| A105 | 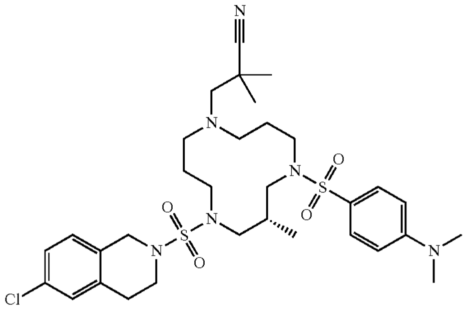 [SMILES: C[C@H]1CN(S(=O)(=O)c2ccc(N(C)C)cc2)CCCN(CC(C)(C)C#N)CCCN(S(=O)(=O)N2CCc3cc(Cl)ccc3C2)C1] |

TABLE A-continued
| No. | Structure |
| --- | --- |
| A106 | 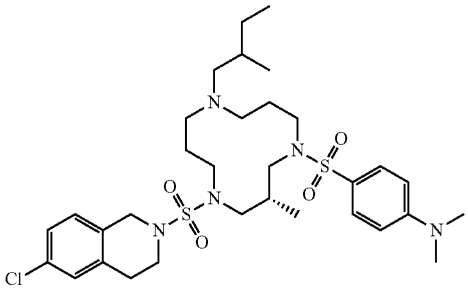 [SMILES: CCC(C)CN1CCCN(S(=O)(=O)c2ccc(N(C)C)cc2)C[C@H](C)CN(S(=O)(=O)N2CCc3cc(Cl)ccc3C2)CCC1] |
| A107 | 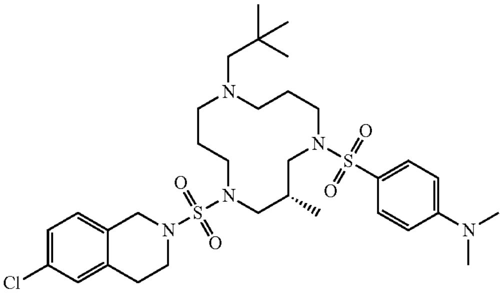 [SMILES: C[C@H]1CN(S(=O)(=O)c2ccc(N(C)C)cc2)CCCN(CC(C)(C)C)CCCN(S(=O)(=O)N2CCc3cc(Cl)ccc3C2)C1] |
| A108 | 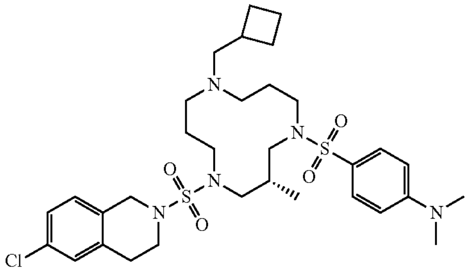 [SMILES: C[C@H]1CN(S(=O)(=O)c2ccc(N(C)C)cc2)CCCN(CC2CCC2)CCCN(S(=O)(=O)N2CCc3cc(Cl)ccc3C2)C1] |
| A109 | 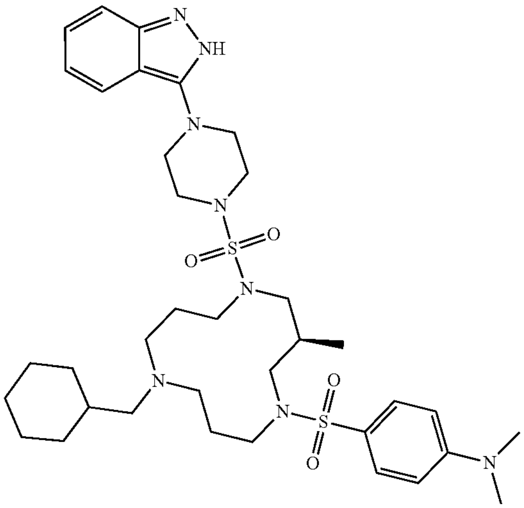 [SMILES: C[C@H]1CN(S(=O)(=O)c2ccc(N(C)C)cc2)CCCN(CC2CCCCC2)CCCN(S(=O)(=O)N2CCN(c3[nH]nc4ccccc34)CC2)C1] |
| A110 | 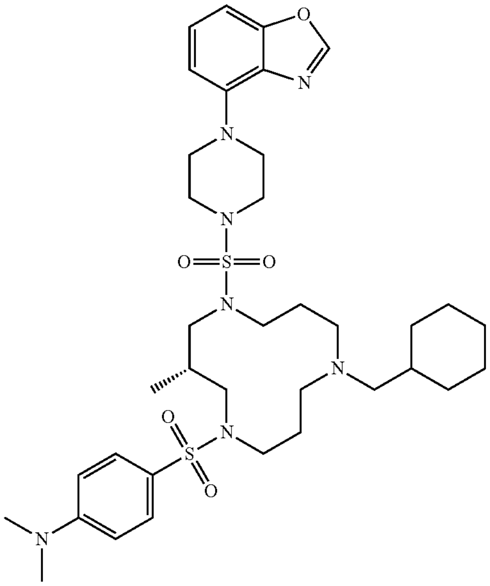 [SMILES: C[C@H]1CN(S(=O)(=O)c2ccc(N(C)C)cc2)CCCN(CC2CCCCC2)CCCN(S(=O)(=O)N2CCN(c3cccc4ocnc34)CC2)C1] |
| A111 | 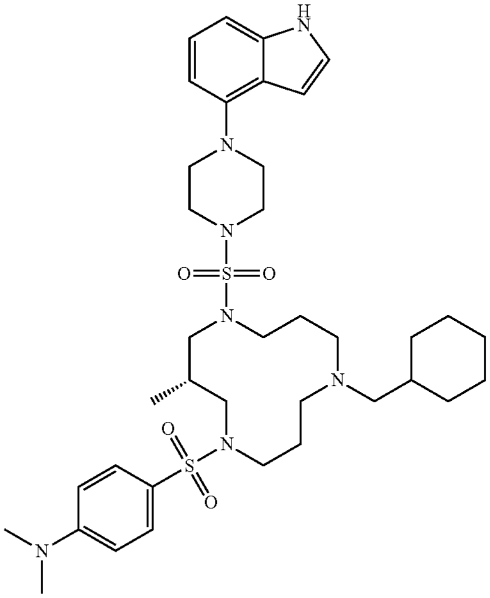 [SMILES: C[C@H]1CN(S(=O)(=O)c2ccc(N(C)C)cc2)CCCN(CC2CCCCC2)CCCN(S(=O)(=O)N2CCN(c3cccc4[nH]ccc34)CC2)C1] |

TABLE A-continued
| No. | Structure |
| --- | --- |
| A112 | 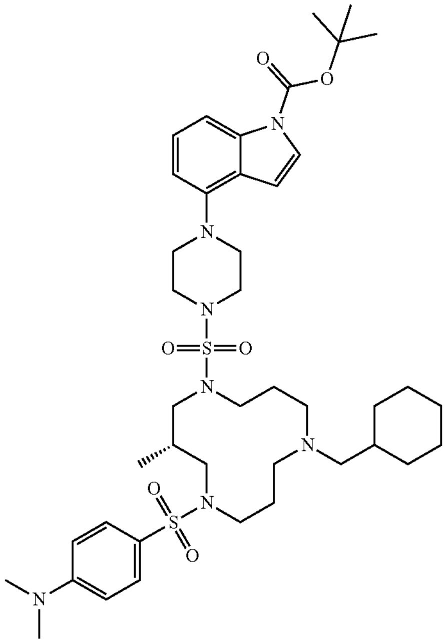 [SMILES: C[C@H]1CN(S(=O)(=O)c2ccc(N(C)C)cc2)CCCN(CC2CCCCC2)CCCN(S(=O)(=O)N2CCN(c3cccc4c3ccn4C(=O)OC(C)(C)C)CC2)C1] |
| A113 | 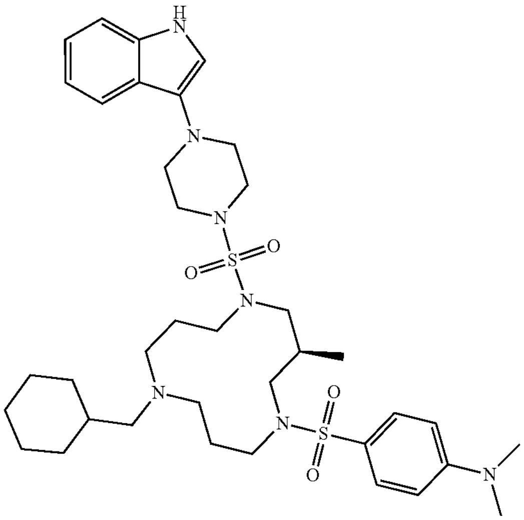 [SMILES: C[C@H]1CN(S(=O)(=O)c2ccc(N(C)C)cc2)CCCN(CC2CCCCC2)CCCN(S(=O)(=O)N2CCN(c3c[nH]c4ccccc34)CC2)C1] |
| A114 | 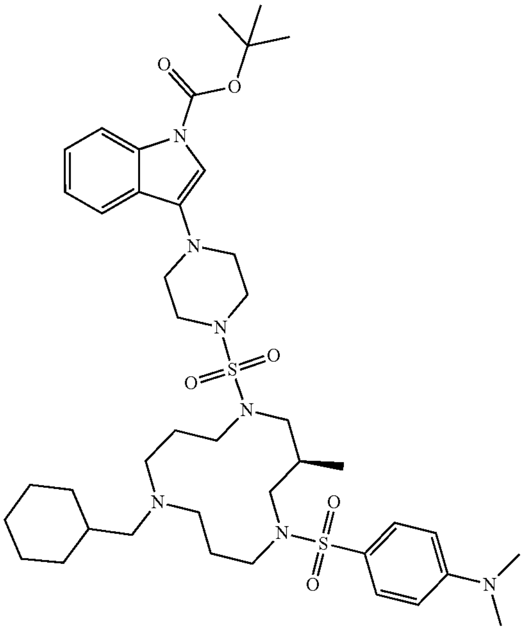 [SMILES: C[C@H]1CN(S(=O)(=O)c2ccc(N(C)C)cc2)CCCN(CC2CCCCC2)CCCN(S(=O)(=O)N2CCN(c3cn(C(=O)OC(C)(C)C)c4ccccc34)CC2)C1] |
| A115 | 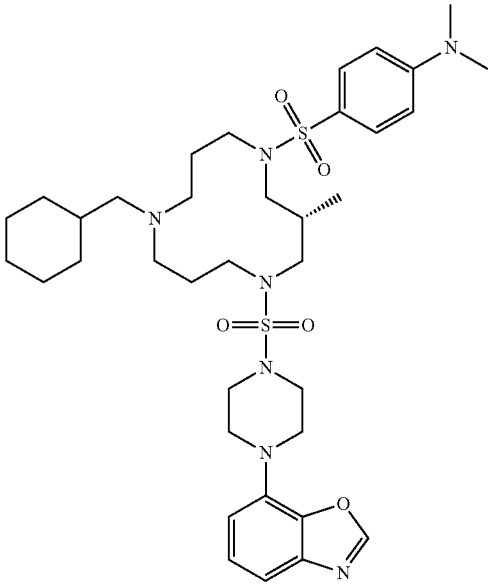 [SMILES: C[C@H]1CN(S(=O)(=O)c2ccc(N(C)C)cc2)CCCN(CC2CCCCC2)CCCN(S(=O)(=O)N2CCN(c3cccc4ncoc34)CC2)C1] |

TABLE A-continued
| No. | Structure |
|---|---|
| A116 | 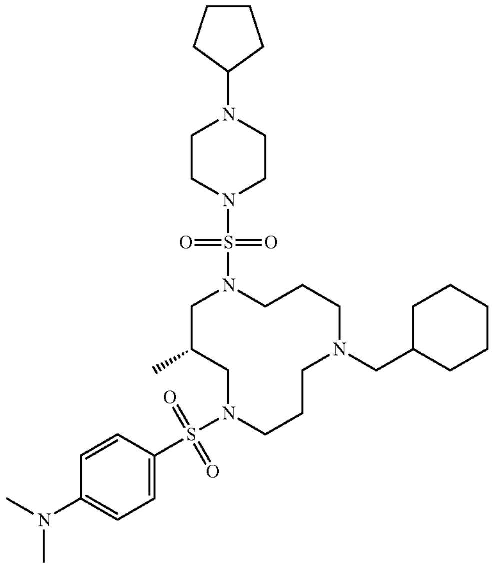 [SMILES: C[C@H]1CN(S(=O)(=O)c2ccc(N(C)C)cc2)CCCN(CC2CCCCC2)CCCN(S(=O)(=O)N2CCN(C3CCCC3)CC2)C1] |
| A117 | 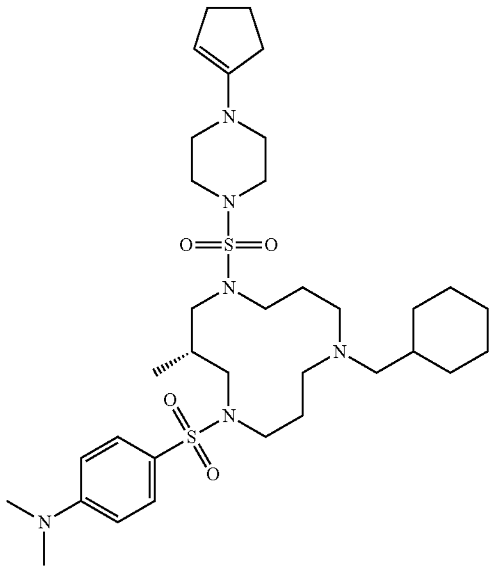 [SMILES: C[C@H]1CN(S(=O)(=O)c2ccc(N(C)C)cc2)CCCN(CC2CCCCC2)CCCN(S(=O)(=O)N2CCN(C3=CCCC3)CC2)C1] |
TABLE A-continued
| No. | Structure |
|---|---|
| A118 | 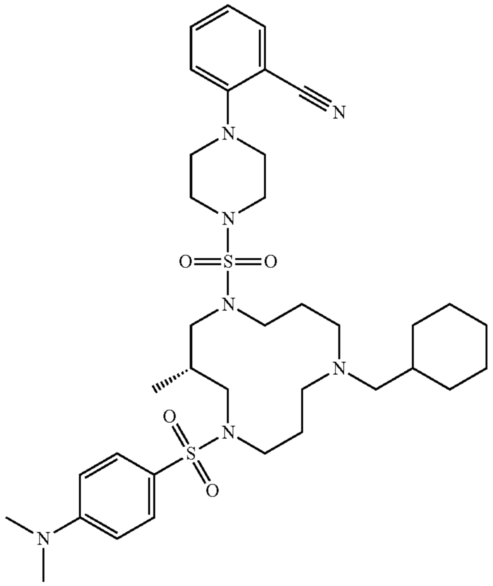 [SMILES: C[C@H]1CN(S(=O)(=O)c2ccc(N(C)C)cc2)CCCN(CC2CCCCC2)CCCN(S(=O)(=O)N2CCN(c3ccccc3C#N)CC2)C1] |
| A119 | 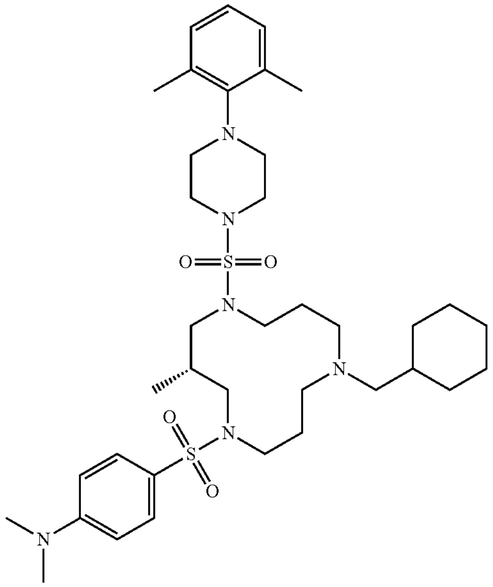 [SMILES: Cc1cccc(C)c1N1CCN(S(=O)(=O)N2CCCN(CC3CCCCC3)CCCN(S(=O)(=O)c3ccc(N(C)C)cc3)C[C@H](C)C2)CC1] |
| A120 | 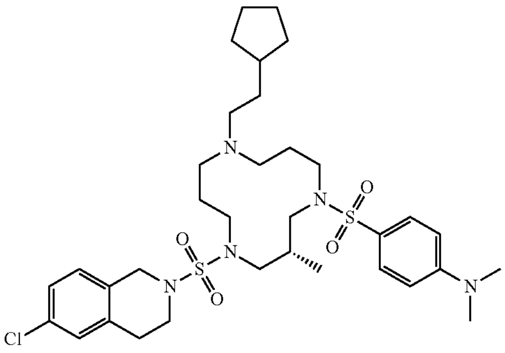 [SMILES: C[C@H]1CN(S(=O)(=O)c2ccc(N(C)C)cc2)CCCN(CCC2CCCC2)CCCN(S(=O)(=O)N2CCc3cc(Cl)ccc3C2)C1] |

TABLE A-continued
| No. | Structure |
|---|---|
| A121 | 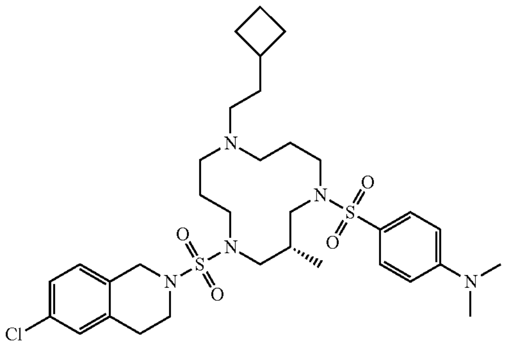 [SMILES: C[C@H]1CN(S(=O)(=O)c2ccc(N(C)C)cc2)CCCN(CCC2CCC2)CCCN(S(=O)(=O)N2CCc3cc(Cl)ccc3C2)C1] |
| A122 | 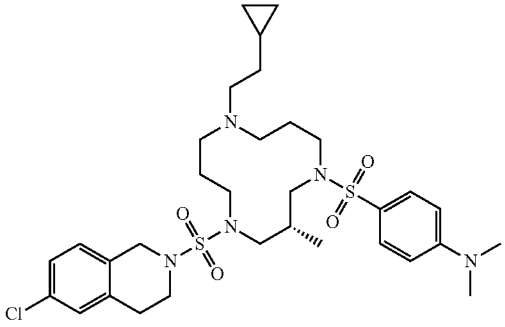 [SMILES: C[C@H]1CN(S(=O)(=O)c2ccc(N(C)C)cc2)CCCN(CCC2CC2)CCCN(S(=O)(=O)N2CCc3cc(Cl)ccc3C2)C1] |
| A123 | 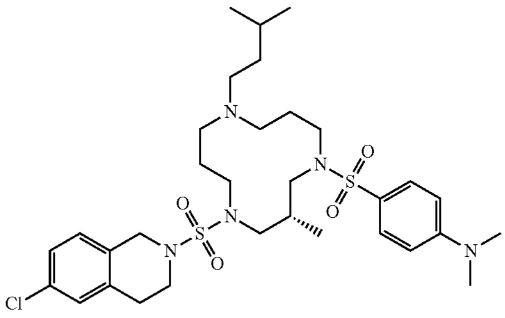 [SMILES: CC(C)CCN1CCCN(S(=O)(=O)c2ccc(N(C)C)cc2)C[C@H](C)CN(S(=O)(=O)N2CCc3cc(Cl)ccc3C2)CCC1] |
| A124 | 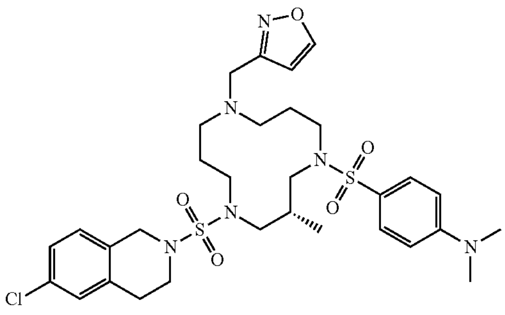 [SMILES: C[C@H]1CN(S(=O)(=O)c2ccc(N(C)C)cc2)CCCN(Cc2ccon2)CCCN(S(=O)(=O)N2CCc3cc(Cl)ccc3C2)C1] |
| A125 | 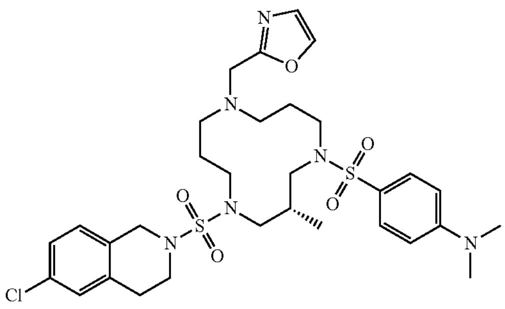 [SMILES: C[C@H]1CN(S(=O)(=O)c2ccc(N(C)C)cc2)CCCN(Cc2ncco2)CCCN(S(=O)(=O)N2CCc3cc(Cl)ccc3C2)C1] |
TABLE A-continued
| No. | Structure |
|---|---|
| A126 | 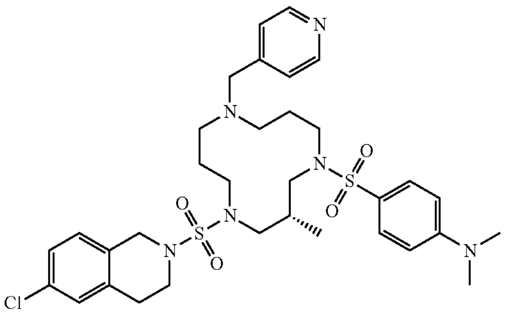 [SMILES: C[C@H]1CN(S(=O)(=O)c2ccc(N(C)C)cc2)CCCN(Cc2ccncc2)CCCN(S(=O)(=O)N2CCc3cc(Cl)ccc3C2)C1] |
| A127 | 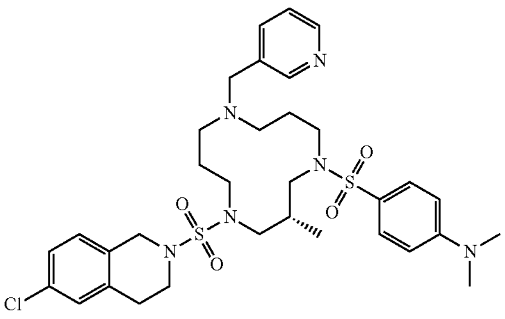 [SMILES: C[C@H]1CN(S(=O)(=O)c2ccc(N(C)C)cc2)CCCN(Cc2cccnc2)CCCN(S(=O)(=O)N2CCc3cc(Cl)ccc3C2)C1] |
| A128 | 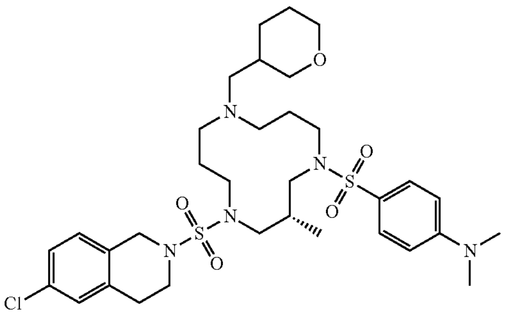 [SMILES: C[C@H]1CN(S(=O)(=O)c2ccc(N(C)C)cc2)CCCN(CC2CCCOC2)CCCN(S(=O)(=O)N2CCc3cc(Cl)ccc3C2)C1] |
| A129 | 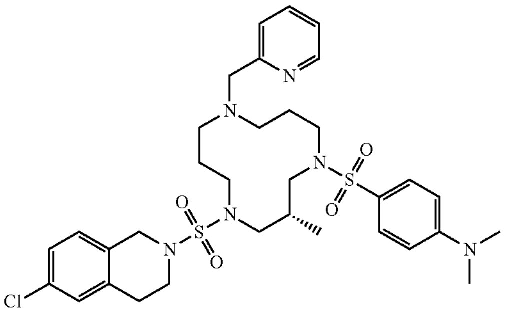 [SMILES: C[C@H]1CN(S(=O)(=O)c2ccc(N(C)C)cc2)CCCN(Cc2ccccn2)CCCN(S(=O)(=O)N2CCc3cc(Cl)ccc3C2)C1] |
| A130 | 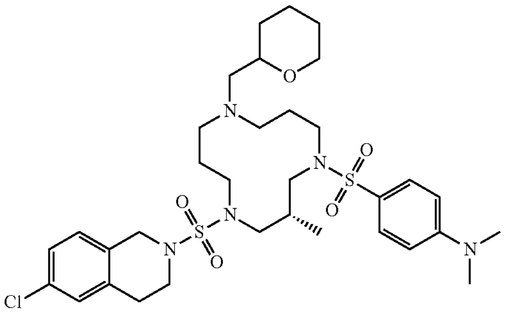 [SMILES: C[C@H]1CN(S(=O)(=O)c2ccc(N(C)C)cc2)CCCN(CC2CCCCO2)CCCN(S(=O)(=O)N2CCc3cc(Cl)ccc3C2)C1] |

TABLE A-continued
| No. | Structure |
|---|---|
| A131 | 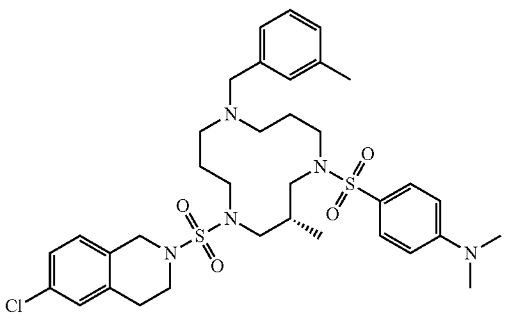 [SMILES: Cc1cccc(CN2CCCN(S(=O)(=O)c3ccc(N(C)C)cc3)C[C@H](C)CN(S(=O)(=O)N3CCc4cc(Cl)ccc4C3)CCC2)c1] |
| A132 | 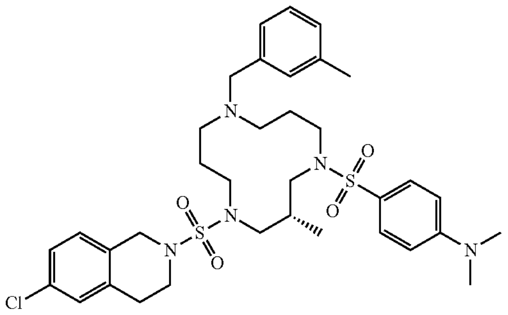 [SMILES: Cc1cccc(CN2CCCN(S(=O)(=O)c3ccc(N(C)C)cc3)C[C@H](C)CN(S(=O)(=O)N3CCc4cc(Cl)ccc4C3)CCC2)c1] |
| A133 | 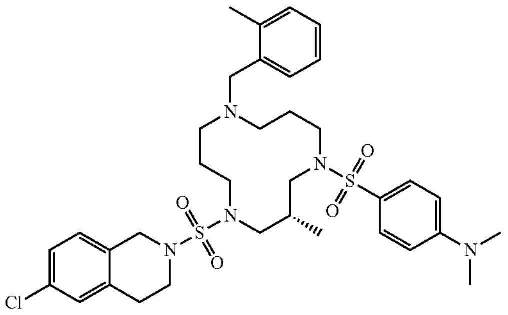 [SMILES: Cc1ccccc1CN1CCCN(S(=O)(=O)c2ccc(N(C)C)cc2)C[C@H](C)CN(S(=O)(=O)N2CCc3cc(Cl)ccc3C2)CCC1] |
| A134 | 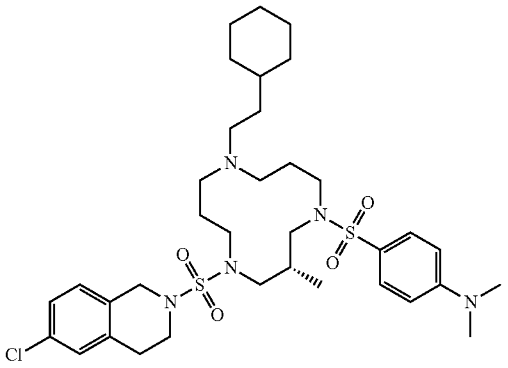 [SMILES: C[C@H]1CN(S(=O)(=O)c2ccc(N(C)C)cc2)CCCN(CCC2CCCCC2)CCCN(S(=O)(=O)N2CCc3cc(Cl)ccc3C2)C1] |
TABLE A-continued
| No. | Structure |
|---|---|
| A135 | 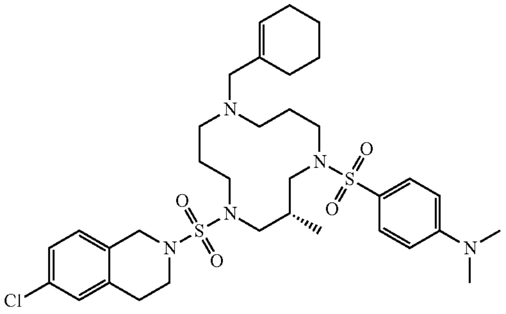 [SMILES: C[C@H]1CN(S(=O)(=O)c2ccc(N(C)C)cc2)CCCN(CC2=CCCCC2)CCCN(S(=O)(=O)N2CCc3cc(Cl)ccc3C2)C1] |
| A136 | 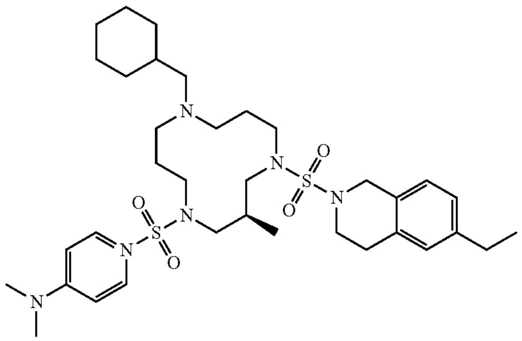 |
| A137 | 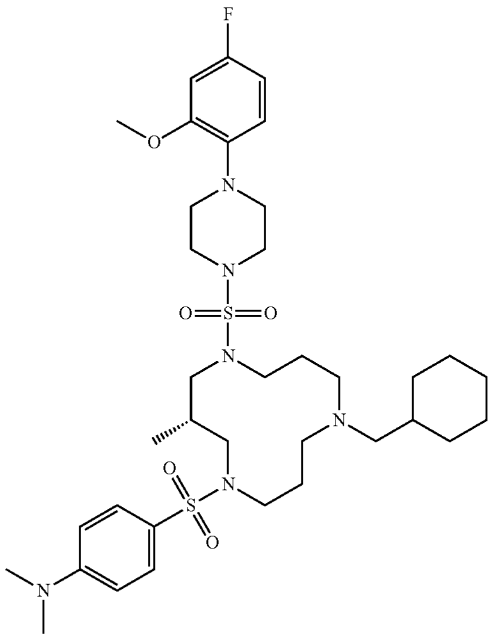 [SMILES: COc1cc(F)ccc1N1CCN(S(=O)(=O)N2CCCN(CC3CCCCC3)CCCN(S(=O)(=O)c3ccc(N(C)C)cc3)C[C@H](C)C2)CC1] |

TABLE A-continued
| No. | Structure |
|---|---|
| A138 | 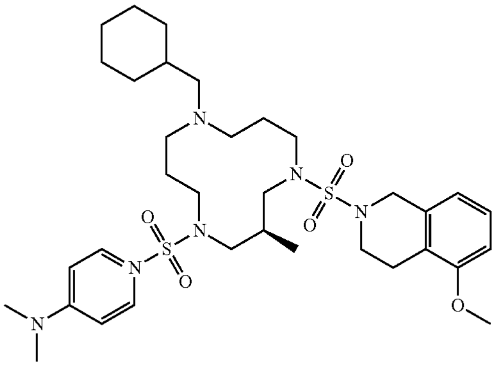 |
| A140 | 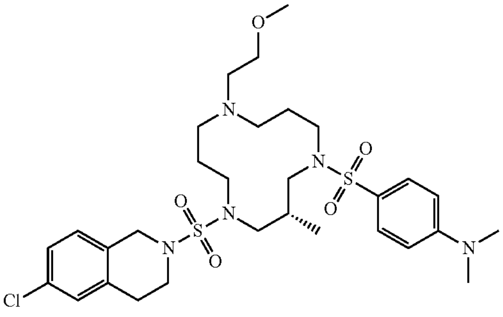 [SMILES: COCCN1CCCN(S(=O)(=O)c2ccc(N(C)C)cc2)C[C@H](C)CN(S(=O)(=O)N2CCc3cc(Cl)ccc3C2)CCC1] |
| A141 | 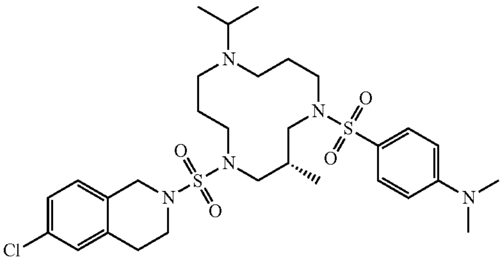 [SMILES: CC(C)N1CCCN(S(=O)(=O)c2ccc(N(C)C)cc2)C[C@H](C)CN(S(=O)(=O)N2CCc3cc(Cl)ccc3C2)CCC1] |
| A142 | 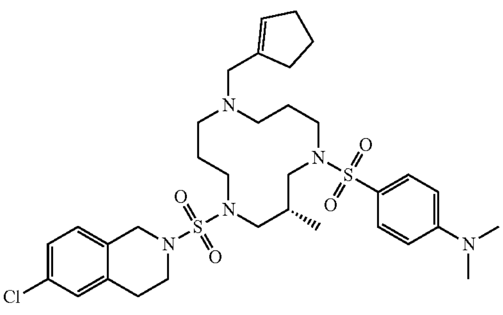 [SMILES: C[C@H]1CN(S(=O)(=O)c2ccc(N(C)C)cc2)CCCN(CC2=CCCC2)CCCN(S(=O)(=O)N2CCc3cc(Cl)ccc3C2)C1] |
TABLE A-continued
| No. | Structure |
|---|---|
| A143 | 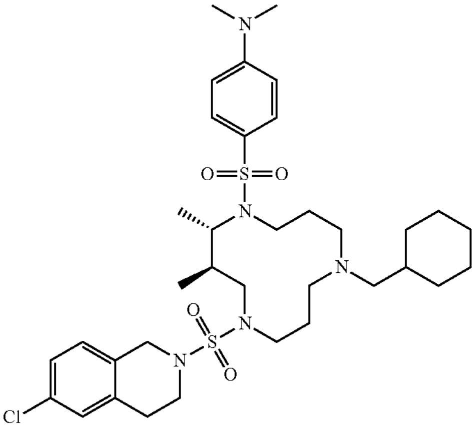 [SMILES: C[C@@H]1CN(S(=O)(=O)N2CCc3cc(Cl)ccc3C2)CCCN(CC2CCCCC2)CCCN(S(=O)(=O)c2ccc(N(C)C)cc2)[C@H]1C] |
| A144 | 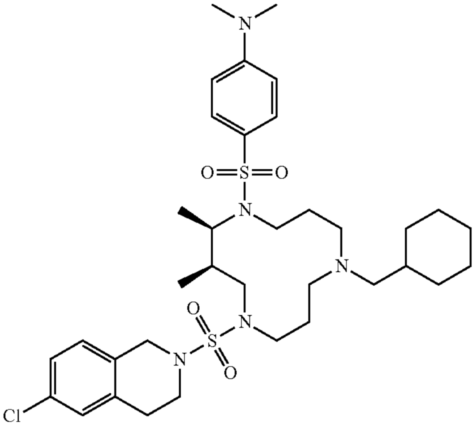 [SMILES: C[C@@H]1CN(S(=O)(=O)N2CCc3cc(Cl)ccc3C2)CCCN(CC2CCCCC2)CCCN(S(=O)(=O)c2ccc(N(C)C)cc2)[C@@H]1C] |
| A145 | 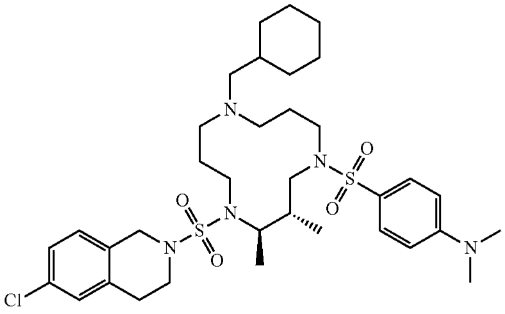 [SMILES: C[C@@H]1[C@@H](C)CN(S(=O)(=O)c2ccc(N(C)C)cc2)CCCN(CC2CCCCC2)CCCN1S(=O)(=O)N1CCc2cc(Cl)ccc2C1] |
| A146 | 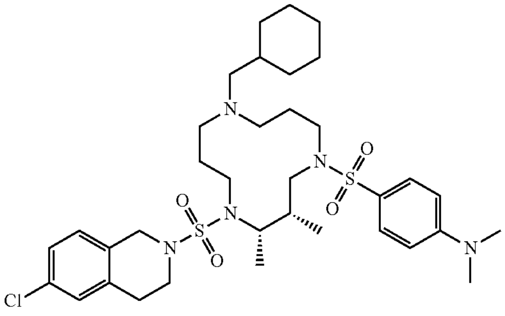 [SMILES: C[C@H]1CN(S(=O)(=O)c2ccc(N(C)C)cc2)CCCN(CC2CCCCC2)CCCN(S(=O)(=O)N2CCc3cc(Cl)ccc3C2)[C@H]1C] |

TABLE A-continued
| No. | Structure |
|---|---|
| A147 | 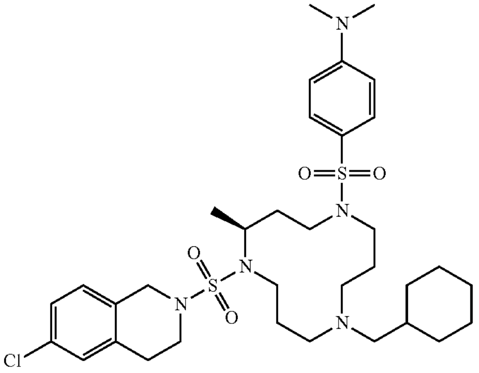 [SMILES: C[C@H]1CCN(S(=O)(=O)c2ccc(N(C)C)cc2)CCCN(CC2CCCCC2)CCCN1S(=O)(=O)N1CCc2cc(Cl)ccc2C1] |
| A148 | 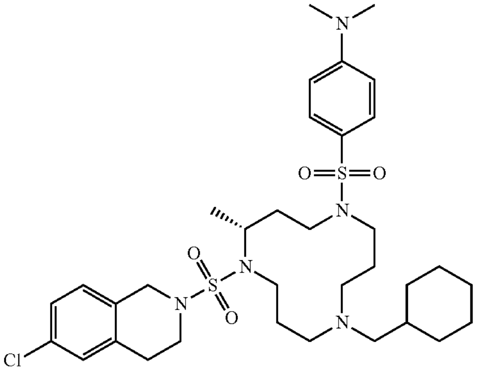 [SMILES: C[C@@H]1CCN(S(=O)(=O)c2ccc(N(C)C)cc2)CCCN(CC2CCCCC2)CCCN1S(=O)(=O)N1CCc2cc(Cl)ccc2C1] |
| A149 | 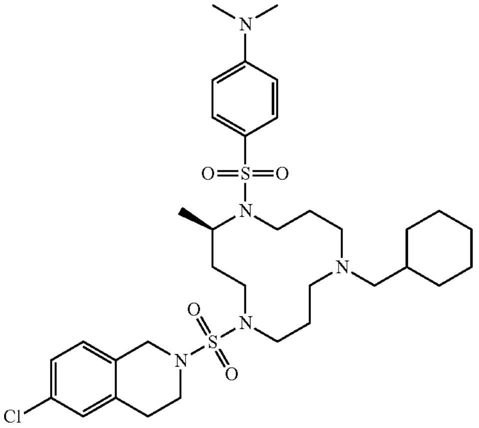 [SMILES: C[C@@H]1CCN(S(=O)(=O)N2CCc3cc(Cl)ccc3C2)CCCN(CC2CCCCC2)CCCN1S(=O)(=O)c1ccc(N(C)C)cc1] |
| A150 | 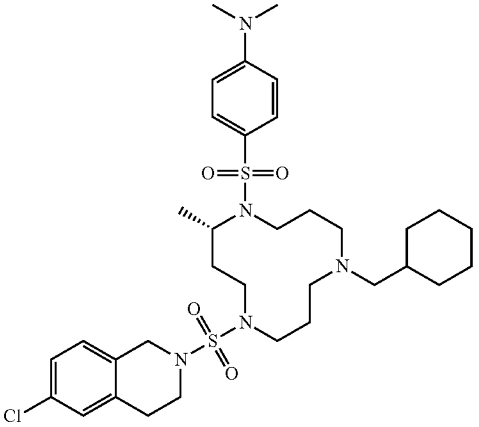 [SMILES: C[C@H]1CCN(S(=O)(=O)N2CCc3cc(Cl)ccc3C2)CCCN(CC2CCCCC2)CCCN1S(=O)(=O)c1ccc(N(C)C)cc1] |
TABLE A-continued
| No. | Structure |
|---|---|
| A151 | 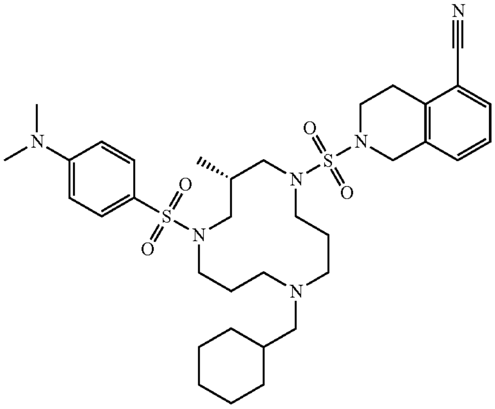 [SMILES: C[C@H]1CN(S(=O)(=O)c2ccc(N(C)C)cc2)CCCN(CC2CCCCC2)CCCN(S(=O)(=O)N2CCc3c(C#N)cccc3C2)C1] |
| A152 | 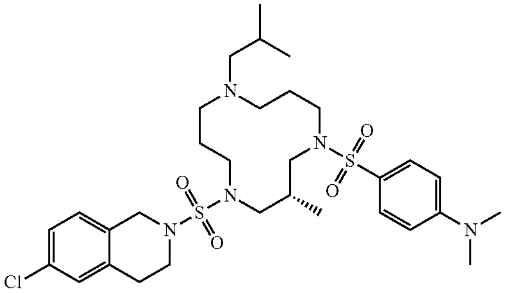 [SMILES: CC(C)CN1CCCN(S(=O)(=O)c2ccc(N(C)C)cc2)C[C@H](C)CN(S(=O)(=O)N2CCc3cc(Cl)ccc3C2)CCC1] |
| A153 | 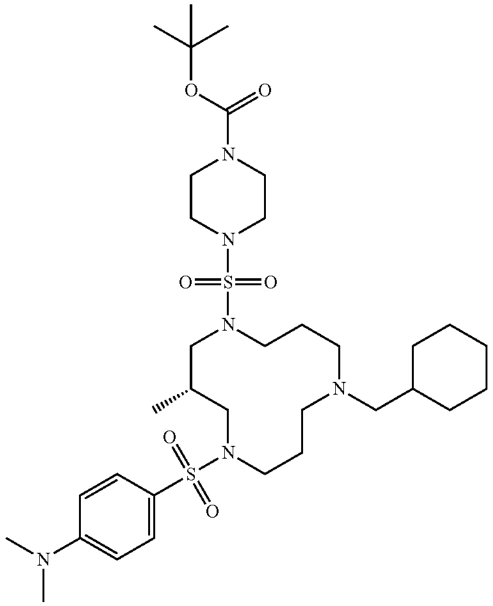 [SMILES: C[C@H]1CN(S(=O)(=O)c2ccc(N(C)C)cc2)CCCN(CC2CCCCC2)CCCN(S(=O)(=O)N2CCN(C(=O)OC(C)(C)C)CC2)C1] |

TABLE A-continued
| No. | Structure |
| --- | --- |
| A154 | 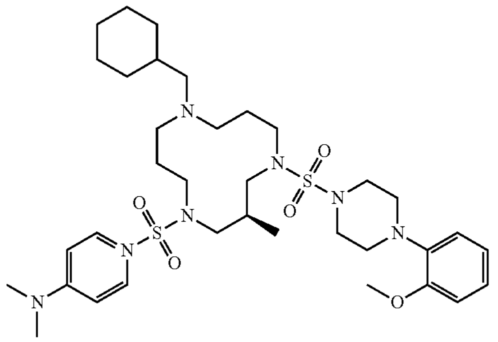 |
| A155 | 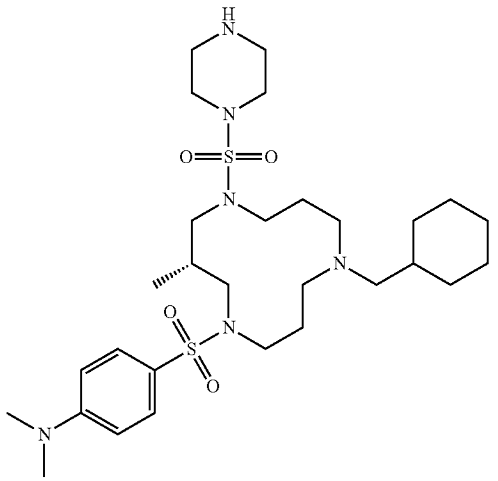 [SMILES: C[C@H]1CN(S(=O)(=O)c2ccc(N(C)C)cc2)CCCN(CC2CCCCC2)CCCN(S(=O)(=O)N2CCNCC2)C1] |
| A156 | 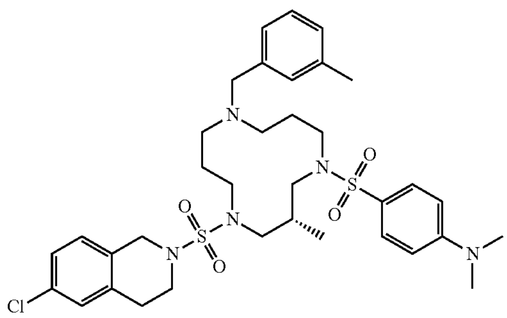 [SMILES: Cc1cccc(CN2CCCN(S(=O)(=O)c3ccc(N(C)C)cc3)C[C@H](C)CN(S(=O)(=O)N3CCc4cc(Cl)ccc4C3)CCC2)c1] |
| A157 | 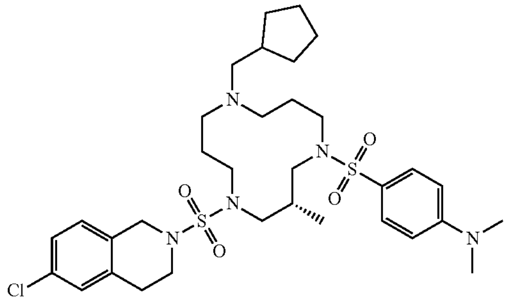 [SMILES: C[C@H]1CN(S(=O)(=O)c2ccc(N(C)C)cc2)CCCN(CC2CCCC2)CCCN(S(=O)(=O)N2CCc3cc(Cl)ccc3C2)C1] |
TABLE A-continued
| No. | Structure |
| --- | --- |
| A160 | 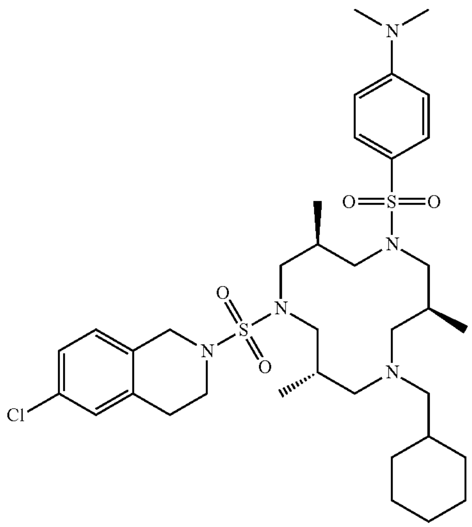 [SMILES: C[C@H]1CN(CC2CCCCC2)C[C@H](C)CN(S(=O)(=O)N2CCc3cc(Cl)ccc3C2)C[C@@H](C)CN(S(=O)(=O)c2ccc(N(C)C)cc2)C1] |
| A161 | 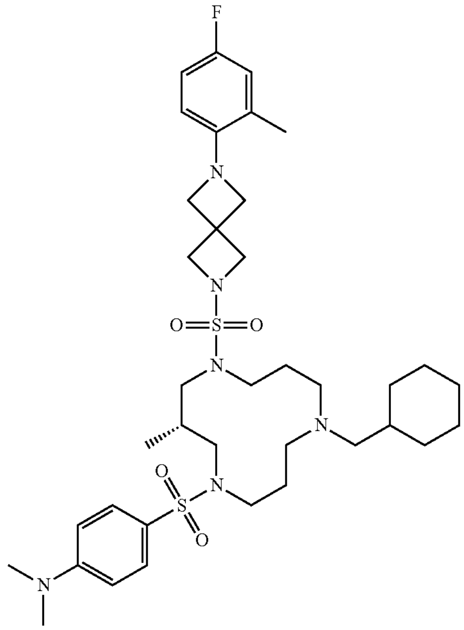 [SMILES: Cc1cc(F)ccc1N1CC2(C1)CN(S(=O)(=O)N1CCCN(CC3CCCCC3)CCCN(S(=O)(=O)c3ccc(N(C)C)cc3)C[C@H](C)C1)C2] |
| A162 | 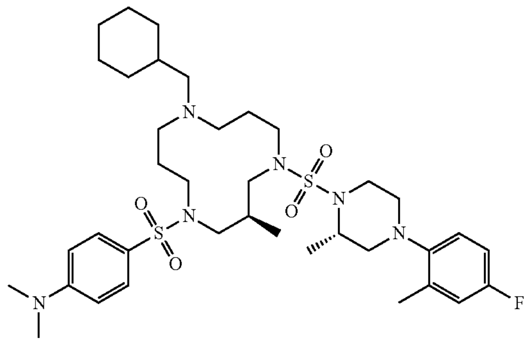 [SMILES: Cc1cc(F)ccc1N1CCN(S(=O)(=O)N2CCCN(CC3CCCCC3)CCCN(S(=O)(=O)c3ccc(N(C)C)cc3)C[C@H](C)C2)[C@@H](C)C1] |

TABLE A-continued
| No. | Structure |
|---|---|
| A163 | 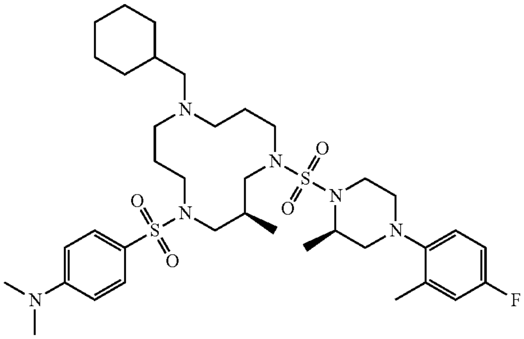 [SMILES: Cc1cc(F)ccc1N1CCN(S(=O)(=O)N2CCCN(CC3CCCCC3)CCCN(S(=O)(=O)c3ccc(N(C)C)cc3)C[C@H](C)C2)[C@H](C)C1] |
| A164 | 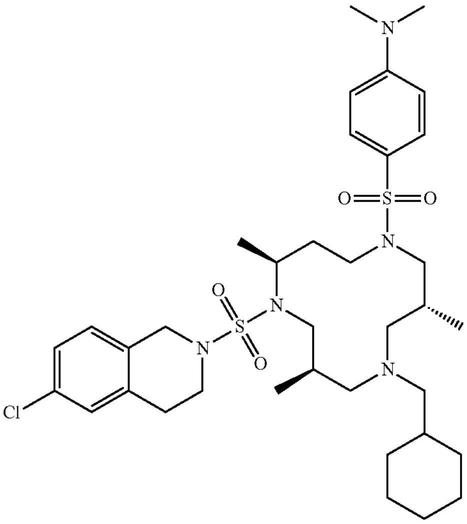 [SMILES: C[C@@H]1CN(CC2CCCCC2)C[C@@H](C)CN(S(=O)(=O)N2CCc3cc(Cl)ccc3C2)[C@@H](C)CCN(S(=O)(=O)c2ccc(N(C)C)cc2)C1] |
| A165 | 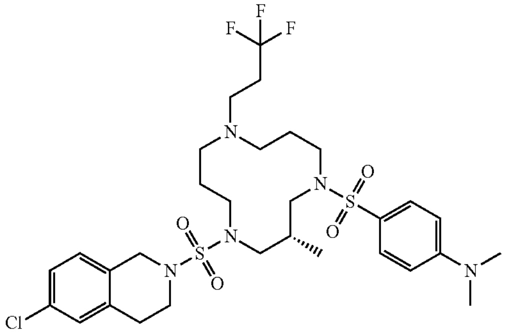 [SMILES: C[C@H]1CN(S(=O)(=O)c2ccc(N(C)C)cc2)CCCN(CCC(F)(F)F)CCCN(S(=O)(=O)N2CCc3cc(Cl)ccc3C2)C1] |
| A166 | 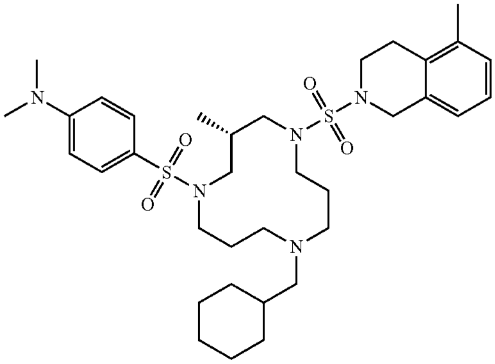 [SMILES: Cc1cccc2c1CCN(S(=O)(=O)N1CCCN(CC3CCCCC3)CCCN(S(=O)(=O)c3ccc(N(C)C)cc3)C[C@H](C)C1)C2] |
TABLE A-continued
| No. | Structure |
|---|---|
| A167 | 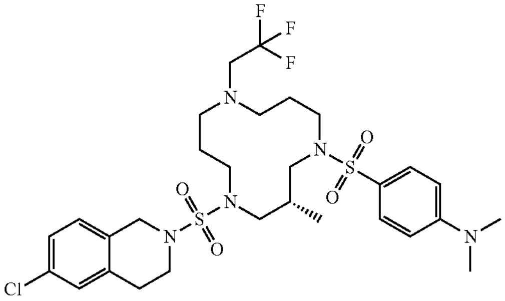 [SMILES: C[C@H]1CN(S(=O)(=O)c2ccc(N(C)C)cc2)CCCN(CC(F)(F)F)CCCN(S(=O)(=O)N2CCc3cc(Cl)ccc3C2)C1] |
| A168 | 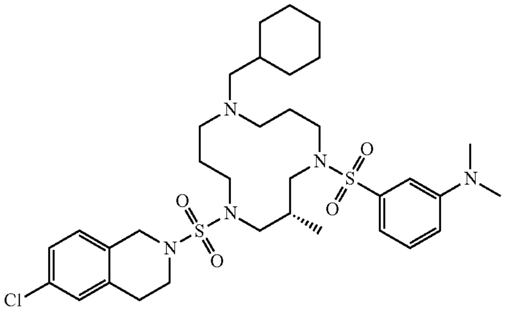 [SMILES: C[C@H]1CN(S(=O)(=O)c2cccc(N(C)C)c2)CCCN(CC2CCCCC2)CCCN(S(=O)(=O)N2CCc3cc(Cl)ccc3C2)C1] |
| A169 | 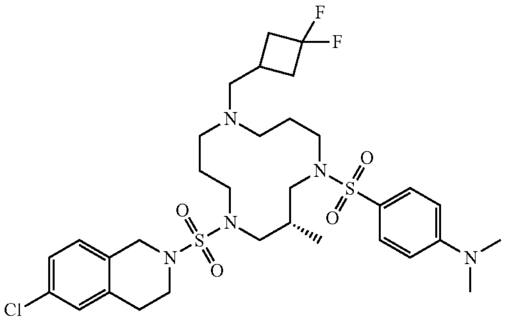 [SMILES: C[C@H]1CN(S(=O)(=O)c2ccc(N(C)C)cc2)CCCN(CC2CC(F)(F)C2)CCCN(S(=O)(=O)N2CCc3cc(Cl)ccc3C2)C1] |
| A170 | 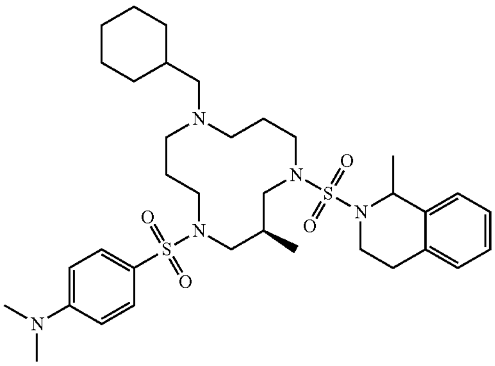 [SMILES: CC1c2ccccc2CCN1S(=O)(=O)N1CCCN(CC2CCCCC2)CCCN(S(=O)(=O)c2ccc(N(C)C)cc2)C[C@H](C)C1] |

TABLE A-continued
| No. | Structure |
| --- | --- |
| A171 | 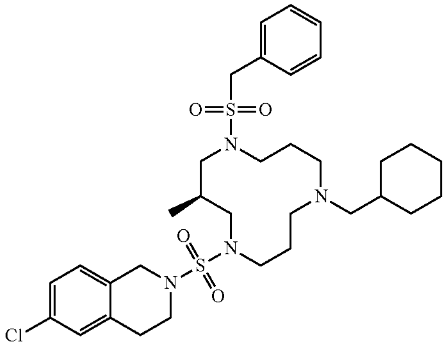 [SMILES: C[C@H]1CN(S(=O)(=O)Cc2ccccc2)CCCN(CC2CCCCC2)CCCN(S(=O)(=O)N2CCc3cc(Cl)ccc3C2)C1] |
| A172 | 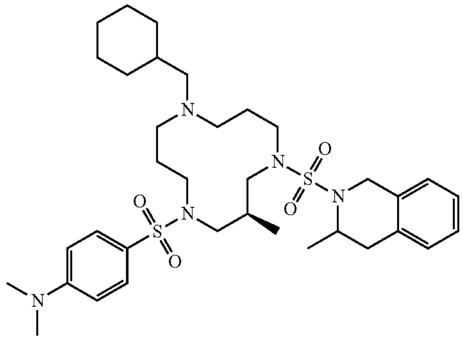 [SMILES: CC1Cc2ccccc2CN1S(=O)(=O)N1CCCN(CC2CCCCC2)CCCN(S(=O)(=O)c2ccc(N(C)C)cc2)C[C@H](C)C1] |
| A173 | 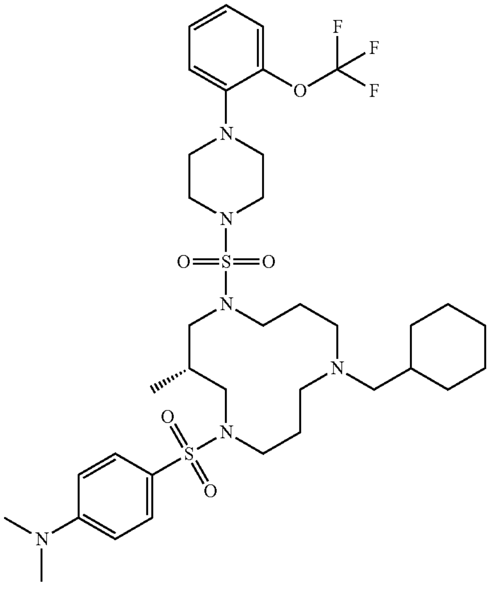 [SMILES: C[C@H]1CN(S(=O)(=O)c2ccc(N(C)C)cc2)CCCN(CC2CCCCC2)CCCN(S(=O)(=O)N2CCN(c3ccccc3OC(F)(F)F)CC2)C1] |
| A174 | 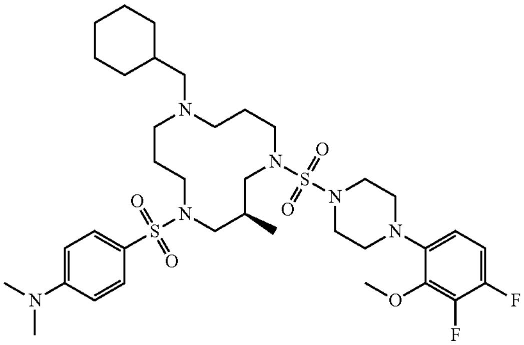 [SMILES: COc1c(N2CCN(S(=O)(=O)N3CCCN(CC4CCCCC4)CCCN(S(=O)(=O)c4ccc(N(C)C)cc4)C[C@H](C)C3)CC2)ccc(F)c1F] |
| A175 | 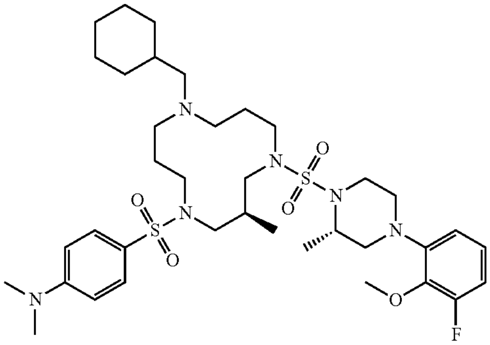 [SMILES: COc1c(F)cccc1N1CCN(S(=O)(=O)N2CCCN(CC3CCCCC3)CCCN(S(=O)(=O)c3ccc(N(C)C)cc3)C[C@H](C)C2)[C@@H](C)C1] |
| A176 | 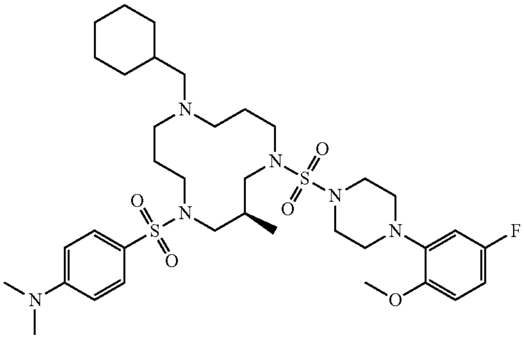 [SMILES: COc1ccc(F)cc1N1CCN(S(=O)(=O)N2CCCN(CC3CCCCC3)CCCN(S(=O)(=O)c3ccc(N(C)C)cc3)C[C@H](C)C2)CC1] |
| A177 | 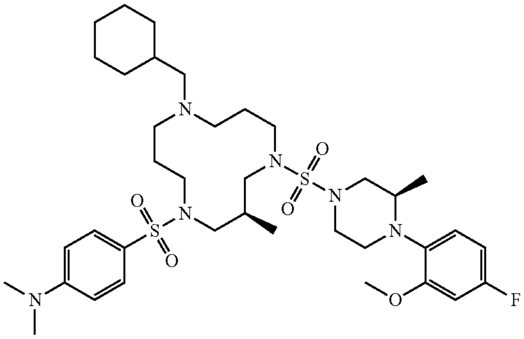 [SMILES: COc1cc(F)ccc1N1CCN(S(=O)(=O)N2CCCN(CC3CCCCC3)CCCN(S(=O)(=O)c3ccc(N(C)C)cc3)C[C@H](C)C2)C[C@H]1C] |

TABLE A-continued
| No. | Structure |
| --- | --- |
| A178 | 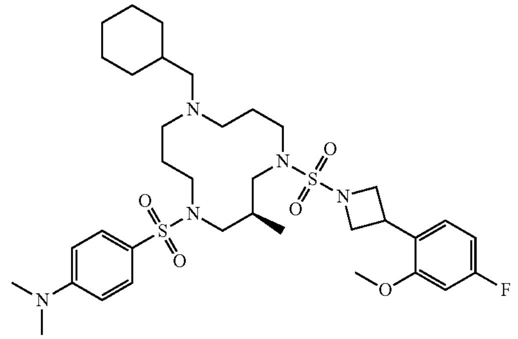 [SMILES: COc1cc(F)ccc1C1CN(S(=O)(=O)N2CCCN(CC3CCCCC3)CCCN(S(=O)(=O)c3ccc(N(C)C)cc3)C[C@H](C)C2)C1] |
| A179 | 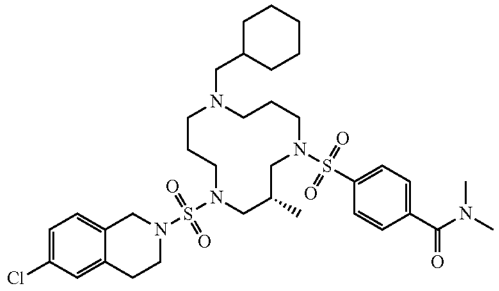 [SMILES: C[C@H]1CN(S(=O)(=O)c2ccc(C(=O)N(C)C)cc2)CCCN(CC2CCCCC2)CCCN(S(=O)(=O)N2CCc3cc(Cl)ccc3C2)C1] |
| A180 | 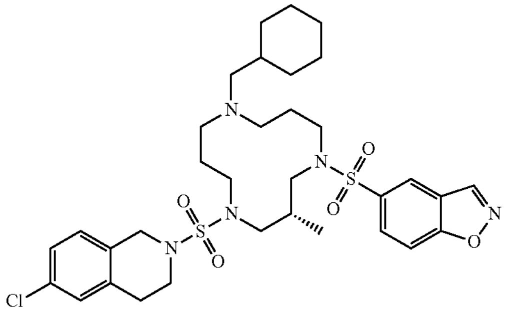 [SMILES: C[C@H]1CN(S(=O)(=O)c2ccc3oncc3c2)CCCN(CC2CCCCC2)CCCN(S(=O)(=O)N2CCc3cc(Cl)ccc3C2)C1] |
| A181 | 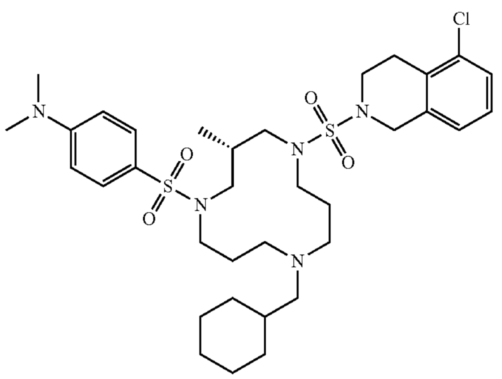 [SMILES: C[C@H]1CN(S(=O)(=O)c2ccc(N(C)C)cc2)CCCN(CC2CCCCC2)CCCN(S(=O)(=O)N2CCc3c(Cl)cccc3C2)C1] |
| A182 | 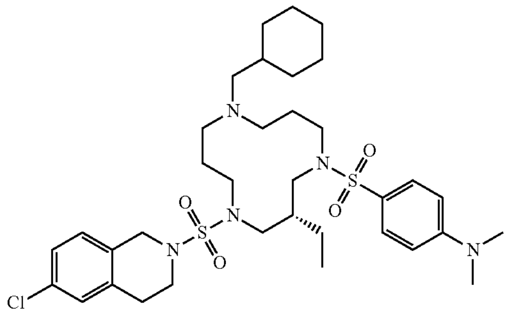 [SMILES: CC[C@H]1CN(S(=O)(=O)c2ccc(N(C)C)cc2)CCCN(CC2CCCCC2)CCCN(S(=O)(=O)N2CCc3cc(Cl)ccc3C2)C1] |
| A183 | 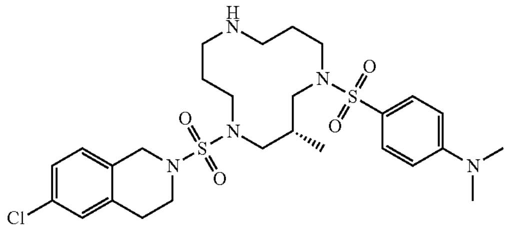 [SMILES: C[C@H]1CN(S(=O)(=O)c2ccc(N(C)C)cc2)CCCNCCCN(S(=O)(=O)N2CCc3cc(Cl)ccc3C2)C1] |
| A184 | 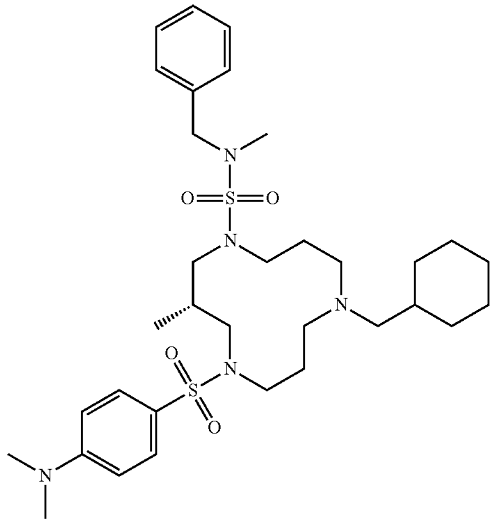 [SMILES: C[C@H]1CN(S(=O)(=O)c2ccc(N(C)C)cc2)CCCN(CC2CCCCC2)CCCN(S(=O)(=O)N(C)Cc2ccccc2)C1] |
| A185 | 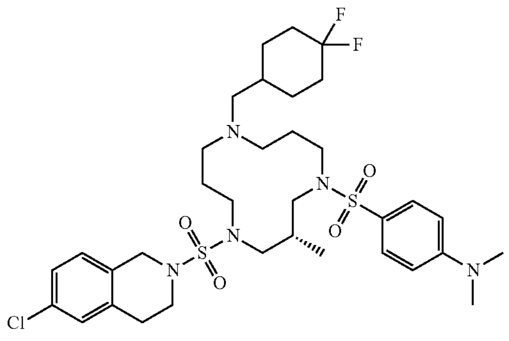 [SMILES: C[C@H]1CN(S(=O)(=O)c2ccc(N(C)C)cc2)CCCN(CC2CCC(F)(F)CC2)CCCN(S(=O)(=O)N2CCc3cc(Cl)ccc3C2)C1] |

TABLE A-continued
| No. | Structure |
|---|---|
| A187 | 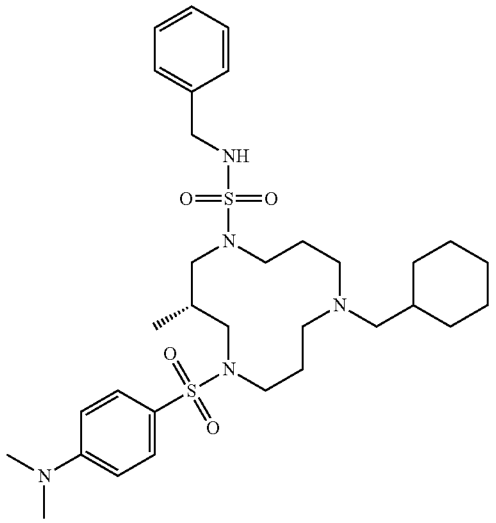 [SMILES: C[C@@H]1CN(S(=O)(=O)NCc2ccccc2)CCCN(CC2CCCCC2)CCCN(S(=O)(=O)c2ccc(N(C)C)cc2)C1] |
| A188 | 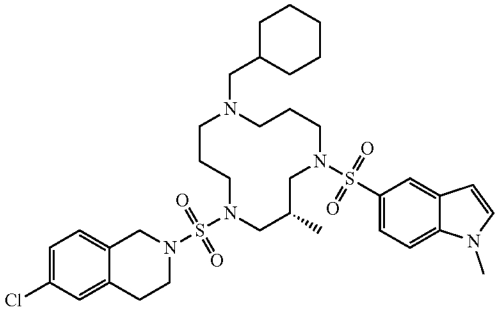 [SMILES: C[C@H]1CN(S(=O)(=O)c2ccc3c(ccn3C)c2)CCCN(CC2CCCCC2)CCCN(S(=O)(=O)N2CCc3cc(Cl)ccc3C2)C1] |
| A189 | 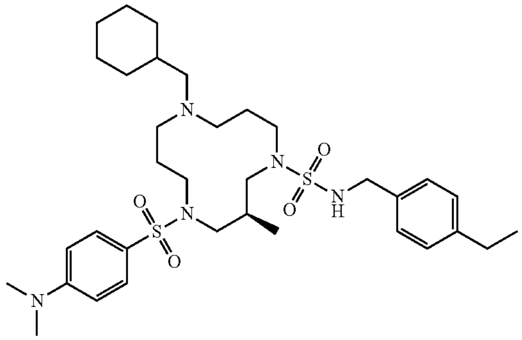 [SMILES: CCc1ccc(CNS(=O)(=O)N2CCCN(CC3CCCCC3)CCCN(S(=O)(=O)c3ccc(N(C)C)cc3)C[C@H](C)C2)cc1] |
| A190 | 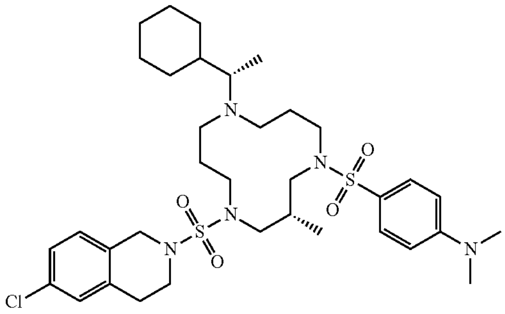 [SMILES: C[C@H]1CN(S(=O)(=O)c2ccc(N(C)C)cc2)CCCN([C@@H](C)C2CCCCC2)CCCN(S(=O)(=O)N2CCc3cc(Cl)ccc3C2)C1] |
TABLE A-continued
| No. | Structure |
|---|---|
| A191 | 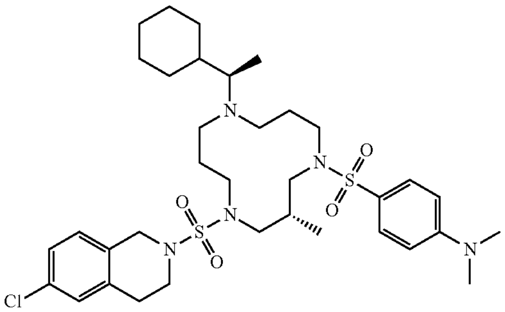 [SMILES: C[C@H]1CN(S(=O)(=O)c2ccc(N(C)C)cc2)CCCN([C@H](C)C2CCCCC2)CCCN(S(=O)(=O)N2CCc3cc(Cl)ccc3C2)C1] |
| A192 | 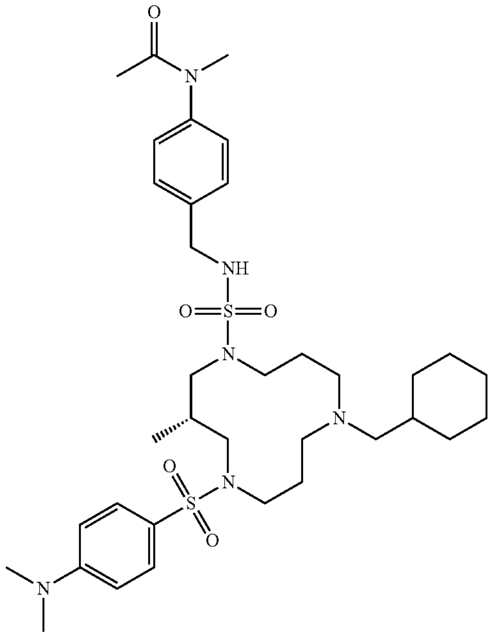 [SMILES: CC(=O)N(C)c1ccc(CNS(=O)(=O)N2CCCN(CC3CCCCC3)CCCN(S(=O)(=O)c3ccc(N(C)C)cc3)C[C@H](C)C2)cc1] |
| A193 | 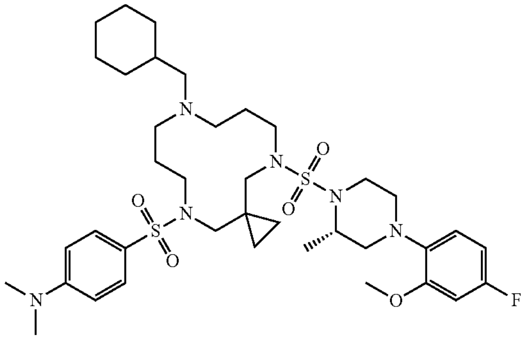 [SMILES: COc1cc(F)ccc1N1CCN(S(=O)(=O)N2CCCN(CC3CCCCC3)CCCN(S(=O)(=O)c3ccc(N(C)C)cc3)CC3(CC3)C2)[C@@H](C)C1] |
| A194 | 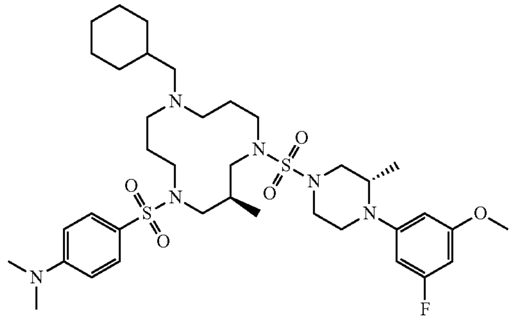 |

TABLE A-continued
| No. | Structure |
|---|---|
| A195 | 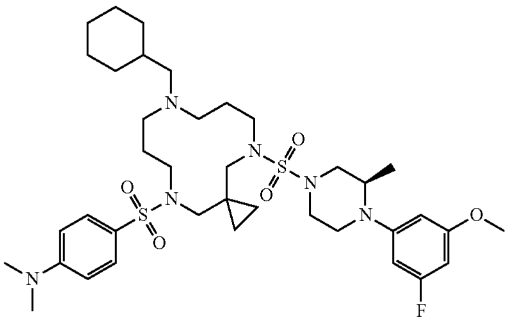 |
| A196 | 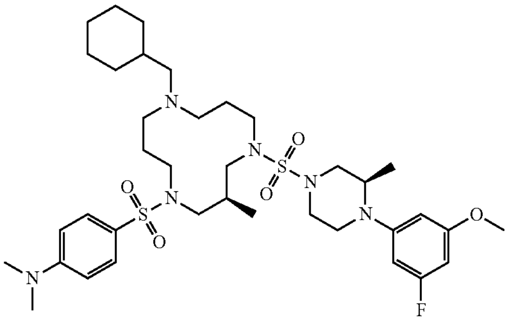 |
| A197 | 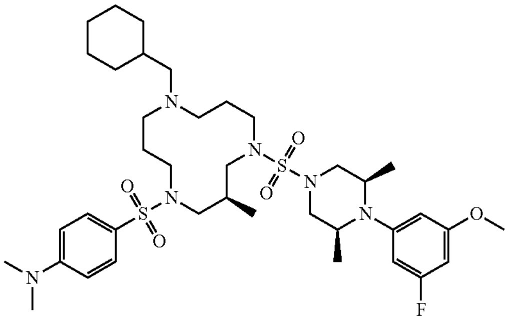 |
| A198 | 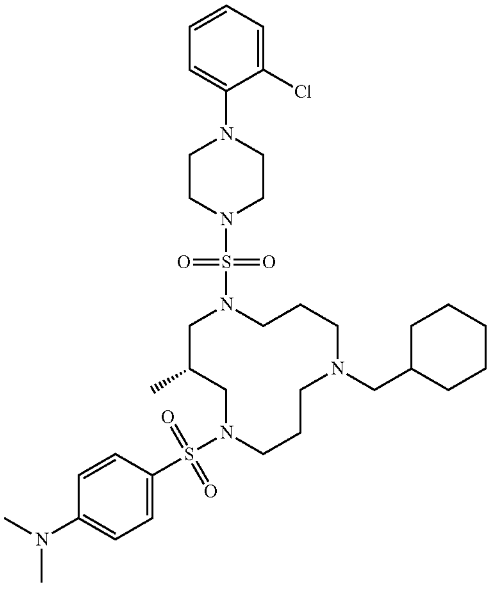 |
TABLE A-continued
| No. | Structure |
|---|---|
| A199 | 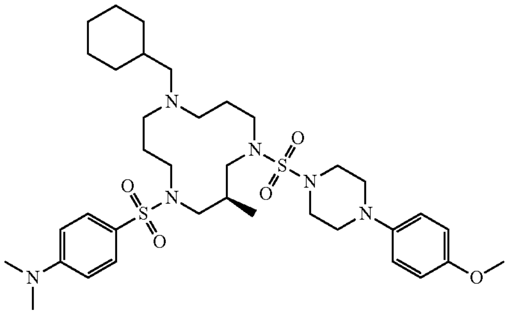 |
| A200 | 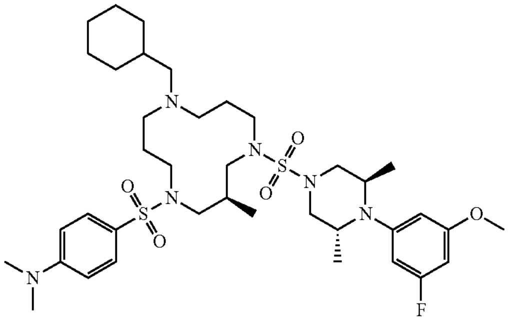 |
| A201 | 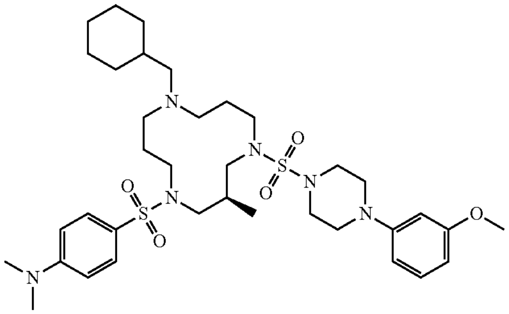 |
| A202 | 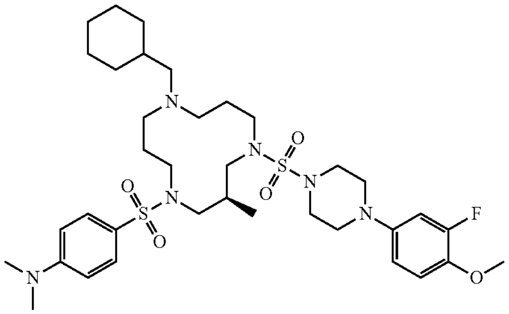 |

TABLE A-continued
| No. | Structure |
| --- | --- |
| A203 | 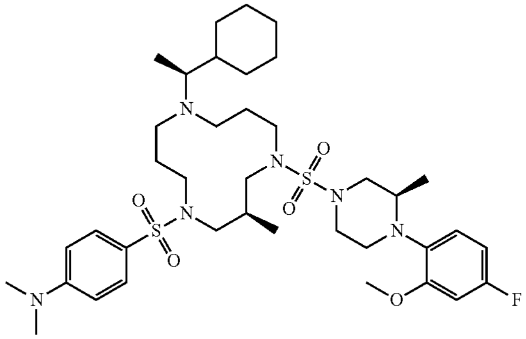 [SMILES: COc1cc(F)ccc1N1CCN(S(=O)(=O)N2CCCN([C@@H](C)C3CCCCC3)CCCN(S(=O)(=O)c3ccc(N(C)C)cc3)C[C@H](C)C2)C[C@H]1C] |
| A204 | 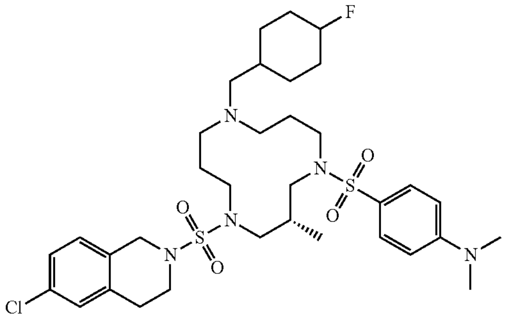 [SMILES: C[C@H]1CN(S(=O)(=O)c2ccc(N(C)C)cc2)CCCN(CC2CCC(F)CC2)CCCN(S(=O)(=O)N2CCc3cc(Cl)ccc3C2)C1] |
| A205 | 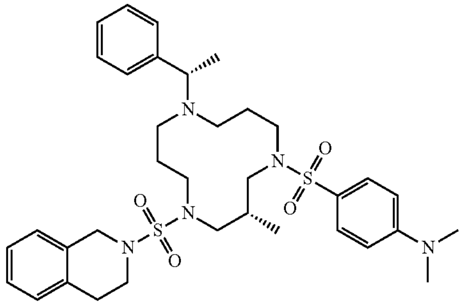 [SMILES: C[C@H]1CN(S(=O)(=O)c2ccc(N(C)C)cc2)CCCN([C@@H](C)c2ccccc2)CCCN(S(=O)(=O)N2CCc3ccccc3C2)C1] |
| A206 | 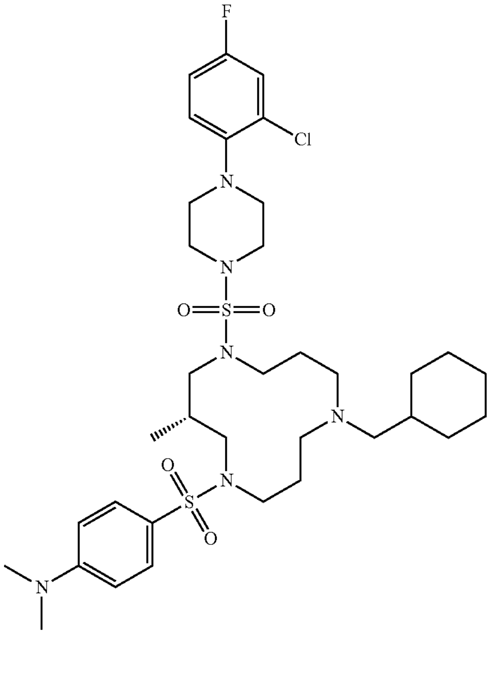 [SMILES: C[C@H]1CN(S(=O)(=O)c2ccc(N(C)C)cc2)CCCN(CC2CCCCC2)CCCN(S(=O)(=O)N2CCN(c3ccc(F)cc3Cl)CC2)C1] |
TABLE A-continued
| No. | Structure |
| --- | --- |
| A207 | 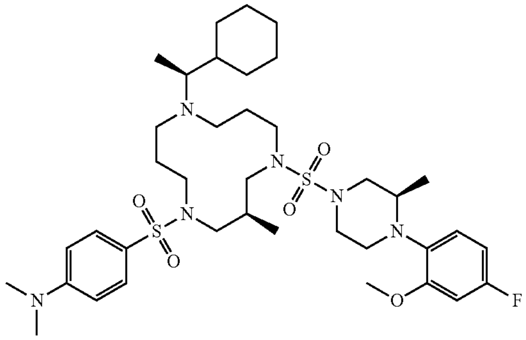 [SMILES: COc1cc(F)ccc1N1CCN(S(=O)(=O)N2CCCN([C@@H](C)C3CCCCC3)CCCN(S(=O)(=O)c3ccc(N(C)C)cc3)C[C@H](C)C2)C[C@H]1C] |
| A208 | 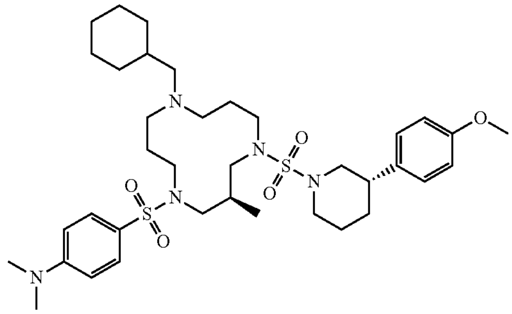 |
| A209 | 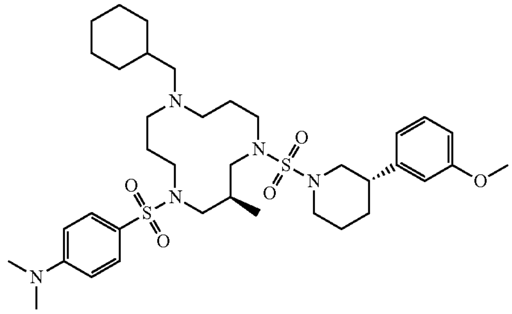 |
| A210 | 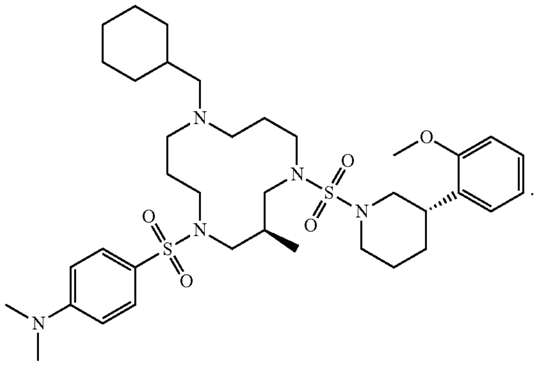 [SMILES: COc1ccccc1[C@@H]1CCCN(S(=O)(=O)N2CCCN(CC3CCCCC3)CCCN(S(=O)(=O)c3ccc(N(C)C)cc3)C[C@H](C)C2)C1] |

In some embodiments, the compounds of the disclosure include
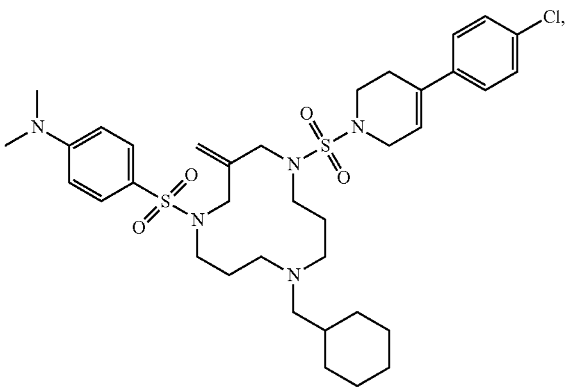
,
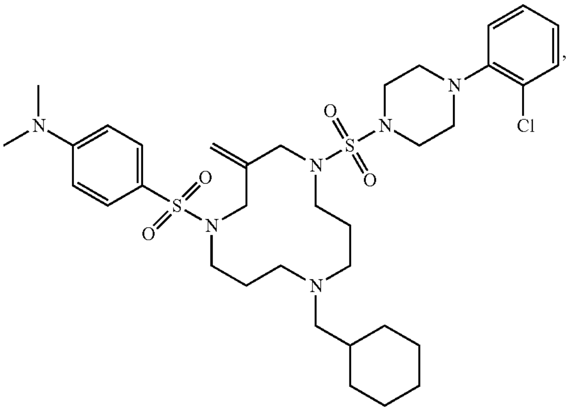
,
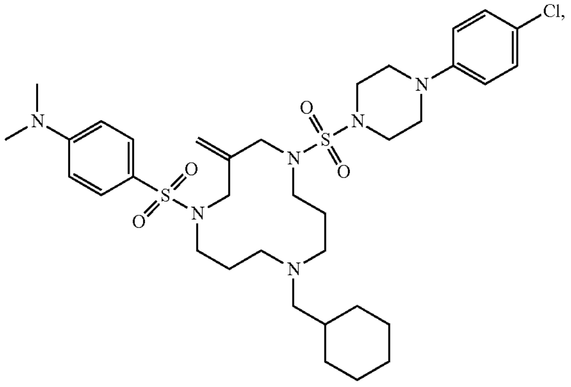
,
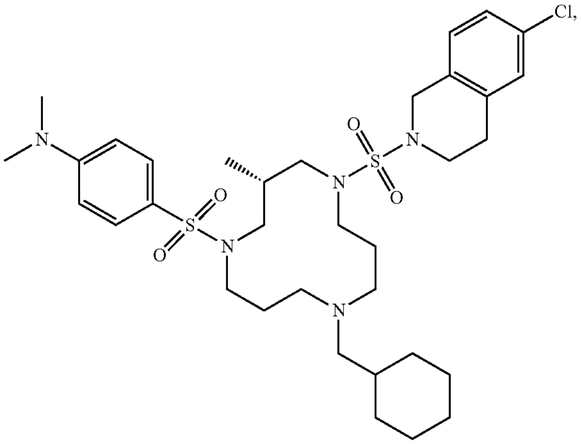
,
-continued
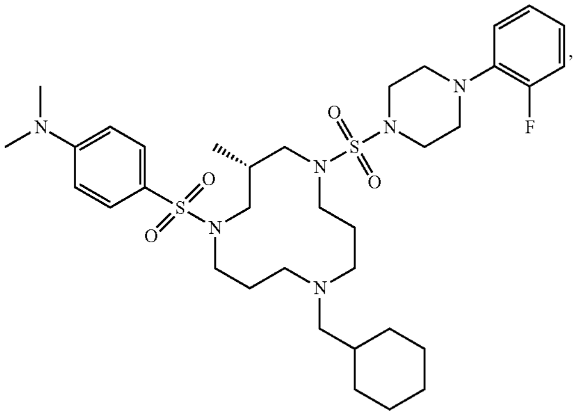
,
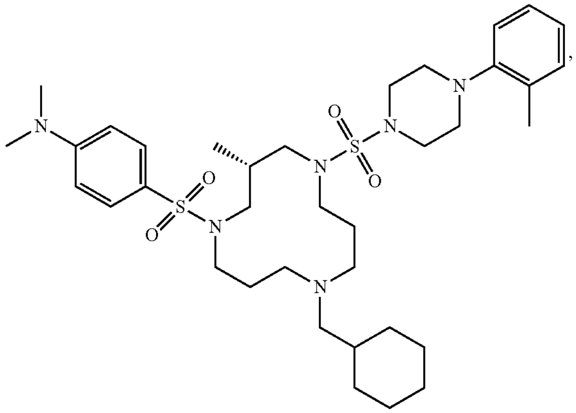
,
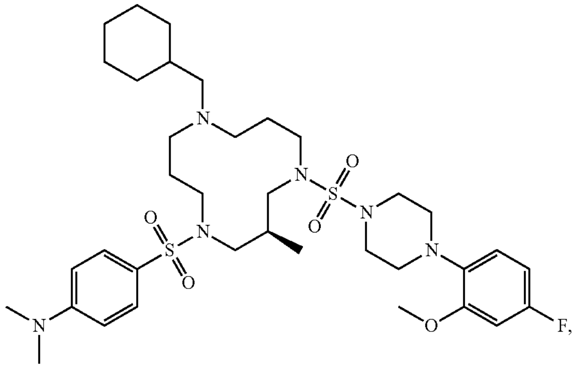
, -continued
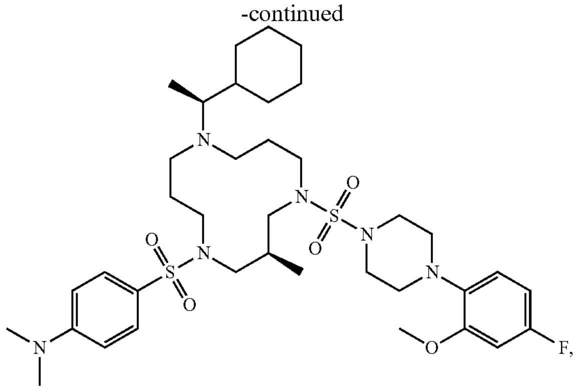
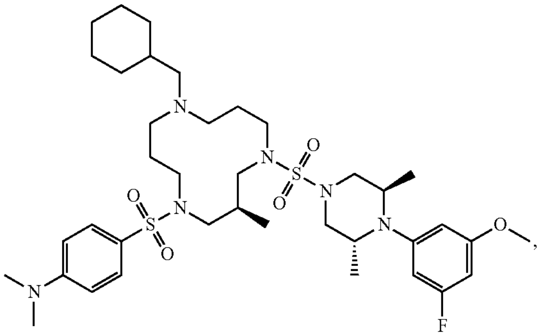
, and
-continued
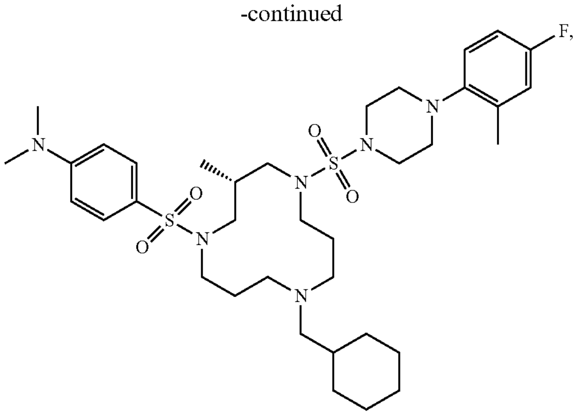
or a pharmaceutically acceptable salt thereof.
Additional compounds of the disclosure are shown in Table B as compounds B1-B22, or a pharmaceutically acceptable salt thereof. In some cases, the compound is a compound of B1-B20, or a pharmaceutically acceptable salt thereof.
TABLE B
| No. | Structure |
| --- | --- |
| B1 | 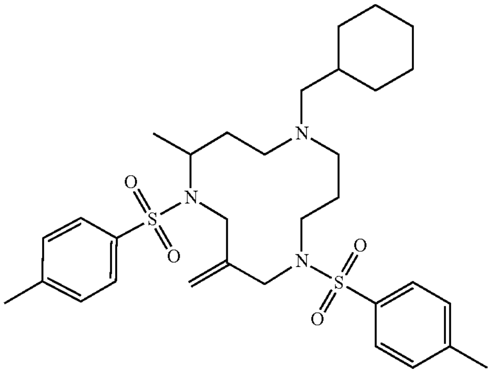 |
| B2 | 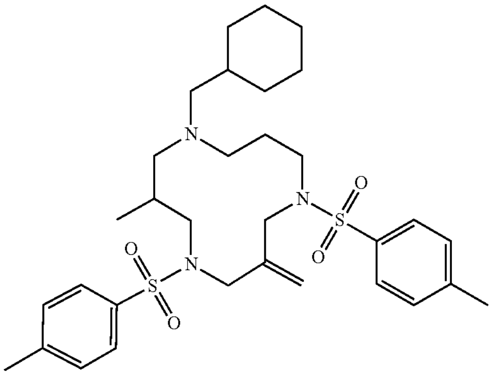 |

TABLE B-continued
| No. | Structure |
|---|---|
| B3 | 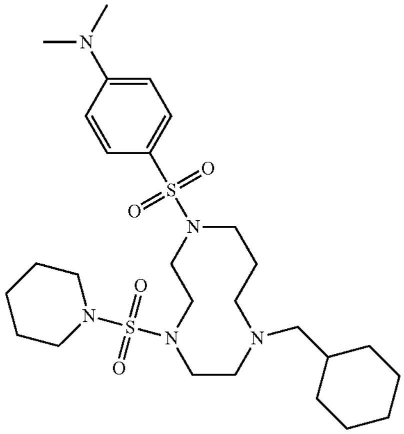 [SMILES: CN(C)c1ccc(S(=O)(=O)N2CCCN(CC3CCCCC3)CCN(S(=O)(=O)N3CCCCC3)CC2)cc1] |
| B4 | 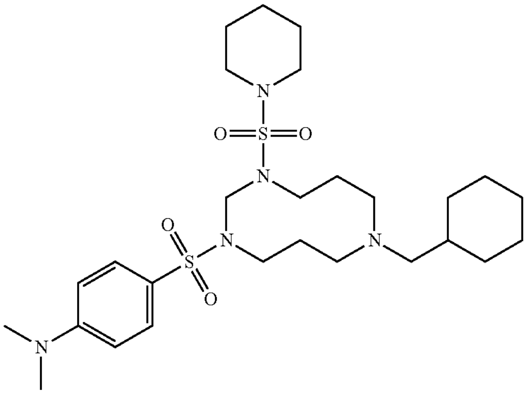 [SMILES: CN(C)c1ccc(S(=O)(=O)N2CCCN(CC3CCCCC3)CCCN(S(=O)(=O)N3CCCCC3)C2)cc1] |
| B5 | 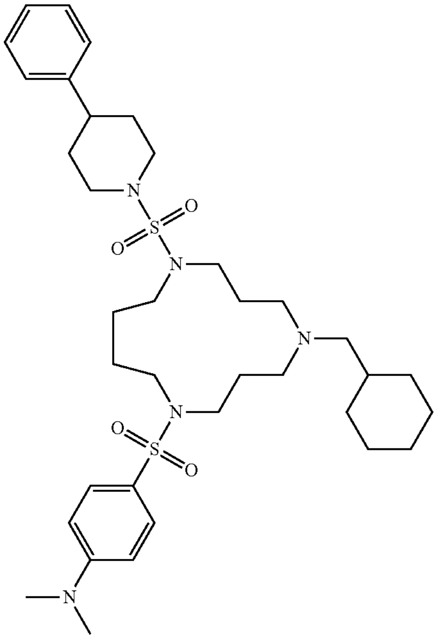 [SMILES: CN(C)c1ccc(S(=O)(=O)N2CCCCN(S(=O)(=O)N3CCC(c4ccccc4)CC3)CCCN(CC3CCCCC3)CCC2)cc1] |

TABLE B-continued
| No. | Structure |
| --- | --- |
| B6 | 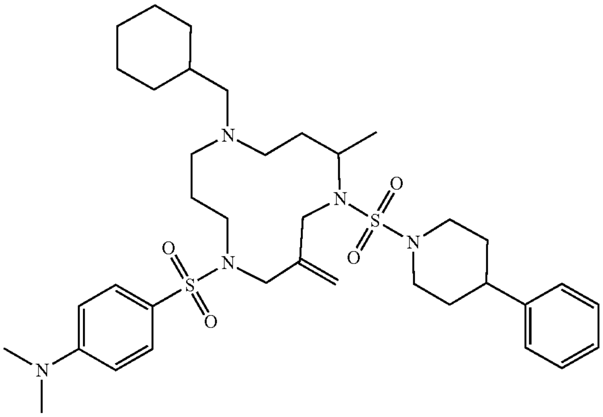 [SMILES: C=C1CN(S(=O)(=O)c2ccc(N(C)C)cc2)CCCN(CC2CCCCC2)CCC(C)N(S(=O)(=O)N2CCC(c3ccccc3)CC2)C1] |
| B7 | 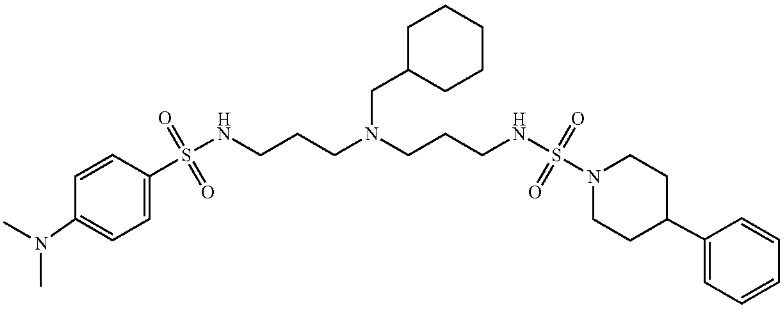 [SMILES: CN(C)c1ccc(S(=O)(=O)NCCCN(CCCNS(=O)(=O)N2CCC(c3ccccc3)CC2)CC2CCCCC2)cc1] |
| B8 | 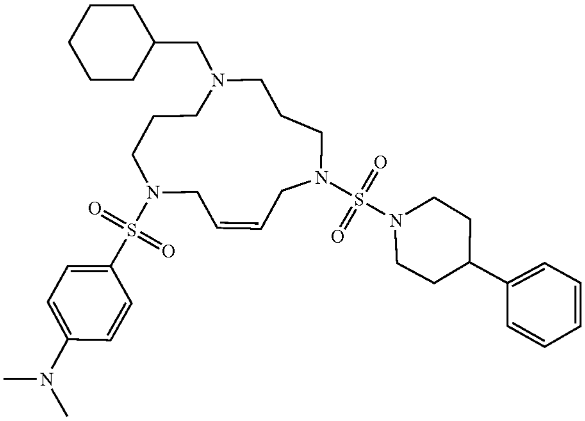 [SMILES: CN(C)c1ccc(S(=O)(=O)N2C/C=C\CN(S(=O)(=O)N3CCC(c4ccccc4)CC3)CCCN(CC3CCCCC3)CCC2)cc1] |

TABLE B-continued
| No. | Structure |
| --- | --- |
| B9 | 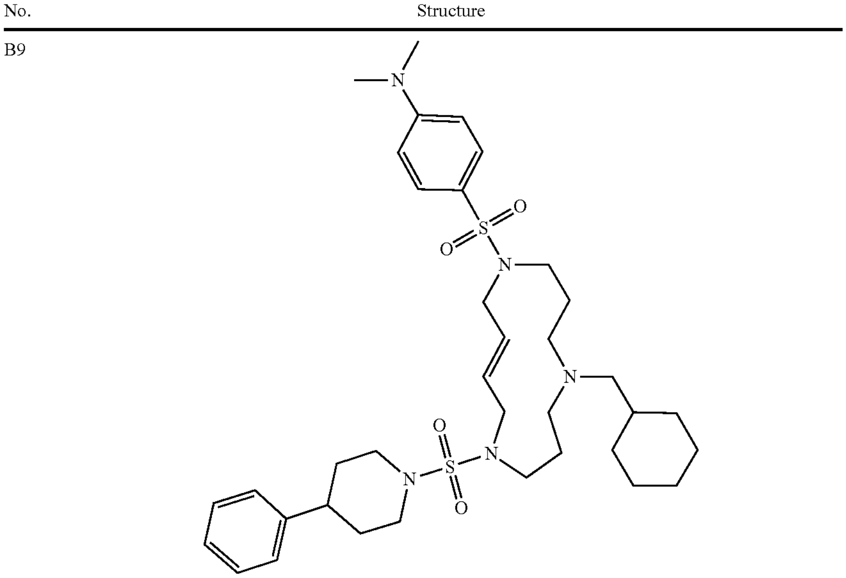 |
| B10 | 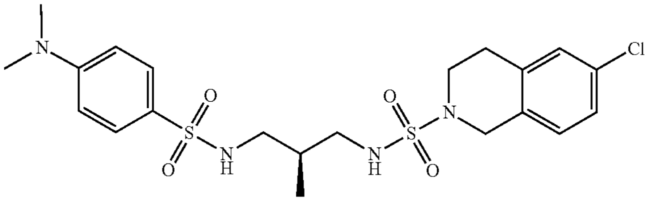 [SMILES: C[C@@H](CNS(=O)(=O)c1ccc(N(C)C)cc1)CNS(=O)(=O)N1CCc2cc(Cl)ccc2C1] |
| B11 | 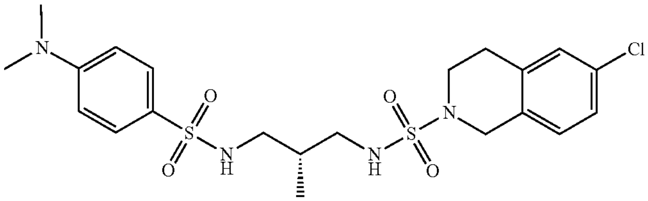 [SMILES: C[C@H](CNS(=O)(=O)c1ccc(N(C)C)cc1)CNS(=O)(=O)N1CCc2cc(Cl)ccc2C1] |
| B12 | 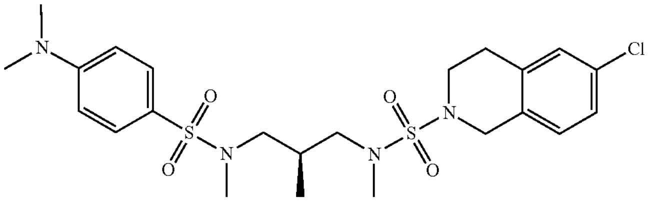 [SMILES: C[C@@H](CN(C)S(=O)(=O)c1ccc(N(C)C)cc1)CN(C)S(=O)(=O)N1CCc2cc(Cl)ccc2C1] |

TABLE B-continued
| No. | Structure |
|---|---|
| B13 | 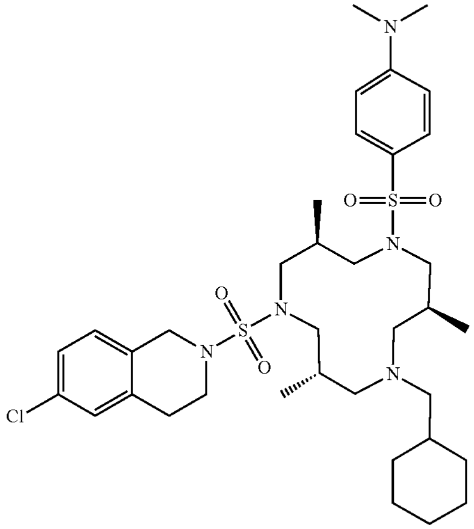 [SMILES: C[C@H]1CN(CC2CCCCC2)C[C@H](C)CN(S(=O)(=O)N2CCc3cc(Cl)ccc3C2)C[C@@H](C)CN(S(=O)(=O)c2ccc(N(C)C)cc2)C1] |
| B14 | 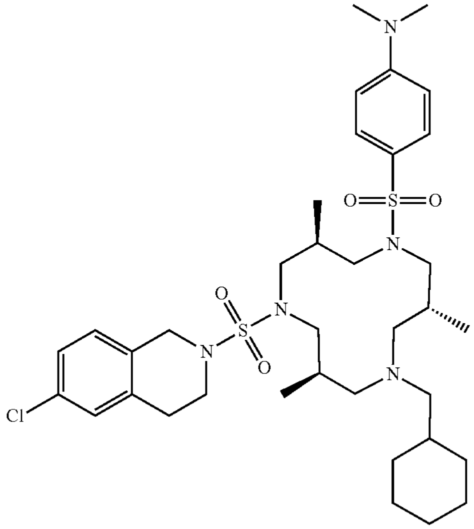 [SMILES: C[C@@H]1CN(CC2CCCCC2)C[C@@H](C)CN(S(=O)(=O)N2CCc3cc(Cl)ccc3C2)C[C@@H](C)CN(S(=O)(=O)c2ccc(N(C)C)cc2)C1] |
| B15 | 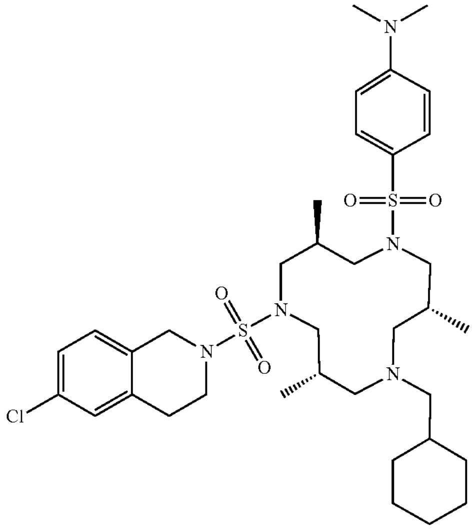 [SMILES: C[C@@H]1CN(CC2CCCCC2)C[C@H](C)CN(S(=O)(=O)N2CCc3cc(Cl)ccc3C2)C[C@@H](C)CN(S(=O)(=O)c2ccc(N(C)C)cc2)C1] |

TABLE B-continued
| No. | Structure |
|---|---|
| B16 | 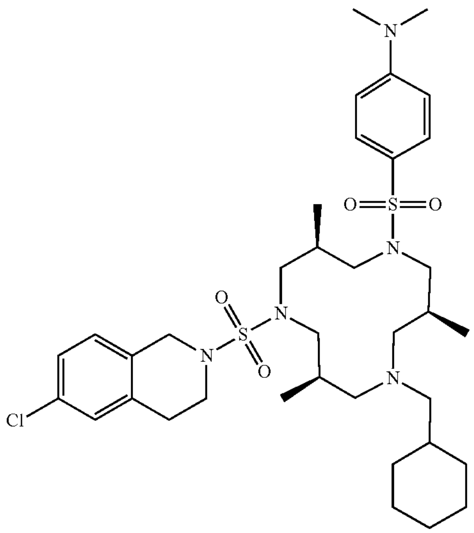 [SMILES: C[C@@H]1CN(CC2CCCCC2)C[C@H](C)CN(S(=O)(=O)c2ccc(N(C)C)cc2)C[C@H](C)CN(S(=O)(=O)N2CCc3cc(Cl)ccc3C2)C1] |
| B17 | 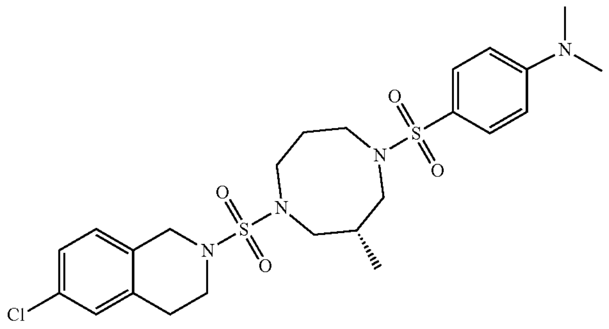 [SMILES: C[C@H]1CN(S(=O)(=O)c2ccc(N(C)C)cc2)CCCN(S(=O)(=O)N2CCc3cc(Cl)ccc3C2)C1] |
| B18 | 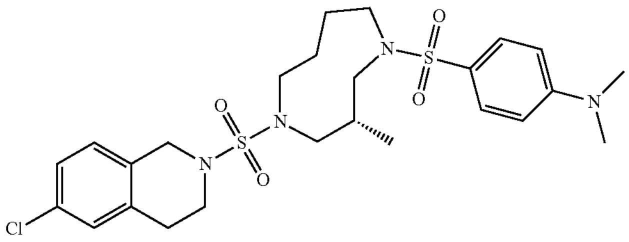 [SMILES: C[C@H]1CN(S(=O)(=O)c2ccc(N(C)C)cc2)CCCCN(S(=O)(=O)N2CCc3cc(Cl)ccc3C2)C1] |
| B19 | 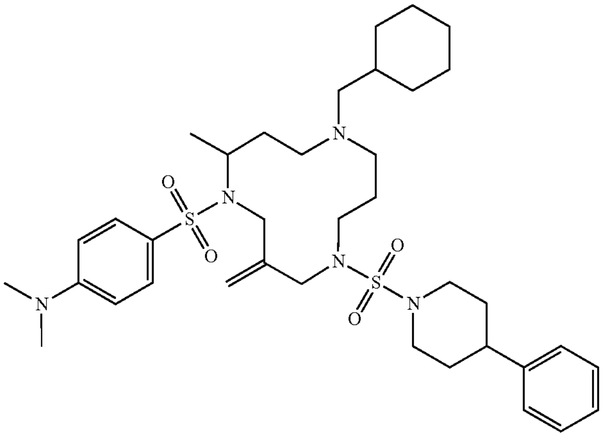 [SMILES: C=C1CN(S(=O)(=O)c2ccc(N(C)C)cc2)C(C)CCN(CC2CCCCC2)CCCN(S(=O)(=O)N2CCC(c3ccccc3)CC2)C1] |

TABLE B-continued

| No. | Structure |
|---|---|
| B20 | 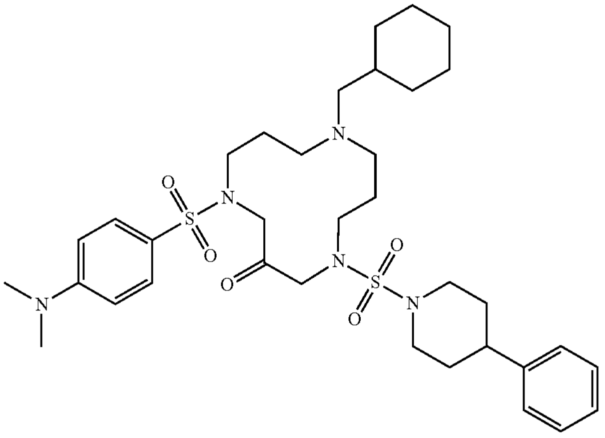 [SMILES: CN(C)c1ccc(S(=O)(=O)N2CCCN(CC3CCCCC3)CCCN(S(=O)(=O)N3CCC(c4ccccc4)CC3)CC(=O)C2)cc1] |
| B21 | 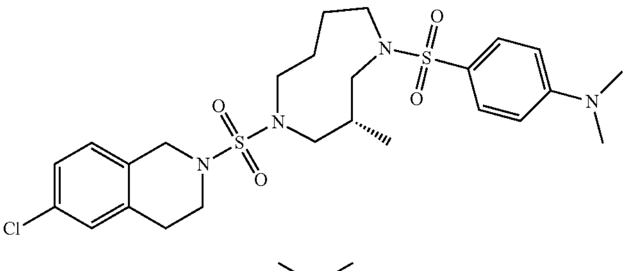 |
| B22 | 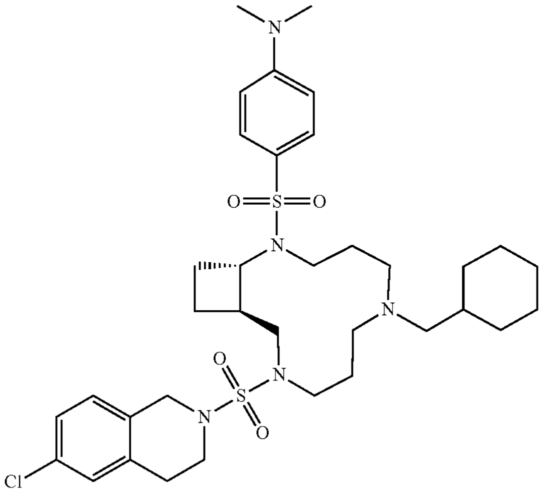 [SMILES: CN(C)c1ccc(S(=O)(=O)N2CCCN(CC3CCCCC3)CCCN(S(=O)(=O)N3CCc4cc(Cl)ccc4C3)C[C@H]3CC[C@@H]32)cc1] |

The chemical structures having one or more stereocenters depicted with dashed and bold bonds (i.e., and ) are meant to indicate absolute stereochemistry of the stereocenter(s) present in the chemical structure. Bonds symbolized by a simple line do not indicate a stereo-preference. Unless otherwise indicated to the contrary, chemical structures that include one or more stereocenters which are illustrated herein without indicating absolute or relative stereochemistry, encompass all possible stereoisomeric forms of the compound (e.g., diastereomers, enantiomers) and mixtures thereof. Structures with a single bold or dashed line, and at least one additional simple line, encompass a single enantiomeric series of all possible diastereomers.

Synthesis of Protein Secretion Inhibitors

The compounds provided herein can be synthesized using conventional techniques readily available starting materials known to those skilled in the art. In general, the compounds provided herein are conveniently obtained via standard organic chemistry synthesis methods.

Synthesis of Final Compounds

In some cases, the compounds described herein can be synthesized by reacting a sulfonyl chloride having a desired $R^2$ group with propane-1,3-diamine, and reacting the resulting product with an aldehyde having a desired $R^3$ group to form N-substituted propyl amine compound. A propyl amino group can be introduced to the N-substituted propyl amine at the $R^4$ position via reaction with 2-(3-bromopropyl) isoindoline-1,3-dione followed by hydrazine, and a desired $R^4$ group can be coupled to the compound by reacting the compound with a sulfonyl chloride functionalized with the desired $R^4$ group. Finally, the compound can be cyclized via a cyclization agent having a desired $R^1$ group, such as 3-chloro-2-chloromethyl-1-propene, 2-methylpropane-1,3-diyl diethanesulfonate, cyclopropane-1,1-diylbis(methylene) diethanesulfonate, 1,3-dichloropropane, or 1,4-dichlorobutane.

In some embodiments, compounds having a methylene group at $R^1$ can be synthesized by coupling a (3-aminopropyl)propane-1,3-diamine group derivatized with the desired $R^3$ and $R^4$ groups with a desired $R^2$-sulfamoyl chloride or $R^2$-sulfanyl chloride group, and then reacting the resulting compound with 3-chloro-2-chloromethyl-1-propene to form the desired triazacyclododecansulfonamide compound, as exemplified by Route 1 in the Examples section.

In various embodiments, compounds having a methylene group at $R^1$ can be synthesized by coupling protected butane-1,3-diamine with an aldehyde having a desired $R^3$ group to form a 3-(azaneyl)-N-butan-1-amine, reacting the amino group at the $R^2$ position with a chloro group functionalized with a desired $R^2$ group, introducing a propyl amino group to the 3-(azaneyl)-N-butan-1-amine at the $R^4$ position via reaction with 2-(3-bromopropyl)isoindoline-1,3-dione followed by hydrazine, reacting the resulting amino group at the $R^4$ position with a chloro group functionalized with a desired $R^4$ group, and then reacting the resulting compound with 3-chloro-2-chloromethyl-1-propene to form the desired triazacyclododecansulfonamide compound, as exemplified by Route 2 in the Examples section.

In some cases, compounds having a Spiro group at $R^1$ can be synthesized by reacting a N-(3-(azaneyl)propyl)propane-1,3-diamino group derivatized with the desired $R^2$, $R^3$, and $R^4$ groups with 1,1-diylbis(methylene)diethanesulfonate derivatized with the desired spiro group, as exemplified by Routes 3, 8, and 9 in the Examples section.

In various cases, compounds provided herein can be synthesized by reducing a benzyl group at $R^2$ on N-(3-(azaneyl)propyl)propane-1,3-diamino functionalized with the desired $R^3$ and $R^4$ groups, and then reacting the resulting product with a desired aldehyde derivatized with a desired $R^2$ group (e.g., dimethyl cyclohexyl), as exemplified by Route 4 in the Examples section.

In some embodiments, compounds having a carboxylate group at $R^2$ can be prepared by reacting triazacyclododensulfonyl group derivatized with desired $R^1$, $R^3$, and $R^4$ groups with a desired alkyl group and triphosgene under basic conditions, as exemplified by Route 5 in the Examples section.

In various embodiments, compounds having piperidinyl group at $R^2$ can be prepared by reacting with DBU/mercaptoethanol a triazacyclododensulfonyl compound having desired $R^1$, $R^3$, and $R^4$ groups and functionalized at $R^2$ with a nitrophenyl group, and then coupling the resulting product with piperidinyl sulfonyl chloride, as exemplified by Route 6 in the Examples section.

In some embodiments, compounds having a hydrogen group at $R^1$ can be synthesized by coupling N-(3-(azaneyl)propyl)propane-1,3-diamino functionalized with the desired $R^2$, $R^3$, and $R^4$ groups with 1,3-dichloropropane or 1,4-dichlorobutane, as exemplified by Route 7 and Route 17 in the Examples section.

In some cases, compounds having a chlorophenylmethanone group at $R^2$ can be synthesized by reacting triazacyclododensulfonyl functionalized with desired $R^1$, $R^3$, and $R^4$ groups with 4-chlorobenzoyl chloride under basic conditions, as exemplified by Route 10 in the Examples section.

In various cases, compounds having a 4-(dimethylamino)-2-methylbenzyl group at $R^4$ and a spiro group at $R^1$ can be prepared by reacting a N-(3-(azaneyl)propyl)propane-1,3-diamino compound functionalized with the desired $R^2$ and $R^3$ groups with 4-(dimethylamino)-2-methylbenzenesulfonyl chloride, and then cyclizing the compound via coupling with 1,1-diylbis(methylene)diethanesulfonate derivatized with the desired Spiro group using methods previously described herein, as exemplified by Route 11 in the Examples section.

In some embodiments, the compounds described herein can be prepared by reacting a sulfonyl chloride having a desired $R^2$ group with propane-1,3-diamine, and reacting the resulting product with an aldehyde having a desired $R^3$ group to form a 3-(azaneyl)-N-butan-1-amine compound. A propyl amino group can be introduced to the 3-(azaneyl)-N-butan-1-amine at the $R^4$ position via reaction with 2-(3-bromopropyl)isoindoline-1,3-dione followed by hydrazine, and a desired $R^4$ group can be coupled to the compound by reacting the compound with desired sulfonyl chloride (e.g., 4-(dimethylamino)-2-methylbenzenesulfonyl chloride). Finally, the compound can be cyclized via an appropriate cyclization agent, such as 3-chloro-2-chloromethyl-1-propene, 2-methylpropane-1,3-diyl diethanesulfonate, cyclopropane-1,1-diylbis(methylene) diethanesulfonate, 1,3-dichloropropane, or 1,4-dichlorobutane, as previously described herein, as exemplified by Route 12 in the Examples section.

In various embodiments, compounds having a 4-phenylpiperidineyl-1-yl sulfonyl group at $R^2$ can be synthesized by reacting a triazacyclododensulfonyl group functionalized with desired $R^1$, $R^3$, and $R^4$ groups with 3-methyl-1-((4-phenylpiperidin-1-yl)sulfonyl)-1H-imidazol-3-ium trifluoromethanesulfonate, as exemplified by Route 14 in the Examples section.

In some cases, compounds having a 4-phenylpiperidineyl-1-yl sulfonyl group at $R^2$ can be synthesized by reacting N-(3-(azaneyl)propyl)propane-1,3-diamino functionalized with the desired $R^3$ and $R^4$ groups with 3-methyl-1-((4-phenylpiperidin-1-yl)sulfonyl)-1H-imidazol-3-ium trifluoromethanesulfonate, and then cyclizing the compound with an appropriate cyclization agent, such as 2-methylpropane-1,3-diyl diethanesulfonate, 3-chloro-2-chloromethyl-1-propene, cyclopropane-1,1-diylbis(methylene) diethanesulfonate, 1,3-dichloropropane or 1,4-dichlorobutane, as previously described herein, as exemplified by Route 15 in the Examples section. Analogous compounds having a methyl group adjacent to the $R^4$ nitrogen can be similarly synthesized using 3-chloro-2-(chloromethyl)prop-1-ene, as exemplified by Route 18 in the Examples section.

In some cases, compounds having an alcohol group for $R^1$ can be synthesized by cyclizing a N-(3-(azaneyl)propyl)propane-1,3-diamino compound with protected 1,3-dichloropropan-2-ol under basic conditions, as exemplified by Route 19 in the Examples section. The alcohol group at $R^1$ can be methylated via reaction with MeI and NaH in toluene, as exemplified by Route 21 in the examples section. The alcohol group at $R^1$ can be oxidized to a carbonyl via reaction with Dess-Martin periodinane, as exemplified by Route 22 in the examples section. The carbonyl group at $R^1$ can be reacted with hydroxylamine hydrochloride to form the oxime compound, as exemplified by Route 25 in the Examples section.

In various cases, compounds having an S-methyl group at $R^1$ can be synthesized by reacting an amino group functionalized with a desired $R^2$ group with 2,3-dimethyl-1-((2-methyl-1H-imidazol-1-yl)sulfonyl)-1H-imidazol-3-ium trifluoromethanesulfonate, followed by $CF_3SO_3Me$, to form 2,3-dimethyl-1H-imidazol-3-ium trifluoromethanesulfonate functionalized with a desired $R^2$ group. The product can be reacted with (R)—N-(3-amino-2-methylpropyl) functionalized with a desired $R^4$ group to form (S)—N,N'-(2-methylpropane-1,3-diamino functionalized with the desired $R^2$ and $R^4$ groups. The resulting product can then be reacted with (azanediyl)bis(propane-3,1-diyl) dimethanesulfonate functionalized with a desired $R^3$ group to result in the desired compound, as exemplified by Route 27 in the Examples section.

SYNTHESIS OF INTERMEDIATES

The intermediates used to prepare the compounds described herein also can be prepared by standard methods known to those skilled in the art, as described in the Examples, section below (e.g., Route 13, Route 16, Route 20, Route 24, Route 26, Route 28, Route 30, Route 31, Route 32, Route 33).

Methods of Use

The compounds disclosed herein (e.g., the compounds of Formula (I), the compounds listed in Tables A and B, and pharmaceutically acceptable salts of the foregoing) can inhibit protein secretion of a protein of interest. The compounds disclosed herein can interfere with the Sec61 protein secretion machinery of a cell. In some cases, a compound as disclosed herein inhibits secretion of one or more of TNFα, VCAM, PRL, IL-2, INFg, CD4, insulin, and PD-1 (mouse and/or human), or each of TNFα, VCAM, PRL, IL-2, INFg, CD4, insulin, and PD-1 (mouse and/or human). In some cases, a compound as disclosed herein can inhibit secretion of a checkpoint protein, or inhibits secretion of a cell surface protein, endoplasmic reticulum-associated protein, or secreted protein involved in regulation of anti-tumor immune responses. In various cases, a compound disclosed herein can inhibit secretion of one or more of PD-1, PD-L1, TIM-1, LAG-3, CTLA4, BTLA, OX-40, B7H1, B7H4, CD137, CD47, CD96, CD73, CD40, VISTA, TIGIT, LAIR1, CD160, 2B4, TGFRβ and combinations thereof. Protein secretion activity can be assessed in a manner as described in the Examples section below.

As used herein, the term "inhibitor" is meant to describe a compound that blocks or reduces an activity of a pharmacological target (for example, a compound that inhibits Sec61 function in the protein secretion pathway). An inhibitor can act with competitive, uncompetitive, or noncompetitive inhibition. An inhibitor can bind reversibly or irreversibly, and therefore, the term includes compounds that are suicide substrates of a protein or enzyme. An inhibitor can modify one or more sites on or near the active site of the protein, or it can cause a conformational change elsewhere on the enzyme. The term inhibitor is used more broadly herein than scientific literature so as to also encompass other classes of pharmacologically or therapeutically useful agents, such as agonists, antagonists, stimulants, co-factors, and the like.

Thus, provided herein are methods of inhibiting protein secretion in a cell. In these methods, a cell is contacted with a compound described herein (e.g., a compound of Formula (I) or a compound listed in Table A or B, and pharmaceutically acceptable salts of the foregoing), or pharmaceutical formulation thereof, in an amount effective to inhibit secretion of the protein of interest. In some embodiments, the cell is contacted in vitro. In various embodiments, the cell is contacted in vivo. In various embodiments, the contacting includes administering the compound or pharmaceutical formulation to a subject.

The biological consequences of Sec61 inhibition are numerous. For example, Sec61 inhibition has been suggested for the treatment or prevention of inflammation and/or cancer in a subject. Therefore, pharmaceutical formulations for Sec61 specific compounds, provide a means of administering a drug to a subject and treating these conditions. As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the invention to an individual in need of such treatment. Within the meaning of the invention, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy. As used herein, the terms "prevent," "preventing," "prevention," are art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population. As used herein, the terms "patient" and "subject" may be used interchangeably and mean animals, such as dogs, cats, cows, horses, and sheep (i.e., non-human animals) and humans. Particular patients are mammals (e.g., humans). The term patient includes males and females.

Inhibition of Sec61-mediated secretion of inflammatory proteins (e.g., TNFα) can disrupt inflammation signaling. Thus, provided herein is a method of treating inflammation in a subject by administering to the subject a therapeutically effective amount of a compound described herein, (i.e., a compound of Formula (I) or a compound listed in Table A or B, or a pharmaceutically acceptable salt of the foregoing).

Further, the viability of cancer cells relies upon increased protein secretion into the ER for survival. Therefore, non-selective or partially selective inhibition of Sec61 mediated protein secretion may inhibit tumor growth. Alternatively, in the immune-oncology setting, selective secretion inhibitors of known secreted or transmembrane immune checkpoint proteins (e.g., PD-1, TIM-3, LAG3, etc.) can result in activation of the immune system to against various cancers.

Accordingly, also provided herein is a method of treating cancer in a subject by administering to the subject a therapeutically effective amount of a compound described herein, (e.g., a compound of Formula (I), a compound listed in Table A or B, or a pharmaceutically acceptable salt of the foregoing). Specifically contemplated cancers that can be treated using the compounds and compositions described herein include, but are not limited to melanoma, multiple myeloma, prostate, lung, non small cell lung carcinoma, squamous cell carcinoma, leukemia, acute myelogenous leukemia, chronic myelogenous leukemia, lymphoma, NPM/ALK-transformed anaplastic large cell lymphoma, diffuse large B cell lymphoma, neuroendocrine tumors, breast, mantle cell lymphoma, renal cell carcinoma, rhabdomyosarcoma, ovarian cancer, endometrial cancer, small cell carcinoma, adenocarcinoma, gastric carcinoma, hepatocellular carcinoma, pancreatic cancer, thyroid carcinoma, anaplastic large cell lymphoma, hemangioma, head and neck cancer, bladder, and colorectal cancers. In some cases, the cancer is a solid tumor. In various cases, the cancer is head and neck cancer, squamous cell carcinoma, gastric carcinoma, or pancreatic cancer.

The compounds described herein are also contemplated to be used in the prevention and/or treatment of a multitude of diseases including, but not limited to, proliferative diseases, neurotoxic/degenerative diseases, ischemic conditions, autoimmune and autoinflammatory disorders, inflammation, immune-related diseases, HIV, cancers, organ graft rejection, septic shock, viral and parasitic infections, conditions associated with acidosis, macular degeneration, pulmonary conditions, muscle wasting diseases, fibrotic diseases, bone and hair growth diseases.

Examples of proliferative diseases or conditions include diabetic retinopathy, macular degeneration, diabetic nephropathy, glomerulosclerosis, IgA nephropathy, cirrhosis, biliary atresia, congestive heart failure, scleroderma, radiation-induced fibrosis, and lung fibrosis (idiopathic pulmonary fibrosis, collagen vascular disease, sarcoidosis, interstitial lung diseases and extrinsic lung disorders).

Inflammatory diseases include acute (e.g., bronchitis, conjunctivitis, myocarditis, pancreatitis) and chronic conditions (e.g., chronic cholecstitis, bronchiectasis, aortic valve stenosis, restenosis, psoriasis and arthritis), along with conditions associated with inflammation such as fibrosis, infection and ischemia.

Immunodeficiency disorders occur when a part of the immune system is not working properly or is not present. They can affect B lymophyctes, T lymphocytes, or phagocytes and be either inherited (e.g., IgA deficiency, severe combined immunodeficiency (SCID), thymic dysplasia and chronic granulomatous) or acquired (e.g., acquired immunodeficiency syndrome (AIDS), human immunodeficiency virus (HIV) and drug-induced immunodeficiencies). Immune-related conditions include allergic disorders such as allergies, asthma and atopic dermatitis like eczema. Other examples of such immune-related conditions include lupus, rheumatoid arthritis, scleroderma, ankylosing spondylitis, dermatomyositis, psoriasis, multiple sclerosis and inflammatory bowel disease (such as ulcerative colitis and Crohn's disease).

Tissue/organ graft rejection occurs when the immune system mistakenly attacks the cells being introduced to the host's body. Graft versus host disease (GVHD), resulting from allogenic transplantation, arises when the T cells from the donor tissue go on the offensive and attack the host's tissues. In all three circumstances, autoimmune disease, transplant rejection and GVHD, modulating the immune system by treating the subject with a compound or composition of the disclosure could be beneficial.

Also provided herein is a method of treating an autoimmune disease in a patient comprising administering a therapeutically effective amount of the compound described herein. An "autoimmune disease" as used herein is a disease or disorder arising from and directed against an individual's own tissues. Examples of autoimmune diseases include, but are not limited to, inflammatory responses such as inflammatory skin diseases including psoriasis and dermatitis (e.g., atopic dermatitis); systemic scleroderma and sclerosis; responses associated with inflammatory bowel disease (such as Crohn's disease and ulcerative colitis); respiratory distress syndrome (including adult respiratory distress syndrome (ARDS)); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g., Type I diabetes mellitus or insulin dependent diabetes mellitus); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia. Compounds provided herein may be useful for the treatment of conditions associated with inflammation, including, but not limited to COPD, psoriasis, asthma, bronchitis, emphysema, and cystic fibrosis.

Also provided herein is the use of a compound as disclosed herein for the treatment of neurodegenerative diseases. Neurodegenerative diseases and conditions includes, but not limited to, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Parkinson's disease, Huntington's disease, multiple sclerosis, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis).

Further guidance for using compounds and compositions described herein (e.g., a compound of Formula (I), a compound listed in Table A or B, or a pharmaceutically acceptable salt of the foregoing) for inhibiting protein secretion can be found in the Examples section, below.

Pharmaceutical Formulations and Administration

The methods provided herein include the manufacture and use of pharmaceutical compositions, which include one or more of the compounds provided herein. Also included are the pharmaceutical compositions themselves. Pharmaceutical compositions typically include a pharmaceutically acceptable carrier. Thus, provided herein are pharmaceutical formulations that include a compound described herein (e.g., a compound of Formula (I), a compound listed in Table A or B, or a pharmaceutically acceptable salt of the foregoing), as previously described herein, and one or more pharmaceutically acceptable carriers.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66:1-19.)

In some embodiments, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent.

Actual dosage levels of the active ingredients in the pharmaceutical compositions provided herein may be varied so as to obtain "therapeutically effective amount," which is an amount of the active ingredient effective to achieve the desired therapeutic response for a particular patient, composition, and mode of administration, without being toxic to the patient.

The concentration of a compound provided herein in a pharmaceutically acceptable mixture will vary depending on several factors, including the dosage of the compound to be administered, the pharmacokinetic characteristics of the compound(s) employed, and the route of administration. In some embodiments, the compositions provided herein can be provided in an aqueous solution containing about 0.1-10% w/v of a compound disclosed herein, among other substances, for parenteral administration. Typical dose ranges can include from about 0.01 to about 50 mg/kg of body weight per day, given in 1-4 divided doses. Each divided dose may contain the same or different compounds. The dosage will be a therapeutically effective amount depending on several factors including the overall health of a patient, and the formulation and route of administration of the selected compound(s).

Dosage forms or compositions containing a compound as described herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Other Embodiments

It is to be understood that while the disclosure is read in conjunction with the detailed description thereof, the foregoing description is intended to illustrate and not limit the scope of the disclosure, which is defined by the scope of the appended claims. Other aspects, advantages, and modifications are within the scope of the following claims.

EXAMPLES

The following examples are provided for illustration and are not intended to limit the scope of the invention.

Route 1

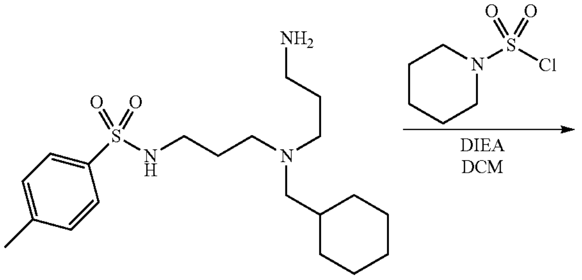

-continued

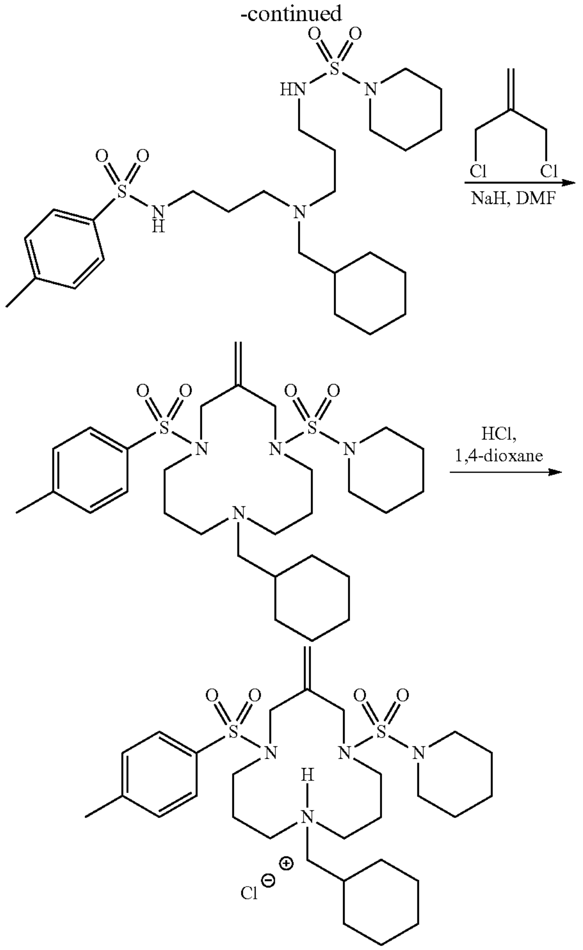

The starting material was synthesized using the method described in *J. Med. Chem.* 2016, 59, 2633-2647. To N-(3-((3-aminopropyl)(cyclohexylmethyl)amino)propyl)-4-methylbenzenesulfonamide (0.200 g, 0.523 mmol) in DCM (2.0 mL) was added DIEA (2 eq, 1.05 mmol, 179 uL) followed by piperidine-1-sulfonyl chloride (0.096 g, 0.523 mmol). After 16 h the reaction was quenched with sodium bicarbonate (sat.), extracted with DCM, dried with sodium sulfate, filtered, and concentrated.

To the crude N-(3-((cyclohexylmethyl)(3-((4-methylphenyl)sulfonamido)propyl)amino)propyl)piperidine-1-sulfonamide in DMF (10 mL) was added NaH (2.5 eq, 1.31 mmol, 0.052 g of a 60% dispersion in mineral oil). The mixture was stirred for 1 h then was heated to 85° C. and 3-chloro-2-chloromethyl-1-propene (0.9 eq, 0.471 mmol, 55 uL dissolved in 0.5 mL DMF) was added over 4 h. After heating for 16 h the mixture was cooled to ambient temp, diluted with brine and water, extracted with ethyl acetate (3×), washed with brine, dried with sodium sulfate, filtered, and concentrated. Flash column chromatography (0-60% hexanes/ethyl acetate+1% DEA) provided the freebase product.

To the freebase was added diethyl ether (1.0 mL) to dissolve and HCl (4 N in dioxane, 1.046 mmol, 262 uL). The HCl salt was filtered and dried under high vacuum to provide compound A5. MS(EI) for $C_{29}H_{48}N_4O_4S_2$, found 581 $[M+H]^+$.

The following compounds were synthesized in a similar manner:

| No. | IUPAC | [M + H]+ |
|---|---|---|
| A6 | 9-(cyclohexylmethyl)-1-(ethanesulfonyl)-5-(4-methylbenzenesulfonyl)-3-methylidene-1,5,9-triazacyclododecane | 526 |
| A7 | 9-(cyclohexylmethyl)-1-(4-methylbenzenesulfonyl)-3-methylidene-5-(propane-2-sulfonyl)-1,5,9-triazacyclododecane | 540 |
| A8 | 1-(cyclohexanesulfonyl)-9-(cyclohexylmethyl)-5-(4-methylbenzenesulfonyl)-3-methylidene-1,5,9-triazacyclododecane | 580 |

Route 2

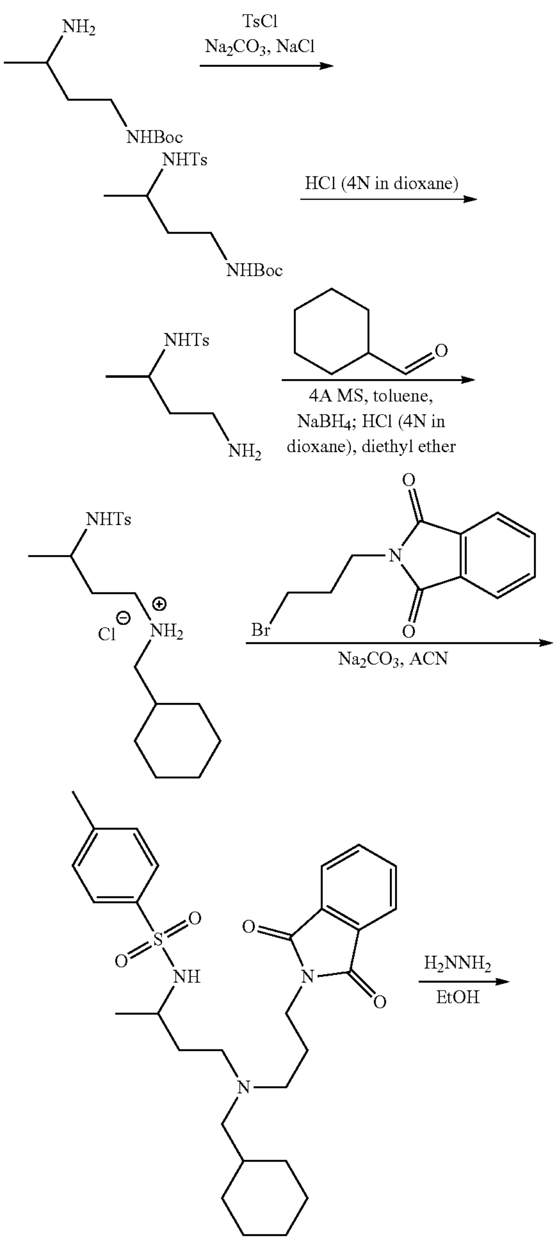

-continued

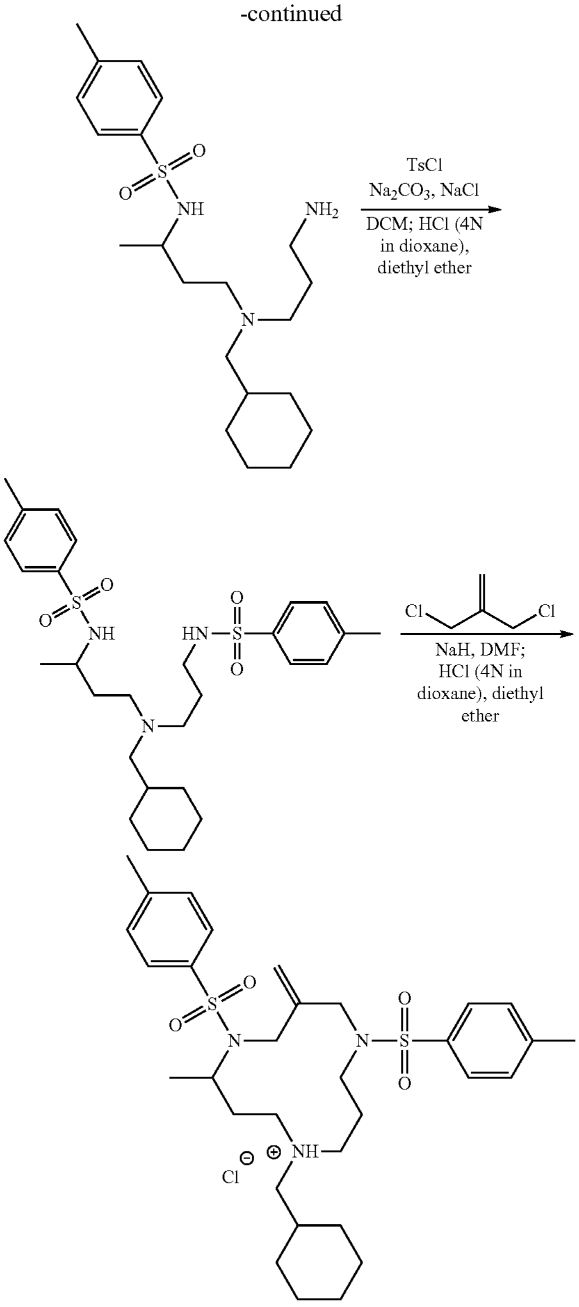

To tert-butyl (3-aminobutyl)carbamate (2.5 g, 13.3 mmol) in DCM (12.5 mL), sat. $Na_2CO_3$ (12.5 mL), and sat. NaCl (12.5 mL) was added TsCl (13.3 mmol, 2.54 g). After 1 h the organic layer was washed with brine, dried with sodium sulfate, filtered, and concentrated to provide tert-butyl (3-((4-methylphenyl)sulfonamido)butyl)carbamate which was carried forward without further purification.

To the tosylate (13.3 mmol) was added TFA (66.5 mmol, 5.09 mL) and DCM (5.09 mL). After 2 h the reaction was concentrated, diluted with NaOH (1N, 30 mL), extracted with DCM (3×30 mL), dried with sodium sulfate, filtered, and concentrated to provide the amine.

To the amine (10.94 mmol) was added toluene (49 mL) and cyclohexanecarboxaldehyde (1.34 g, 12.0 mmol). The mixture was refluxed with a dean stark apparatus overnight (external temperature of 185° C.) then concentrated, diluted with ethanol (absolute, 19 mL) and $NaBH_4$ (0.827 g, 21.8 mmol) was added portion-wise while the internal temperature was maintained at <20° C. After stirring for 2 h the mixture was diluted with water (10 mL), stirred for 20 min, extracted with DCM (3×), washed with brine, dried with sodium sulfate, filtered, and concentrated to provide the amine. The amine was diluted with diethyl ether (20 mL) and HCl (conc., ~0.3 mL) was added dropwise. The HCl salt crashed out within 5 min and was filtered using diethyl ether to wash. The product was dried under vacuum overnight to provide N-(4-((cyclohexylmethyl)amino)butan-2-yl)-4-methylbenzenesulfonamide hydrochloride.

To the HCl salt (3.5 mmol) was added acetonitrile (9 mL), sodium carbonate (0.99 g, 9.2 mmol), LiI (0.114 g), and 3-bromopropylphthalimide (2.30 g). The mixture was heated to 70° C. for 5 h at which time it was filtered and concentrated. The crude phthalimide was carried forward without further purification.

To the pthalimide (3.5 mmol) was added hydrazine monohydrate (4.2 mL) and ethanol (15 mL). After heating to 80° C. for 30 min the reaction was complete and the precipitate was filtered washing with ethanol. The filtrate was concentrated and diluted with HCl (2 N, 30 mL) then allowed to stand for 1 h. To the aqueous mixture was added NaOH (1 N) to basify to pH 10. The mixture was then extracted with DCM (3×), dried with sodium sulfate, filtered, and concentrated to provide crude N-(4-((3-aminopropyl)(cyclohexylmethyl)amino)butan-2-yl)-4-methylbenzenesulfonamide.

To the amine (695 mg, 1.76 mmol) was added DCM (9 mL), sat. $Na_2CO_3$ (9 mL), sat. NaCl (9 mL), TsCl (1.76 mmol, 336 mg). After stirring for 1 h the mixture was extracted with DCM (3×), dried with sodium sulfate, filtered, and concentrated to provide the freebase. The HCl salt was made by diluting the freebase in diethyl ether (50 mL) and adding HCl (conc., 300 uL). After placing under high vacuum for 2 h the HCl salt (1.02 g) was collected.

To the HCl salt (0.400 g, 0.683 mmol) in DMF (14 mL) was added NaH (3.5 eq, 2.39 mmol, 60% dispersion in mineral oil, 80.3 mg). After stirring for 1 h, 3-chloro-2-chloromethyl-1-propene (0.9 eq, 0.615 mmol, 71 uL in 7 mL DMF) was added dropwise over 3 h. After heating an additional 2 h the mixture was cooled to ambient temperature, diluted with brine, water, and ethyl acetate. The mixture was extracted with ethyl acetate (2×), washed with brine, dried with sodium sulfate, filtered, and concentrated. Flash column chromatography (0-90% hexanes/ethyl acetate+1% DEA) provided the product. The HCl salt was formed by diluting the freebase in diethyl ether (20 vol.) and adding HCl (4N in dioxane, 4 eq) to provide 5-(cyclohexylmethyl)-2-methyl-11-methylene-1,9-ditosyl-1,5,9-triazacyclododecane hydrochloride, compound B1. MS(EI) for $C_{32}H_{47}N_3O_4S_2$, found 602 $[M+H]^+$.

The following compounds were synthesized in a similar manner:

| No. | IUPAC | $[M + H]^+$ |
|---|---|---|
| B2 | 1-(cyclohexylmethyl)-3-methyl-5,9-bis(4-methylbenzenesulfonyl)-7-methylidene-1,5,9-triazacyclododecane | 602 |
| A9 | N,N-dimethyl-4-{[5-(4-methylbenzenesulfonyl)-3-methylidene-9-[(oxan-4-yl)methyl]-1,5,9-triazacyclododecan-1-yl]sulfonyl}aniline | 619 |

Route 3

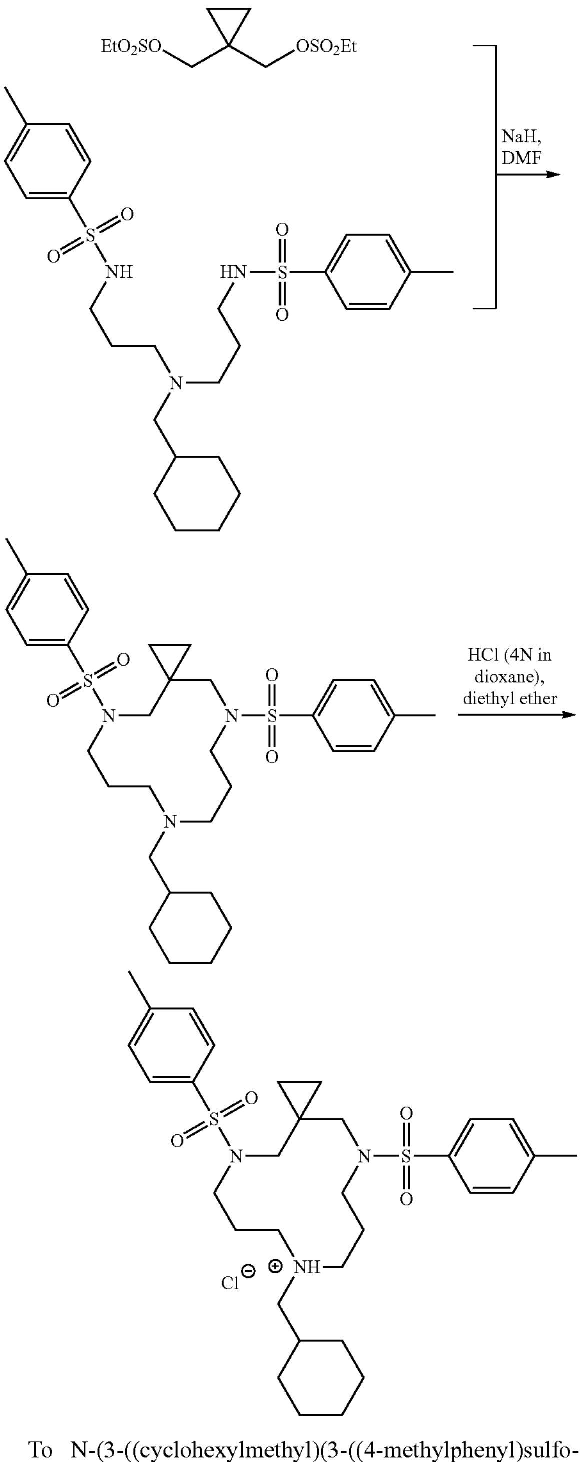

To N-(3-((cyclohexylmethyl)(3-((4-methylphenyl)sulfonamido)butyl)amino)propyl)-4-methylbenzenesulfonamide (0.099 mmol) in DMF (10.0 mL) was added sodium hydride (0.350 mmol of a 60% dispersion in mineral oil). The mixture was stirred at ambient temperature for 30 min then heated to 80° C. before cyclopropane-1,1-diylbis(methylene) diethanesulfonate (0.099 mmol dissolved in 1.0 mL DMF) over the course of 2 h. After stirring an additional 4 h at 80° C. the mixture was cooled to ambient temperature, quenched with brine, extracted with ethyl acetate (3×). The combined organics were washed with brine (2×), dried with sodium sulfate, filtered, and concentrated. Flash column chromatography (0-60% hexanes (1% DEA)/ethyl acetate) provided the freebase product which was dissolved in diethyl ether (2 mL) and HCl (0.1 mL of a 4 N solution in 1,4-dioxane) was added. The mixture was concentrated to provide 4-{[9-(cyclohexylmethyl)-13-(4-methylbenzenesulfonyl)-5,9,13-triazaspiro[2.11]tetradecan-5-yl]sulfonyl}-N,N-dimethylaniline hydrochloride, compound A11. MS(EI) for $C_{33}H_{50}N_4O_4S_2$, found 631 $[M+H]^+$.

Route 4

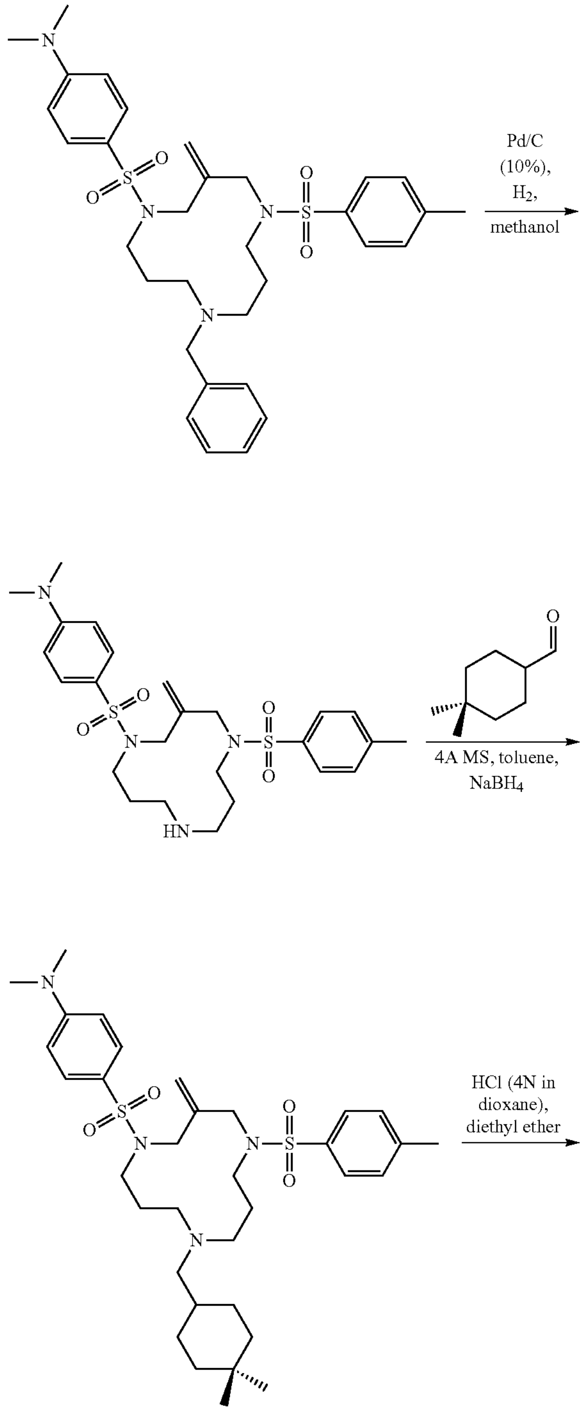

-continued

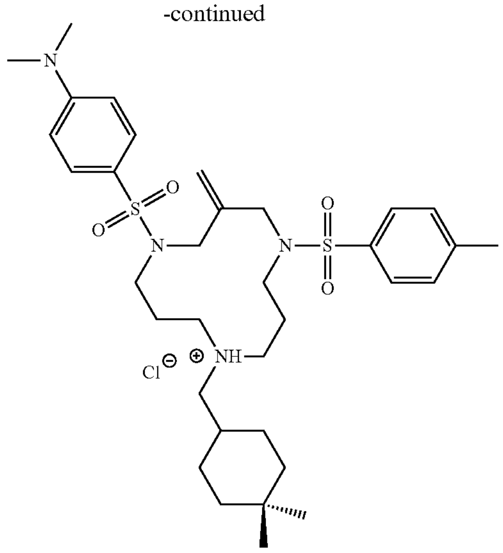

The starting material was synthesized using the method described in *J. Med. Chem.* 2016, 59, 2633-2647. To the starting material (0.327 mmol) in methanol (2.0 mL) under argon was added Pd/C (20 mg). A hydrogen atmosphere was established and the mixture was stirred at ambient temp. After 3 h the reaction was filtered and purified by flash column chromatography (0-80% hexanes (1% DEA)/ethyl acetate) to provide the product.

To the starting material (0.028 mmol) was added toluene (5 mL) followed by the aldehyde (0.028 mmol). The mixture was stirred for 3 h at reflux then concentrated. To the imine was added ethanol followed by sodium borohydride. The mixture was stirred at ambient temp for 30 min then diluted with water (1 mL), extracted, with DCM (3×1 mL), dried with sodium sulfate, filtered, and concentrated. The product was purified by flash column chromatography (0-60% hexanes (1% DEA)/ethyl acetate). The freebase was diluted with ethyl ether (1 mL) and HCl (7 μL, 4 N in dioxane) was added. The mixture was filtered to provide 4-((9-((4,4-dimethylcyclohexyl)methyl)-3-methylene-5-tosyl-1,5,9-triazacyclododecan-1-yl)sulfonyl)-N,N-dimethylaniline hydrochloride (compound A10). MS(EI) for $C_{34}H_{52}N_4O_4S_2$, found 645 $[M+H]^+$.

Route 5

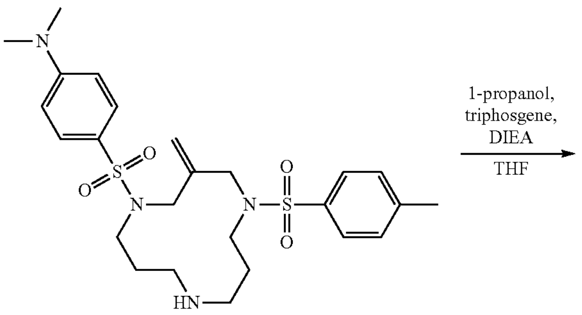

-continued

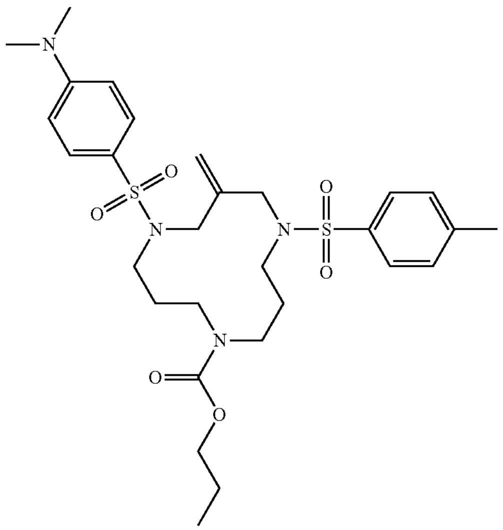

To triphosgene (0.0316 mmol, 9.4 mg) in DCM (100 uL) was added 1-propanol (0.190 mmol 14 uL). After stirring for 45 min this solution was added to the amine (0.0158 mmol, 8.2 mg), DIEA (0.126 mmol, 22 uL), and DCM (100 uL). The mixture was stirred at ambient temperature for 1 h then purified directly by flash column chromatography (0-70% hexanes/ethyl acetate) to provide propyl 5-((4-(dimethyl-amino)phenyl)sulfonyl)-7-methylene-9-tosyl-1,5,9-triaza-cyclododecane-1-carboxylate (compound A12). MS(EI) for $C_{29}H_{42}N_4O_6S_2$, found 607 $[M+H]^+$.

Route 6

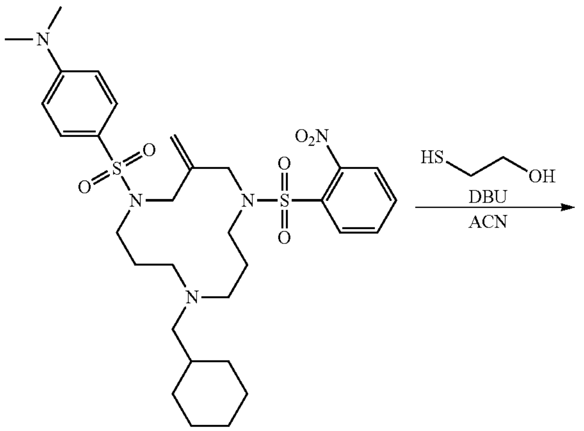

-continued

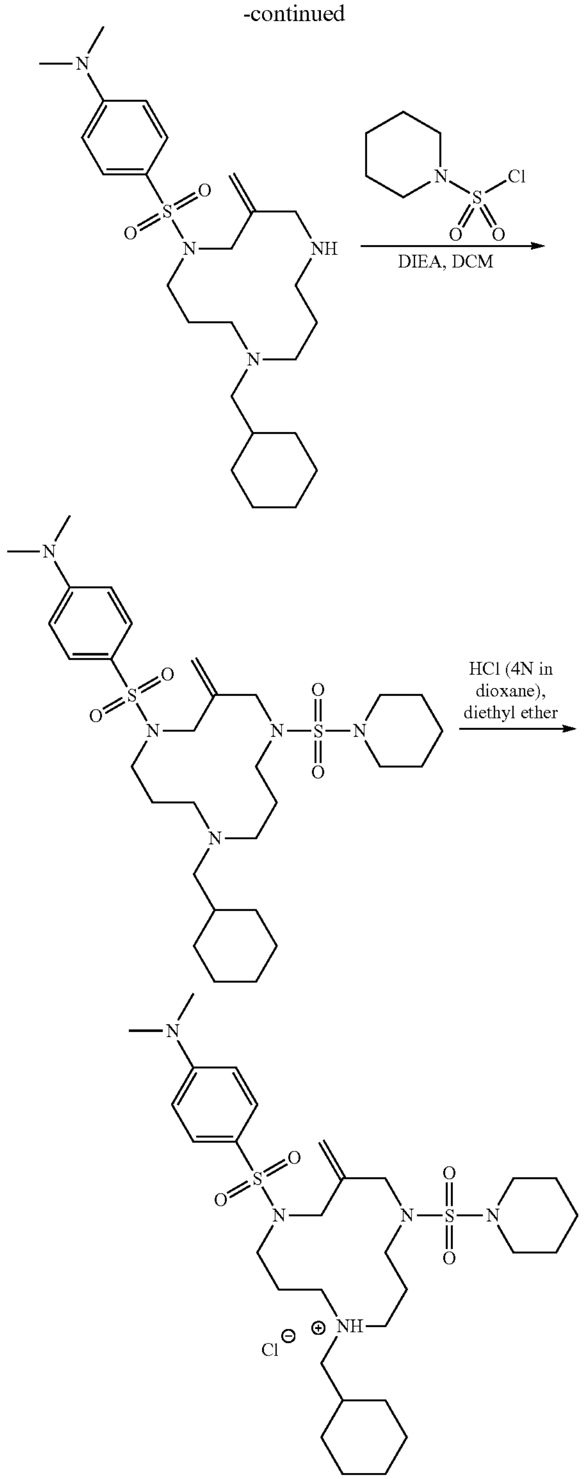

The starting material, 4-((9-(cyclohexylmethyl)-3-methylene-5-((2-nitrophenyl)sulfonyl)-1,5,9-triazacyclododecan-1-yl)sulfonyl)-N,N-dimethylaniline, was synthesized using a similar method described in Route 2 substituting with the appropriate sulfonyl chlorides.

To the starting material (1.09 g, 1.68 mmol) in ACN (12.3 mL) was added DBU (0.780 mL, 5.22 mmol) followed by 2-mercaptoethanol (0.135 mL, 1.92 mmol). The mixture was stirred at ambient temperature for 2 h then an additional aliquot of 2-mercaptoethanol (1.14 eq) was added. After stirring an additional 2 h the mixture was concentrated and purified directly by FCC (0-100% hexanes (1% DEA)/ethyl acetate). 4-((9-(Cyclohexylmethyl)-3-methylene-1,5,9-triazacyclododecan-1-yl)sulfonyl)-N,N-dimethylaniline.

To the amine (70 mg, 0.152 mmol) in DCM (2 mL) was added DIEA (0.303 mmol, 52 uL) followed by piperidine-1-sulfonyl chloride (0.152 mmol, 28 mg). After allowing to stand overnight the reaction was purified directly by flash column chromatography (hexanes (1% DEA)/ethyl acetate 0-60%). The HCl salt of the product was made by dissolving the freebase in diethyl ether (1 mL) and adding HCl (4 N in dioxane, 38 uL). The filtrate was collected to provide 4-((9-(cyclohexylmethyl)-3-methylene-5-(piperidin-1-ylsulfonyl)-1,5,9-triazacyclododecan-1-yl)sulfonyl)-N,N-dimethylaniline hydrochloride (compound A15). MS(EI) for $C_{30}H_{51}N_5O_4S_2$, found 610 $[M+H]^+$.

The following compounds were synthesized in a similar manner:

| No. | IUPAC | $[M+H]^+$ |
|---|---|---|
| A16 | 9-(cyclohexylmethyl)-5-[4-(dimethylamino)benzenesulfonyl]-N,N-dimethyl-3-methylidene-1,5,9-triazacyclododecane-1-sulfonamide | 570 |
| A13 | 4-{[9-(cyclohexylmethyl)-3-methylidene-5-(piperidine-1-sulfonyl)-1,5,9-triazacyclododecan-1-yl]sulfonyl}-N,N-dimethylaniline | 610 |

Route 7

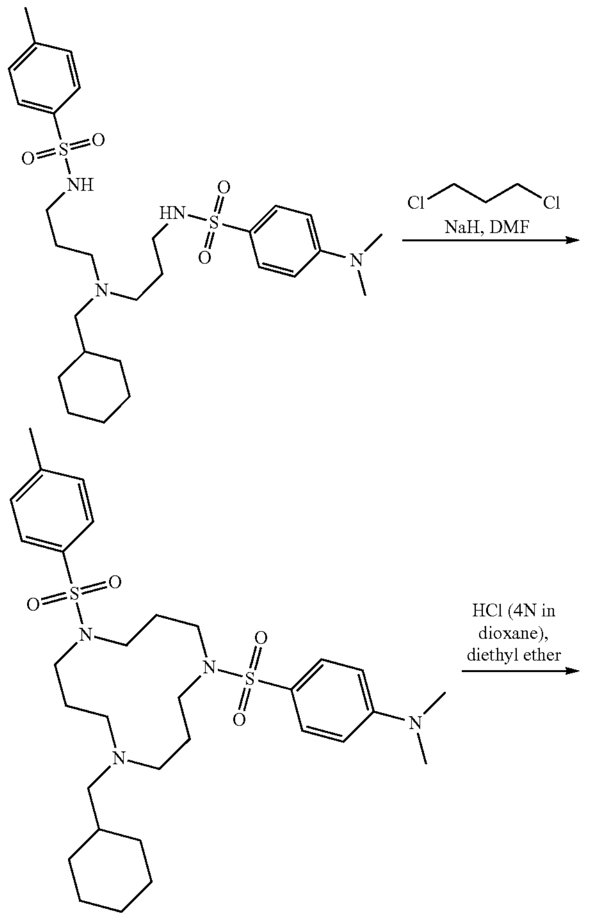

-continued

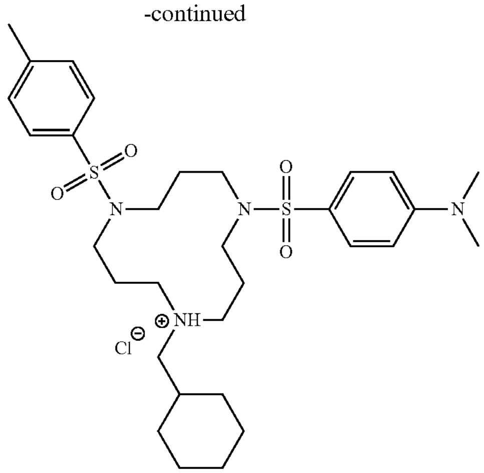

The starting material, N-(3-((cyclohexylmethyl)(3-((4-(dimethylamino)phenyl)sulfonamido)propyl)amino)propyl)-4-methylbenzenesulfonamide, was synthesized using the same method described in Route 1 substituting with the appropriate sulfonyl chloride.

To the diamine (49 mg, 0.087 mmol) in DMF (2.5 mL) was added NaH (0.22 mmol, 9 mg). After stirring for 30 min at ambient temperature, 1,3-dichloropropane (0.087 mmol, 8.3 uL in 0.5 mL DMF) was slowly added over 1 h while heating at 80° C. After 3 h the mixture was cooled to ambient temp, diluted with brine (10 mL), water (5 mL), and ethyl acetate (10 mL). The aqueous layer was extracted with ethyl acetate (3×5 mL), the organics were combined and washed with brine (1×5 mL), dried with sodium sulfate, and concentrated. Flash column chromatography (0-50% hexanes (1% DEA/ethyl acetate) provided the freebase product that was converted to the HCl salt with the addition of ether (1 mL) then HCl (20 uL, 4 N in dioxane). The filtrate was collected and concentrated to provide 4-((5-(cyclohexylmethyl)-9-tosyl-1,5,9-triazacyclododecan-1-yl)sulfonyl)-N,N-dimethylaniline (compound A14). MS(EI) for $C_{31}H_{48}N_4O_4S_2$, found 605 $[M+H]^+$.

The following compound was synthesized in a similar manner:

| No. | IUPAC | $[M+H]^+$ |
|---|---|---|
| A17 | 4-{[10-(cyclohexylmethyl)-14-(piperidine-1-sulfonyl)-2-oxa-6,10,14-triazaspiro[3.11]pentadecan-6-yl]sulfonyl}-N,N-dimethylaniline | 640 |

Route 8

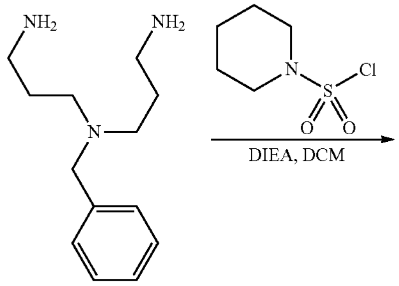

-continued

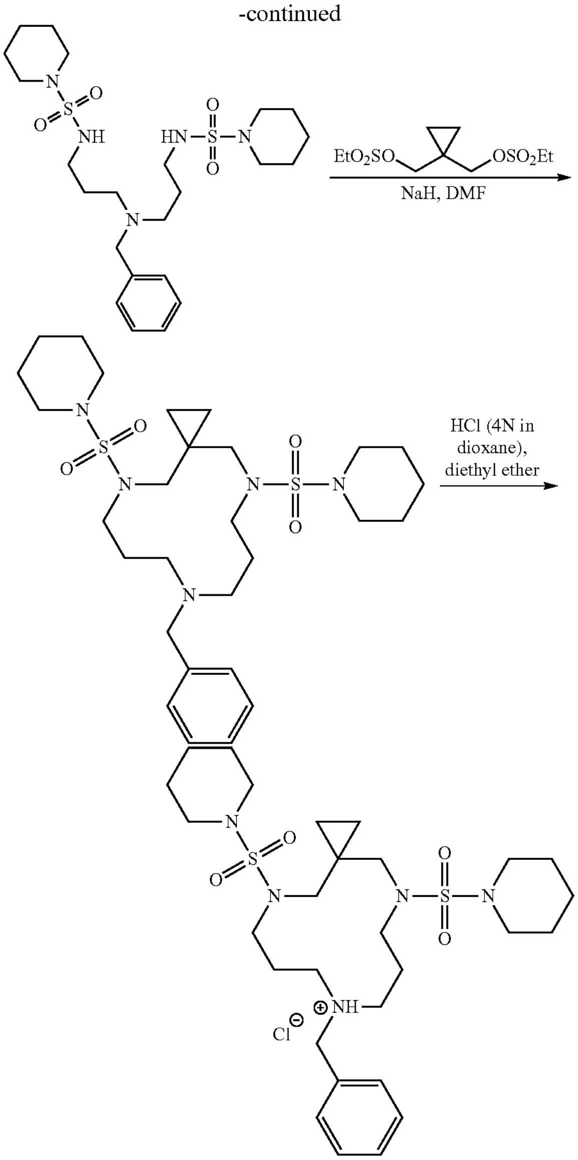

The starting material was synthesized using the method described in *J. Med. Chem.* 2006, 49, 1291-1312. To N1-(3-aminopropyl)-N1-benzylpropane-1,3-diamine (363 mg, 1.64 mmol) in DCM (2 mL) was added DIEA (1.14 mL, 6.56 mL) then the sulfonyl chloride (345 μL, 2.46 mmol). The solution was allowed to stand overnight at ambient temp. Concentration and purification by flash column chromatography (0-80% hexanes (1% DEA)/ethyl acetate) provided the product.

To the starting material (260 mg, 504 μL) in DMF (20 mL) was added NaH (50 mg of a 60% dispersion in mineral oil, 1.26 mmol). The mixture was stirred at 80° C. for 20 min then the bis-sulfonate (144 mg, 504 μL) was added over the course of 1 h. After heating for 4 h the reaction was complete and was diluted with ethyl acetate (40 mL) and brine (40 mL), extracted with ethyl acetate (2×20 mL). The combined organics were washed with brine (20 mL), dried with sodium sulfate, filtered, and concentrated. Flash column chromatography (hexanes (1% DEA)/ethyl acetate 0-50%) provided the product which was diluted with ethyl ether (5 mL) and HCl (4 N in dioxane, 100 uL) was added. The mixture was concentrated, washed with diethyl ether, and dried to provide 9-benzyl-5,13-bis(piperidin-1-ylsulfonyl)-5,9,13-triazaspiro[2.11]tetradecane hydrochloride (compound A18). MS(EI) for $C_{28}H_{47}N_5O_4S_2$, found 581 $[M+H]^+$.

Route 9

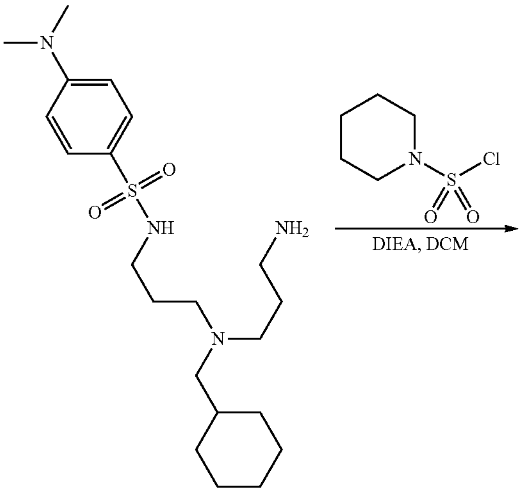

-continued

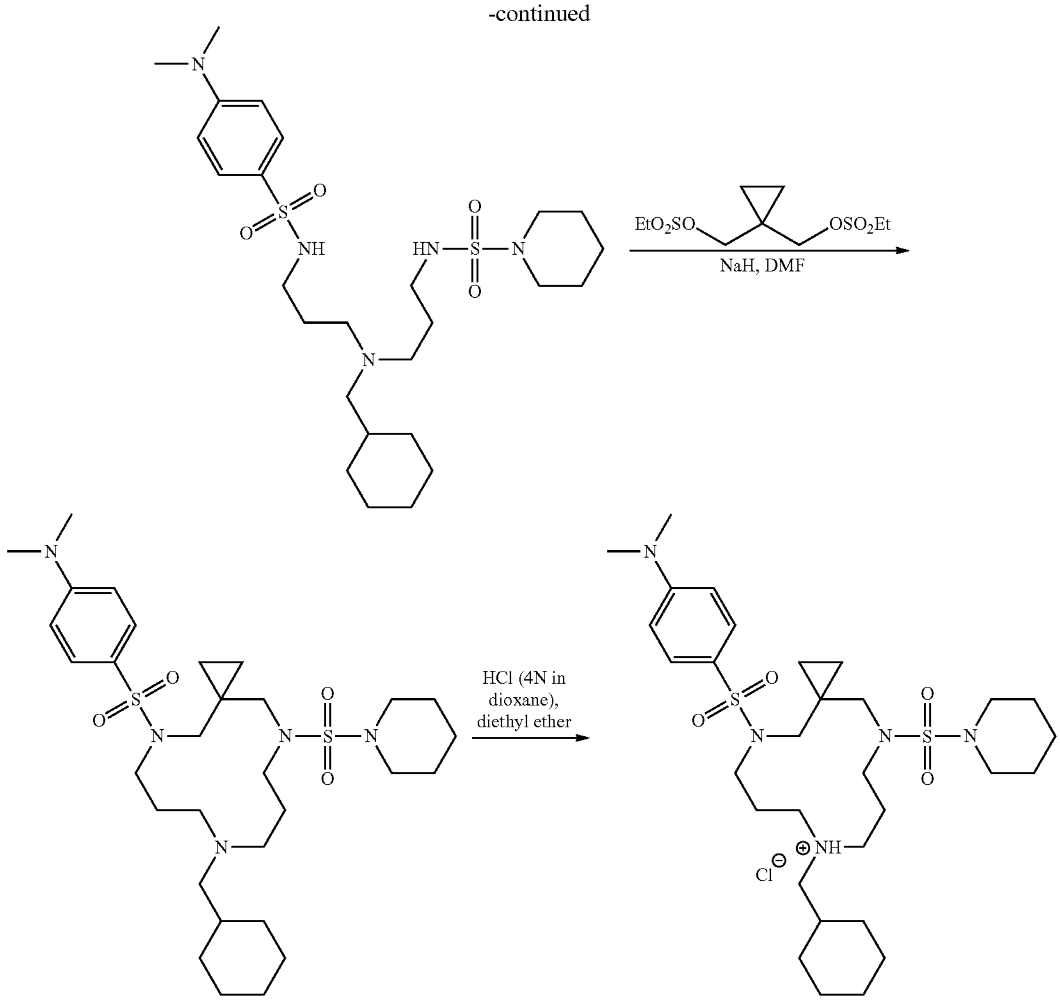

The starting material, N-(3-((3-aminopropyl)(cyclohexylmethyl)amino)propyl)-4-(dimethylamino)benzenesulfonamide, was synthesized using a similar method as described in Route 2.

To N-(3-((3-aminopropyl)(cyclohexylmethyl)amino)propyl)-4-(dimethylamino)benzenesulfonamide (559 mg, 1.36 mmol) in DCM (2 mL) was added DIEA (0.71 mL, 4.08 mmol) then the sulfonyl chloride (250 mg, 1.36 mmol). The solution was allowed to stand overnight at ambient temp. Concentration and purification by flash column chromatography (0-80% hexanes (1% DEA)/ethyl acetate) provided the product.

The cyclization of N-(3-((cyclohexylmethyl)(3-((4-(dimethylamino)phenyl)sulfonamido)propyl)amino)propyl)piperidine-1-sulfonamide and salt formation was carried out in a similar manner to Route 8 to provide 4-((9-(cyclohexylmethyl)-13-(piperidin-1-ylsulfonyl)-5,9,13-triazaspiro [2.11]tetradecan-5-yl)sulfonyl)-N,N-dimethylaniline hydrochloride (compound A19). MS(EI) for $C_{31}H_{53}N_5O_4S_2$, found 624 $[M+H]^+$.

The following compounds were synthesized in a similar manner. The cyclization of compounds A25, A26, A27, A28, and A29 was carried out using NMP as the solvent.

| No. | IUPAC | $[M+H]^+$ |
|---|---|---|
| A20 | 4-{[9-(cyclohexylmethyl)-13-[(2-methylpiperidin-1-yl)sulfonyl]-5,9,13-triazaspiro[2.11]tetradecan-5-yllsulfonyl]-N,N-dimethylaniline | 638 |
| A21 | 4-{[9-(cyclohexylmethyl)-13-[(3-methylpiperidin-1-yl)sulfonyl]-5,9,13-triazaspiro[2.11]tetradecan-5-yl]sulfonyl}-N,N-dimethylaniline | 638 |
| A22 | 4-{[9-(cyclohexylmethyl)-13-[(4-methylpiperidin-1-yl)sulfonyl]-5,9,13-triazaspiro[2.11]tetradecan-5-yl]sulfonyl}-N,N-dimethylaniline | 638 |
| A23 | 4-{[9-(cyclohexylmethyl)-13-(pyrrolidine-1-sulfonyl)-5,9,13-triazaspiro[2.11]tetradecan-5-yl]sulfonyl}-N,N-dimethylaniline | 610 |
| B3 | 4-{[8-(cyclohexylmethyl)-4-(piperidine-1-sulfonyl)-1,4,8-triazacycloundecan-1-yl]sulfonyl}-N,N-dimethylaniline | 584 |
| B4 | 4-{[7-(cyclohexylmethyl)-3-(piperidine-1-sulfonyl)-1,3,7-triazecan-1-yl]sulfonyl}-N,N-dimethylaniline | 570 |
| A25 | 4-{[13-(azepane-1-sulfonyl)-9-(cyclohexylmethyl)-5,9,13-triazaspiro[2.11]tetradecan-5-yl]sulfonyl}-N,N-dimethylaniline | 638 |
| A26 | 4-{[9-(cyclohexylmethyl)-13-[(4,4-dimethylpiperidin-1-yl)sulfonyl]-5,9,13-triazaspiro[2.11]tetradecan-5-yl]sulfonyl}-N,N-dimethylaniline | 652 |
| A27 | 4-{[9-(cyclohexylmethyl)-13-[(4-methoxypiperidin-1-yl)sulfonyl]-5,9,13-triazaspiro[2.11]tetradecan-5-yl]sulfonyl}-N,N-dimethylaniline | 654 |

-continued

| No. | IUPAC | [M + H]+ |
|---|---|---|
| A28 | 1-{[9-(cyclohexylmethyl)-13-[4-(dimethylamino)benzenesulfonyl]-5,9,13-triazaspiro[2.11]tetradecan-5-yl]sulfonyl}piperidin-4-ol | 640 |
| A29 | 4-{[9-(cyclohexylmethyl)-13-[(4-phenylpiperidin-1-yl)sulfonyl]-5,9,13-triazaspiro[2.11]tetradecan-5-yl]sulfonyl}-N,N-dimethylaniline | 700 |

Route 10

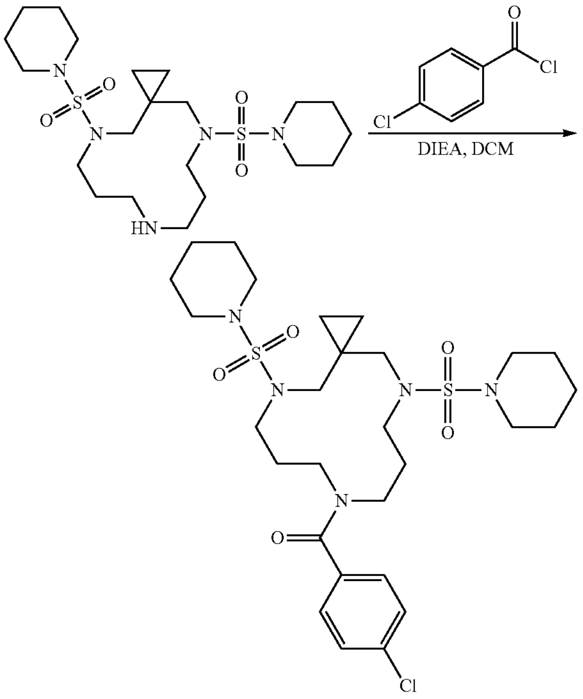

To the amine (67 mg, 0.14 mmol) in DCM (12 mL) was added DIEA (35 mg, 0.27 mmol) followed by 4-chlorobenzoyl chloride (24 mg, 0.14 mmol). After standing at ambient temperature for 30 min the reaction was quenched with sodium bicarbonate (sat.), extracted with DCM (3×), dried with sodium sulfate, and filtered. Flash column chromatography (0-60% hexanes (1% DEA)/ethyl acetate) provided (5,13-bis(piperidin-1-ylsulfonyl)-5,9,13-triazaspiro[2.11]tetradecan-9-yl)(4-chlorophenyl)methanone (compound A24). MS(EI) for $C_{28}H_{44}ClN_5O_5S_2$, found 630 [M+H]+.

Route 11

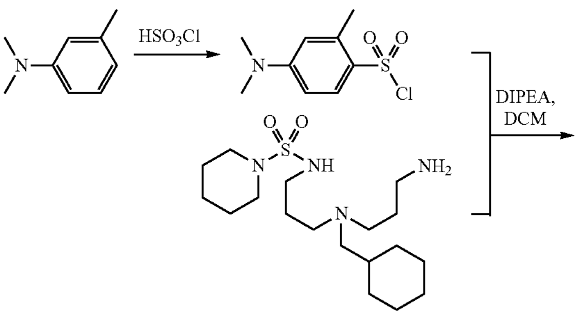

-continued

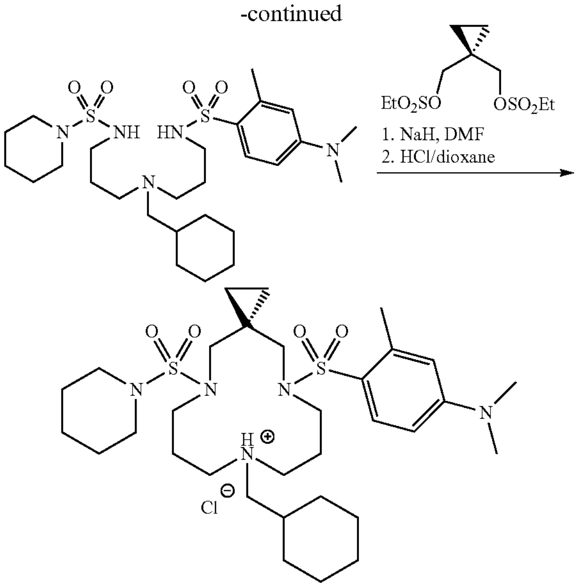

To a solution of N,N-3-trimethylaniline (1.35 g, 10.0 mmol) in $CHCl_3$ (4 mL) was added chlorosulfonic acid (4 mL). The reaction mixture was heated at 80° C. for 18 h. The mixture was cooled to ambient temperature and diluted with DCM (20 mL). The resulting mixture was poured into ice-water (30 mL) and then adjusted to pH=7~8 with saturated aqueous $Na_2CO_3$. The organic layer was separated, washed with saturated aqueous $NaHCO_3$, dried over anhydrous $Na_2SO_4$ and concentrated. The residue was recrystallized from petroleum ether/EtOAc (10:1, 10 mL) to provide 4-(dimethylamino)-2-methylbenzenesulfonyl chloride. $^1H$ NMR (400 MHz, $CDCl_3$): δ 7.88 (d, J=9.6 Hz, 1H), 6.53 (m, 2H), 3.09 (s, 6H), 2.70 (s, 3H).

4-{[9-(cyclohexylmethyl)-13-(piperidine-1-sulfonyl)-5,9,13-triazaspiro[2.11]tetradecan-5-yl]sulfonyl}-N,N,3-trimethylaniline was prepared following the procedure described in Route 12 to provide compound A30. $^1H$ NMR (400 MHz, DMSO-$d_6$): δ 9.57 (br s, 1H), 7.50 (d, J=8.8 Hz, 2H), 6.85 (m, 2H), 3.95 (br s, 1H), 2.8-93.55 (m, 24H), 1.4-51.90 (m, 15H), 1.28 (m, 4H), 0.95 (m, 2H), 0.66 (br s, 4H). MS(EI) for $C_{32}H_{55}N_5O_4S_2$, found 638 [M+H]+.

The following compound was synthesized in a similar manner:

| No. | IUPAC | [M + H]+ | $^1H$ NMR |
|---|---|---|---|
| A41 | 5-(cyclohexanesulfonyl)-9-(cyclohexylmethyl)-13-(piperidine-1-sulfonyl)-5,9,13-triazaspiro[2.11]tetradecane | 587 | $^1H$ NMR (400 MHz, DMSO-$d_6$): δ 9.46 (br s, 1 H), 3.37-2.95 (m, 15 H), 2.01-1.01 (m, 33 H), 0.95 (m, 2 H), 0.73 (m, 4 H). |

Route 12

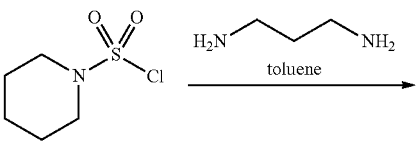

-continued

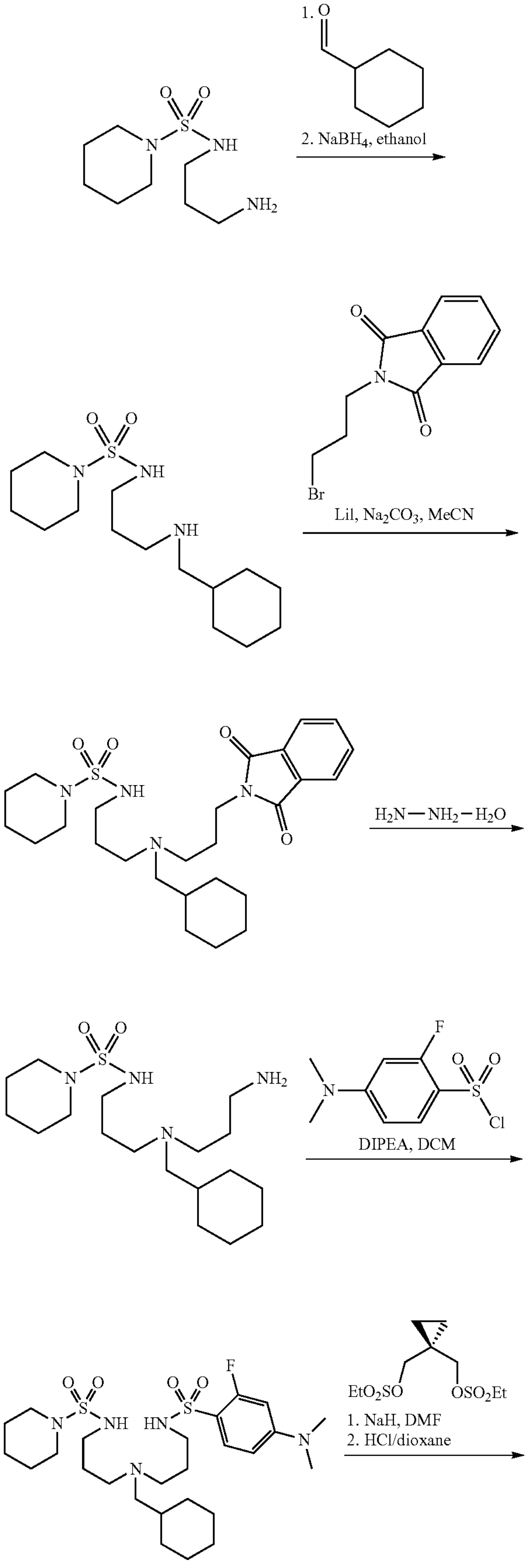

-continued

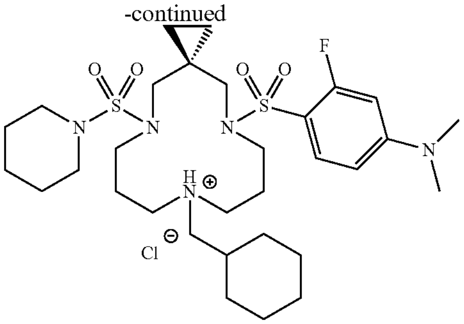

To a solution of piperidine-1-sulfonyl chloride (68.3 g, 0.37 mol) in toluene (350 mL) was added dropwise a solution of propane-1,3-diamine (83.4 g, 1.12 mol) in toluene (150 mL). The reaction mixture was stirred overnight at ambient temperature. The resulting slurry was filtered and the filtrate was concentrated. The residue was purified by column chromatography on silica gel (DCM/MeOH=50:1 to 20:1) to afford N-(3-aminopropyl)piperidine-1-sulfonamide. $^1$H NMR (400 MHz, $CDCl_3$): δ 3.17 (m, 6H), 2.88 (t, J=6.0 Hz, 2H), 1.65 (m, 6H), 1.54 (m, 2H).

A mixture of N-(3-aminopropyl)piperidine-1-sulfonamide (22.62 mmol) and cyclohexanecarbaldehyde (2.8 g, 24.89 mmol) in toluene (90.0 mL) was heated under reflux overnight with removal of water by means of a Dean-Stark apparatus. The mixture was cooled to ambient temperature and concentrated under vacuum. The resulting product was dissolved in ethanol (35 mL) and $NaBH_4$ (1.66 g, 43.7 mmol) was added. The reaction mixture was stirred at ambient temperature overnight. The reaction was quenched with 2N aqueous HCl (30 mL) and then adjusted to pH=10 with aqueous NaOH. The resulting mixture was extracted with ethyl acetate (50 mL) and the organic layer was concentrated. The residue was purified by column chromatography on silica gel (DCM/MeOH=50:1 to 40:1) to provide N-(3-(cyclohexylmethylamino)propyl)piperidine-1-sulfonamide. NMR (400 MHz, $CDCl_3$): δ 3.17 (m, 6H), 2.78 (t, J=6.0 Hz, 2H), 2.45 (d, J=6.4 Hz, 2H), 1.75 (m, 12H), 1.44 (m, 1H), 1.23 (m, 3H), 0.96 (m, 2H). MS(EI) for $C_{15}H_{31}N_3O_2S$, found 318 $[M+H]^+$.

To a solution of N-(3-(cyclohexylmethylamino)propyl) piperidine-1-sulfonamide (2.8 g, 8.83 mmol) in $CH_3CN$ (50 mL) were added $Na_2CO_3$ (0.97 g, 9.19 mmol), LiI (0.28 g, 2.12 mmol) and 3-bromopropylphthalimide (5.66 g, 21.19 mmol). The reaction mixture was heated under reflux overnight. The mixture was cooled to ambient temperature and filtered. The filtrate was concentrated and the residue was purified by column chromatography on silica gel (EtOAc/Petroleum ether=1:3) to provide N-(3-((cyclohexylmethyl)(3-(1,3-dioxoisoindolin-2-yl)propyl)amino)propyl) piperidine-1-sulfonamide. $^1$H NMR (400 MHz, $CDCl_3$): δ 7.85 (m, 2H), 7.73 (m, 2H), 5.82 (br s, 1H), 3.68 (t, J=7.2 Hz, 2H), 3.17 (m, 6H), 2.46 (m, 4H), 2.14 (m, 2H), 1.82 (m, 2H), 1.67 (m 12H), 1.45 (m, 3H), 1.18 (m, 2H), 0.87 (m, 2H).

To a solution of N-(3-((cyclohexylmethyl)(3-(1,3-dioxoisoindolin-2-yl)propyl)amino)propyl) piperidine-1-sulfonamide (500 mg, 0.10 mmol) in EtOH (5 mL) was added $NH_2NH_2$ (1.5 mL, 2.55 mmol). The reaction mixture was stirred at ambient temperature overnight. The solvent was removed under reduced pressure and the residue was diluted with ethyl acetate (20 mL). The resulting mixture was washed with water (2×10 mL). The organic layer was dried over anhydrous sodium sulfate and concentrated to provide N-(3-((3-aminopropyl)(cyclohexylmethyl)amino)propyl)piperidine-1-sulfonamide (380 mg, quantitative). $^1$H NMR (400 MHz, $CDCl_3$): δ 3.17 (m, 6H), 2.78 (t, J=6.8 Hz, 2H), 2.45 (m, 4H), 2.14 (d, J=7.2 Hz, 2H), 1.82 (m, 2H), 1.67 (m 12H), 1.45 (m, 3H), 1.18 (m, 2H), 0.87 (m, 2H). MS(EI) for $C_{18}H_{38}N_4O_2S$, found 375 $[M+H]^+$.

To a solution of N-(3-((3-aminopropyl)(cyclohexylmethyl)amino)propyl)piperidine-1-sulfonamide (2.42 g, 6.49 mmol) and DIEA (1.31 g, 10.3 mmol) in DCM (50 mL) was added the sulfonyl chloride (1.69 g, 7.13 mmol). The reaction mixture was stirred at ambient temperature for 2 h. The mixture was washed with water (50 mL). The organic phase was dried over anhydrous $Na_2SO_4$ and concentrated. The residue was purified by column chromatography on silica gel (MeOH/DCM=1:80 to 1:30) to provide N-(3-((Cyclohexylmethyl)(3-(4-(dimethylamino)-2-fluorophenylsulfonamido) propyl)amino)propyl)piperidine-1-sulfonamide. $^1$H NMR (400 MHz, $CDCl_3$): δ 7.66 (m, 1H), 6.43 (m, 2H), 5.58 (br s, 2H), 3.15 (m, 6H), 3.03 (s, 6H), 2.99 (br s, 2H) 2.46 (br s, 4H), 2.12 (br s, 2H), 1.30-1.70 (m, 18H), 1.21 (m, 4H), 0.82 (m, 2H). MS(EI) for $C_{26}H_{46}FN_5O_4S_2$, found 575 $[M+H]^+$.

To a solution of N-(3-((Cyclohexylmethyl)(3-(4-(dimethylamino)-2-fluorophenylsulfonamido) propyl)amino)propyl)piperidine-1-sulfonamide (2.28 g, 3.97 mmol) in DMF (20 mL) was added sodium hydride (400 mg, 3.97 mmol). The mixture was stirred for 30 min at ambient temperature. Cyclopropane-1,1-diylbis(methylene) diethanesulfonate (1.3 g, 3.97 mmol) was added and the reaction mixture was stirred at 80° C. for 2 h. The mixture was cooled to ambient temperature and poured into water (150 mL). The resulting mixture was extracted with ethyl acetate (100 mL). The organic layer was washed with water (50 mL×2), dried over anhydrous sodium sulfate and concentrated. The residue was purified by column chromatography on silica gel (EtOAc/Petroleum ether=1:15 to 1:8) to provide the freebase which was dissolved in ether (5 mL). Hydrochloric acid (1.5 mL or a 3 N solution in 1,4-dioxane) was added and the mixture was stirred for 0.5 h. The solvent was removed under vacuum and the residue was triturated with ether three times to provide compound A40. $^1$H NMR (400 MHz, DMSO-$d_6$): δ 9.89 (br s, 1H), 7.54 (m, 1H), 6.63 (m, 2H), 3.67 (br s, 1H), 3.55-2.89 (m, 23H), 1.90-1.45 (m, 15H), 1.28 (m, 4H), 0.95 (m, 2H), 0.69 (m, 4H). MS(EI) for $C_{31}H_{52}FN_5O_4S_2$, found 643 $[M+H]^+$.

The following compounds were synthesized in a similar manner:

Route 13

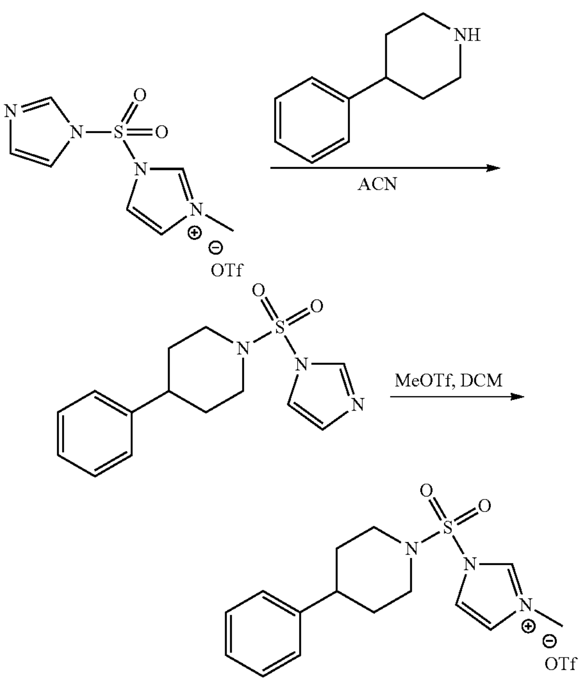

To 1-((1H-imidazol-1-yl)sulfonyl)-3-methyl-1H-imidazol-3-ium trifluorosulfonate (1.69 g, 4.65 mmol, reference: *J. Org. Chem.* 2002, 68, 115-119.) and 4-phenylpiperidine (750 mg, 4.65 mmol) was added ACN (16 mL) and the solution was allowed to stand for 2 h then concentrated and purified directly by flash column chromatography (0-80% hexanes/ethyl acetate) to provide the product.

To 1-((1H-imidazol-1-yl)sulfonyl)-4-phenylpiperidine (600 mg, 2.06 mmol) in DCM at 0° C. was added methyl triflate (0.23 mL, 2.06 mmol) over 5 min. After allowing to stand for 30 min the mixture was concentrated to provide 3-methyl-1-((4-phenylpiperidin-1-yl)sulfonyl)-1H-imidazol-3-ium trifluoromethanesulfonate which was carried forward without further purification. MS(EI) for $C_{15}H_{20}N_3O_2S$, found 307 $[M]^+$.

| No. | IUPAC | [M + H]$^+$ | $^1$H NMR |
|---|---|---|---|
| A31 | 9-(cyclohexylmethyl)-5-(4-methoxybenzenesulfonyl)-13-(piperidine-1-sulfonyl)-5,9,13-triazaspiro[2.11]tetradecane | 611 | $^1$H NMR (400 MHz, DMSO-$d_6$): δ 9.75 (brs, 1 H), 7.73 (d, J = 8.8 Hz, 2 H), 7.16 (d, J = 8.8 Hz, 2 H), 3.85 (s, 3 H), 3.55-2.89 (m, 18 H), 1.90-1.45 (m, 15 H), 1.28 (m, 4 H), 0.95 (m, 2 H), 0.66 (m, 4 H). |
| A32 | 9-(cyclohexylmethyl)-5-(3-methoxybenzenesulfonyl)-13-(piperidine-1-sulfonyl)-5,9,13-triazaspiro[2.11]tetradecane | 611 | $^1$H NMR (400 MHz, DMSO-$d_6$): δ 9.89 (br s, 1 H), 7.57 (m, 1 H), 7.32 (m, 2 H), 7.23 (s, 1 H), 3.85 (s, 3 H), 3.55-2.89 (m, 18 H), 2.04-1.45 (m, 15 H), 1.28 (m, 4 H), 0.95 (m, 2 H), 0.67 (m, 4 H). |
| A33 | 9-(cyclohexylmethyl)-5-(2-methoxybenzenesulfonyl)-13-(piperidine-1-sulfonyl)-5,9,13-triazaspiro[2.11]tetradecane | 611 | $^1$H NMR (400 MHz, DMSO-$d_6$): δ 9.35 (br s, 1 H), 7.80 (m, 1 H), 7.68 (m, 1 H), 7.28 (m, 1 H), 7.13 (m, 1 H), 3.89 (s, 3 H), 3.55-2.89 (m, 18 H), 1.90-1.45 (m, 15 H), 1.28 (m, 4 H), 0.95 (m, 2 H), 0.66 (br s, 2 H), 0.51 (brs, 2 H). |
| A34 | 5-(benzenesulfonyl)-9-(cyclohexylmethyl)-13-(piperidine-1-sulfonyl)-5,9,13-triazaspiro[2.11]tetradecane | 581 | $^1$H NMR (400 MHz, DMSO-$d_6$): δ 10.26 (br s, 1 H), 7.76 (m, 4 H), 3.41-2.89 (m, 18 H), 1.90-1.45 (m, 15 H), 1.28 (m, 4 H), 0.95 (m, 2 H), 0.73 (brs, 4 H). |

The following compounds were synthesized in a similar manner:

1-((8-chloro-3,4-dihydroisoquinolin-2(1H)-yl)sulfonyl)-3-methyl-1H-imidazol-3-ium trifluoromethanesulfonate (Intermediate for compound A51).

1-((7-chloro-3,4-dihydroisoquinolin-2(1H)-yl)sulfonyl)-3-methyl-1H-imidazol-3-ium trifluoromethanesulfonate (Intermediate for compound A52).

1-((6-chloro-3,4-dihydroisoquinolin-2(1H)-yl)sulfonyl)-3-methyl-1H-imidazol-3-ium trifluoromethanesulfonate (Intermediate for compound A53).

1-((5-chloro-3,4-dihydroisoquinolin-2(1H)-yl)sulfonyl)-3-methyl-1H-imidazol-3-ium trifluoromethanesulfonate (Intermediate for compound A54).

1-((6-fluoro-3,4-dihydroisoquinolin-2(1H)-yl)sulfonyl)-3-methyl-1H-imidazol-3-ium trifluoromethanesulfonate (Intermediate for compound A59).

1-((6-bromo-3,4-dihydroisoquinolin-2(1H)-yl)sulfonyl)-3-methyl-1H-imidazol-3-ium trifluoromethanesulfonate (Intermediate for compound A60).

1-((4-isopropoxypiperidin-1-yl)sulfonyl)-3-methyl-1H-imidazol-3-ium trifluoromethanesulfonate hydrochloride (Intermediate for compound A66).

1-((4-(cyclopent-1-en-1-yl)-3,6-dihydropyridin-1(2H)-yl)sulfonyl)-3-methyl-1H-imidazol-3-ium trifluoromethanesulfonate (Intermediate for compound A67).

1-((4-(cyclohex-1-en-1-yl)-3,6-dihydropyridin-1(2H)-yl)sulfonyl)-3-methyl-1H-imidazol-3-ium trifluoromethanesulfonate (Intermediate for compound A68).

1-((4-(3-chlorophenyl)-3,6-dihydropyridin-1(2H)-yl)sulfonyl)-3-methyl-1H-imidazol-3-ium trifluoromethanesulfonate (Intermediate for compound A69).

1-((4-(2-chlorophenyl)-3,6-dihydropyridin-1(2H)-yl)sulfonyl)-3-methyl-1H-imidazol-3-ium trifluoromethanesulfonate (Intermediate for compound A73).

1-((4-(4-chlorophenyl)-3,6-dihydropyridin-1(2H)-yl)sulfonyl)-3-methyl-1H-imidazol-3-ium trifluoromethanesulfonate (Intermediate for compound A74).

1-((4-(1H-pyrazol-1-yl)piperidin-1-yl)sulfonyl)-3-methyl-1H-imidazol-3-ium trifluoromethanesulfonate (Intermediate for compound A79).

1-((4-(benzo[d]oxazol-2-yl)piperidin-1-yl)sulfonyl)-3-methyl-1H-imidazol-3-ium trifluoromethanesulfonate (Intermediate for compound A80).

3-methyl-1-((4-(pyrimidin-2-yl)piperidin-1-yl)sulfonyl)-1H-imidazol-3-ium trifluoromethanesulfonate (Intermediate for compound A81).

1-((2-chloro-7,8-dihydro-1,6-naphthyridin-6(5H)-yl)sulfonyl)-3-methyl-1H-imidazol-3-ium trifluoromethanesulfonate (Intermediate for compound A82).

1-((5-chloroisoindolin-2-yl)sulfonyl)-3-methyl-1H-imidazol-3-ium trifluoromethanesulfonate (Intermediate for compound A89).

Route 14

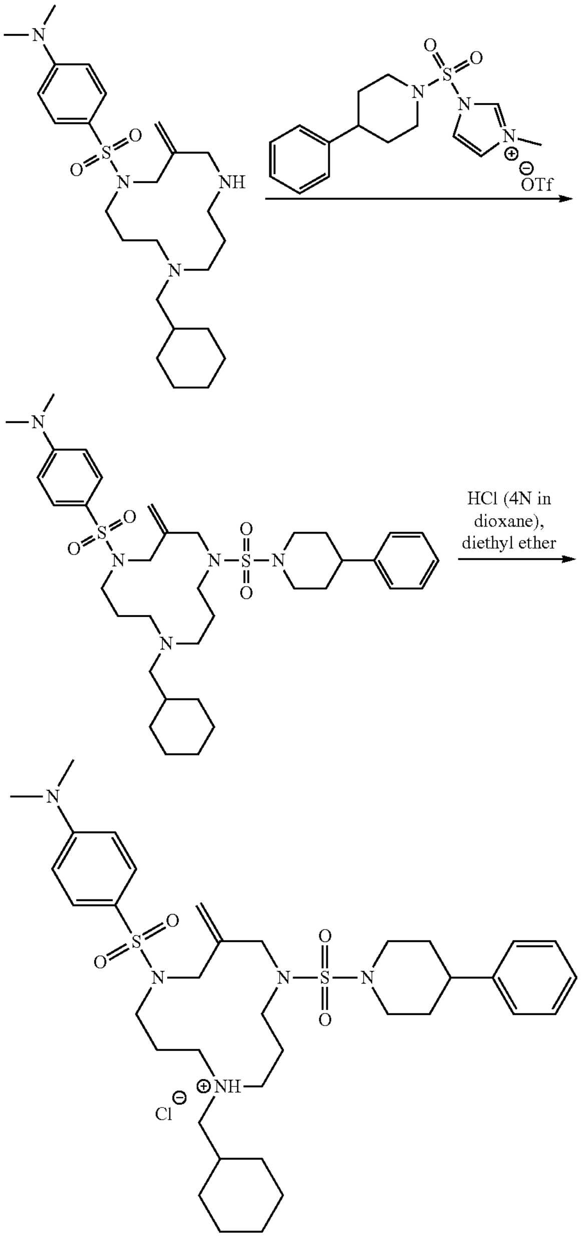

To 4-((9-(cyclohexylmethyl)-3-methylene-1,5,9-triazacyclododecan-1-yl)sulfonyl)-N,N-dimethylaniline (97 mg, 0.21 mmol) in ACN (0.8 mL) was added 3-methyl-1-((4-phenylpiperidin-1-yl)sulfonyl)-1H-imidazol-3-ium trifluoromethanesulfonate (95 mg, 0.21 mmol) and the mixture was heated to 80° C. for 8 h then concentrated and purified directly by flash column chromatography (0-70% hexanes (1% DEA)/ethyl acetate) to provide the freebase. To this was added diethyl ether (5 mL) and HCl (52 μL of a 4 N HCl in 1,4-dioxane) and the mixture was allowed to stand for 10 min then concentrated to provide 4-{[9-(cyclohexylmethyl)-3-methylidene-5-[(4-phenylpiperidin-1-yl)sulfonyl]-1,5,9-triazacyclododecan-1-yl]sulfonyl}-N,N-dimethylaniline hydrochloride (compound A35). MS(EI) for $C_{36}H_{55}N_5O_4S_2$, found 686 $[M+H]^+$.

The following compounds were synthesized in a similar manner:

| No. | IUPAC | [M + H]$^+$ |
|---|---|---|
| A36 | 4-{[9-(cyclohexylmethyl)-3-methylidene-5-[(4-phenylpiperazin-1-yl)sulfonyl]-1,5,9-triazacyclododecan-1-yl]sulfonyl}-N,N-dimethylaniline | 687 |
| A37 | 4-{[9-(cyclohexylmethyl)-3-methylidene-5-[(4-phenoxypiperidin-1-yl)sulfonyl]-1,5,9-triazacyclododecan-1-yl]sulfonyl}-N,N-dimethylaniline | 702 |
| A38 | 4-{[9-(cyclohexylmethyl)-3-methylidene-5-[(3-phenylpiperidin-1-yl)sulfonyl]-1,5,9-triazacyclododecan-1-yl]sulfonyl}-N,N-dimethylaniline | 686 |
| A39 | $^{1}$-{[9-(cyclohexylmethyl)-5-[4-(dimethylamino)benzenesulfonyl]-3-methylidene-1,5,9-triazacyclododecan-1-yl]sulfonyl}piperidine-4-carbonitrile | 635 |
| A42 | 4-{[5-(cyclohexylmethyl)-9-[(4-phenylpiperidin-1-yl)sulfonyl]-1,5,9-triazacyclododecan-1-yl]sulfonyl}-N,N-dimethylaniline | 674 |

-continued

| No. | IUPAC | [M + H]$^+$ |
|---|---|---|
| A43 | 4-{[9-(cyclohexylmethyl)-3-methylidene-5-{[(3S)-3-phenylpiperidin-1-yl]sulfonyl}-1,5,9-triazacyclododecan-1-yl]sulfonyl}-N,N-dimethylaniline | 686 |
| A46 | 4-{[9-(cyclohexylmethyl)-5-{[(3R)-3-methyl-4-phenylpiperazin-1-yl]sulfonyl}-3-methylidene-1,5,9-triazacyclododecan-1-yl]sulfonyl}-N,N-dimethylaniline | 701 |
| A47 | 4-{[9-(cyclohexylmethyl)-5-{[(3S)-3-methyl-4-phenylpiperazin-1-yl]sulfonyl}-3-methylidene-1,5,9-triazacyclododecan-1-yl]sulfonyl}-N,N-dimethylaniline | 701 |
| A48 | 4-{[9-(cyclohexylmethyl)-5-[4-(dimethylamino)benzenesulfonyl]-3-methylidene-1,5,9-triazacyclododecan-1-yl]sulfonyl}-1-phenylpiperazin-2-one | 701 |
| A49 | 4-{[9-(cyclohexylmethyl)-3-methylidene-5-{[(3R)-3-phenylpiperidin-1-yl]sulfonyl}-1,5,9-triazacyclododecan-1-yl]sulfonyl}-N,N-dimethylaniline | 686 |
| A50 | 4-{[9-(cyclohexylmethyl)-3-methylidene-5-(1,2,3,4-tetrahydroisoquinoline-2-sulfonyl)-1,5,9-triazacyclododecan-1-yl]sulfonyl}-N,N-dimethylaniline | 658 |

Route 15

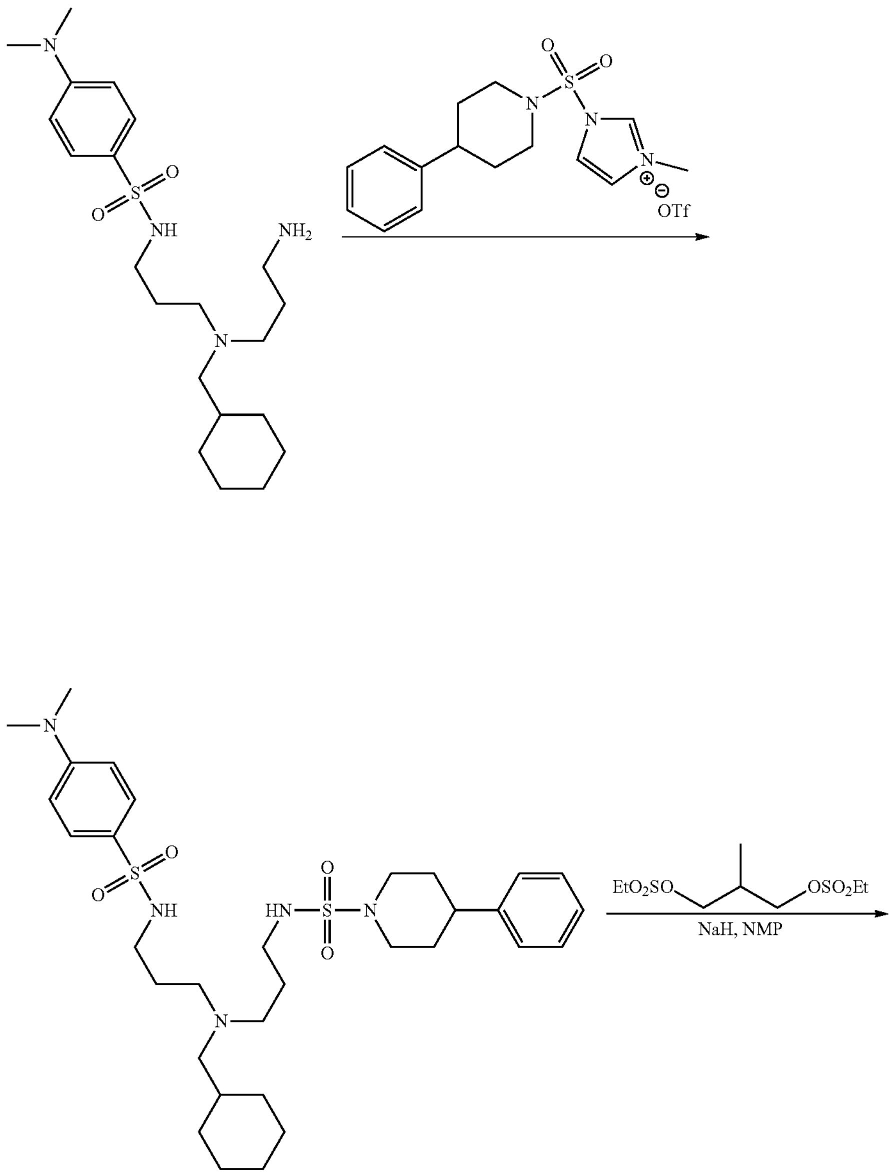

-continued

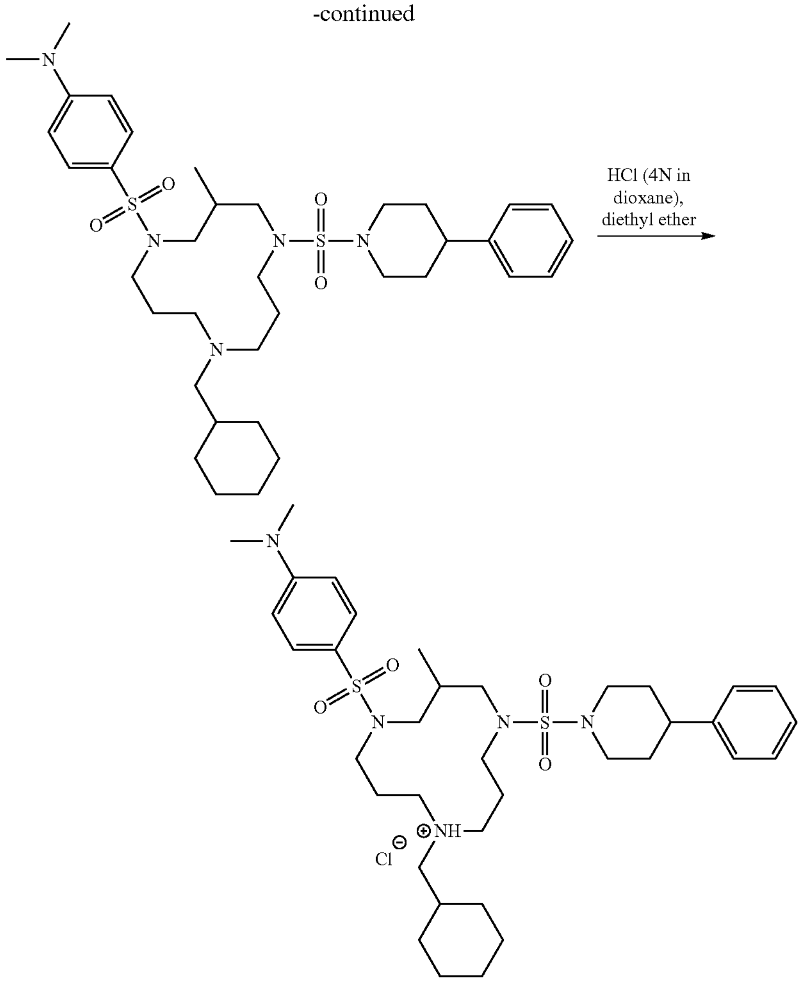

To N-(3-((3-aminopropyl)(cyclohexylmethyl)amino)propyl)-4-(dimethylamino)benzenesulfonamide (838 mg, 1.84 mmol) in ACN (5 mL) was added 3-methyl-1-((4-phenylpiperidin-1-yl)sulfonyl)-1H-imidazol-3-ium trifluoromethanesulfonate (838 mg, 1.84 mmol) and the mixture was heated to 80° C. for 8 h the concentrated and purified directly by flash column chromatography (0-70% hexanes (1% DEA)/ethyl acetate) to provide the product. $^1$H NMR (400 MHz, $CDCl_3$): δ 7.68 (d, J=8.8 Hz, 2H), 7.33 (m, 5H), 6.68 (d, J=8.8 Hz, 2H), 5.75 (br s, 2H), 3.84 (m, 2H), 3.18 (m, 2H), 3.05 (s, 6H), 2.91 (m, 4H), 2.65 (m, 1H), 2.43 (m, 4H), 2.08 (m, 2H), 1.73 (m, 12H), 1.40 (m, 1H), 1.15 (m, 4H), 0.85 (m, 2H).

To 4-((9-(cyclohexylmethyl)-3-methyl-5-((4-phenylpiperidin-1-yl)sulfonyl)-1,5,9-triazacyclododecan-1-yl)sulfonyl)-N,N-dimethylaniline (123 mg, 0.194 mmol) in NMP (10 mL) was added sodium hydride (19 mg of a 60% dispersion in mineral oil, 0.485 mmol) over 20 min. The mixture was stirred at ambient temperature for 30 min then 80° C. for an additional 20 min. The bis-sulfonate was then added over the course of 1 h. After 8 h at 80° C. the mixture was cooled to ambient temp., diluted with brine and ethyl acetate, extracted with ethyl acetate (3×), the combined organics were washed with brine (3×), dried with sodium sulfate, filtered, and concentrated. Flash column chromatography (0-50% hexanes (1% DEA)/ethyl acetate) provided the freebase. The freebase was converted to the HCl salt with the addition of ethyl ether (5 mL) and HCl (4N in dioxane, 50 uL). Concentration after 10 min provided 4-{[9-(cyclohexylmethyl)-3-methyl-5-[(4-phenylpiperidin-1-yl)sulfonyl]-1,5,9-triazacyclododecan-1-yl]sulfonyl}-N,N-dimethylaniline hydrochloride (compound A44). MS(EI) for $C_{36}H_{57}N_5O_4S_2$, found 688 $[M+H]^+$.

The following compound was synthesized in a similar manner:

| No. | IUPAC | $[M + H]^+$ |
|---|---|---|
| B7 | N-{3-[(cyclohexylmethyl)(3-{[(4-phenylpiperidin-1-yl)sulfonyl]amino}propyl)amino]propyl}-4-(dimethylamino)benzene-1-sulfonamide | 634 |

Route 16

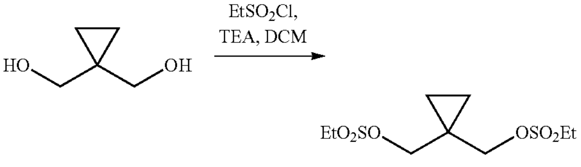

To 1,1-bis(hydroxymethyl)cyclopropane (5.00, 49.0 mmol) in acetone (20 mL) was added TEA (2.2 eq, 108 mmol) and the mixture was cooled to 0-5° C. Ethanesulfonyl chloride was added at a rate to maintain the internal temperature below 10° C. (=1 h). After stirring an additional 2 h at ambient temperature the mixture was diluted with 150 mL of water, extracted with ethyl acetate (2×50 mL), washed with brine, dried with sodium sulfate, filtered, and concentrated to provide the product. $^{1}H$ NMR (400 MHz, $CDCl_3$): δ 4.16 (s, 4H), 3.20 (m, 4H), 1.46 (t, J=7.2 Hz, 6H), 0.83 (s, 4H). MS(EI) for $C_3H_{18}O_6S_2$, found 287 $[M+H]^+$.

The following compound was synthesized in a similar manner 2-methylpropane-1,3-diyldiethanesulfonate (Intermediate for compound A44).

Route 17

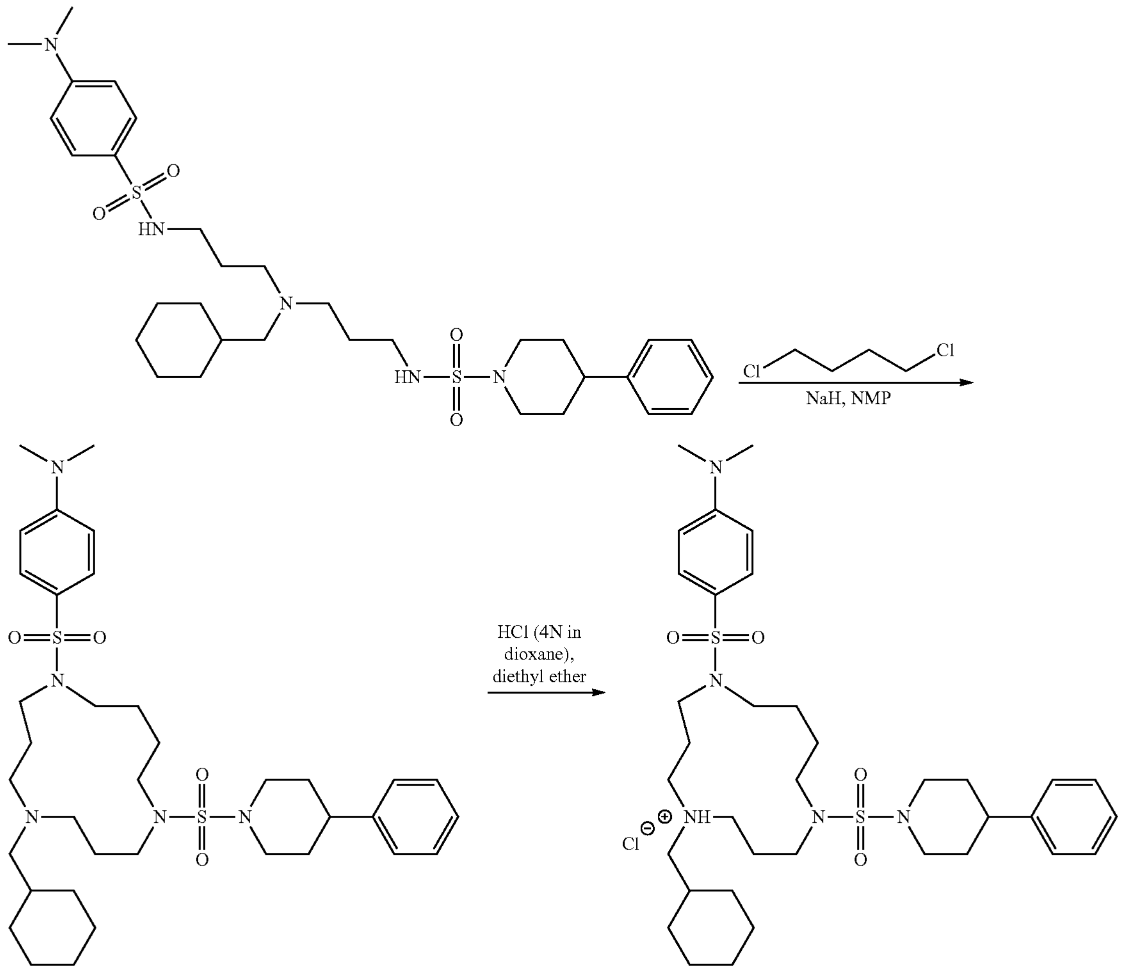

To N-(3-((cyclohexylmethyl)(3-((4-(dimethylamino)phenyl)sulfonamido)propyl)amino)propyl)-4-phenylpiperidine-1-sulfonamide (89 mg, 0.14 mmol) in NMP (7 mL) was added NaH (14 mg of a 60% dispersion in mineral oil, 0.35 mmol) portion-wise over 20 min. The mixture was stirred at ambient temperature for 30 min then 80° C. for 20 min. The dichloride was then added and the mixture was heated at 80° C. After 8 h at 80° C. the mixture was cooled to ambient temp, diluted with brine and ethyl acetate, extracted with ethyl acetate (3×), the combined organics were washed with brine (3×), dried with sodium sulfate, filtered, and concentrated. Flash column chromatography (0-50% hexanes (1% DEA)/ethyl acetate) provided the product. The product was converted to the HCl salt with the addition of ethyl ether (5 mL) and HCl (4N in dioxane, 35 uL). The mixture was concentrated to provide 4-{[5-(cyclohexylmethyl)-9-[(4-phenylpiperidin-1-yl)sulfonyl]-1,5,9-triazacyclotridecan-1-yl]sulfonyl}-N,N-dimethylaniline hydrochloride (compound B5). MS(EI) for $C_{36}H_{57}N_5O_4S_2$, found 688 $[M+H]^+$.

The following compounds were synthesized in a similar manner:

| No. | IUPAC | $[M + H]^+$ |
|---|---|---|
| B8 | 4-{(11Z)-5-(cyclohexylmethyl)-9-[(4-phenylpiperidin-1-yl)sulfonyl]-1,5,9-triazacyclotridec-11-en-1-yl]sulfonyl}-N,N-dimethylaniline | 686 |
| B9 | 4-{[(11E)-5-(cyclohexylmethyl)-9-[(4-phenylpiperidin-1-yl)sulfonyl]-1,5,9-triazacyclotridec-11-en-1-yl]sulfonyl}-N,N-dimethylaniline | 686 |

Route 18

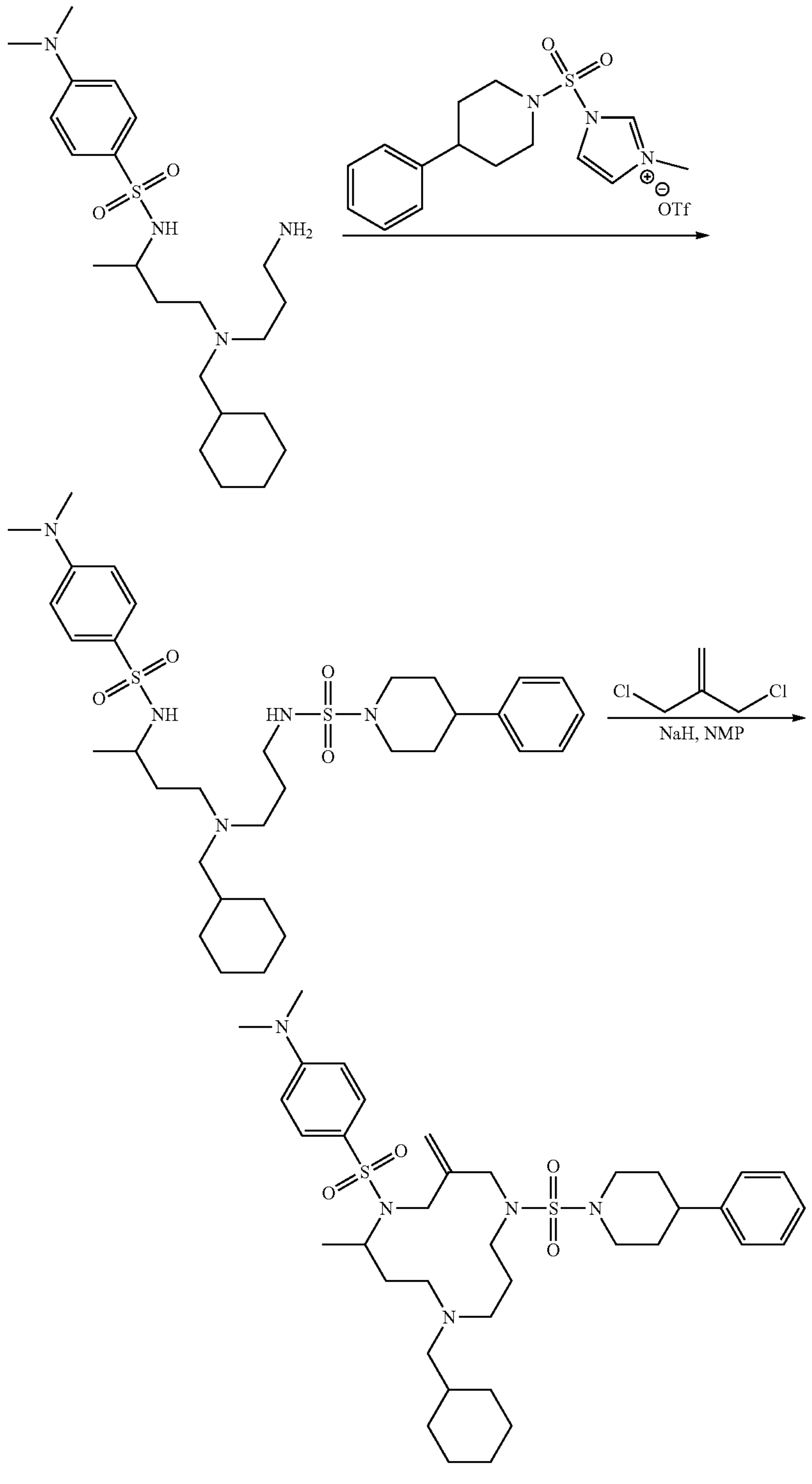

N-(4-((3-aminopropyl)(cyclohexylmethyl)amino)butan-2-yl)-4-(dimethylamino)benzenesulfonamide was synthesized following Route 2 with substitution of the appropriate sulfonyl chloride.

4-((5-(cyclohexylmethyl)-2-methyl-11-methylene-9-((4-phenylpiperidin-1-yl)sulfonyl)-1,5,9-triazacyclododecan-1-yl)sulfonyl)-N,N-dimethylaniline was synthesized following the procedure described in Route 15 substituting with 3-chloro-2-(chloromethyl)prop-1-ene to provide 4-((5-(cyclohexylmethyl)-2-methyl-11-methylene-9-((4-phenylpiperidin-1-yl)sulfonyl)-1,5,9-triazacyclododecan-1-yl)sulfonyl)-N,N-dimethylaniline (compound B6). MS(EI) for $C_{37}H_{57}N_5O_4S_2$, found 700 $[M+H]^+$.

The following compounds were synthesized in a similar manner:

| No. | IUPAC | [M + H]+ | 1H NMR |
|---|---|---|---|
| B19 | 4-{[5-(cyclohexylmethyl)-2-methyl-11-methylidene-9-[(4-phenylpiperidin-1-yl)sulfonyl]-1,5,9-triazacyclododecan-1-yl]sulfonyl}-N,N-dimethylaniline | 700 | |
| A51 | 4-({5-[(8-chloro-1,2,3,4-tetrahydroisoquinolin-2-yl)sulfonyl]-9-(cyclohexylmethyl)-3-methylidene-1,5,9-triazacyclododecan-1-yl}sulfonyl)-N,N-dimethylaniline | 692 | |
| A52 | 4-({5-[(7-chloro-1,2,3,4-tetrahydroisoquinolin-2-yl)sulfonyl]-9-(cyclohexylmethyl)-3-methylidene-1,5,9-triazacyclododecan-1-yl}sulfonyl)-N,N-dimethylaniline | 692 | |
| A53 | 4-({5-[(6-chloro-1,2,3,4-tetrahydroisoquinolin-2-yl)sulfonyl]-9-(cyclohexylmethyl)-3-methylidene-1,5,9-triazacyclododecan-1-yl}sulfonyl)-N,N-dimethylaniline | 692 | $^1$H NMR (400 MHz, $CDCl_3$): δ 7.59 (d, J = 8.8 Hz, 2 H), 7.15 (m, 2 H), 7.04 (m, 1 H), 6.70 (d, J = 8.8 Hz, 2 H), 5.25 (s, 1 H), 5.13 (S, 1 H), 4.34 (S, 2 H), 4.12 (S, 2 H), 4.10 (s, 2 H), 3.51 (m, 6 H), 3.05 (s, 6 H), 2.88 (m, 4 H), 2.41 (m, 2 H), 2.25 (m, 2 H), 1.95 (m, 2 H), 1.85 (m, 2 H), 1.67 (m, 6 H), 1.23 (m, 4 H), 0.85 (m, 1 H). |
| A54 | 4-({5-[(5-chloro-1,2,3,4-tetrahydroisoquinolin-2-yl)sulfonyl]-9-(cyclohexylmethyl)-3-methylidene-1,5,9-triazacyclododecan-1-yl}sulfonyl)-N,N-dimethylaniline | 692 | |
| A56 | 4-({5-[(6-chloro-1,2,3,4-tetrahydroisoquinolin-2-yl)sulfonyl]-9-(cyclohexylmethyl)-3-methylidene-1,5,9-triazacyclododecan-1-yl}sulfonyl)-3-fluoro-N,N-dimethylaniline | 710 | |
| A57 | 4-[(5-{[4-(2-chlorophenyl)piperidin-1-yl]sulfonyl}-9-(cyclohexylmethyl)-3-methylidene-1,5,9-triazacyclododecan-1-yl)sulfonyl]-N,N-dimethylaniline | 720 | |
| A58 | 4-[(5-{[4-(3-chlorophenyl)piperidin-1-yl]sulfonyl}-9-(cyclohexylmethyl)-3-methylidene-1,5,9-triazacyclododecan-1-yl)sulfonyl]-N,N-dimethylaniline | 720 | |
| A59 | 4-{[9-(cyclohexylmethyl)-5-[(6-fluoro-1,2,3,4-tetrahydroisoquinolin-2-yl)sulfonyl]-3-methylidene-1,5,9-triazacyclododecan-1-yl]sulfonyl}-N,N-dimethylaniline | 676 | |
| A60 | 4-({5-[(6-bromo-1,2,3,4-tetrahydroisoquinolin-2-yl)sulfonyl]-9-(cyclohexylmethyl)-3-methylidene-1,5,9-triazacyclododecan-1-yl}sulfonyl)-N,N-dimethylaniline | 736 | |

-continued

| No. | IUPAC | [M + H]$^+$ | $^1$H NMR |
|---|---|---|---|
| A64 | 4-{[9-(cyclohexylmethyl)-5-[(4-cyclopentylpiperidin-1-yl)sulfonyl]-3-methylidene-1,5,9-triazacyclododecan-1-yl]sulfonyl}-N,N-dimethylaniline | 678 | |
| A65 | 4-{[9-(cyclohexylmethyl)-5-[(4-cyclohexylpiperidin-1-yl)sulfonyl]-3-methylidene-1,5,9-triazacyclododecan-1-yl]sulfonyl}-N,N-dimethylaniline | 692 | |
| A66 | 4-{[9-(cyclohexylmethyl)-3-methylidene-5-{[4-(propan-2-yloxy)piperidin-1-yl]sulfonyl}-1,5,9-triazacyclododecan-1-yl]sulfonyl}-N,N-dimethylaniline | 668 | |
| A67 | 4-{[9-(cyclohexylmethyl)-5-{[4-(cyclopent-1-en-1-yl)-1,2,3,6-tetrahydropyridin-1-yl]sulfonyl}-3-methylidene-1,5,9-triazacyclododecan-1-yl]sulfonyl}-N,N-dimethylaniline | 674 | |
| A68 | 4-[(5-{[4-(cyclohex-1-en-1-yl)-1,2,3,6-tetrahydropyridin-1-yl]sulfonyl}-9-(cyclohexylmethyl)-3-methylidene-1,5,9-triazacyclododecan-1-yl)sulfonyl]-N,N-dimethylaniline | 688 | |
| A69 | 4-[(5-{[4-(3-chlorophenyl)-1,2,3,6-tetrahydropyridin-1-yl]sulfonyl}-9-(cyclohexylmethyl)-3-methylidene-1,5,9-triazacyclododecan-1-yl)sulfonyl]-N,N-dimethylaniline | 718 | |
| A70 | 2-{[9-(cyclohexylmethyl)-5-[4-(dimethylamino)benzenesulfonyl]-3-methylidene-1,5,9-triazacyclododecan-1-yl]sulfonyl}-1,2,3,4-tetrahydroisoquinoline-6-carbonitrile | 683 | |
| A71 | 4-{[9-(cyclohexylmethyl)-5-[(6-methoxy-1,2,3,4-tetrahydroisoquinolin-2-yl)sulfonyl]-3-methylidene-1,5,9-triazacyclododecan-1-yl]sulfonyl}-N,N-dimethylaniline | 688 | |
| A72 | 4-[(5-44-(4-chlorophenyl)piperidin-1-yl]sulfonyl}-9-(cyclohexylmethyl)-3-methylidene-1,5,9-triazacyclododecan-1-yl)sulfonyll-N,N-dimethylaniline | 720 | |
| A73 | 4-[(5-{[4-(2-chlorophenyl)-1,2,3,6-tetrahydropyridin-1-yl]sulfonyl}-9-(cyclohexylmethyl)-3-methylidene-1,5,9-triazacyclododecan-1-yl)sulfonyl]-N,N-dimethylaniline | 718 | |
| A74 | 4-[(5-{[4-(4-chlorophenyl)-1,2,3,6-tetrahydropyridin-1-yl]sulfonyl}-9-(cyclohexylmethyl)-3-methylidene-1,5,9-triazacyclododecan-1-yl)sulfonyl]-N,N-dimethylaniline | 718 | |

-continued

| No. | IUPAC | [M + H]+ | $^1$H NMR |
|---|---|---|---|
| A78 | 4-{[9-(cyclohexylmethyl)-3-methylidene-5-{[4-(oxan-4-yl)piperidin-1-yl]sulfonyl}-1,5,9-triazacyclododecan-1-yl]sulfonyl}-N,N-dimethylaniline | 694 | |
| A79 | 4-{[9-(cyclohexylmethyl)-3-methylidene-5-{[4-(1H-pyrazol-1-yl)piperidin-1-yl]sulfonyl}-1,5,9-triazacyclododecan-1-yllsulfonyl}-N,N-dimethylaniline | 676 | |
| A80 | 4-[(5-{[4-(1,3-benzoxazol-2-yl)piperidin-1-yl]sulfonyl}-9-(cyclohexylmethyl)-3-methylidene-1,5,9-triazacyclododecan-1-yl)sulfonyl]-N,N-dimethylaniline | 727 | |
| A81 | 4-{[9-(cyclohexylmethyl)-3-methylidene-5-{[4-(pyrimidin-2-yl)piperidin-1-yl]sulfonyl}-1,5,9-triazacyclododecan-1-yl}sulfonyl}-N,N-dimethylaniline | 688 | |
| A82 | 4-({5-[(2-chloro-5,6,7,8-tetrahydro-1,6-naphthyridin-6-yl)sulfonyl]-9-(cyclohexylmethyl)-3-methylidene-1,5,9-triazacyclododecan-1-yl}sulfonyl)-N,N-dimethylaniline | 693 | |
| A88 | (3Z)-9-(cyclohexylmethyl)-1-[4-(dimethylamino)benzenesulfonyl]-N-methoxy-5-[(4-phenylpiperidin-1-yl)sulfonyl]-1,5,9-triazacyclododecan-3-imine | 717 | |
| A83 | 4-[(5-[4-(2-chlorophenyl)piperazin-1-yl]sulfonyl}-9-(cyclohexylmethyl)-3-methylidene-1,5,9-triazacyclododecan-1-yl)sulfonyl]-N,N-dimethylaniline | 721 | $^1$H NMR (400 MHz, $CDCl_3$): δ 7.61 (d, J = 8.8 Hz, 2 H), 7.39 (m, 2 H), 7.05 (m, 2 H), 6.82 (d, J = 8.8 Hz, 2 H), 5.35 (m, 2 H), 4.10 (m, 2 H), 3.41 (m, 6 H), 3.10 (m, 4 H), 3.05 (s, 6 H), 2.88 (m, 2 H), 2.41 (m, 3 H), 2.21 (m, 4 H), 2.01 (m, 3 H), 1.85 (m, 6 H), 1.55 (m, 11 H), 1.15 (m, 9 H), 0.82 (m, 3 H). |
| A84 | 4-[(5-{[4-(3-chlorophenyl)piperazin-1-yl]sulfonyl}-9-(cyclohexylmethyl)-3-methylidene-1,5,9-triazacyclododecan-1-yl)sulfonyl]-N,N-dimethylaniline | 721 | $^1$H NMR (400 MHz, $CDCl_3$): δ 7.59 (d, J = 8.8 Hz, 2 H), 7.18 (m, 1 H), 6.85 (m, 3 H), 6.78 (d, J = 8.8 Hz, 2 H), 5.25 (m, 2 H), 4.10 (m, 2 H), 3.51 (m, 2 H), 3.20 (m, 10 H), 3.05 (s, 6 H), 2.88 (m, 2 H), 2.41 (m, 2 H), 2.01 (m,2 H), 1.85 (m, 4 H), 1.65 (m, 6 H), 1.25 (m, 5 H), 0.82 (m, 1 H). |
| A85 | 4-[(5-{[4-(4-chlorophenyl)piperazin-1-yl]sulfonyl}-9-(cyclohexylmethyl)-3-methylidene-1,5,9-triazacyclododecan-1-yl)sulfonyl]-N,N-dimethylaniline | 721 | $^1$H NMR (400 MHz, $CDCl_3$): δ 7.59 (d, J = 8.8 Hz, 2 H), 7.26 (d, J = 8.0 Hz, 2 H), 6.87 (d, J = 8.0 Hz, 2 H), 6.70 (d, J = 8.8 Hz, 2 H), 5.25 (m, 2 H), 4.10 (m, 2 H), 3.51 (m, 2 H), 3.20 (m, 10 H), 3.05 (s, 6 H), 2.88 (m, 2 H), 2.41 (m, 2 H), 2.01 (m,2 H), 1.85 (m, 4 H), 1.65 (m,6 H), 1.27 (m, 5 H), 0.85 (m, 1 H). |
| A89 | 4-({5-[(5-chloro-2,3-dihydro-1H-isoindol-2-yl)sulfonyl]-9-(cyclohexylmethyl)-3-methylidene-1,5,9-triazacyclododecan-1-yl}sulfonyl)-N,N-dimethylaniline | 678 | $^1$H NMR (400 MHz, $CDCl_3$): δ 7.59 (d, J = 8.8 Hz, 2 H), 7.25 (m, 4 H), 6.68 (d, J = 8.8 Hz, 2 H), 5.28 (s, 1 H), 5.12 (s, 1 H), 4.64 (m, 4 H), 4.12 (s, 2 H), 3.45 (m, 4 H), 3.05 (s, 6 H), 2.88 (m, 2 H), 2.25 (m, 2 H), 1.95 (m, 2 H), 1.65 (m, 8 H), 1.23 (m, 8 H), 0.85 (m, 1 H). |

Route 19

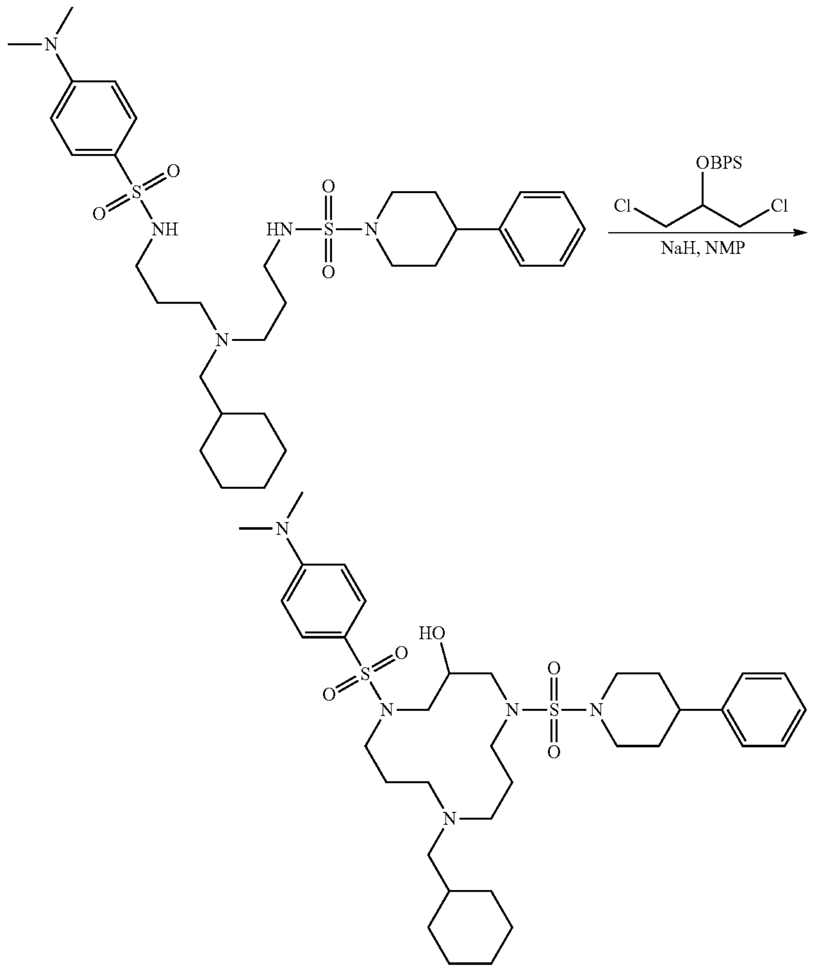

To N-(3-((cyclohexylmethyl)(3-((4-(dimethylamino)phenyl)sulfonamido)propyl)amino)propyl)-4-phenylpiperidine-1-sulfonamide (33 mg, 0.052 mmol) in NMP (3 mL) was added sodium hydride (4.6 mg of a 60% dispersion in mineral oil, 0.11 mmol). The mixture was stirred at ambient temperature for 30 min then 80° C. for an additional 20 min. The dichloride (19 mg, 0.052 mmol) was then added. After 2 h at 80° C. the mixture was cooled to ambient temp, diluted with brine and ethyl acetate, extracted with ethyl acetate (3×), the combined organics were washed with brine (3×), dried with sodium sulfate, filtered, and concentrated. Flash column chromatography (0-50% hexanes (1% DEA)/ethyl acetate) provided 9-(cyclohexylmethyl)-1-[4-(dimethylamino)benzenesulfonyl]-5-[(4-phenylpiperidin-1-yl)sulfonyl]-1,5,9-triazacyclododecan-3-ol (compound A55). MS(EI) for $C_{35}H_{55}N_5O_5S_2$, found 690 $[M+H]^+$.

Route 20

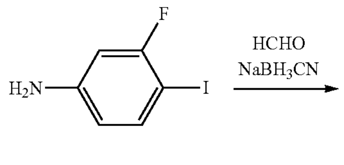

-continued

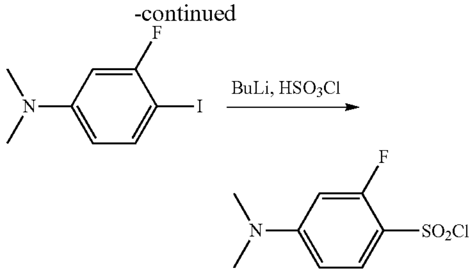

To a solution of 3-fluoro-4-iodoaniline (1.11 g, 4.68 mmol) in acetonitrile (15.00 mL) were added 37% aqueous formaldehyde (8.0 mL, 99.9 mmol) and sodium cyanoborohydride (1.88 g, 29.97 mmol). Then acetic acid (1 mL) was added dropwise over 10 min and the reaction mixture was stirred at ambient temperature overnight. Aqueous NaOH (1N, 30 mL) was added and the resulting mixture was extracted with ethyl acetate (50 mL). The organics were washed with brine, dried over anhydrous sodium sulfate and concentrated to provide 3-fluoro-4-iodo-N,N-dimethylaniline. $^1H$ NMR (400 MHz, $CDCl_3$): δ 7.47 (m, 1H), 6.43 (m, 1H), 6.28 (m, 1H), 2.94 (s, 6H).

To a solution of 3-fluoro-4-iodo-N,N-dimethylaniline (500 mg, 1.89 mmol) in ether (5 mL) was added n-BuLi (0.8 mL, 1.89 mmol) at −78° C. The mixture was stirred for 0.5 h at this temperature. Sulfuryl dichloride (405 mg, 3 mmol) was added and the reaction mixture was stirred for 1 h. The reaction was quenched with water (10 mL) and then adjusted to pH=8 with saturated aqueous $NaHCO_3$. The resulting mixture was extracted with ethyl acetate (10 mL). The organic phase was separated and concentrated. The residue was purified by column chromatography on silica gel to provide 4-(dimethylamino)-2-fluorobenzene-1-sulfonyl chloride. $^1H$ NMR (400 MHz, $CDCl_3$): δ 7.73 (m, 1H), 6.43 (m, 2H), 3.15 (s, 3H).

Route 21

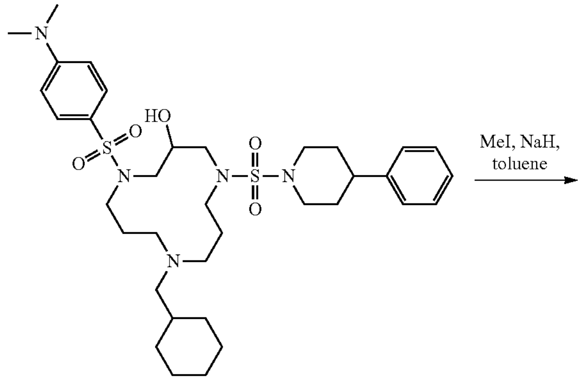

-continued

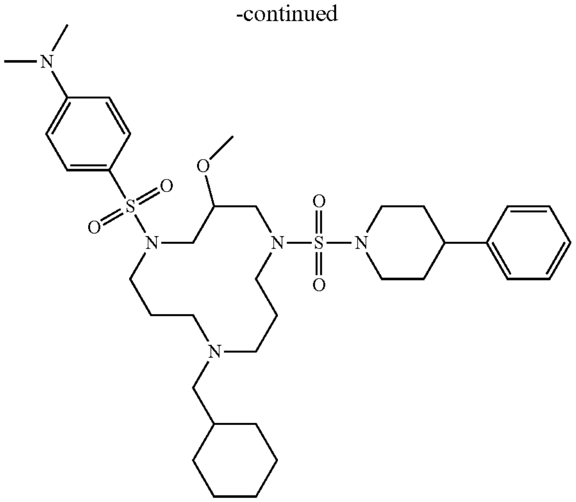

To 9-(cyclohexylmethyl)-1-((4-(dimethylamino)phenyl) sulfonyl)-5-((4-phenylpiperidin-1-yl)sulfonyl)-1,5,9-triaza-cyclododecan-3-ol (30 mg, 0.043 mmol) in toluene (0.5 mL) was added NaH (1.6 mg of a 60% dispersion in mineral oil, 0.065 mmol) followed by iodomethane (14 μL, 0.22 mmol). After stirring for 1 h the mixture was quenched with water, extracted with DCM (2×), the organics were combined and dried with sodium sulfate, filtered, and concentrated. Flash column chromatography (0-50% hexanes/ethyl acetate+1% DEA) provided 4-{[9-(cyclohexylmethyl)-3-methoxy-5-[(4-phenylpiperidin-1-yl)sulfonyl]-1,5,9-triazacyclododecan-1-yl]sulfonyl}-N,N-dimethylaniline (compound A61). MS(EI) for $C_{36}H_{57}N_5O_5S_2$, found 704 $[M+H]^+$.

Route 22

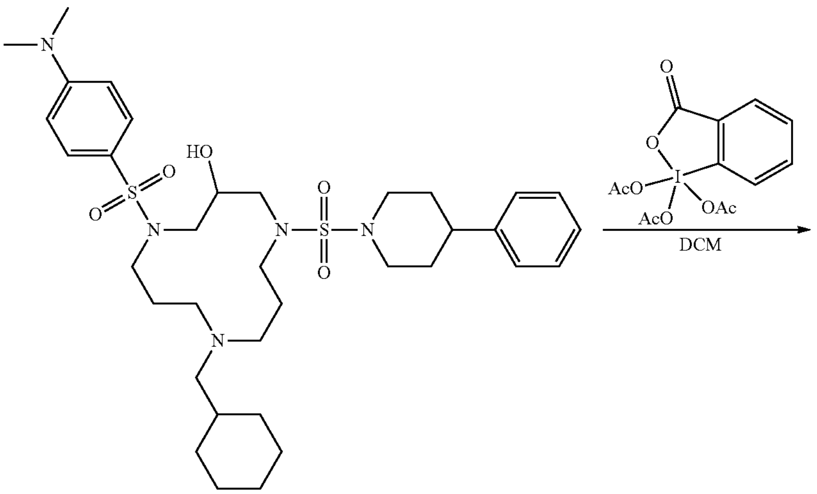

-continued

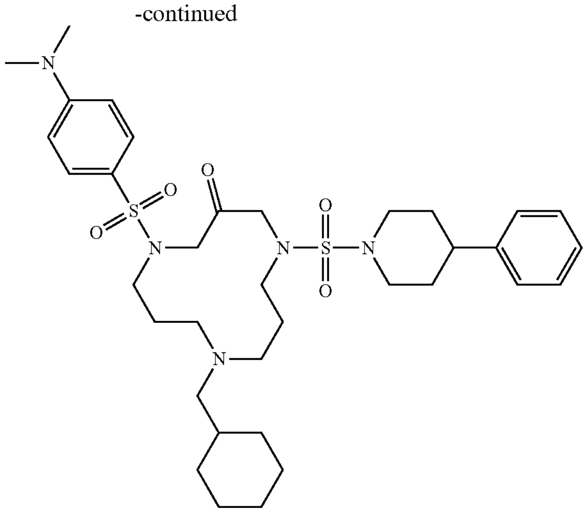

To 9-(cyclohexylmethyl)-1-((4-(dimethylamino)phenyl) sulfonyl)-5-((4-phenylpiperidin-1-yl)sulfonyl)-1,5,9-triazacyclododecan-3-ol (171 mg, 0.248 mmol) was added DCM (10 mL) followed by Dess-Martin periodinane (126 mg, 0.297 mmol). The mixture was allowed to stand for 2 h at rt then it was concentrated and purified directly by FCC (0-60% hexanes (1% DEA)/ethyl acetate) to provide 9-(cyclohexylmethyl)-1-((4-(dimethylamino)phenyl)sulfonyl)-5-((4-phenylpiperidin-1-yl)sulfonyl)-1,5,9-triazacyclododecan-3-one (compound B20). MS(EI) for $C_{35}H_{53}N_5O_5S_2$, found 688 $[M+H]^+$.

Route 23

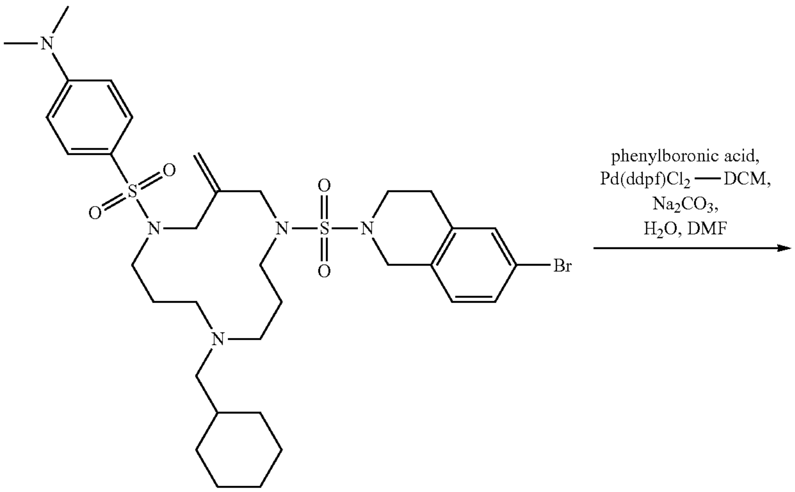

-continued

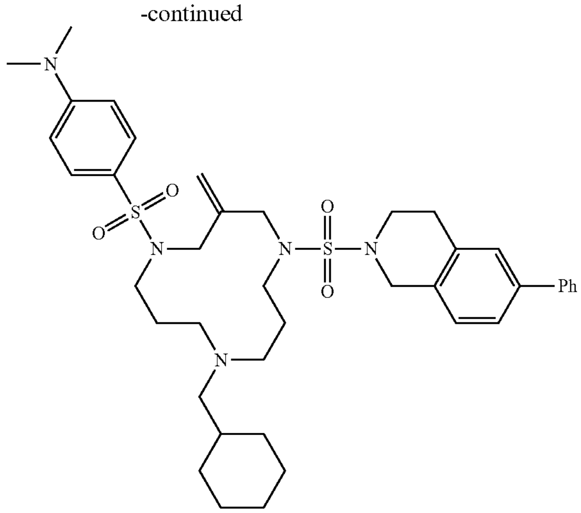

To 4-((5-((6-bromo-3,4-dihydroisoquinolin-2(1H)-yl)sulfonyl)-9-(cyclohexylmethyl)-3-methylene-1,5,9-triazacyclododecan-1-yl)sulfonyl)-N,N-dimethylaniline (70 mg, 0.095 mmol) in DMF (0.7 mL) was added water (0.1 mL), phenylboronic acid (13 mg, 0.10 mmol), Pd(dppf)$Cl_2$-DCM (7.8 mg, 0.001 mmol), and sodium carbonate (30 mg, 0.29 mmol). The mixture was heated to 80° C. for 1 h then diluted with brine, extracted with ethyl acetate (2×), dried with sodium sulfate, filtered, and concentrated. Flash column chromatography (0-50% hexanes (1% DEA)/ethyl acetate) provided 4-((9-(cyclohexylmethyl)-3-methylene-5-((6-phenyl-3,4-dihydroisoquinolin-2(1H)-yl)sulfonyl)-1,5,9-triazacyclododecan-1-yl)sulfonyl)-N,N-dimethylaniline (compound A63). MS(EI) for $C_{40}H_{53}N_5O_4S_2$, found 734 $[M+H]^+$.

Route 24

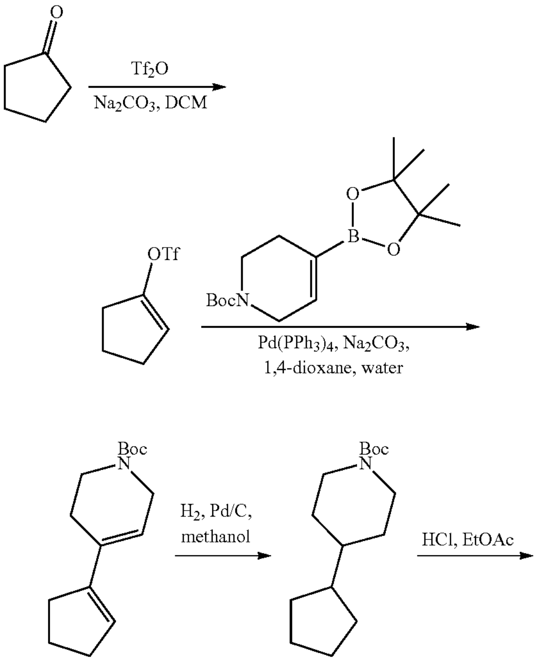

-continued

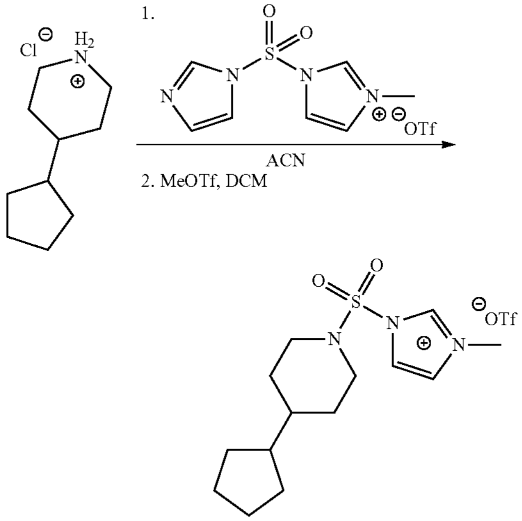

To a mixture of cyclopentanone (5.50 g, 65.5 mmol) and $Na_2CO_3$ (10.4 g, 98.2 mmol) in DCM (130 mL) was added $Tf_2O$ (18.6 g, 72.0 mmol) at −20° C. The reaction mixture was allowed to warm to ambient temperature and stirred overnight. The solid was filtered off and the filtrate was concentrated to provide cyclopentenyl trifluoromethanesulfonate.

A solution of cyclopentenyl trifluoromethanesulfonate (7.7 g, 35.6 mmol) in 1,4-dioxane (105 mL) and water (50 mL) was degassed and then filled with argon. tert-Butyl 4-(4,4,5,5-tetramethyl-1,3-dioxolan-2-yl)-5,6-dihydropyridine-1(2H)-carboxylate (6.0 g, 19.4 mmol), $Pd(PPh_3)_4$ (1.02 g, 0.88 mmol) and sodium carbonate (10.3 g, 97.1 mmol) were added. The reaction mixture was stirred overnight at 90° C. and then cooled to ambient temperature. The mixture was poured into water and extracted with ethyl acetate. The combined organic layers were washed with brine, dried over anhydrous $Na_2SO_4$, and concentrated under reduced pressure. Purification by flash column chromatography on silica gel (ethyl acetate/hexanes=1:99 to 5:95) provided tert-Butyl 4-cyclopentenyl-5,6-dihydropyridine-1(2H)-carboxylate.

$^1H$ NMR (400 MHz, $CDCl_3$): δ 5.73 (br s, 1H), 5.56 (br s,

1H), 4.00 (br s, 2H), 3.45 (br s, 2H), 2.47 (m, 4H), 2.33 (br s, 2H), 1.94 (m, 2H), 1.48 (s, 9H).

To a solution of tert-Butyl 4-cyclopentenyl-5,6-dihydropyridine-1(2H)-carboxylate (3.3 g, 15.3 mmol) in methanol (30 mL) was added Pd/C (0.6 g). The mixture was hydrogenated under 15 psi pressure for 5 h. The mixture was filtered and the filtrate was concentrated under reduced pressure to provide tert-Butyl 4-cyclopentylpiperidine-1-carboxylate.

To a solution of tert-Butyl 4-cyclopentylpiperidine-1-carboxylate (2.9 g, 11.5 mmol) in ethyl acetate (15 mL) was added EtOAc/HCl (4N, 20 mL). The mixture was stirred for 2 h and the solvent was removed. The resulting product was washed with ether to provide 4-cyclopentylpiperidine hydrochloride. 1H NMR (400 MHz, $D_2O$): δ 3.25 (m, 2H), 2.75 (m, 2H), 1.84 (m, 2H), 1.61 (m, 2H), 1.45 (m, 8H), 0.96 (m, 2H).

4-Cyclopentylpiperidine hydrochloride (1.4 g, 9.5 mmol) and 1-(1H-imidazol-1-ylsulfonyl)-3-methyl-1H-imidazol-3-ium trifluoromethanesulfonate (3.45 g, 9.5 mmol) were mixed in $CH_3CN$ (20 mL). The mixture was stirred at ambient temperature overnight. The solvent was removed. The residue was purified by column chromatography on silica gel (EtOAc/petroleum ether=1:9 to 1:3) to provide 1-(1H-Imidazol-1-ylsulfonyl)-4-cyclopentylpiperidine. 1H NMR (400 MHz, $CDCl_3$): δ 7.91 (s, 1H), 7.24 (s, 1H), 7.14 (s, 1H), 3.87 (m, 2H), 2.51 (m, 2H), 1.83 (m, 4H), 1.54 (m, 5H), 1.33 (m, 2H), 1.08 (m, 3H).

To a solution of 1-(1H-Imidazol-1-ylsulfonyl)-4-cyclopentylpiperidine (500 mg, 1.8 mmol) in DCM (5 mL) was added MeOTf (0.3 g, 1.8 mmol). The reaction mixture was stirred at ambient temperature overnight. The solvent was removed and the resulting product was washed with ether to provide 1-((4-cyclopentylpiperidin-1-yl)sulfonyl)-3-methyl-1H-imidazol-3-ium trilfluoromethanesulfonate. $^1H$ NMR (400 MHz, $CD_3OD$): δ 9.59 (s, 1H), 8.02 (s, 1H), 7.78 (s, 1H), 4.00 (s, 3H), 3.95 (m, 2H), 2.87 (m, 2H), 1.81 (m, 4H), 1.54 (m, 6H), 1.23 (m, 4H).

The following compounds were synthesized in a similar manner:

1-((4-cyclohexylpiperidin-1-yl)sulfonyl)-3-methyl-1H-imidazol-3-ium trifluoromethanesulfonate (Intermediate for compound A65).

3-methyl-1-((4-(tetrahydro-2H-pyran-4-yl)piperidin-1-yl)sulfonyl)-1H-imidazol-3-ium trifluoromethanesulfonate (Intermediate for compound A78).

Route 25

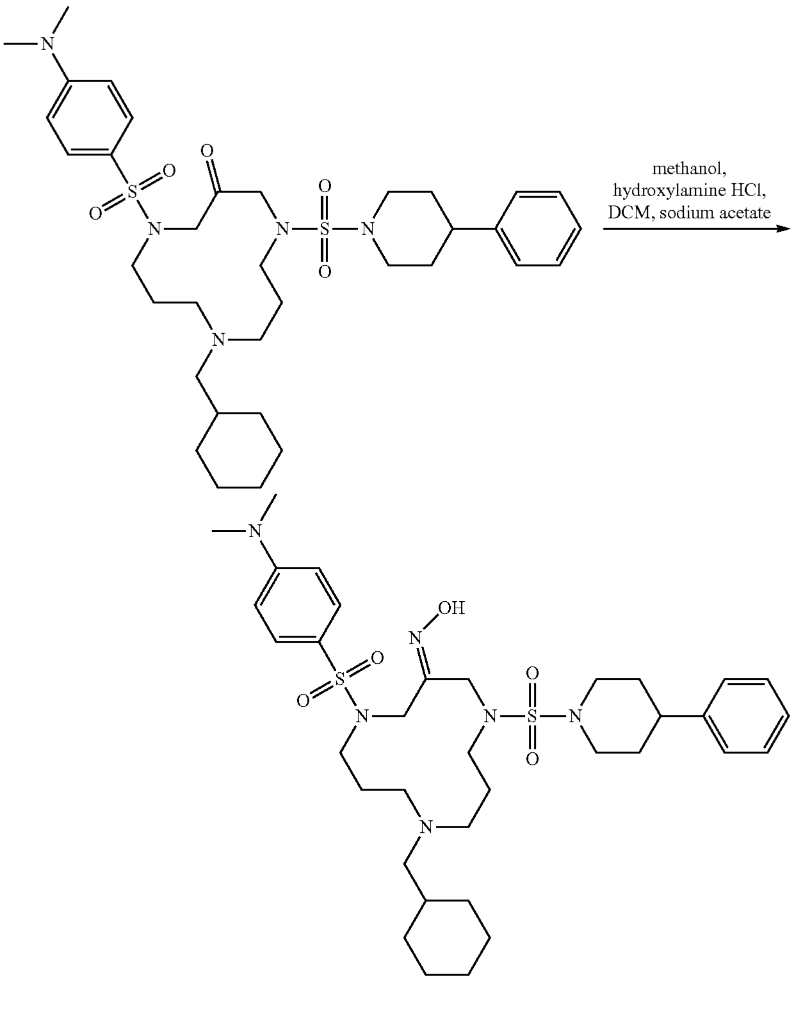

To 9-(cyclohexylmethyl)-1-((4-(dimethylamino)phenyl)sulfonyl)-5-((4-phenylpiperidin-1-yl)sulfonyl)-1,5,9-triazacyclododecan-3-one (19 mg, 0.028 mmol) in DCM (0.5 mL) and methanol (0.05 mL) was added hydroxylamine hydrochloride (5.8 mg, 0.083 mmol) and sodium acetate (6.8 mg, 0.083 mmol). The mixture was stirred for 6 h at ambient temperature then concentrated and purified by flash column chromatography (0-60% hexanes (1% DEA)/ethyl acetate) to provide 9-(cyclohexylmethyl)-1-((4-(dimethylamino) phenyl)sulfonyl)-5-((4-phenylpiperidin-1-yl)sulfonyl)-1,5,9-triazacyclododecan-3-one oxime (compound A75). MS(EI) for $C_{35}H_{54}N_6O_5S_2$, found 703 $[M+H]^+$.

Route 26

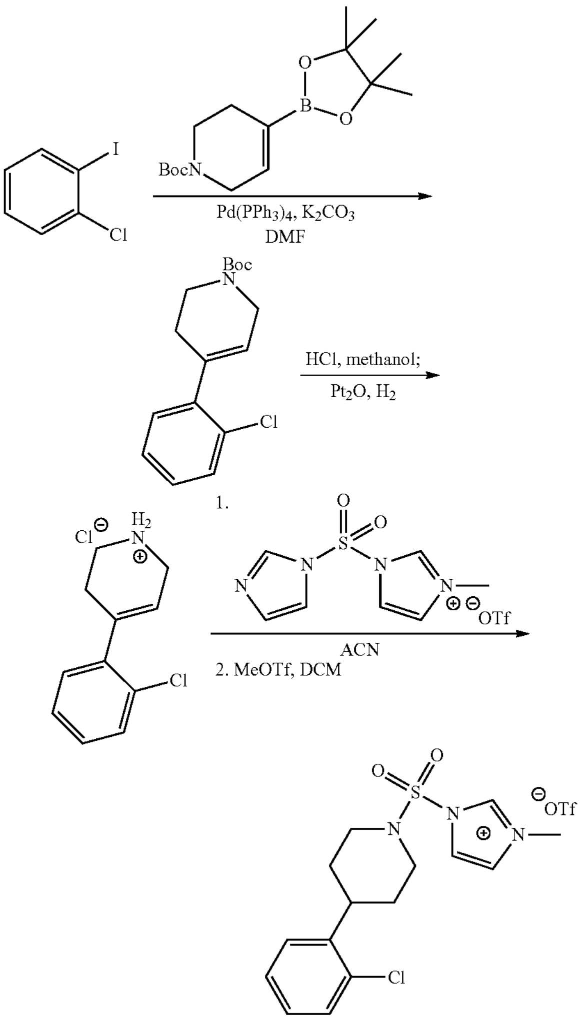

A solution of 1-chloro-2-iodobenzene (5.0 g, 21.1 mmol) in DMF (150 mL) was degassed and then filled with argon. tert-Butyl 4-(4,4,5,5-tetramethyl-1,3-dioxolan-2-yl)-5,6-dihydropyridine-1(2H)-carboxylate (7.13 g, 23.0 mmol), $Pd(dppf)Cl_2$ (1.7 g, 2.1 mmol) and potassium carbonate (8.69 g, 63.0 mmol) were added. The reaction mixture was stirred overnight at 110° C. and then cooled to ambient temperature. The mixture was poured into water and extracted with ethyl acetate. The combined organic layers were washed with brine, dried over anhydrous $Na_2SO_4$ and concentrated under reduced pressure. Purification by flash column chromatography on silica gel (ethyl acetate/hexanes=1:9 to 1:4) provided tert-Butyl 4-(2-chlorophenyl)-5,6-dihydropyridine-1(2M-carboxylate. $^1H$ NMR (400 MHz, $CDCl_3$): δ 7.37 (m, 1H), 7.18 (m, 3H), 5.67 (m, 1H), 4.06 (m, 2H), 3.64 (m, 2H), 2.46 (br s, 2H), 1.51 (s, 9H).

To a solution of tert-Butyl 4-(2-chlorophenyl)-5,6-dihydropyridine-1(2H)-carboxylate (2.0 g, 6.8 mmol) in MeOH (20 mL) was added HCl/MeOH (3M, 20 mL). The mixture was stirred at ambient temperature for 2 h. The resulting solution of 4-(2-chlorophenyl)-1,2,3,6-tetrahydropyridine hydrochloride was used directly in the next step.

To the solution of 4-(2-chlorophenyl)piperidine hydrochloride in MeOH/HCl was added $PtO_2$ (0.1 g). The mixture was hydrogenated at ambient temperature under 15 psi for 3 h. The catalyst was filtered off and the filtrate was concentrated to provide the product. $^1H$ NMR (400 MHz, DMSO-$d_6$): δ 9.19 (br s, 2H), 7.37 (m, 1H), 7.36 (m, 4H), 3.44 (m, 1H), 3.33 (m, 2H), 3.08 (m, 2H), 1.95 (m, 4H).

The free base (0.95 g, 4.8 mmol) and 1-(1H-imidazol-1-ylsulfonyl)-3-methyl-1H-imidazol-3-ium trifluoromethanesulfonate (1.76 g, 4.8 mmol) were mixed in $CH_3CN$ (10 mL). The mixture was stirred at ambient temperature overnight. The solvent was removed, and the residue was purified by column chromatography on silica gel to provide 1-(1H-imidazol-1-ylsulfonyl)-4-(2-chlorophenyl)piperidine. $^1H$ NMR (400 MHz, $CDCl_3$): δ 8.01 (s, 1H), 7.36 (m, 2H), 7.18 (m, 4H), 4.07 (m, 2H), 3.06 (m, 1H), 2.74 (m, 2H), 1.99 (m, 2H), 1.81 (m, 2H).

To a solution of 1-(1H-imidazol-1-ylsulfonyl)-4-(2-chlorophenyl)piperidine (501 mg, 1.5 mmol) in DCM (5 mL) was added MeOTf (0.27 g, 1.63 mmol). The mixture was stirred at ambient temperature overnight. The solvent was removed. The resulting product was washed with ether to provide 1-((4-(2-chlorophenyl)piperidin-1-yl)sulfonyl)-3-methyl-1H-imidazol-3-ium trifluoromethanesulfonate (Intermediate for compound A57). 1H NMR (400 MHz, $CD_3OD$): δ 9.65 (s, 1H), 8.08 (s, 1H), 7.82 (s, 1H), 7.39 (m, 4H), 4.16 (m, 2H), 4.02 (s, 3H), 3.31 (m, 3H), 2.03 (m, 2H), 1.85 (m, 2H).

The following compounds were synthesized in a similar manner:

1-((4-(3-chlorophenyl)piperidin-1-yl)sulfonyl)-3-methyl-1H-imidazol-3-ium trifluoromethanesulfonate (Intermediate for compound A58).

1-((4-(4-chlorophenyl)piperidin-1-yl)sulfonyl)-3-methyl-1H-imidazol-3-ium trifluoromethanesulfonate (Intermediate for compound A72).

Route 27

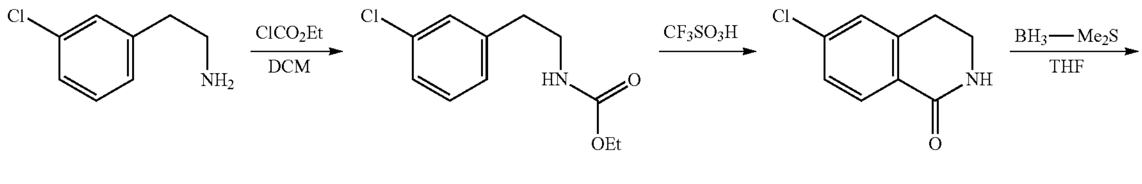

-continued

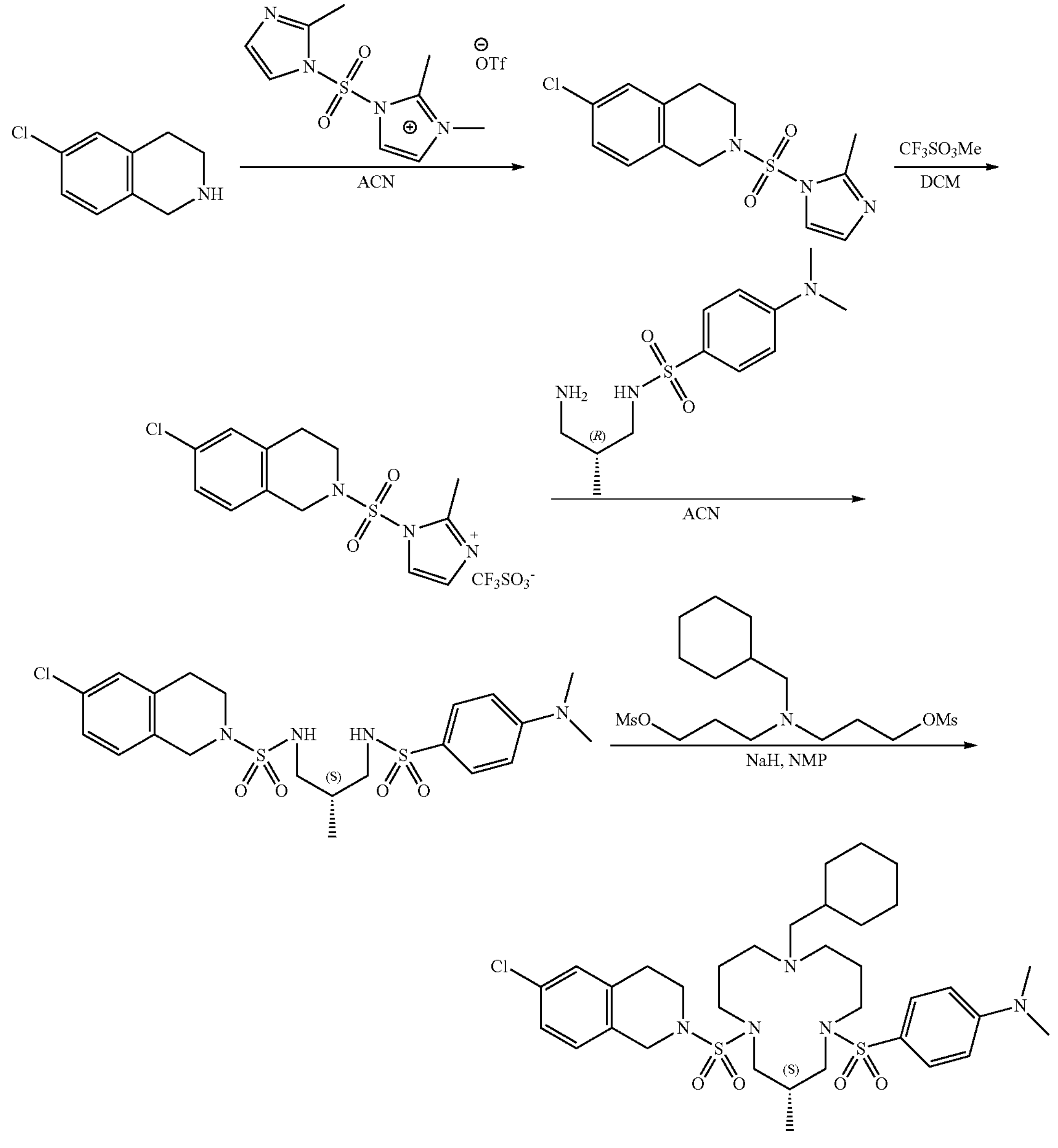

To a solution of 2-(3-chlorophenyl)ethanamine (149 g, 0.95 mol) and TEA (144 g, 1.42 mol) in DCM (1.5 L) was added dropwise ethyl carbonochloridate (107 g, 1.14 mol) at 0° C. The reaction mixture was stirred for 3 h and then washed with 1 N aqueous HCl (1 L) and saturated aqueous $NaHCO_3$ (600 mL). The DCM layer was dried over anhydrous sodium sulfate and concentrated to provide methyl 3-chlorophenethylcarbamate. $^1H$ NMR (400 MHz, $CDCl_3$): δ 7.27 (m, 3H), 7.08 (m, 1H), 4.77 (m, 1H), 3.78 (s, 3H), 3.44 (m, 2H), 2.80 (m, 2H).

Methyl 3-chlorophenethylcarbamate (193 g, 0.9 mol) was dissolved in $CF_3SO_3H$ (1.36 kg). The mixture was heated at 120° C. overnight. The mixture was cooled to ambient temperature and then poured into ice-water (4 L). The resulting product was collected by filtration and washed with ether to provide 6-chloro-3,4-dihydroisoquinolin-1(2H)-one. $^1H$ NMR (400 MHz, $CDCl_3$): δ 8.01 (m, 1H), 7.35 (m, 1H), 7.25 (m, 2H), 6.21 (br s, 1H), 3.60 (m, 2H), 3.01 (m, 2H).

To a solution of 6-chloro-3,4-dihydroisoquinolin-1(2H)-one (33 g, 182 mmol) in THF (330 mL) was added dropwise $BH_3$-$Me_2S$ (73 mL, 729 mmol). The reaction mixture was refluxed overnight. The mixture was cooled to ambient temperature and then quenched with 6N aqueous HCl (300 mL). THF was removed under reduced pressure and the remaining solution was refluxed overnight. The mixture was concentrated to a certain volume and then basified with 2N aqueous NaOH. The resulting mixture was extracted with DCM. The DCM layer was dried over anhydrous sodium sulfate and concentrated to provide 6-chloro-1,2,3,4-tetrahydroisoquinoline.

To a solution of 6-chloro-1,2,3,4-tetrahydroisoquinoline (18.5 g, 0.11 mol) in $CH_3CN$ (180 mL) was added compound 2,3-dimethyl-1-((2-methyl-1H-imidazol-1-yl)sulfonyl)-1H-imidazol-3-ium trifluoromethanesulfonate (43.5 g, 0.11 mol, Reference: *J. Org. Chem.* 2002, 68, 115-119.). The reaction mixture was stirred overnight at 30° C. The solvent was removed and the residue was purified by column chromatography on silica gel (EtOAc/Petroleum ether=1:1) to provide 6-chloro-2-(2-methyl-1H-imidazol-1-ylsulfonyl)-1,2,3,4-tetrahydroisoquinoline. $^1$H NMR (400 MHz, $CDCl_3$): δ 7.21 (m, 1H), 7.18 (s, 1H), 7.02 (m, 1H), 6.94 (m, 1H), 4.45 (s, 2H), 3.62 (m, 2H), 2.92 (m, 2H), 2.67 (s, 3H).

To a solution of 6-chloro-2-(2-methyl-1H-imidazol-1-ylsulfonyl)-1,2,3,4-tetrahydroisoquinoline (25.5 g, 82 mmol) in DCM (260 mL) was added $CF_3SO_3Me$ (13.45 g, 82 mmol). The reaction mixture was stirred at ambient temperature overnight. The solvent was removed and the residue was washed with ether to provide 1-(6-chloro-3,4-dihydroisoquinolin-2(1H)-ylsulfonyl)-2,3-dimethyl-1H-imidazol-3-ium trifluoromethanesulfonate.

To a solution of 1-(6-Chloro-3,4-dihydroisoquinolin-2(1H)-ylsulfonyl)-2,3-dimethyl-1H-imidazol-3-ium trifluoromethanesulfonate (8.7 g, 18.4 mmol) in $CH_3CN$ (100 mL) was added (R)—N-(3-amino-2-methylpropyl)-4-(dimethylamino)benzenesulfonamide (5.0 g, 18.4 mmol). The reaction mixture was stirred overnight at 30° C. The solvent was removed and the residue was purified by column chromatography on silica gel (EtOAc/Petroleum ether=1:3 to 1:1) to provide (S)-6-chloro-N-(3-((4-(dimethylamino)phenyl)sulfonamido)-2-methylpropyl)-3,4-dihydroisoquinoline-2(1H)-sulfonamide (compound B10). $^1$H NMR (400 MHz, $CDCl_3$): δ 7.85 (m, 2H), 7.43 (m, 2H), 7.18 (m, 2H), 7.03 (m, 1H), 4.35 (s, 2H), 3.48 (m, 2H), 3.18 (s, 6H), 3.15 (m, 1H), 2.95 (m, 6H), 2.85 (m, 1H), 1.89 (m, 1H), 0.89 (m, 3H).

(S)-6-Chloro-N-(3-((4-(dimethylamino)phenyl)sulfonamido)-2-methylpropyl)-3,4-dihydroisoquinoline-2(1H)-sulfonamide (300 mg, 0.6 mmol) was dissolved in NMP (3 mL) and NaH (60%, 96 mg, 2.4 mmol) was added. The mixture was stirred for 30 min at ambient temperature and then heated at 80° C. for 20 min. The mixture was cooled to ambient temperature. A solution of ((cyclohexylmethyl)azanediyl)bis(propane-3,1-diyl) dimethanesulfonate (231 mg, 0.6 mmol) in NMP (1 mL) was added. The reaction mixture was heated at 80° C. for 1 h then cooled to ambient temperature and quenched with water (10 mL). The resulting mixture was extracted with ethyl acetate (15 mL). The extract was washed with brine and concentrated. The residue was purified by column chromatography on silica gel (EtOAc/petroleum ether=1:8 to 1:3) to provide compound A87. MS(EI) for $C_{34}H_{52}ClN_5O_4S_2$, found 695 $[M+H]^+$. $^1$H NMR (400 MHz, $CDCl_3$): δ 7.59 (d, J=8.8 Hz, 2H), 7.15 (m, 2H), 7.00 (m, 1H), 6.68 (d, J=8.8 Hz, 2H), 4.34 (m, 2H), 3.71 (m, 2H), 3.45 (m, 2H), 3.17 (m, 3H), 3.05 (s, 6H), 2.88 (m, 4H), 2.25 (m, 2H), 2.15 (m, 6H), 1.95 (m, 2H), 1.65 (m, 8H), 1.23 (m, 6H), 0.95 (m, 5H).

The following compounds were synthesized in a similar manner:

| No. | IUPAC | $[M + H]^+$ | $^1$H NMR |
|---|---|---|---|
| B11 | N-[(2R)-3-{[(6-chloro-1,2,3,4-tetrahydroisoquinolin-2-yl)sulfonyl]amino}-2-methylpropyl]-4-(dimethylamino)benzene-1-sulfonamide | 501 | |
| A90 | 4-{[(3S)-9-(cyclohexylmethyl)-3-methyl-5-{[(3S)-3-phenylpyrrolidin-1-yl]sulfonyl}-1,5,9-triazacyclododecan-1-yl]sulfonyl}-N,N-dimethylaniline | 674 | |
| A91 | 4-{[(3S)-9-(cyclohexylmethyl)-3-methyl-5-{[(3R)-3-phenylpyrrolidin-1-yl]sulfonyl}-1,5,9-triazacyclododecan-1-yl]sulfonyl}-N,N-dimethylaniline | 674 | |
| A92 | 4-{[(3S)-9-(cyclohexylmethyl)-3-methyl-5-[(4-phenoxypiperidin-1-yl)sulfonyl]-1,5,9-triazacyclododecan-1-yl]sulfonyl}-N,N-dimethylaniline | 704 | |
| A93 | 4-{[(3S)-9-(cyclohexylmethyl)-3-methyl-5-{[4-(pyrimidin-2-yl)piperazin-1-yl]sulfonyl}-1,5,9-triazacyclododecan-1-yl]sulfonyl}-N,N-dimethylaniline | 691 | |
| A94 | 4-{[(3S)-9-(cyclohexylmethyl)-5-{[4-(2-fluorophenyl)piperazin-1-yl]sulfonyl}-3-methyl-1,5,9-triazacyclododecan-1-yl]sulfonyl}-N,N-dimethylaniline | 707 | |
| A95 | 4-{[(3S)-9-(cyclohexylmethyl)-5-{[4-(3-fluorophenyl)piperazin-1-yl]sulfonyl}-3-methyl-1,5,9-triazacyclododecan-1-yl]sulfonyl}-N,N-dimethylaniline | 707 | |
| A96 | 4-{[(3S)-9-(cyclohexylmethyl)-5-{[4-(4-fluorophenyl)piperazin-1-yl]sulfonyl}-3-methyl-1,5,9-triazacyclododecan-1-yl]sulfonyl}-N,N-dimethylaniline | 707 | |
| A97 | 4-{[(3S)-9-(cyclohexylmethyl)-3-methyl-5-{[4-(2-methylphenyl)piperazin-1-yl]sulfonyl}-1,5,9-triazacyclododecan-1-yl]sulfonyl}-N,N-dimethylaniline | 703 | |

-continued

| No. | IUPAC | [M + H]+ | $^1$H NMR |
|---|---|---|---|
| A98 | 4-{[(3S)-9-(cyclohexylmethyl)-3-methyl-5-{[4-(3-methylphenyl)piperazin-1-yl]sulfonyl}-1,5,9-triazacyclododecan-1-yl]sulfonyl}-N,N-dimethylaniline | 703 | |
| A99 | 4-{[(3S)-9-(cyclohexylmethyl)-3-methyl-5-{[4-(4-methylphenyl)piperazin-1-yl]sulfonyl}-1,5,9-triazacyclododecan-1-yl]sulfonyl}-N,N-dimethylaniline | 703 | |
| A100 | 4-{[(3S)-5-[(4-benzoylpiperazin-1-yl)sulfonyl]-9-(cyclohexylmethyl)-3-methyl-1,5,9-triazacyclododecan-1-yl]sulfonyl}-N,N-dimethylaniline | 717 | |
| A101 | 4-{[(3S)-9-(cyclohexylmethyl)-3-methyl-5-[(3-phenylazetidin-1-yl)sulfonyl]-1,5,9-triazacyclododecan-1-yl]sulfonyl}-N,N-dimethylaniline | 660 | |
| A102 | 4-{[(3S)-9-(cyclohexylmethyl)-5-{[4-(4-fluoro-2-methylphenyl)piperazin-1-yl]sulfonyl}-3-methyl-1,5,9-triazacyclododecan-1-yl]sulfonyl}-N,N-dimethylaniline | 721 | |
| A76 | 4-{[(3R)-9-(cyclohexylmethyl)-3-methyl-5-[(4-phenylpiperidin-1-yl)sulfonyl]-1,5,9-triazacyclododecan-1-yl]sulfonyl}-N,N-dimethylaniline | 688 | $^1$H NMR (400 MHz, $CDCl_3$): δ 7.60 (d, J = 8.8 Hz, 2 H), 7.33 (m, 5 H), 6.82 (d, J = 8.8 Hz, 2 H), 3.77 (m, 4 H), 3.28 (m, 1 H), 3.18 (m, 3 H), 3.05 (s, 6 H), 2.88 (m, 4 H), 2.61 (m, 1 H), 2.41 (m, 1 H), 2.21 (m, 4 H), 2.01 (m, 3 H), 1.85 (m, 8 H), 1.25 (m, 6 H), 0.93 (m, 3 H), 0.82 (m, 4 H). |
| A77 | 4-{[(3S)-9-(cyclohexylmethyl)-3-methyl-5-[(4-phenylpiperidin-1-yl)sulfonyl]-1,5,9-triazacyclododecan-1-yl]sulfonyl}-N,N-dimethylaniline | 688 | $^1$H NMR (400 MHz, $CDCl_3$): δ 7.60 (d, J = 8.8 Hz, 2 H), 7.33 (m, 5 H), 6.82 (d, J = 8.8 Hz, 2 H), 3.77 (m, 4 H), 3.28 (m, 1 H), 3.18 (m, 3 H), 3.05 (s, 6 H), 2.88 (m, 4 H), 2.61 (m, 1 H), 2.41 (m, 1 H), 2.21 (m, 4 H), 2.01 (m, 3 H), 1.85 (m, 8 H), 1.25 (m, 6 H), 0.93 (m, 3 H), 0.82 (m, 4 H). |

Route 28

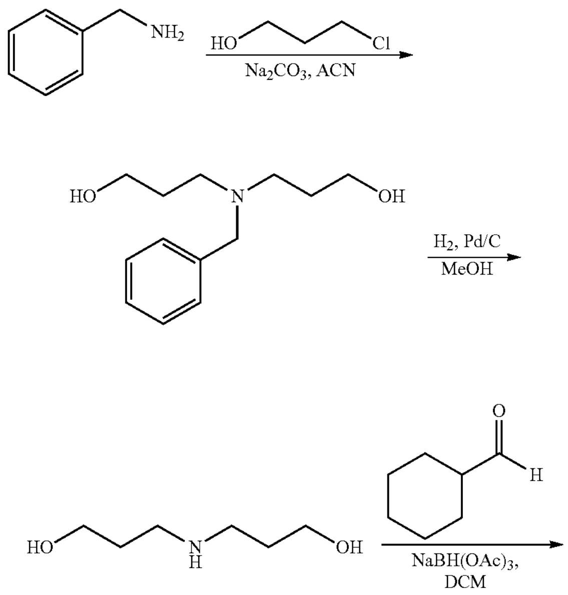

-continued

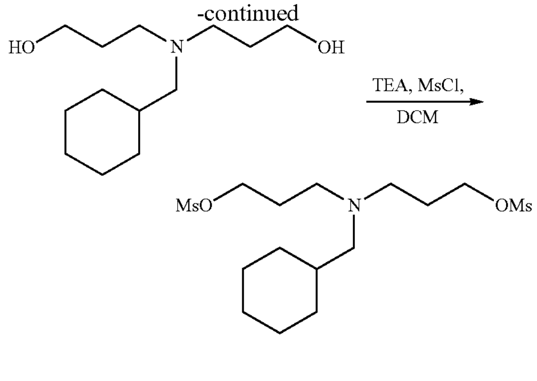

To a solution of benzylamine (37.7 g, 0.350 mol) in $CH_3CN$ (1 L) were added 3-chloropropan-1-ol (100 g, 1.06 mol) and $Na_2CO_3$ (131 g, 1.24 mol). The reaction mixture was refluxed for 50 h and then cooled to ambient temperature. The mixture was filtered and the filtrate was concentrated under reduced pressure. The residue was purified by column chromatography on silica gel (MeOH/DCM=1:99 to 3:97) to provide 3,3'-(benzylazanediyl)dipropan-1-ol. $^1$H NMR (400 MHz, $CDCl_3$): δ 7.34 (m, 5H), 3.70 (m, 4H), 3.61 (s, 2H), 3.48 (s, 2H), 2.68 (m, 4H), 1.78 (m, 4H).

To a solution of 3,3'-(benzylazanediyl)dipropan-1-ol (55 g) in MeOH (500 mL) was added Pd/C (10 g). The mixture was hydrogenated at ambient temperature under 15 kg pressure for 6 h. The mixture was filtered and the filtrate was concentrated to provide 3,3'-azanediyldipropan-1-ol. $^1$H NMR (400 MHz, $CDCl_3$): δ 3.78 (m, 4H), 3.46 (s, 2H), 2.84 (m, 4H), 1.75 (m, 4H).

To a solution of 3,3'-azanediyldipropan-1-ol (15 g, 113 mmol) in DCM (300 mL) were added cyclohexanecarbaldehyde (18.8 g, 141 mmol) and $NaBH(OAc)_3$ (72.5 g, 0.34 mol). The mixture was stirred for 0.5 h and HOAc (20.4 g, 0.34 mol) was added. The reaction mixture was stirred at ambient temperature overnight. The mixture was quenched with water (150 mL) and then adjusted to pH=12 with NaOH. The organic layer was separated, dried over anhydrous sodium sulfate and concentrated. The residue was purified by column chromatography on silica gel (MeOH/DCM=3:97 to 1:9) to provide 3,3'-((cyclohexylmethyl)azanediyl)bis(propan-1-ol). $^1$H NMR (400 MHz, $CDCl_3$): δ 3.75 (m, 4H), 2.64 (m, 4H), 2.18 (m, 2H), 1.75 (m, 9H), 1.55 (m, 1H), 1.21 (m, 3H), 0.89 (m, 1H).

To a solution of compound 3,3'-((cyclohexylmethyl)azanediyl)bis(propan-1-ol) (1.2 g, 5.2 mmol) and TEA (1.0 g, 10.4 mmol) in DCM (15 mL) was added MsCl (1.18 g, 10.4 mmol) at 0° C. The reaction mixture was stirred for 4 h and then quenched with water (15 mL). The DCM layer was separated, dried over anhydrous sodium sulfate and concentrated to provide compound ((cyclohexylmethyl)azanediyl)bis(propane-3,1-diyl) dimethanesulfonate. The dimesylate was used immediately without further purification.

Route 29

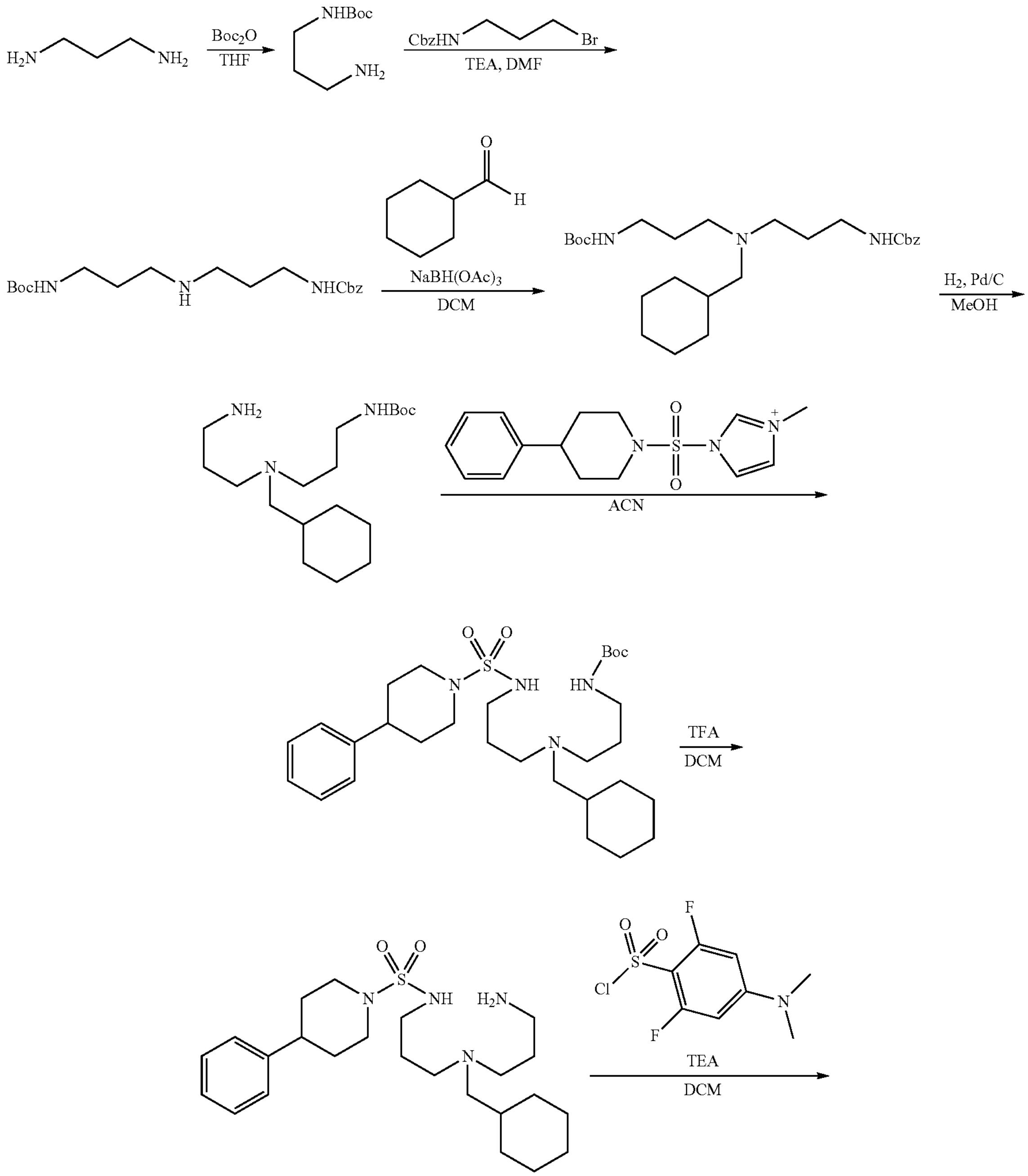

-continued

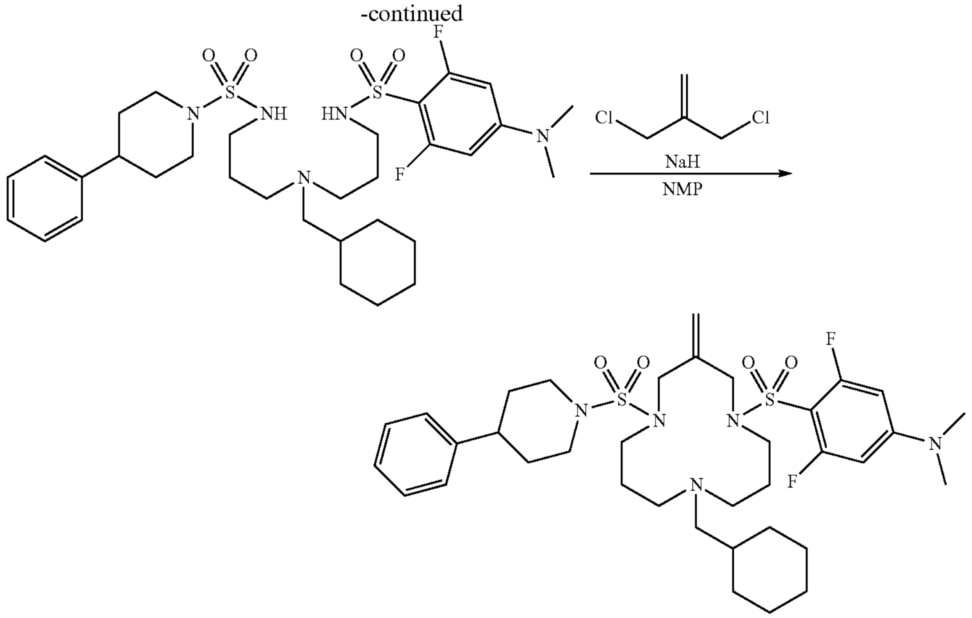

To a solution of propane-1,3-diamine (100 g, 1.35 mol) in THF (800 mL) was added a solution of $Boc_2O$ (73.6 g, 0.34 mol) in THF (200 mL) at 0=10° C. The reaction mixture was stirred for 3 h and water (1 L) was added. The resulting mixture was extracted with ethyl acetate (500 mL×2). The organic layers were combined and concentrated to a volume of 400 mL. Hexane (300 mL) was added and to the resulting solution was added 15% aqueous oxalic acid (1 L). The mixture was stirred for 0.5 h. The organic layer was decanted and the aqueous layer was adjusted to pH=10 with 3N aqueous NaOH. The resulting mixture was extracted with DCM (600 mL×2). The combined extracts were dried over anhydrous sodium sulfate and concentrated to provide tert-Butyl 3-aminopropylcarbamate. $^1H$ NMR (400 MHz, $CDCl_3$): δ 5.03 (br s, 1H), 3.23 (br s, 2H), 2.69 (m, 2H), 1.71 (m, 2H), 1.44 (s, 9H).

Triethylamine (4.70 g, 46.5 mmol) was added dropwise to a stirred mixture of benzyl 3-bromopropylcarbamate (4.2 g, 15.5 mmol) to provide tert-Butyl 3-aminopropylcarbamate (2.7 g, 15.5 mmol) in DMF (50 mL) at ambient temperature. The reaction mixture was heated at 70° C. for 1 h. The majority of DMF was removed under vacuum and the remaining mixture was diluted with water (120 mL) and washed with ether (150 mL×4) to remove most of the dialkylated by-product. The aqueous layer was adjusted to pH=11 with 1 N aqueous NaOH and extracted with ether (200 mL). The extract was washed with water (150 mL×3) to remove unreacted tert-Butyl 3-aminopropylcarbamate, dried with anhydrous sodium sulfate and concentrated to provide tert-butyl (3-((3-(((benzyloxy)carbonyl)amino)propyl)amino)propyl)carbamate. $^1H$ NMR (400 MHz, $CDCl_3$): 7.36 (m, 5H), 5.60 (br s, 1H), 5.11 (m, 3H), 3.30 (m, 2H), 3.20 (m, 2H), 2.68 (m, 4H), 1.70 (m, 5H), 1.44 (s, 9H).

To a solution of tert-butyl (3-((3-(((benzyloxy)carbonyl) amino)propyl)amino)propyl)carbamate (100 mg, 0.27 mmol) in DCM (5 mL) was added cyclohexanecarbaldehyde (31 mg, 0.27 mmol) and HOAc (30 mg, 1.1 mmol). The mixture was stirred for 0.5 h and $NaBH(OAc)_3$ (235 g, 1.1 mmol) was added in one portion. The reaction mixture was stirred for 4 h. TLC analysis showed 50% conversion and another portion of cyclohexane carbaldehyde (15 mg, 0.13 mmol) was added. The reaction mixture was stirred overnight at ambient temperature. Water (10 mL) was added to quench the reaction and the mixture was adjusted to pH=2 by addition of HOAc. The mixture was stirred for another 0.5 h and then adjusted to pH=12 with aqueous NaOH (1N). The organic layer was separated and concentrated to provide tert-butyl (3-((3 (((benzyloxy)carbonyl)amino)propyl)(cyclohexylmethyl)amino)propyl)carbamate. $^1H$ NMR (400 MHz, $CDCl_3$): δ 7.27 (m, 5H), 6.12 (br s, 1H), 5.55 (br s, 1H), 5.01 (s, 3H), 3.34 (m, 2H), 3.18 (m, 2H), 3.08 (m, 2H), 2.80 (m, 4H), 1.65 (m, 9H), 1.44 (s, 9H), 1.12 (m, 6H).

To a solution of tert-butyl (3-((3-(((benzyloxy)carbonyl) amino)propyl) (cyclohexylmethyl)amino)propyl)carbamate (0.50 g, 1.1 mmol) in MeOH (5 mL) was added Pd/C (0.1 g). The mixture was hydrogenated under 15 psi pressure for 3 h. The mixture was filtered and the filtrate was concentrated to provide tert-butyl (3-((3-aminopropyl)(cyclohexylmethyl)amino)propyl)carbamate. $^1H$ NMR (400 MHz, $CDCl_3$): δ 5.78 (br s, 1H), 3.19 (br s, 2H), 2.78 (m, 2H), 2.40 (m, 4H), 2.13 (m, 2H), 1.98 (br s, 2H), 1.67 (m, 9H), 1.44 (s, 9H), 1.12 (m, 4H), 0.89 (m, 2H).

To a solution of tert-butyl (3-((3-aminopropyl)(cyclohexylmethyl)amino)propyl) carbamate (1.2 g, 3.7 mmol) in $CH_3CN$ (10 mL) was added 3-methyl-1-(4-phenylpiperidin-1-ylsulfonyl)-1H-imidazol-3-ium (1.47 g, 3.7 mmol). The reaction mixture was stirred at ambient temperature overnight. The solvent was removed and the residue was purified by column chromatography on silica gel to provide tert-butyl 3-((cyclohexylmethyl)(3-(4-phenylpiperidine-1-sulfonamido)propyl) amino)propylcarbamate.

To a solution of tert-butyl 3-((cyclohexylmethyl)(3-(4-phenylpiperidine-1-sulfonamido)propyl) amino)propylcarbamate (0.85 g, 1.5 mmol) in DCM (15 mL) was added TFA (10 mL). The reaction mixture was stirred at ambient temperature for 3 h. The solvent was removed and the residue was dissolved in DCM (50 mL). The solution was basified with 1 N aqueous NaOH. The DCM layer was dried over anhydrous $Na_2SO_4$ and concentrated to provide N-(3-((3-aminopropyl)(cyclohexylmethyl)amino)propyl)-4-phenylpiperidine-1-sulfonamide.

To a solution of N-(3-((3-aminopropyl)(cyclohexylmethyl)amino)propyl)-4-phenylpiperidine-1-sulfonamide (90 mg, 0.20 mmol) in DCM (5 mL) was added TEA (40 mg, 0.4 mmol). The mixture was cooled 0° C. and a solution of 4-(dimethylamino)-2,6-difluorobenzene-1-sulfonyl chloride (60 mg, 0.24 mmol) in DCM (1 mL) was added. The reaction mixture was stirred at ambient temperature for 2 h. The mixture was diluted with DCM (30 mL) and then washed with water (20 mL). The organic layer was dried over anhydrous $Na_2SO_4$ and concentrated. The residue was purified by column chromatography on silica gel to provide N-(3-((cyclohexylmethyl)(3-(4-(dimethylamino)phenylsulfonamido)propyl) amino)propyl)-4-phenylpiperidine-1-sulfonamide.

To a solution of N-(3-((cyclohexylmethyl)(3-(4-(dimethylamino)phenylsulfonamido)propyl) amino)propyl)-4-phenylpiperidine-1-sulfonamide (80 mg, 0.123 mmol) in NMP (2 mL) was added NaH (12 mg, 0.29 mmoL). The mixture was heated at 80° C. for 0.5 h. The mixture was cooled to ambient temperature and a solution of 3-chloro-2-(chloromethyl)prop-1-ene (15 mg, 0.12 mmol) in NMP (0.1 mL) was added. The reaction mixture was heated at 80° C. for 2 h. The mixture was cooled to ambient temperature and water (20 mL) was added. The resulting mixture was extracted with ethyl acetate (15 mL). The organic layer was dried over anhydrous sodium sulfate and concentrated. The residue was purified by column chromatography on silica gel (ethyl acetate/hexane=10:30 to 20:10) to provide compound A86. MS(EI) for $C_{36}H_{53}F_2N_5O_4S_2$, found 733 $[M+H]^+$. $^1H$ NMR (400 MHz, $CDCl_3$): δ 7.31 (m, 5H), 6.18 (m, 2H), 5.25 (m, 2H), 4.05 (s, 2H), 3.87 (m, 4H), 3.20 (m, 4H), 3.05 (s, 6H), 2.88 (m, 2H), 2.41 (m, 4H), 2.05 (m, 5H), 1.75 (m, 9H), 1.27 (m, 6H), 0.85 (m, 2H).

Route 30

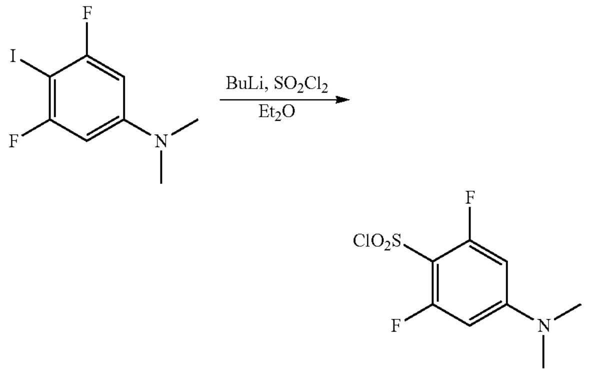

To a solution of 3,5-difluoro-4-iodo-N,N-dimethylaniline (500 mg, 1.77 mmol) in ether (5 mL) was added dropwise n-BuLi (0.71 mL, 1.77 mmol) at −78° C. The mixture was stirred for 0.5 h at −78° C. Sulfuryl dichloride (358 mg, 1.5 mmol) was added. The reaction mixture was stirred for another 0.5 h. The mixture was quenched with water (10 mL) and then extracted with ethyl acetate (15 mL). The organic layer was dried over anhydrous $Na_2SO_4$ and concentrated. The residue was purified by column chromatography on silica gel to provide the crude product, which was further recrystallized from hexane/EtOAc (10:1) to provide 4-(dimethylamino)-2,6-difluorobenzene-1-sulfonyl chloride. $^1H$ NMR (400 MHz, $CDCl_3$): δ 6.21 (s, 1H), 6.18 (s, 1H), 3.09 (s, 6H).

Route 31

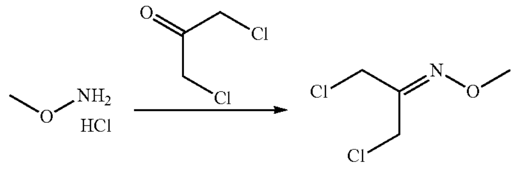

To a suspension of 1, 3-dichloropropan-2-one (5.0 g, 39.5 mmol) in $H_2O$ (50 mL) was added O-methylhydroxylamine hydrochloride (3.5 g, 41.5 mmol) and the reaction mixture was stirred at ambient temperature for 1 h. The organic layer was separated, diluted with ether and concentrated under vacuum (<30° C.) to provide 1,3-dichloropropan-2-one O-methyl oxime. $^1H$ NMR (400 MHz, $CDCl_3$): δ4.33 (s, 2H), 4.27 (s, 2H), 3.94 (s, 3H).

Route 32

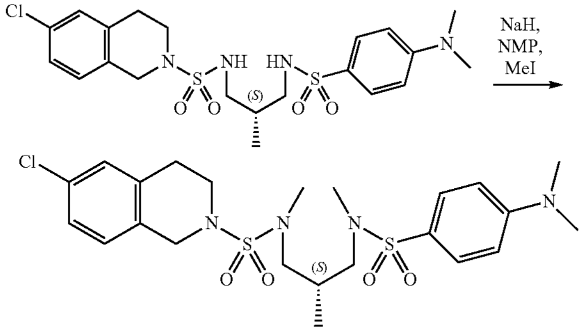

To (S)-6-chloro-N-(3-((4-(dimethylamino)phenyl)sulfonamido)-2-methylpropyl)-3,4-dihydroisoquinoline-2(1H)-sulfonamide (100.0 mg, 0.200 mmol) in dry NMP (3 mL) at 0° C. was added NaH (24.0 mg, 0.600 mmol) and the mixture was stirred at ambient temp for 20 min and turned from a cloudy mixture to nearly transparent during this time. Iodomethane (27 μL, 0.440 mmol) was added and the mixture was allowed to stir at ambient temp for 1 h and did not progress past ~50% completion, so the same amount of NaH and methyl iodide was added again and the reaction was complete after an additional hour at ambient temp. Brine (10 mL) and EA (10 mL) was added. The aqueous layer was extracted with EA (1×5 mL) and the organics were combined, washed with brine (3×10 mL), dried with sodium sulfate, filtered and concentrated. FCC (hexanes/EA 0-70%) provided compound B12. MS(EI) for $C_{23}H_{33}ClN_4O_4S_2$, found 529 $[M+H]^+$.

Route 33

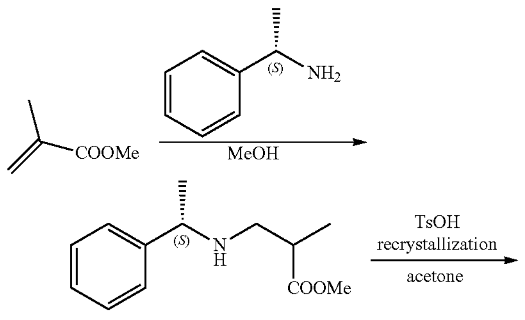

mixture)

-continued

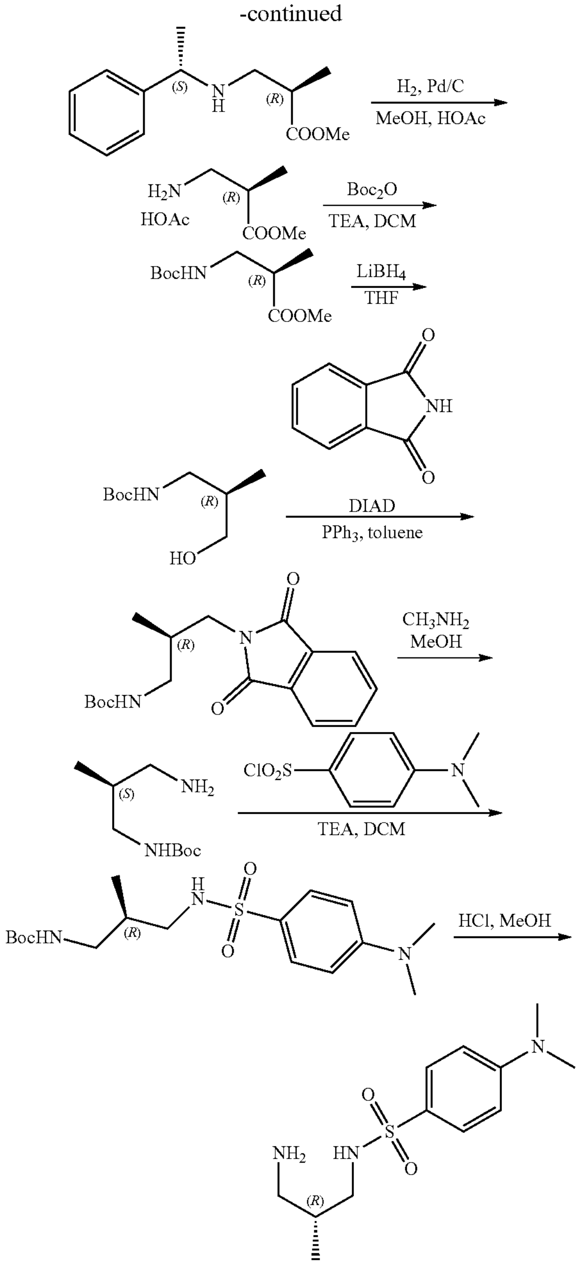

To a solution of methyl methacrylate (300 g, 3.0 mol) in MeOH (1.5 L) was added (S)-1-phenylethanamine (363 g, 3 mol). The reaction mixture was refluxed for 5 days. The mixture was concentrated and the residue was purified by column chromatography on silica gel (EtOAc/Petroleum ether=1:9 to 1:1) to provide methyl 2-methyl-3-((S)-1-phenylethylamino)propanoate. $^1$H NMR (400 MHz, $CDCl_3$): δ 7.25 (m, 5H), 3.75 (m, 1H), 3.69 (s, 3H), 2.75 (m, 3H), 1.39 (m, 1H), 1.28 (m, 3H), 1.09 (m, 3H).

To a solution of 2-methyl-3-((S)-1-phenylethylamino) propanoate (440 g, 1.99 mol) in acetone (6 L) was added TsOH—$H_2O$ (378 g, 1.99 mol). The mixture was stirred at ambient temperature for 1 h. The precipitated solid was collected by filtration and dried to provide a salt (300 g) which was suspended in acetone (2 L) and refluxed for 1 h. The mixture was cooled to ambient temperature and the resulting precipitate was collected by filtration to provide a salt which was suspended in DCM (2 L) and saturated aqueous $K_2CO_3$ (1.5 L). The mixture was stirred for 0.5 h and the solid was dissolved. The DCM layer was separated, dried over anhydrous $Na_2SO_4$ and concentrated to provide (R)-methyl 2-methyl-3-((S)-1-phenylethylamino)propanoate.

To a solution of (R)-methyl 2-methyl-3-((S)-1-phenylethylamino)propanoate (140 g, 0.630 mol) in MeOH (1.4 L) were added HOAc (30 mL) and Pd/C (15 g). The mixture was hydrogenated under 20 kg pressure at 60° C. for 6 h. The catalyst was removed by filtration and the filtrate was concentrated to provide (R)-methyl 3-amino-2-methylpropanoate. $^1$H NMR (400 MHz, $CDCl_3$): δ 5.09 (br, 3H), 3.72 (s, 3H), 3.05 (m, 1H), 2.93 (m, 1H), 2.75 (m, 1H), 1.23 (d, J=7.2 Hz, 3H).

To a solution of (R)-methyl 3-amino-2-methylpropanoate (112 g, 0.63 mol) in dichloromethane (1 L) were added TEA (160 g, 1.58 mol) and $Boc_2O$ (152 g, 0.69 mol) at 0-5° C. The reaction mixture was allowed to warm to ambient temperature and stirred overnight. The mixture was washed with water (1 L), 2N aqueous HCl (1 L) and saturated aqueous $NaHCO_3$ (1 L), respectively. The organic layer was dried over anhydrous $Na_2SO_4$ and concentrated. The residue was purified by column chromatography on silica gel to provide (R)-methyl 3-(tert-butoxycarbonylamino)-2-methylpropanoate. $^1$H NMR (400 MHz, $CDCl_3$): δ 4.94 (br s, 1H), 3.70 (s, 3H), 3.31 (m, 2H), 2.70 (m, 1H), 1.52 (s, 9H), 1.18 (d, J=7.2 Hz, 3H).

To a solution of (R)-methyl 3-(tert-butoxycarbonylamino)-2-methylpropanoate (6 g, 51.3 mmol) in THF (60 mL) was added $LiBH_4$ (1.12 g, 102 mmol). The reaction mixture was stirred overnight at ambient temperature. The mixture was quenched with water (30 mL) followed by addition of 1 N aqueous HCl to adjust pH=2~3. The resulting mixture was extracted with ethyl acetate and the extract was washed with saturated aqueous $NaHCO_3$, dried over anhydrous $Na_2SO_4$ and concentrated to provide (R)-tert-Butyl 3-hydroxy-2-methylpropylcarbamate. $^1$H NMR (400 MHz, $CDCl_3$): δ 3.57 (m, 1H), 3.37 (m, 2H), 3.05 (m, 1H), 1.77 (m, 1H), 1.48 (s, 9H), 0.88 (d, J=7.2 Hz, 3H).

To a solution of (R)-tert-Butyl 3-hydroxy-2-methylpropylcarbamate (2.5 g, 13.2 mmol) in toluene (25 mL) were added $PPh_3$ (4.15 g, 15.8 mmol) and isoindoline-1,3-dione (2.72 g, 18.5 mmol). The mixture was cooled to 0~5° C. and DIAD (3.2 g, 15.8 mmol) was added dropwise. The reaction mixture was stirred at ambient temperature for 3 h. The precipitated solid was filtered off and the filtrate was concentrated. The residue was purified by column chromatography on silica gel (EtOAc/Petroleum ether=1:9 to 1:1) to provide (R)-tert-Butyl 3-(1,3-dioxoisoindolin-2-yl)-2-methylpropylcarbamate. $^1$H NMR (400 MHz, $CDCl_3$): δ 7.85 (m, 2H), 7.47 (m, 2H), 5.23 (br s, 1H), 3.64 (m, 2H), 3.03 (br s, 2H), 2.13 (m, 1H), 1.43 (s, 9H), 0.96 (d, J=6.4 Hz, 3H).

To a solution of (R)-tert-Butyl 3-(1,3-dioxoisoindolin-2-yl)-2-methylpropylcarbamate (40 g, 8.83 mmol) in MeOH (200 mL) was added methylamine solution (7.8 g, 30% in MeOH). The reaction mixture was heated at 60° C. for 6 h. The solvent was removed under reduced pressure. The residue was suspended in ether (300 mL) and then stirred for 0.5 h. The solid was filtered off and the filtrate was concentrated under reduced pressure to provide (S)-tert-Butyl 3-amino-2-methylpropylcarbamate.

To a solution of (S)-tert-Butyl 3-amino-2-methylpropylcarbamate (12.5 g, 66.5 mmol) in DCM (250 mL) was added TEA (10.3 g, 101.7 mmol). The mixture was cooled to 0-5° C. and 4-(dimethylamino) benzene-1-sulfonyl chloride (16 g, 72 mmol) was added. The reaction mixture was stirred at ambient temperature for 3 h. The mixture was washed with water and the organic phase was concentrated under reduced pressure. The residue was purified by column chromatography on silica gel (EtOAc/Petroleum ether=1:9 to 3:7) to provide (R)-tert-Butyl 3-(4-(dimethylamino)phenylsulfonamido)-2-methylpropylcarbamate. $^1$H NMR (400 MHz, $CDCl_3$): δ 7.70 (d, J=8.8 Hz, 2H), 6.71 (d, J=8.8 Hz, 2H), 5.45 (m, 1H), 4.72 (m, 1H), 3.18 (m, 1H), 3.04 (s, 6H), 2.98 (m, 2H), 2.75 (m, 1H), 1.78 (m, 1H), 1.41 (s, 9H), 0.87 (m, J=6.8 Hz, 3H).

To a solution of (R)-tert-Butyl 3-(4-(dimethylamino)phenylsulfonamido)-2-methylpropylcarbamate (21 g, 59.3 mmol) in MeOH (150 mL) was added 4N HCl/MeOH (150 mL). The mixture was stirred for 3 h at ambient temperature. The solvent was removed under reduced pressure. The resulting solid was suspended in DCM (200 mL) and saturated aqueous $K_2CO_3$ (150 mL) was added. The mixture was stirred for 5 min and the organic layer was separated, dried over anhydrous $Na_2SO_4$, and concentrated to provide compound (R)—N-(3-amino-2-methylpropyl)-4-(dimethylamino)benzenesulfonamide. $^1$H NMR (400 MHz, $CDCl_3$): δ 7.70 (d, J=8.8 Hz, 2H), 6.68 (d, J=8.8 Hz, 2H), 3.04 (s, 6H), 2.98 (m, 1H), 2.75 (m, 2H), 2.58 (m, 1H), 1.78 (m, 2H), 0.87 (m, J=7.2 Hz, 3H).

Using a similar method (S)—N-(3-amino-2-methylpropyl)-4-(dimethylamino)benzenesulfonamide was synthesized (Intermediate for compound A76).

Route 34

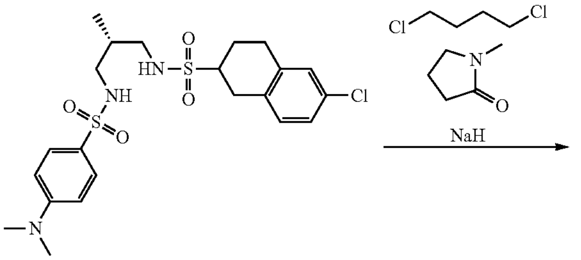

-continued

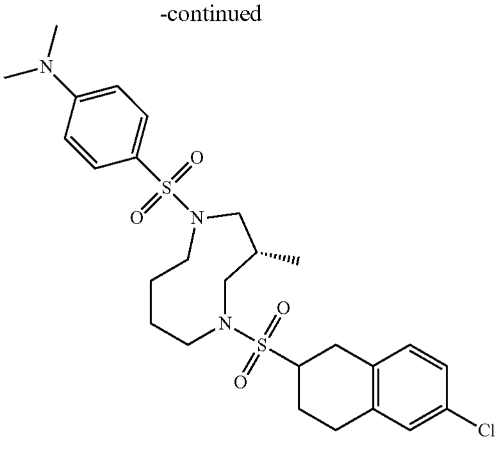

To 6-chloro-N—((R)-3-((4-(dimethylamino)phenyl)sulfonamido)-2-methylpropyl)-1,2,3,4-tetrahydronaphthalene-2-sulfonamide (100 mg, 200 μM) in dry NMP (4 mL) at 0° C. was added NaH (24 mg, 600 μmol) and the mixture was stirred at ambient temp for 20 min over which time it turned from a cloudy mixture to nearly transparent. The dichloride (21.3 μL, 200 μmol) was added and the mixture was heated to 80° C. After 40 min the reaction was quenched with brine and the aqueous layer was extracted with ethyl acetate (2×), the combined organics were washed with brine (3×), dried with sodium sulfate, filtered, and concentrated. Column chromatography (0-50% hexanes+1% diethylamine)/ethyl acetate) provided the product (compound B21). MS(EI) for $C_{25}H_{35}ClN_4O_4S_2$, found 555 $[M+H]^+$.

Route 35

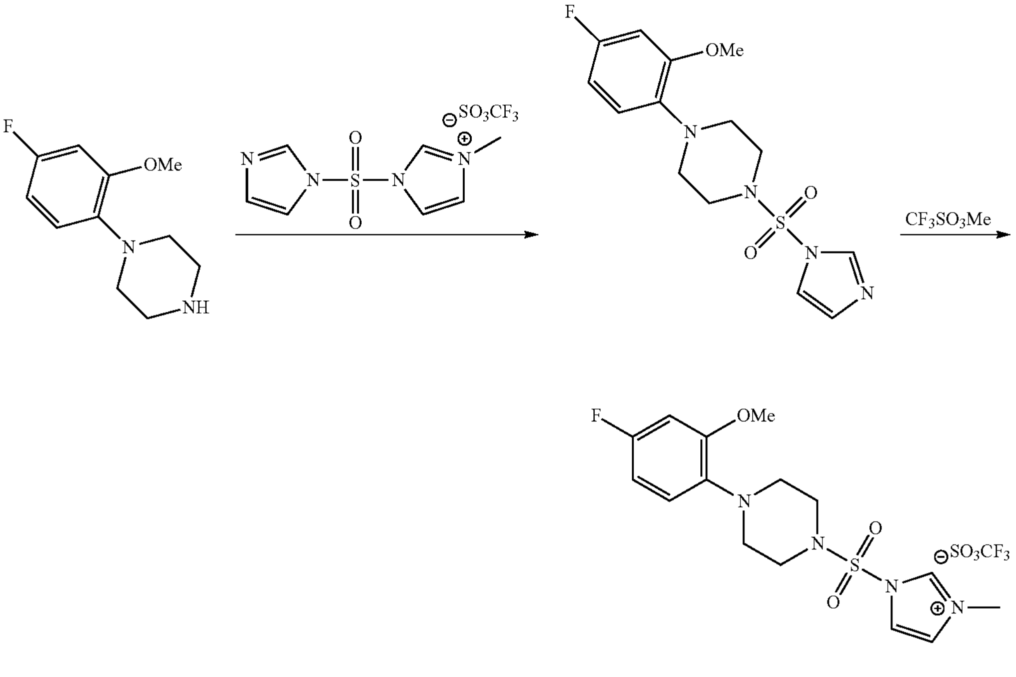

-continued

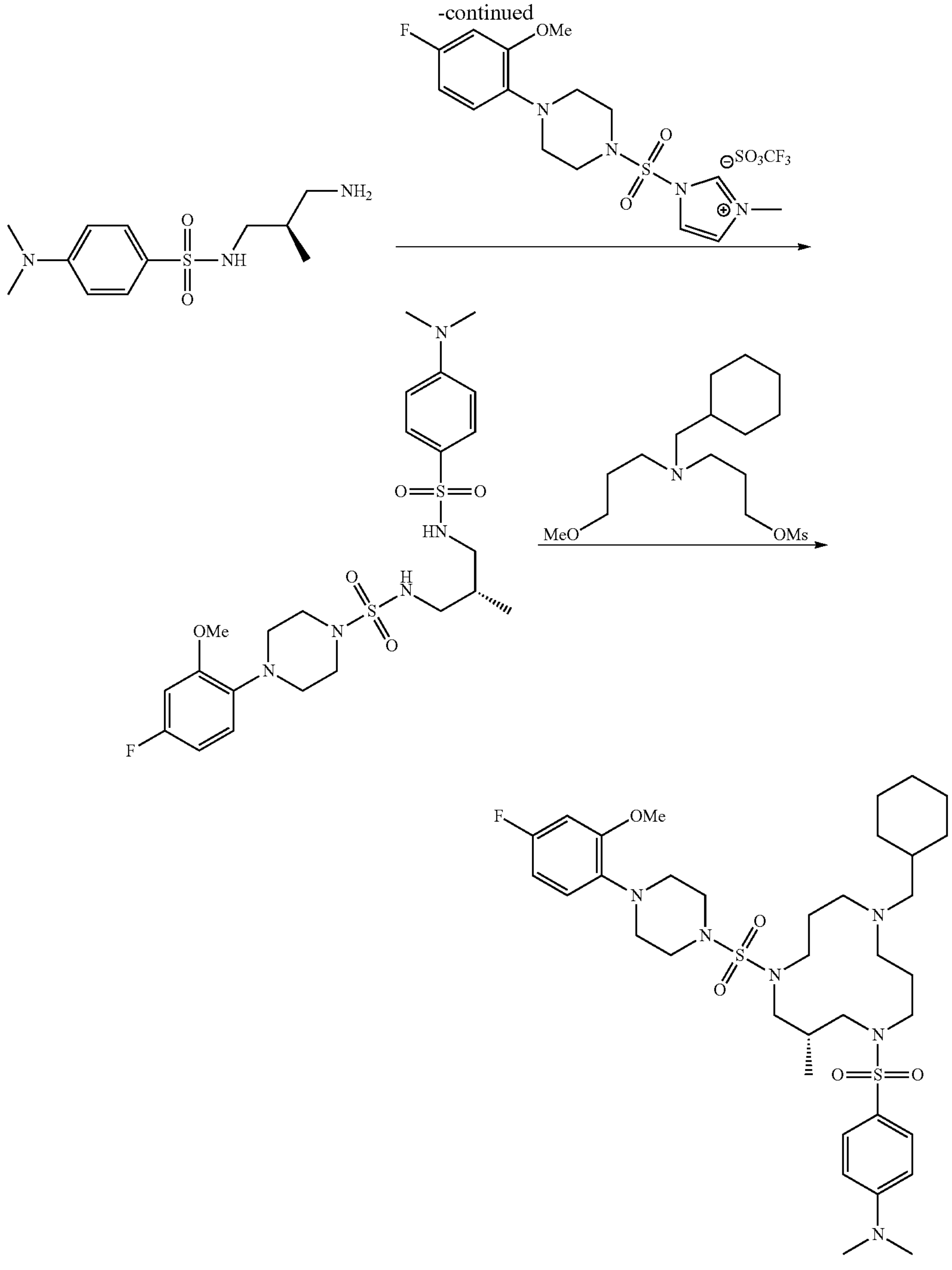

To a solution of 1-(4-fluoro-2-methoxyphenyl)piperazine (1.4 g, 6.8 mmol) in $CH_3CN$ (15 mL) was added 1-(1H-imidazol-1-ylsulfonyl)-3-methyl-1H-imidazol-3-ium trifluoromethanesulfonate (2.7 g, 6.8 mmol). The reaction mixture was stirred at ambient temperature overnight. The mixture was then concentrated and the residue was purified by column chromatography to provide 1-((1H-imidazol-1-yl)sulfonyl)-4-(4-fluoro-2-methoxyphenyl)piperazine.

To a solution of 1-((1H-imidazol-1-yl)sulfonyl)-4-(4-fluoro-2-methoxyphenyl)piperazin (0.92 g, 2.7 mmol) in DCM (10 mL) was added $CF_3SO_3Me$ (0.45 g, 2.7 mmol) at 0° C. The reaction mixture was stirred at ambient temperature for 5 h then concentrated and the resulting product was washed with ether to provide 1-((4-(4-fluoro-2-methoxyphenyl)piperazin-1-yl)sulfonyl)-3-methyl-1H-imidazol-3-ium trifluoromethanesulfonate.

To a solution of (R)—N-(3-amino-2-methylpropyl)-4-(dimethylamino)benzenesulfonamide (0.6 g, 2.2 mmol) in $CH_3CN$ (6 mL) was added 1-((4-(4-fluoro-2-methoxyphenyl)piperazin-1-yl)sulfonyl)-3-methyl-1H-imidazol-3-ium trifluoromethanesulfonate (1.1 g, 2.2 mmol). The reaction mixture was stirred at ambient temperature overnight. The mixture was concentrated and the residue was purified by column chromatography to provide (S)—N-(3-((4-(dimethylamino)phenyl)sulfonamido)-2-methylpropyl)-4-(4-fluoro-2-methoxyphenyl)piperazine-1-sulfonamide.

To a solution of (S)—N-(3-((4-(dimethylamino)phenyl) sulfonamido)-2-methylpropyl)-4-(4-fluoro-2-methoxyphenyl)piperazine-1-sulfonamide (771 mg, 1.42 mmol) in NMP (7 mL) was added NaH (140 mg, 3.48 mmol, 60%). The mixture was stirred for 0.5 h at 80° C. The mixture was cooled to 70° C. and ((cyclohexylmethyl)azanediyl)bis(propane-3,1-diyl) dimethanesulfonate (820 mg, 2.1 mmol) was added. The reaction mixture was stirred for 2 h at 70° C. then cooled and poured into water. The resulting mixture was extracted with ethyl acetate. The extract was concentrated and the residue was purified by column chromatography (petroleum ether/EtOAc=10:1) to provide compound A137. MS (EI) for $C_{36}H_{57}FN_6O_5S_2$, found 737 $[M+H]^+$. $^1H$ NMR (400 MHz, $CDCl_3$): δ 7.62 (d, J=8.8 Hz, 2H), 7.16 (m, 2H), 7.05 (m, 1H), 6.86 (d, J=8.8 Hz, 2H), 4.35 (m, 2H), 3.62 (m, 4H), 3.19 (m, 2H), 3.04 (s, 6H), 2.87 (m 4H), 2.46 (m, 5H), 1.92 (m, 1H), 1.79 (m, 2H), 1.66 (m, 4H).

The following compounds were synthesized in a similar manner:

| No. | IUPAC | $[M + H]^+$ |
|---|---|---|
| A153 | tert-butyl4-{[(3S)-9-(cyclohexylmethyl)-5-[4-(dimethylamino)benzenesulfonyl]-3-methyl-1,5,9-triazacyclododecan-1-yl]sulfonyl}piperazine-1-carboxylate | 714 |
| A118 | 2-(4-{[(3S)-9-(cyclohexylmethyl)-5-[4-(dimethylamino)benzenesulfonyl]-3-methyl-1,5,9-triazacyclododecan-1-yl]sulfonyl}piperazin-1-yl)benzonitrile | 715 |
| A154 | 4-{[(3S)-9-(cyclohexylmethyl)-5-{[4-(2-methoxyphenyl)piperazin-1-yl]sulfonyl}-3-methyl-1,5,9-triazacyclododecan-1-yl]sulfonyl}-N,N-dimethylaniline | 720 |
| A155 | 4-{[(3S)-9-(cyclohexylmethyl)-3-methyl-5-(piperazine-1-sulfonyl)-1,5,9-triazacyclododecan-1-yl]sulfonyl}-N,N-dimethylaniline | 613 |
| A119 | 4-{[(3S)-9-(cyclohexylmethyl)-5-{[4-(2,6-dimethylphenyl)piperazin-1-yl]sulfonyl}-3-methyl-1,5,9-triazacyclododecan-1-yl]sulfonyl}-N,N-dimethylaniline | 717 |
| A136 | 4-{[(3S)-9-(cyclohexylmethyl)-5-[(6-ethyl-1,2,3,4-tetrahydroisoquinolin-2-yl)sulfonyl]-3-methyl-1,5,9-triazacyclododecan-1-yl]sulfonyl}-N,N-dimethylaniline | 688 |
| A161 | 4-{[(3S)-9-(cyclohexylmethyl)-5-{[6-(4-fluoro-2-methylphenyl)-2,6-diazaspiro[3.3]heptan-2-yl]sulfonyl}-3-methyl-1,5,9-triazacyclododecan-1-yl]sulfonyl}-N,N-dimethylaniline | 733 |
| A162 | 4-{[(3S)-9-(cyclohexylmethyl)-5-{[(2S)-4-(4-fluoro-2-methylphenyl)-2-methylpiperazin-1-yl]sulfonyl}-3-methyl-1,5,9-triazacyclododecan-1-yl]sulfonyl}-N,N-dimethylaniline | 735 |
| A163 | 4-{[(3S)-9-(cyclohexylmethyl)-5-{[(2R)-4-(4-fluoro-2-methylphenyl)-2-methylpiperazin-1-yl]sulfonyl}-3-methyl-1,5,9-triazacyclododecan-1-yl]sulfonyl}-N,N-dimethylaniline | 735 |
| A166 | 4-{[(3S)-9-(cyclohexylmethyl)-3-methyl-5-[(5-methyl-1,2,3,4-tetrahydroisoquinolin-2-yl)sulfonyl]-1,5,9-triazacyclododecan-1-yl]sulfonyl}-N,N-dimethylaniline | 674 |
| A138 | 4-{[(3S)-9-(cyclohexylmethyl)-5-[(5-methoxy-1,2,3,4-tetrahydroisoquinolin-2-yl)sulfonyl]-3-methyl-1,5,9-triazacyclododecan-1-yl]sulfonyl}-N,N-dimethylaniline | 690 |
| A151 | 2-{[(3S)-9-(cyclohexylmethyl)-5-[4-(dimethylamino)benzenesulfonyl]-3-methyl-1,5,9-triazacyclododecan-1-yl]sulfonyl}-1,2,3,4-tetrahydroisoquinoline-5-carbonitrile | 685 |
| A170 | 4-{[(3S)-9-(cyclohexylmethyl)-3-methyl-5-[(1-methyl-1,2,3,4-tetrahydroisoquinolin-2-yl)sulfonyl]-1,5,9-triazacyclododecan-1-yl]sulfonyl}-N,N-dimethylaniline | 674 |
| A172 | 4-{[(3S)-9-(cyclohexylmethyl)-3-methyl-5-[(3-methyl-1,2,3,4-tetrahydroisoquinolin-2-yl)sulfonyl]-1,5,9-triazacyclododecan-1-yl]sulfonyl}-N,N-dimethylaniline | 674 |
| A173 | 4-{[(3S)-9-(cyclohexylmethyl)-3-methyl-5-({4-[2-(trifluoromethoxy)phenyl]piperazin-1-yijsulfonyl)-1,5,9-triazacyclododecan-1-yl]sulfonyl}-N,N-dimethylaniline | 773 |
| A174 | 4-{[(3S)-9-(cyclohexylmethyl)-5-{[4-(3,4-difluoro-2-methoxyphenyl)piperazin-1-yl]sulfonyl}-3-methyl-1,5,9-triazacyclododecan-1-yl]sulfonyl}-N,N-dimethylaniline | 755 |
| A175 | 4-{[(3S)-9-(cyclohexylmethyl)-5-{[4-(3-fluoro-2-methoxyphenyl)piperazin-1-yl]sulfonyl}-3-methyl-1,5,9-triazacyclododecan-1-yl]sulfonyl}-N,N-dimethylaniline | 737 |
| A176 | 4-{[(3S)-9-(cyclohexylmethyl)-5-{[4-(5-fluoro-2-methoxyphenyl)piperazin-1-yl]sulfonyl}-3-methyl-1,5,9-triazacyclododecan-1-yl]sulfonyl}-N,N-dimethylaniline | 737 |
| A177 | 4-{[(3S)-9-(cyclohexylmethyl)-5-{[(3R)-4-(4-fluoro-2-methoxyphenyl)-3-methylpiperazin-1-yl]sulfonyl}-3-methyl-1,5,9-triazacyclododecan-1-yl]sulfonyl}-N,N-dimethylaniline | 751 |
| A178 | 4-{[(3S)-9-(cyclohexylmethyl)-5-{[3-(4-fluoro-2-methoxyphenyl)azetidin-1-yl]sulfonyl}-3-methyl-1,5,9-triazacyclododecan-1-yl]sulfonyl}-N,N-dimethylaniline | 708 |
| A181 | 4-{[(3S)-5-[(5-chloro-1,2,3,4-tetrahydroisoquinolin-2-yl)sulfonyl]-9-(cyclohexylmethyl)-3-methyl-1,5,9-triazacyclododecan-1-yl]sulfonyl}-N,N-dimethylaniline | 694 |
| A187 | (3S)-N-benzyl-9-(cyclohexylmethyl)-5-[4-(dimethylamino)benzenesulfonyl]-3-methyl-1,5,9-triazacyclododecane-1-sulfonamide | 634 |

-continued

| No. | IUPAC | [M + H]+ |
|---|---|---|
| A198 | 4-{[(3S)-5-{[4-(2-chlorophenyl)piperazin-1-yl]sulfonyl}-9-(cyclohexylmethyl)-3-methyl-1,5,9-triazacyclododecan-1-yl]sulfonyl}-N,N-dimethylaniline | 723 |
| A199 | 4-{[(3S)-9-(cyclohexylmethyl)-5-{[4-(4-methoxyphenyl)piperazin-1-yl]sulfonyl}-3-methyl-1,5,9-triazacyclododecan-1-yl]sulfonyl}-N,N-dimethylaniline | 719 |
| A201 | 4-{[(3S)-9-(cyclohexylmethyl)-5-{[4-(3-methoxyphenyl)piperazin-1-yl]sulfonyl}-3-methyl-1,5,9-triazacyclododecan-1-yl]sulfonyl}-N,N-dimethylaniline | 719 |
| A202 | 4-{[(3S)-9-(cyclohexylmethyl)-5-{[4-(3-fluoro-4-methoxyphenyl)piperazin-1-yl]sulfonyl}-3-methyl-1,5,9-triazacyclododecan-1-yl]sulfonyl}-N,N-dimethylaniline | 737 |
| A206 | 4-{[(3S)-5-{[4-(2-chloro-4-fluorophenyl)piperazin-1-yl]sulfonyl}-9-(cyclohexylmethyl)-3-methyl-1,5,9-triazacyclododecan-1-yl]sulfonyl}-N,N-dimethylaniline | 741 |
| A147 | 4-{[(4S)-5-[(6-chloro-1,2,3,4-tetrahydroisoquinolin-2-yl)sulfonyl]-9-(cyclohexylmethyl)-4-methyl-1,5,9-triazacyclododecan-1-yl]sulfonyl}-N,N-dimethylaniline | 694 |
| A148 | 4-{[(4R)-5-[(6-chloro-1,2,3,4-tetrahydroisoquinolin-2-yl)sulfonyl]-9-(cyclohexylmethyl)-4-methyl-1,5,9-triazacyclododecan-1-yl]sulfonyl}-N,N-dimethylaniline | 694 |
| A150 | 4-{[(2S)-5-[(6-chloro-1,2,3,4-tetrahydroisoquinolin-2-yl)sulfonyl]-9-(cyclohexylmethyl)-2-methyl-1,5,9-triazacyclododecan-1-yl]sulfonyl}-N,N-dimethylaniline | 694 |
| A149 | 4-{[(2R)-5-[(6-chloro-1,2,3,4-tetrahydroisoquinolin-2-yl)sulfonyl]-9-(cyclohexylmethyl)-2-methyl-1,5,9-triazacyclododecan-1-yl]sulfonyl}-N,N-dimethylaniline | 694 |
| A190 | 4-{[(3S)-5-[(6-chloro-1,2,3,4-tetrahydroisoquinolin-2-yl)sulfonyl]-9-[(1S)-1-cyclohexylethyl]-3-methyl-1,5,9-triazacyclododecan-1-yl]sulfonyl}-N,N-dimethylaniline | 708 |
| A191 | 4-{[(3S)-5-[(6-chloro-1,2,3,4-tetrahydroisoquinolin-2-yl)sulfonyl]-9-[(1R)-1-cyclohexylethyl]-3-methyl-1,5,9-triazacyclododecan-1-yl]sulfonyl}-N,N-dimethylaniline | 708 |
| A207 | 4-I(3S)-9-(1S)-1-cyclohexylethyl]-5-{[(3R)-4-(4-fluoro-2-methoxyphenyl)-3-methylpiperazin-1-yl]sulfonyl}-3-methyl-1,5,9-triazacyclododecan-1-yl]sulfonyl}-N,N-dimethylaniline | 765 |
| A205 | N,N-dimethyl-4-{[(3S)-3-methyl-9-[(1S)-1-phenylethyl]-5-(1,2,3,4-tetrahydroisoquinoline-2-sulfonyl)-1,5,9-triazacyclododecan-1-yl]sulfonyl}aniline | 668 |

Route 36

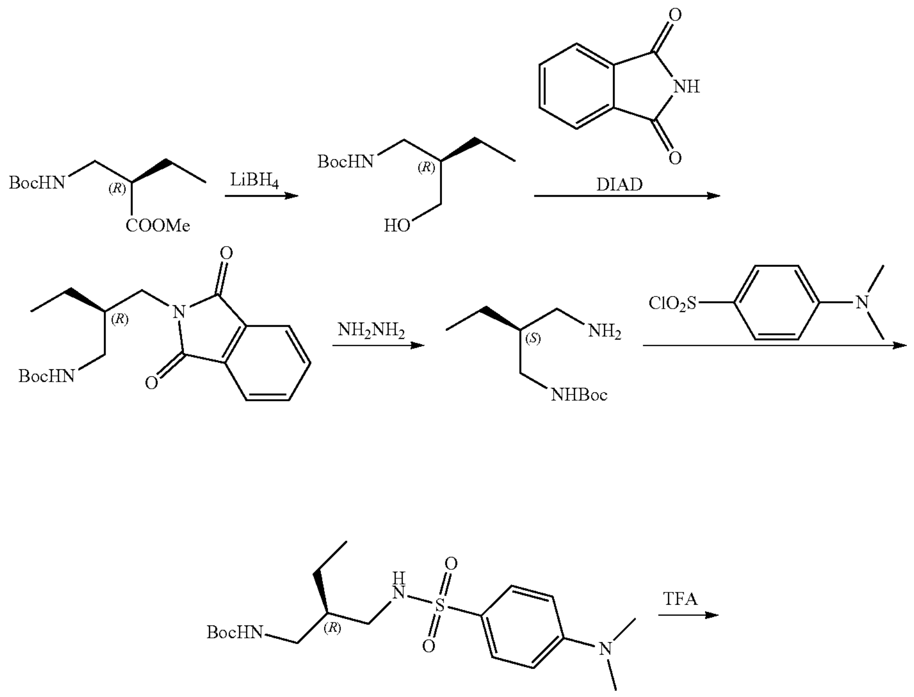

-continued

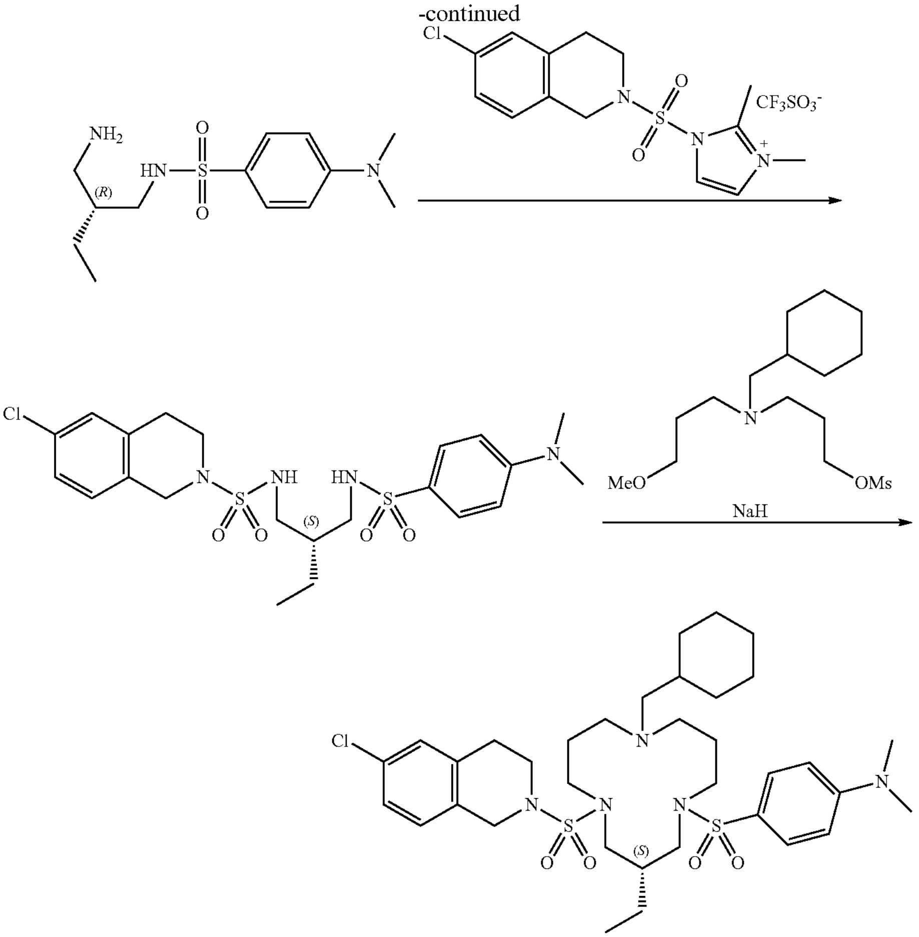

To a solution of (R)-methyl 2-((tert-butoxycarbonylamino)methyl)butanoate (4.8 g, 20.8 mmol) in THF (50 mL) was added $LiBH_4$ (0.7 g, 33 mmol). The reaction mixture was stirred overnight at ambient temperature. The mixture was quenched with water (30 mL) followed by addition of 1 N aqueous HCl dropwise to adjust to pH=2~3. The resulting mixture was extracted with ethyl acetate and the extract was washed with saturated aqueous $NaHCO_3$, dried over anhydrous sodium sulfate, and concentrated to provide (R)-tert-butyl 2-(hydroxymethyl)butylcarbamate.

To a solution of (R)-tert-butyl 2-(hydroxymethyl)butylcarbamate (3.4 g, 16.7 mmol) in toluene (40 mL) was added $PPh_3$ (6.2 g, 17.4 mmol) and isoindoline-1,3-dione (3.7 g, 25 mmol). The mixture was cooled to 0~5° C. and DIAD (4.3 g, 22 mmol) was added dropwise. The reaction mixture was stirred at ambient temperature for 3 h. The resulting precipitate was filtered and the filtrate was concentrated. The residue was purified by column chromatography (petroleum ether/EtOAc=9:1 to 1:1) to provide 1-(4-fluoro-2-methoxyphenyl)-4-(2-methyl-1H-imidazol-1-ylsulfonyl)piperazine.

To a solution of 1-(4-fluoro-2-methoxyphenyl)-4-(2-methyl-1H-imidazol-1-ylsulfonyl)piperazine (3.8 g, 11.4 mmol) in EtOH (70 mL) was added hydrazine hydrate (1.1 g, 80%). The reaction mixture was refluxed for 6 h. The resulting product was filtered and the filtrate was concentrated under reduced pressure. The residue was dissolved in 1 N aqueous NaOH (20 mL) then extracted with DCM (50 mL). The organic layer was dried over anhydrous sodium sulfate and concentrated to provide (S)-tert-butyl 2-(aminomethyl)butylcarbamate.

To a solution of (S)-tert-butyl 2-(aminomethyl)butylcarbamate (1.87 g, 9.2 mmol) in DCM (20 mL) was added TEA (1.01 g, 10.1 mol). The mixture was cooled to 0-5° C. and 4-(dimethylamino)benzene-1-sulfonyl chloride (2.0 g, 9.2 mmol) was added. The reaction mixture was stirred at ambient temperature for 3 h. The mixture was washed with water then concentrated. The residue was purified by column chromatography (petroleum ether/EtOAc=9:1 to 7:3) to provide (R)-tert-butyl 2-((4-(dimethylamino)phenylsulfonamido)methyl) butylcarbamate.

To a solution of (R)-tert-butyl 2-((4-(dimethylamino)phenylsulfonamido)methyl) butylcarbamate (2.9 g, 7.5 mmol) in MeOH (10 mL) was added 4N HCl/MeOH (15 mL). The mixture was stirred for 3 h at ambient temperature. The solvent was removed under reduced pressure. The resulting product was suspended in DCM (100 mL) and saturated aqueous $K_2CO_3$ (450 mL) was added. The mixture was stirred for 5 min. The DCM layer was separated, dried over anhydrous sodium sulfate, and concentrated to provide (R)—N-(2-(aminomethyl)butyl)-4-(dimethylamino)benzenesulfonamide.

To a solution of (R)—N-(2-(aminomethyl)butyl)-4-(dimethylamino) benzenesulfonamide (0.9 g, 3.2 mmol) in $CH_3CN$ (9 mL) was added 1-((6-chloro-3,4-dihydroisoquinolin-2(1H)-yl)sulfonyl)-2,3-dimethyl-1H-imidazol-3-ium trifluoromethanesulfonate (0.59 g, 3.2 mmol). The reaction mixture was stirred overnight at ambient temperature. The mixture was concentrated and the residue was purified by column chromatography (petroleum ether/EtOAc=8:1 to 2:1) to provide (S)-6-chloro-N-(2-((4-(dimethylamino)phenylsulfonamido)methyl)butyl)-3,4-dihydroisoquinoline-2 (1H)-sulfonamide.

To a solution of (S)-6-chloro-N-(2-((4-(dimethylamino) phenylsulfonamido)methyl)butyl)-3,4-dihydroisoquinoline-2(1H)-sulfonamide (0.8 g, 1.5 mmol) in NMP (3 mL) was added NaH (159 mg, 3.9 mmol, 60%). The mixture was stirred for 0.5 h at 80° C. The mixture was cooled to 70° C. and cyclopropane-1,1-diylbis(methylene) dimethanesulfonate (510 mg, 2.0 mmol) was added. The reaction mixture was stirred for 2 h at 70° C. The solvent was removed and the residue was purified by column chromatography (petroleum ether/EtOAc=15:1) to provide compound A182. LC-MS: m/z 708.2 $[M+H]^+$. $^1H$ NMR (400 MHz, $CDCl_3$): δ 7.59 (m, 2H), 7.15 (m, 2H), 7.05 (m, 1H), 6.68 (m, 2H), 4.34 (m, 2H), 3.55 (m, 4H), 3.19 (m, 6H), 3.04 (s, 6H), 2.87 (m, 4H), 2.15 (m, 4H), 1.89 (m, 10H), 1.32 (m, 8H), 0.88 (m, 3H).

Route 37

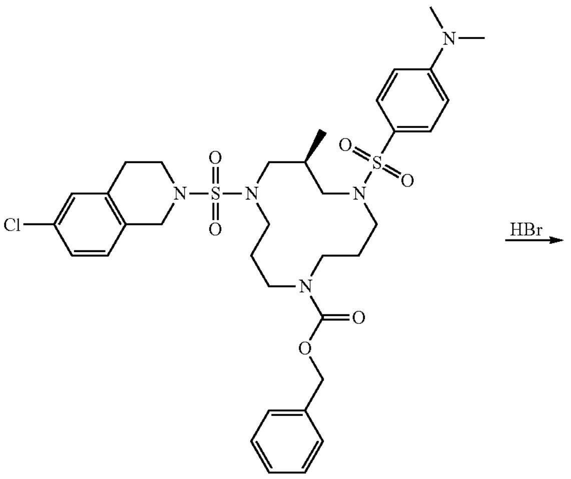

-continued

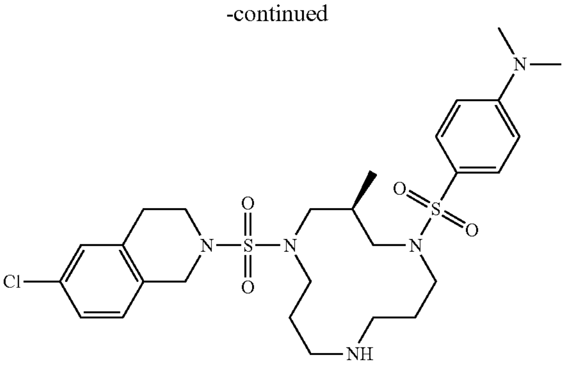

To benzyl (S)-5-((6-chloro-3,4-dihydroisoquinolin-2 (1H)-yl)sulfonyl)-9-((4-(dimethylamino)phenyl)sulfonyl)-7-methyl-1,5,9-triazacyclododecane-1-carboxylate (25 mg) was added HBr (33% in acetic acid, 0.5 mL). After 30 min at ambient temperature the mixture was diluted with diethyl ether and water (1:1 mix, 10 mL) and the organic layer was removed. The aqueous layer was washed with diethyl ether (1×5 mL), basified with NaOH (4 N) to pH ~12, then extracted with DCM (3×2 mL). The organics were dried with sodium sulfate, filtered, and concentrated. Addition of hexanes (~2 mL) followed by concentration was used to facilitate precipitation of the product. Drying under vacuum provided compound A183. MS(EI) for $C_{27}H_{40}ClN_5O_4S_2$, found 598 $[M+H]^+$.

Route 38

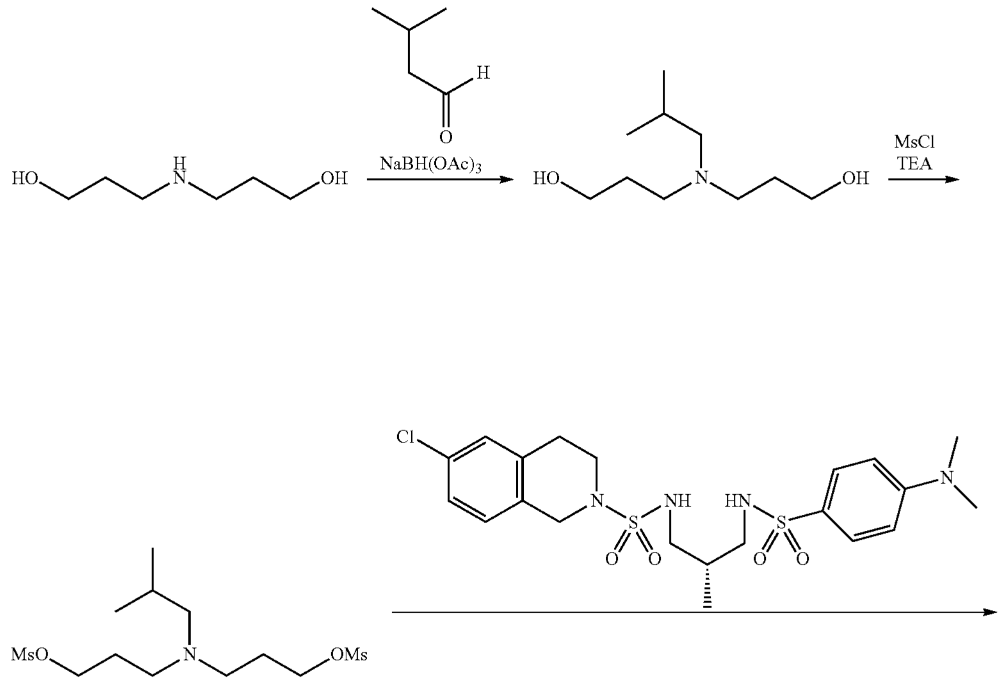

-continued

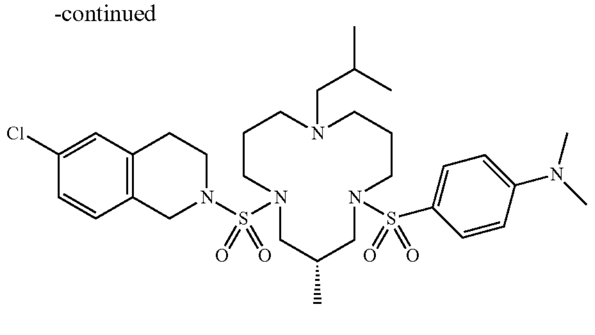

To a solution of 3,3'-azanediyldipropan-1-ol (1.0 g, 7.5 mmol) in DCM (20 mL) was added isobutyraldehyde (1.22 g, 11.3 mmol). The mixture was stirred for 30 min at ambient temperature. Acetic acid (1.8 g, 30.1 mmol) was added and the mixture was stirred for another 30 min. Sodium triacetoxyborohydride (6.40 g, 30.1 mmol) was then added and the reaction mixture was stirred overnight at ambient temperature. The mixture was adjusted to pH=1-2 with 3N aqueous HCl and then stirred for 1 h. To the mixture was added 20% aqueous NaOH (to adjust pH to 10-11) then it was extracted with DCM (50 mL). The extract was washed with brine, dried over anhydrous sodium sulfate, and concentrated to provide 3,3'-(isobutylazanediyl)bis(propan-1-ol).

To a solution of 3,3'-(isobutylazanediyl)bis(propan-1-ol) (780 mg, 4.1 mmol) in DCM (10 mL) was added $NEt_3$ (820 mg, 8.2 mmol). MsCl (935 mg, 8.2 mmol) was then added slowly at 0° C. The reaction mixture was stirred for 3 h at ambient temperature. The mixture was diluted with DCM (20 mL) and then washed with water (25 mL). The organic layer was dried over anhydrous sodium sulfate and concentrated to provide 3,3'-(Isobutylazanediyl)bis(propane-3,1-diyl) dimethanesulfonate.

To a solution of (S)-6-chloro-N-(3-((4-(dimethylamino)phenyl)sulfonamido)-2-methylpropyl)-3,4-dihydroisoquinoline-2(1H)-sulfonamide (0.515 g, 1.03 mmol) in dry N-methyl pyrrolidone was added NaH (0.25 g, 2.26 mmol) at ambient temperature. The mixture was heated at 80° C. with stirring for 30 min and then cooled to ambient temperature. 3,3'-(Isobutylazanediyl)bis(propane-3,1-diyl) dimethanesulfonate (0.5 g, 1.5 mmol) was added and the reaction mixture was heated at 80° C. for 2 h. The reaction was quenched with water then extracted with ethyl acetate. The extract was dried over anhydrous sodium sulfate and concentrated. The residue was purified by flash column chromatography to afford compound A152. MS (EI) for $C_{31}H_{48}ClN_5O_4S_2$, found 654.4 $[M+H]^+$. $^1H$ NMR (400 MHz, $CDCl_3$): δ 7.59 (d, 2H), 7.16 (m, 2H), 7.04 (m, 1H), 6.69 (d, 2H), 4.32 (m, 2H), 3.60 (m, 4H), 3.31 (m, 3H), 3.04 (s, 6H), 2.90 (m, 4H), 2.27 (m, 4H), 1.93 (m, 2H), 1.79 (m, 1H), 0.87 (m, 9H).

The following compounds were synthesized in a similar manner:

| No. | IUPAC | $[M + H]^+$ |
|---|---|---|
| A123 | 4-{[(3S)-5-[(6-chloro-1,2,3,4-tetrahydroisoquinolin-2-yl)sulfonyl]-3-methyl-9-(3-methylbutyl)-1,5,9-triazacyclododecan-1-yl]sulfonyl}-N,N-dimethylaniline | 668 |
| A156 | 4-{[(3S)-5-[(6-chloro-1,2,3,4-tetrahydroisoquinolin-2-yl)sulfonyl]-3-methyl-9-[(3-methylphenyl)methyl]-1,5,9-triazacyclododecan-1-yl]sulfonyl}-N,N-dimethylaniline | 702 |
| A131 | 4-{[(3S)-5-[(6-chloro-1,2,3,4-tetrahydroisoquinolin-2-yl)sulfonyl]-3-methyl-9-[(4-methylphenyl)methyl]-1,5,9-triazacyclododecan-1-yl]sulfonyl}-N,N-dimethylaniline | 702 |
| A157 | 4-{[(3S)-5-[(6-chloro-1,2,3,4-tetrahydroisoquinolin-2-yl)sulfonyl]-9-(cyclopentylmethyl)-3-methyl-1,5,9-triazacyclododecan-1-yl]sulfonyl}-N,N-dimethylaniline | 680 |
| A106 | 4-{[(3S)-5-[(6-chloro-1,2,3,4-tetrahydroisoquinolin-2-yl)sulfonyl]-3-methyl-9-(2-methylbutyl)-1,5,9-triazacyclododecan-1-yl]sulfonyl}-N,N-dimethylaniline | 668 |
| A108 | 4-{[(3S)-5-[(6-chloro-1,2,3,4-tetrahydroisoquinolin-2-yl)sulfony]-9-(cyclobutylmethyl)-3-methyl-1,5,9-triazacyclododecan-1-yl]sulfonyl}-N,N-dimethylaniline | 666 |
| A134 | 4-{[(3S)-5-[(6-chloro-1,2,3,4-tetrahydroisoquinolin-2-yl)sulfonyl]-9-(2-cyclohexylethyl)-3-methyl-1,5,9-triazacyclododecan-1-yl]sulfonyl}-N,N-dimethylaniline | 708 |
| A122 | 4-{[(3S)-5-[(6-chloro-1,2,3,4-tetrahydroisoquinolin-2-yl)sulfonyl]-9-(2-cyclopropylethyl)-3-methyl-1,5,9-triazacyclododecan-1-yl]sulfonyl}-N,N-dimethylaniline | 666 |
| A120 | 4-{[(3S)-5-[(6-chloro-1,2,3,4-tetrahydroisoquinolin-2-yl)sulfonyl]-9-(2-cyclopentylethyl)-3-methyl-1,5,9-triazacyclododecan-1-yl]sulfonyl}-N,N-dimethylaniline | 694 |
| A165 | 4-{[(3S)-5-[(6-chloro-1,2,3,4-tetrahydroisoquinolin-2-yl)sulfonyl]-3-methyl-9-(3,3,3-trifluoropropyl)-1,5,9-triazacyclododecan-1-yl]sulfonyl}-N,N-dimethylaniline | 694 |
| A141 | 4-{[(3S)-5-[(6-chloro-1,2,3,4-tetrahydroisoquinolin-2-yl)sulfonyl]-3-methyl-9-(propan-2-yl)-1,5,9-triazacyclododecan-1-yl]sulfonyl}-N,N-dimethylaniline | 640 |

-continued

| No. | IUPAC | [M + H]+ |
|---|---|---|
| A176 | 4-{[(3S)-5-[(6-chloro-1,2,3,4-tetrahydroisoquinolin-2-yl)sulfonyl]-9-[(cyclopent-1-en-1-yl)methyl]-3-methyl-1,5,9-triazacyclododecan-1-yl]sulfonyl}-N,N-dimethylaniline | 678 |
| A135 | 4-{[(3S)-5-[(6-chloro-1,2,3,4-tetrahydroisoquinolin-2-yl)sulfonyl]-9-[(cyclohex-1-en-1-yl)methyl]-3-methyl-1,5,9-triazacyclododecan-1-yl]sulfonyl}-N,N-dimethylaniline | 692 |
| A167 | 4-{[(3S)-5-[(6-chloro-1,2,3,4-tetrahydroisoquinolin-2-yl)sulfonyl]-3-methyl-9-(2,2,2-trifluoroethyl)-1,5,9-triazacyclododecan-1-yl]sulfonyl}-N,N-dimethylaniline | 680 |
| A169 | 4-{[(3S)-5-[(6-chloro-1,2,3,4-tetrahydroisoquinolin-2-yl)sulfonyl]-9-[(3,3-difluorocyclobutyl)methyl]-3-methyl-1,5,9-triazacyclododecan-1-yl]sulfonyl}-N,N-dimethylaniline | 702 |
| A133 | 4-{[(3S)-5-[(6-chloro-1,2,3,4-tetrahydroisoquinolin-2-yl)sulfonyl]-3-methyl-9-[(2-methylphenyl)methyl]-1,5,9-triazacyclododecan-1-yl]sulfonyl}-N,N-dimethylaniline | 702 |
| A140 | 4-{[(3S)-5-[(6-chloro-1,2,3,4-tetrahydroisoquinolin-2-yl)sulfonyl]-9-(2-methoxyethyl)-3-methyl-1,5,9-triazacyclododecan-1-yl]sulfonyl}-N,N-dimethylaniline | 656 |
| A125 | 4-{[(3S)-5-[(6-chloro-1,2,3,4-tetrahydroisoquinolin-2-yl)sulfonyl]-3-methyl-9-[(1,3-oxazol-2-yl)methyl]-1,5,9-triazacyclododecan-1-yl]sulfonyl}-N,N-dimethylaniline | 679 |
| A124 | 4-{[(3S)-5-[(6-chloro-1,2,3,4-tetrahydroisoquinolin-2-yl)sulfonyl]-3-methyl-9-[(1,2-oxazol-3-yl)methyl]-1,5,9-triazacyclododecan-1-yl]sulfonyl}-N,N-dimethylaniline | 679 |
| A183 | 4-{[(3S)-5-[(6-chloro-1,2,3,4-tetrahydroisoquinolin-2-yl)sulfonyl]-3-methyl-1,5,9-triazacyclododecan-1-yl]sulfonyl}-N,N-dimethylaniline | 598 |
| A185 | 4-{[(3S)-5-[(6-chloro-1,2,3,4-tetrahydroisoquinolin-2-yl)sulfonyl]-9-[(4,4-difluorocyclohexyl)methyl]-3-methyl-1,5,9-triazacyclododecan-1-yl]sulfonyl}-N,N-dimethylaniline | 730 |
| A107 | 4-{[(3S)-5-[(6-chloro-1,2,3,4-tetrahydroisoquinolin-2-yl)sulfonyl]-9-(2,2-dimethylpropyl)-3-methyl-1,5,9-triazacyclododecan-1-yl]sulfonyl}-N,N-dimethylaniline | 668 |
| A204 | 4-{[(3S)-5-[(6-chloro-1,2,3,4-tetrahydroisoquinolin-2-yl)sulfonyl]-9-[(4-fluorocyclohexyl)methyl]-3-methyl-1,5,9-triazacyclododecan-1-yl]sulfonyl}-N,N-dimethylaniline | 712 |

Route 39

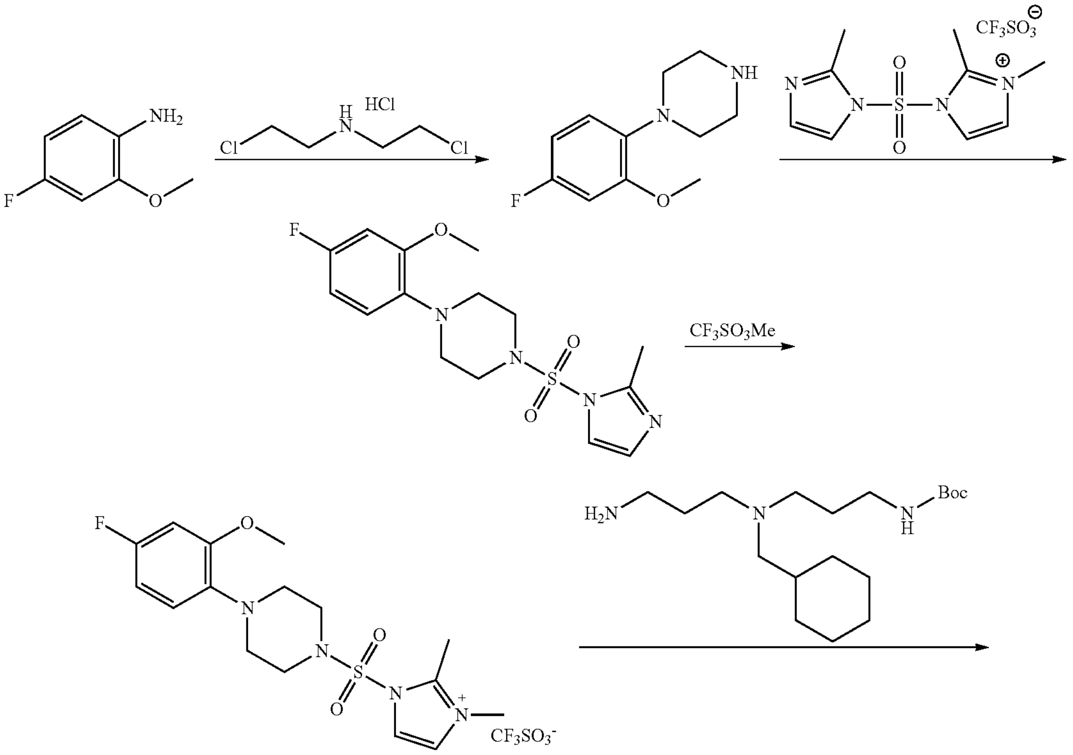

-continued

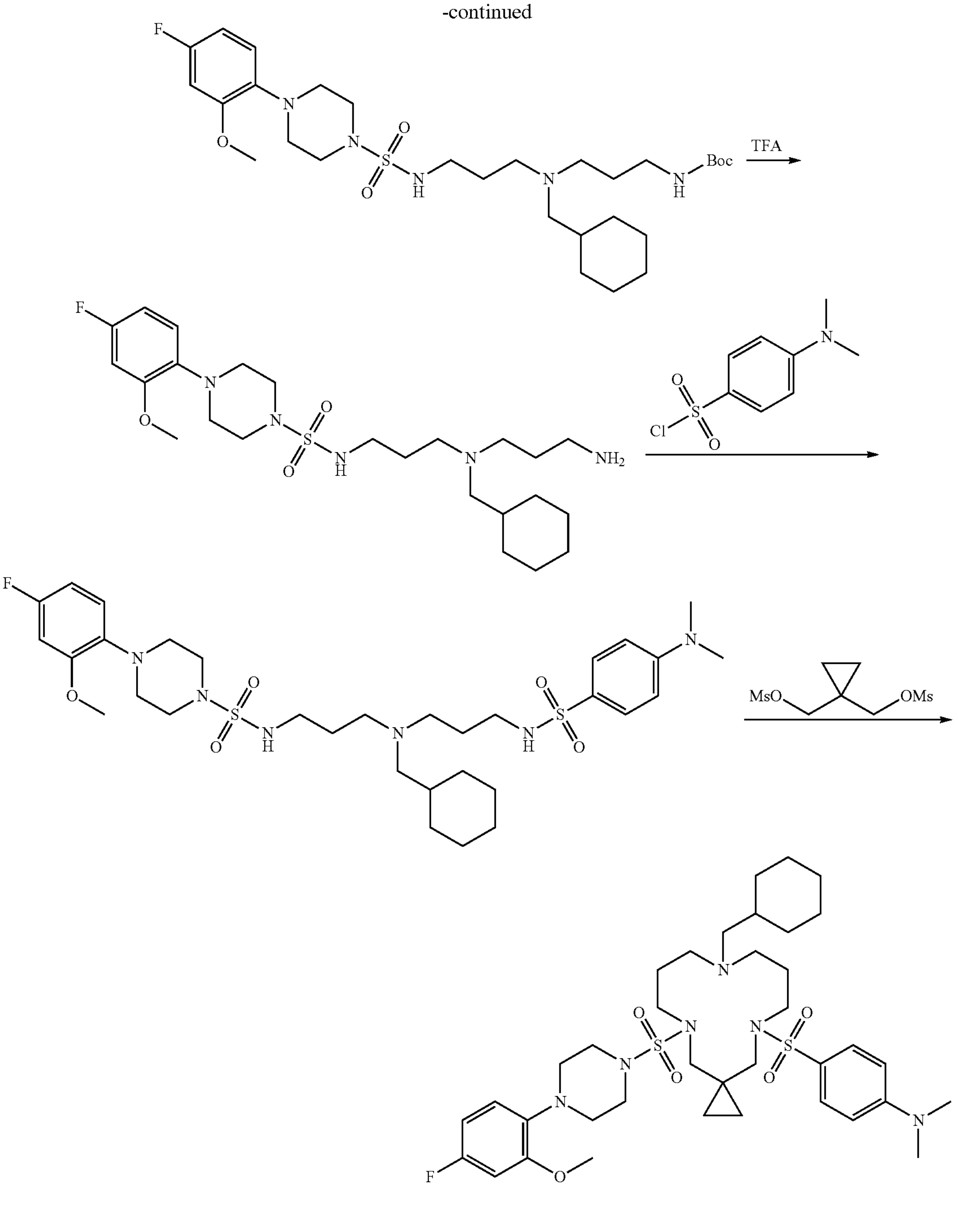

To a mixture of 4-fluoro-2-methoxyaniline (25.0 g, 177 mmol), $K_2CO_3$ (36.7 g, 266 mmol) and NaI (10.6 g, 0.07 mmol) in i-PrOH (250 mL) was added bis(2-chloroethyl) amine hydrochloride (47 g, 177 mmol). The reaction mixture was refluxed overnight. The solvent was removed and the residue was purified by column chromatography (petroleum ether/EtOAc=10:1) to provide 1-(4-fluoro-2-methoxyphenyl)piperazine. MS: m/z 212.36 $[M+H]^+$.

A solution of 1-(4-fluoro-2-methoxyphenyl)piperazine (4.0 g, 19 mmol) in MeCN (40 mL) was added 2,3-dimethyl-1-(2-methyl-1H-imidazol-1-ylsulfonyl)-1H-imidazol-3-ium (7.5 g, 19 mmol). The reaction mixture was stirred overnight at ambient temperature. The solvent was removed and the residue was purified by column chromatography (petroleum ether/EtOAc=20:1) to provide 1-(4-fluoro-2-methoxyphenyl)-4-(2-methyl-1H-imidazol-1-ylsulfonyl)piperazine. MS: m/z 355.36 $[M+H]^+$.

To a solution of 1-(4-fluoro-2-methoxyphenyl)-4-(2-methyl-1H-imidazol-1-ylsulfonyl)piperazine (6.0 g, 17 mmol) in DCM (60 mL) was added $CF_3SO_3Me$ (2.78 g, 17 mmol). The reaction mixture was stirred for 2 h at ambient temperature. The solvent was removed and the residue was washed with ether to provide 1-(4-(4-fluoro-2-methoxyphenyl)piperazin-1-ylsulfonyl)-2,3-dimethyl-1H-imidazol-3-ium trifluoromethanesulfonate.

To a solution of 1-(4-(4-fluoro-2-methoxyphenyl)piperazin-1-ylsulfonyl)-2,3-dimethyl-1H-imidazol-3-ium trifluoromethanesulfonate (740 mg, 2.3 mmol) in $CH_3CN$ (8 mL)

was added tert-butyl 3-((3-aminopropyl)(cyclohexylmethyl) amino)propylcarbamate (1.17 g, 2.3 mmol). The reaction mixture was stirred overnight at ambient temperature. The mixture was concentrated and the residue was purified by column chromatography (petroleum ether/EtOAc=8:1 to 2:1) to provide tert-butyl-3-((cyclohexylmethyl)(3-(4-(4-fluoro-2-methoxyphenyl)piperazine-1-sulfonamido)propyl) amino)propylcarbamate.

To a solution of tert-butyl-3-((cyclohexylmethyl)(3-(4-(4-fluoro-2-methoxyphenyl)piperazine-1-sulfonamido)propyl) amino)propylcarbamate (600 mg, 1 mmol) in DCM (30 mL) was added TFA (30 mL). The mixture was stirred for 2 h at ambient temperature. The solvent was removed and the residue was dissolved in ethyl acetate then washed with saturated aqueous $NaHCO_3$. The organic phase was dried over anhydrous sodium sulfate and concentrated to provide N-(3-((3-aminopropyl)(cyclohexylmethyl)amino)propyl)-4-(4-fluoro-2-methoxy phenyl)piperazine-1-sulfonamide.

To a solution of N-(3-((3-aminopropyl)(cyclohexylmethyl)amino)propyl)-4-(4-fluoro-2-methoxy phenyl)piperazine-1-sulfonamide (416 mg, 0.83 mmol) in DCM (5 mL) was added $Et_3N$ (170 mg, 1.66 mmol) and 4-(dimethylamino)benzenesulfonyl chloride (365 mg, 1.66 mmol). The reaction mixture was stirred overnight at ambient temperature. The mixture was concentrated and purified by column chromatography (petroleum ether/EtOAc=8:1 to 2:1) to provide N-(3-((cyclohexylmethyl)(3-(4-(dimethylamino)phenylsulfonamido)propyl) amino)propyl)-4-(4-fluoro-2-methoxyphenyl)piperazine-1-sulfonamide.

To a solution of N-(3-((cyclohexylmethyl)(3-(4-(dimethylamino)phenylsulfonamido)propyl) amino)propyl)-4-(4-fluoro-2-methoxyphenyl)piperazine-1-sulfonamide (320 mg, 0.45 mmol) in NMP (3 mL) was added NaH (53 mg, 1.32 mmol, 60% dispersion). The mixture was stirred for 0.5 h at 80° C. then cooled to 70° C. and cyclopropane-1,1-diylbis(methylene) dimethanesulfonate (170 mg, 0.66 mmol) was added. The reaction mixture was stirred for 2 h at 70° C. The solvent was removed and the residue was purified by column chromatography (petroleum ether/EtOAc=15:1) to provide compound A193. MS (EI) for $C_{37}H_{57}FN_6O_3S_2$, found 745.0 $[M+H]^+$. $^1H$ NMR (400 MHz, $CDCl_3$): δ 7.57 (t, 2H), 6.64 (t, 1H), 6.63 (br s, 4H), 3.86 (s, 3H), 3.19 (m, 4H), 3.04 (m, 8H), 2.87 (m, 12H), 2.36 (m, 2H), 1.56 (m, 15H), 0.43 (m, 4H).

Route 40

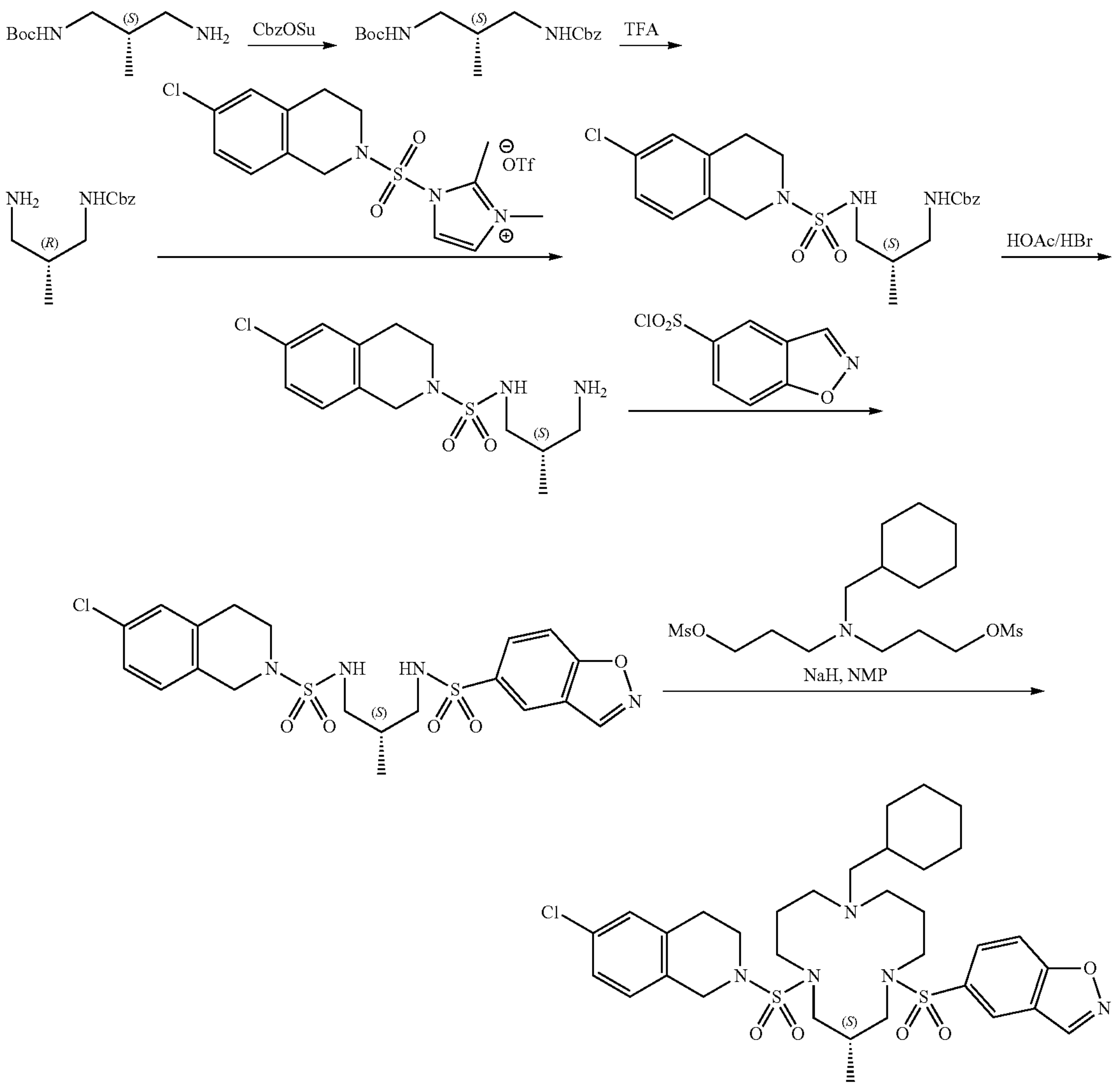

To a solution of (S)-tert-butyl 3-amino-2-methylpropylcarbamate (4.0 g, 21.3 mmol) in THF (20 mL) and water (20 mL) was added CbzOSu (5.83 g, 23.5 mmol). Aqueous NaOH (4N) was added to adjust to pH=11. The reaction mixture was stirred at ambient temperature for 2 h. The mixture was diluted with water (15 mL) and then extracted with ethyl acetate (50 mL). The organic phase was washed with 1 N aqueous HCl, dried over anhydrous sodium sulfate, and concentrated. The residue was purified by column chromatography to provide benzyl tert-butyl (2-methylpropane-1,3-diyl)(S)-dicarbamate.

To a solution of benzyl tert-butyl (2-methylpropane-1,3-diyl)(S)-dicarbamate (4.5 g, 14.0 mmol) in DCM (25 mL) was added TFA (20 mL). The reaction mixture was stirred at ambient temperature for 3 h. The mixture was concentrated and the residue was dissolved in DCM (50 mL). The resulting solution was washed with saturated aqueous $K_2CO_3$ and the DCM layer was dried over anhydrous sodium sulfate and concentrated to provide (R)-benzyl 3-amino-2-methylpropylcarbamate.

To a solution of (R)-benzyl 3-amino-2-methylpropylcarbamate (2.7 g, 12.2 mmol) in $CH_3CN$ (25 mL) was added 1-(6-chloro-3,4-dihydroisoquinolin-2(1H)-ylsulfonyl)-2,3-dimethyl-1H-imidazol-3-ium (5.7 g, 12.2 mmol). The reaction mixture was stirred at ambient temperature overnight. The mixture was concentrated and the residue was purified by column chromatography to provide (S)-benzyl 3-(6-chloro-1,2,3,4-tetrahydroisoquinoline-2-sulfonamido)-2-methyl propylcarbamate.

(S)-Benzyl 3-(6-chloro-1,2,3,4-tetrahydroisoquinoline-2-sulfonamido)-2-methyl propylcarbamate (2.7 g, 6.0 mmol) was dissolved in HBr (48%)/HOAc (20 mL). The mixture was stirred at ambient temperature for 1 h. The mixture was diluted with water (100 mL) and then washed with ether (50 mL). The aqueous layer was basified with NaOH to pH=10. The resulting mixture was extracted with DCM (100 mL). The DCM layer was dried over anhydrous sodium sulfate and concentrated to provide (S)—N-(3-amino-2-methylpropyl)-6-chloro-3,4-dihydroisoquinoline-2(1H)-sulfonamide.

To a solution of (S)—N-(3-amino-2-methylpropyl)-6-chloro-3,4-dihydroisoquinoline-2(1H)-sulfonamide (0.6 g, 1.9 mmol) and TEA (270 mg, 2.7 mmol) in DCM (6 mL) was added benzo[d]isoxazole-5-sulfonyl chloride (420 mg, 1.9 mmol) at 0° C. The reaction mixture was stirred at ambient temperature for 2 h. The mixture was washed with water and then concentrated. The residue was purified by column chromatography to provide (S)—N-(3-(6-chloro-1,2,3,4-tetrahydroisoquinoline-2-sulfonamido)-2-methylpropyl)benzo[c]isoxazole-5-sulfonamide.

To a solution of (S)—N-(3-(6-chloro-1,2,3,4-tetrahydroisoquinoline-2-sulfonamido)-2-methylpropyl)benzo[d]isoxazole-5-sulfonamide (0.61 g, 1.22 mmol) in NMP (6 mL) was added NaH (122 mg, 3.05 mmol, 60%). The mixture was stirred for 0.5 h at 80° C. The mixture was cooled to 70° C. and 3,3'-(cyclohexylmethylazanediyl)bis(propane-3,1-diyl) dimethanesulfonate (0.74 g, 1.83 mmol) was added. The reaction mixture was stirred for 2 h at 70° C. The mixture was cooled and poured into water. The resulting mixture was extracted with ethyl acetate. The organic phase was concentrated and the residue was purified by column chromatography (petroleum ether/EtOAc=12:1) to provide compound A180. LC-MS (ESI): m/z 692.2 $[M+H]^+$. $^1H$ NMR (400 MHz, $CDCl_3$): δ 7.84 (S, 1H), 7.61 (m, 1H), 7.13 (m, 3H), 6.69 (m, 2H), 4.32 (m, 2H), 3.66 (m, 5H), 3.21 (m, 5H), 2.91 (m, 4H), 2.77 (m, 4H), 1.91 (m, 4H), 1.57 (m, 6H), 1.13 (m, 6H), 0.89 (m, 3H).

The following compounds were synthesized in a similar manner:

| No. | IUPAC | $[M + H]^+$ |
|---|---|---|
| A168 | 3-{[(3S)-5-[(6-chloro-1,2,3,4-tetrahydroisoquinolin-2-yl)sulfonyl-9-(cyclohexylmethyl)-3-methyl-1,5,9-triazacyclododecan-1-yl]sulfonyl}-N,N-dimethylaniline | 694 |
| A171 | 6-chloro-2-{[(3S)-9-(cyclohexylmethyl)-3-methyl-5-phenylmethanesulfonyl-1,5,9-triazacyclododecan-1-yl]sulfonyl}-1,2,3,4-tetrahydroisoquinoline | 665 |
| A179 | 4-{[(3S)-5-[(6-chloro-1,2,3,4-tetrahydroisoquinolin-2-yl)sulfonyl]-9-(cyclohexylmethyl)-3-methyl-1,5,9-triazacyclododecan-1-yl]sulfonyl}-N,N-dimethylbenzamide | 722 |
| A184 | (3S)-N-benzyl-9-(cyclohexylmethyl)-5-[4-(dimethylamino)benzenesulfonyl]-N,3-dimethyl-1,5,9-triazacyclododecane-1-sulfonamide | 648 |
| A188 | 6-chloro-2-{[(3S)-9-(cyclohexylmethyl)-3-methyl-5-[(1-methyl-1H-indol-5-yl)sulfonyl]-1,5,9-triazacyclododecan-1-yl]sulfonyl}-1,2,3,4-tetrahydroisoquinoline | 704 |
| A189 | (3S)-9-(cyclohexylmethyl)-5-[4-(dimethylamino)benzenesulfonyl]-N-[(4-ethylphenyl)methyl]-3-methyl-1,5,9-triazacyclododecane-1-sulfonamide | 662 |
| A192 | N-{4-[({[(3S)-9-(cyclohexylmethyl)-5-[4-(dimethylamino)benzenesulfonyl]-3-methyl-1,5,9-triazacyclododecan-1-yl]sulfonyl}amino)methyl]phenyl}-N-methylacetamide | 705 |

Route 41
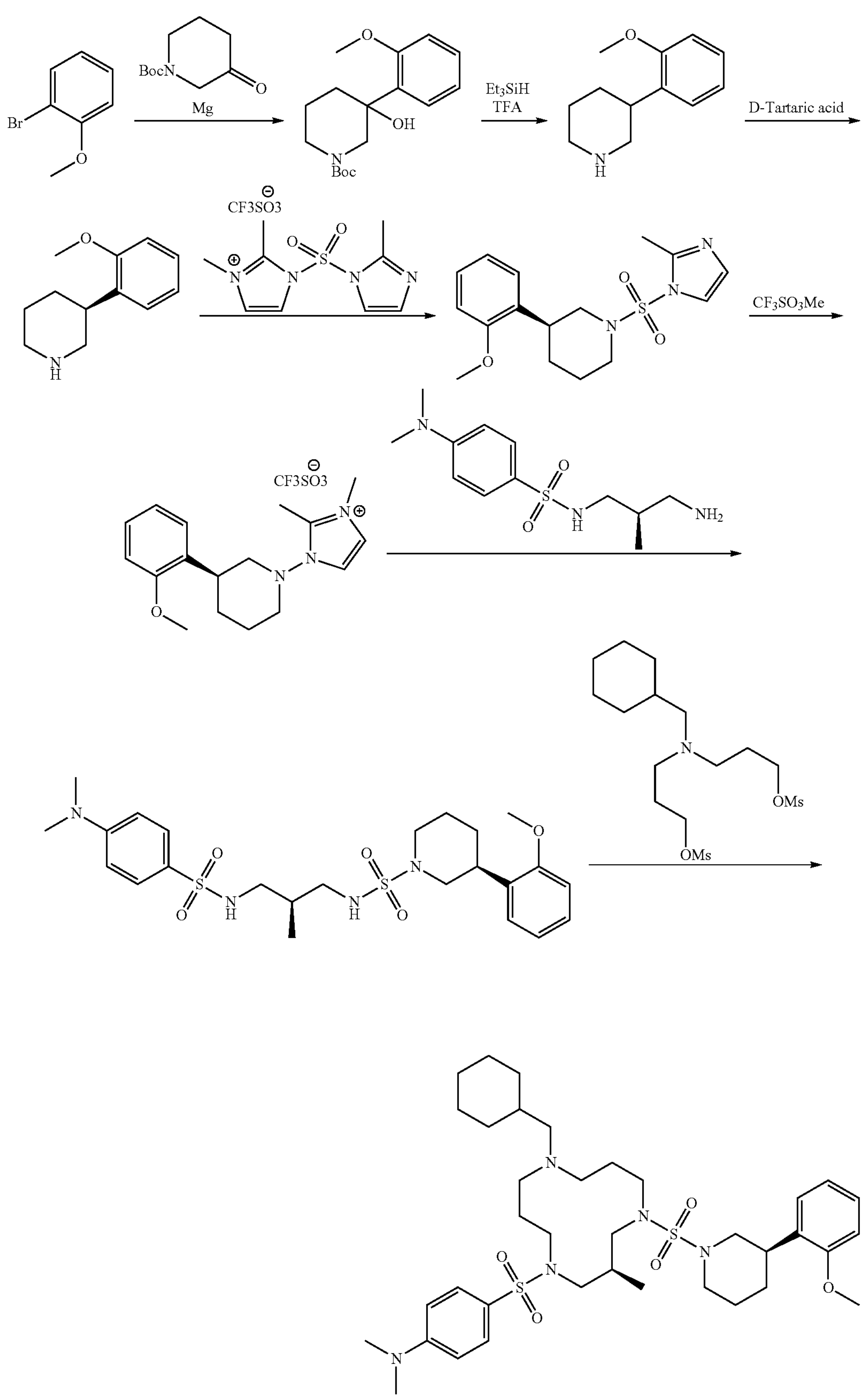

To a suspension of Mg (4.4 g, 181 mmol) in THF (200 mL) was added 1-bromo-2-methoxybenzene (40 g, 214 mmol). The mixture was stirred at 80° C. for 0.5 h. The mixture was cooled to 0° C. and a solution of tert-butyl 3-oxopiperidine-1-carboxylate (35.5 g, 181 mmol) in THF was added. The reaction mixture was stirred at ambient temperature for 2 h. The residue was purified by column chromatography to provide tert-butyl 3-hydroxy-3-(2-methoxyphenyl)piperidine-1-carboxylate. $^1$H NMR (400 MHz, $CDCl_3$): δ 7.48 (m, 1H), 7.32 (m, 1H), 6.98 (m, 2H), 4.08 (m, 1H), 3.96 (s, 3H), 3.82 (m, 1H), 3.31 (s, 1H), 2.98 (m, 1H), 2.25 (m, 1H), 1.99 (m, 2H), 1.62 (m, 2H), 1.63 (m, 9H).

A solution of tert-butyl 3-hydroxy-3-(2-methoxyphenyl)piperidine-1-carboxylate (23.0 g, 75 mmol) and triethylsilane (44 ml) in DCM (230 mL) was cooled to −30° C. and TFA (27 mL) was added. The reaction mixture was stirred at −30° C. for 2.5 h and then allowed to warm to ambient temperature and stirred for another 3.5 h. The mixture was poured into ice-water and the solution was adjusted to pH=9 with saturated aqueous sodium hydroxide. The resulting mixture was extracted three times with DCM. The combined organic phases were dried over anhydrous sodium sulfate and concentrated. The residue was purified by column chromatography to provide 3-(2-methoxyphenyl)piperidine.

A solution of 3-(2-methoxyphenyl)piperidine (6.5 g, 34 mmol) and D-tartaric acid (5.1 g, 34 mmol) in MeOH (25 mL) was refluxed for 2 h. The mixture was cooled to ambient temperature and filtered to provide the tartrate salt. This tartrate salt was recrystallized twice from MeOH and then treated with aqueous NaOH. The resulting mixture was extracted with DCM. The DCM layer was dried over anhydrous sodium sulfate and concentrated to provide (S)-3-(2-methoxyphenyl)piperidine.

A solution of (S)-3-(2-methoxyphenyl)piperidine (500 mg, 2.6 mmol) and 2,3-dimethyl-1-((2-methyl-1H-imidazol-1-yl)sulfonyl)-1H-imidazol-3-ium trifluromethanesulfonate (1.1 g, 2.7 mmol) in MeCN (15 ml) was stirred overnight at ambient temperature. The solvent was removed. The residue was purified by column chromatography (petroleum ether/EtOAc=20:1) to provide (S)-3-(2-methoxyphenyl)-1-((2-methyl-1H-imidazol-1-yl)sulfonyl)piperidine. LC-MS (ESI): m/z 336.06 [M+H]$^+$.

To a solution of (S)-3-(2-methoxyphenyl)-1-((2-methyl-1H-imidazol-1-yl)sulfonyl)piperidine (800 g, 2.4 mmol) in DCM (10 ml) was added $CF_3SO_3Me$ (398 mg, 2.4 mmol). The reaction mixture was stirred for 2 h at ambient temperature. The solvent was removed and the residue was washed with ether to provide (S)-1-(3-(2-methoxyphenyl)piperidin-1-yl)-2,3-dimethyl-1H-imidazol-3-ium trifluoromethanesulfonate.

To a solution of (S)-1-(3-(2-methoxyphenyl)piperidin-1-yl)-2,3-dimethyl-1H-imidazol-3-ium trifluoromethanesulfonate (1 g, 2 mmol) in $CH_3CN$ (24 ml) was added (R)—N-(3-amino-2-methylpropyl)-4-(dimethylamino)benzenesulfonamide (0.55 g, 2 mmol). The reaction mixture was stirred overnight at ambient temperature. The mixture was concentrated. The residue was purified by column chromatography (petroleum ether/EtOAc=8:1 to 2:1) to provide (S)—N—((S)-3-((4-(dimethylamino)phenyl)sulfonamido)-2-methylpropyl)-3-(2-methoxyphenyl)piperidine-1-sulfonamide.

To a solution of (S)—N—((S)-3-((4-(dimethylamino)phenyl)sulfonamido)-2-methylpropyl)-3-(2-methoxyphenyl)piperidine-1-sulfonamide (454 mg, 0.86 mmol) in NMP (14 mL) was added NaH (104 mg, 2.6 mmol, 60%). The mixture was stirred for 0.5 h at 80° C. The mixture was cooled to 70° C. and ((cyclohexylmethyl)azanediyl)bis(propane-3,1-diyl) dimethanesulfonate (500 mg, 1.3 mmol) was added. The reaction mixture was stirred for 2 h at 70° C. The mixture was cooled to 0-5° C. and poured into water. The resulting mixture was extracted with ethyl acetate. The organic phase was dried over anhydrous sodium sulfate and concentrated. The residue was purified by prep-HPLC to provide compound A210. LC-MS (ESI): m/z 718.17 [M+H]$^+$. $^1$H NMR (400 MHz, $CDCl_3$): δ 7.60 (m, 2H), 7.23 (m, 2H), 6.95 (m, 2H), 6.68 (m, 2H), 3.82 (s, 3H), 3.73 (m, 5H), 3.26 (m, 4H), 3.12 (s, 6H), 2.76 (m, 5H), 2.36 (m, 4H), 1.76 (m, 9H), 1.33 (m, 10H), 0.86 (m, 6H).

The following compound was synthesized in a similar manner:

| No. | IUPAC | [M + H]$^+$ |
|---|---|---|
| A208 | 4-{[(3S)-9-(cyclohexylmethyl)-5-{[(3S)-3-(4-methoxyphenyl)piperidin-1-yl]sulfonyl}-3-methyl-1,5,9-triazacyclododecan-1-yl]sulfonyl}-N,N-dimethylaniline | 718 |

Route 42

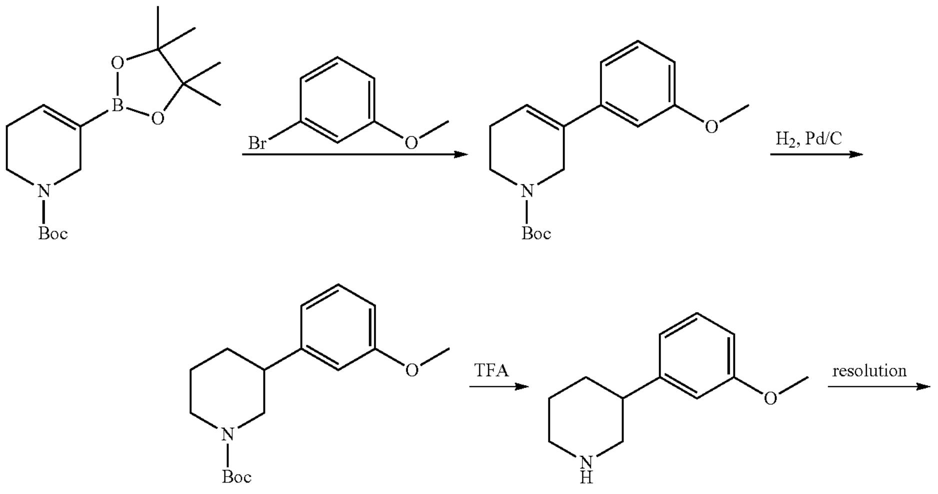

-continued

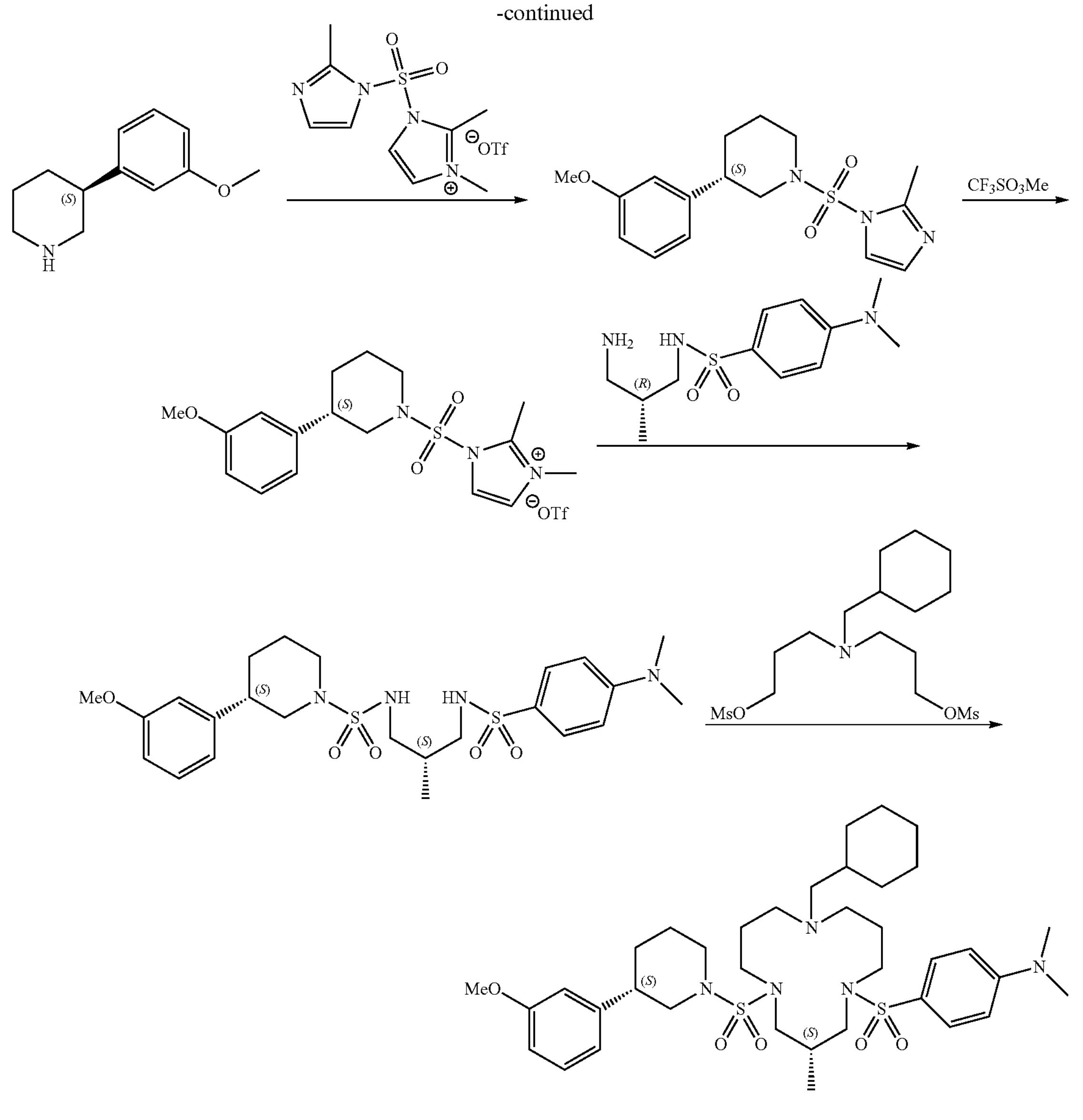

To a solution of tert-butyl 3-(4,4,5,5-tetramethyl-1,3,2-dioxaborolan-2-yl)-5,6-dihydropyridine-1(2H)-carboxylate (10.92 g, 35 mmol), 1-bromo-3-methoxybenzene (6.6 g, 35 mmol) and $Cs_2CO_3$ (3.44 g, 106 mmol) in 1,4-dioxane (50 mL) and $H_2O$ (10 mL) was added Pd(dppf)$Cl_2$ (1.32 g, 1.75 mmol). The reaction mixture was stirred overnight at 80° C. The solvent was removed. The residue was purified by column chromatography (petroleum ether/EtOAc=10:1) to provide tert-butyl 3-(3-methoxyphenyl)-5,6-dihydropyridine-1(214)-carboxylate. LC-MS (ESI): m/z 290.12 $[M+H]^+$. $^1H$ NMR (400 MHz, $CDCl_3$): δ 7.26 (m, 1H), 6.96 (m, 1H), 6.89 (s, 1H), 6.81 (m, 1H), 6.19 (s, 1H), 4.25 (s, 2H), 3.81 (s, 3H), 3.54 (m, 2H), 2.30 (s, 2H), 1.49 (s, 9H).

To a solution of tert-butyl 3-(3-methoxyphenyl)-5,6-dihydropyridine-1(2H)-carboxylate (9.46 g, 32 mmol) in MeOH (75 mL) and EtOAc (25 mL) was added Pd/C (2 g). The mixture was stirred at ambient temperature for 4 h under $H_2$ atmosphere. The mixture was filtered and the filtrate was concentrated to provide tert-butyl 3-(3-methoxyphenyl)piperidine-1-carboxylate. $^1H$ NMR (400 MHz, $CDCl_3$): δ 7.25 (m, 1H), 6.81 (m, 3H), 3.99 (m, 2H), 3.73 (s, 3H), 2.65 (m, 1H), 2.55 (m, 1H), 2.50 (m, 2H), 1.98 (m, 1H), 1.65 (m, 2H), 1.44 (s, 9H).

A solution of tert-butyl 3-(3-methoxyphenyl)piperidine-1-carboxylate (7.85 g, 27 mmol) in HCl/MeOH (80 mL) was stirred at ambient temperature for 4 h. The mixture was treated with water and then adjusted to pH=12 with 3N aqueous NaOH. The resulting mixture was extracted with EtOAc (100 mL×2). The combined extracts were dried over anhydrous sodium sulfate and concentrated to provide 3-(3-methoxyphenyl). LC-MS (ESI): m/z 192.09 $[M+H]^+$.

To a solution of D-(−)-tartaric acid (2.5 g, 16.7 mmol) in MeOH (12.5 mL) was added 3-(3-methoxyphenyl)piperidine (3.2 g, 16.7 mmol). The mixture was stirred at 80° C. for 24 h then cooled to ambient temperature. The resulting precipitate was collected by filtration and then recrystallized three times from MeOH to provide (S)-3-(3-methoxyphenyl)piperidine.

To a solution of (S)-3-(3-methoxyphenyl)piperidine (1.28 g, 6.7 mmol) in $CH_3CN$ (10 mL) was added 1-(1H-imidazol-1-ylsulfonyl)-3-methyl-1H-imidazol-3-ium trifluoromethanesulfonate (2.87 g, 7.3 mmol). The reaction mixture was stirred at ambient temperature overnight. The solvent was removed. The residue was purified by column chromatography (petroleum ether/EtOAc=9:1 to 8:2) to provide (S)-3-(3-methoxyphenyl)-1-(2-methyl-1H-imidazol-1-ylsulfonyl)piperidine. NMR (400 MHz, $CDCl_3$): δ 7.27 (m, 1H), 7.21 (s, 1H), 6.93 (s, 1H), 6.79 (m, 2H), 6.72 (s, 1H), 3.93 (m, 2H), 3.82 (s, 3H), 2.68 (m, 1H), 2.65 (m, 2H), 2.62 (s, 3H), 2.06 (m, 1H), 1.95 (m, 1H), 1.82 (m, 1H), 1.62 (m, 1H).

To a solution of (S)-3-(3-methoxyphenyl)-1-(2-methyl-1H-imidazol-1-ylsulfonyl)piperidine (1.6 mg, 4.7 mmol) in DCM (20 mL) was added $CF_3CO_2Me$ (782 mg, 4.7 mmol). The reaction mixture was stirred at ambient temperature for 2 h. The solvent was removed. The resulting product was washed with ether to provide (S)-1-(3-(3-methoxyphenyl) piperidin-1-ylsulfonyl)-2,3-dimethyl-1H-imidazol-3-ium trifluoromethanesulfonate.

mixture was stirred for 30 min at 80° C. The mixture was cooled to 70° C. and a solution of ((cyclohexylmethyl) azanediyl)bis(propane-3,1-diyl) dimethanesulfonate (606 mg, 1.57 mmol) in NMP (3 mL) was added. The reaction mixture was stirred at 70° C. for 1 h. The mixture was cooled to ambient temperature and poured into water (10 mL). The resulting mixture was extracted with ethyl acetate (20 mL). The organic layer was washed with water (15 mL×2), dried over anhydrous sodium sulfate and concentrated. The residue was purified by column chromatography (EtOAc/Petroleum ether=1:15 to 1:5) to provide compound A209. LC-MS (ESI): m/z 719.2 $[M+H]^+$. $^1H$ NMR (400 MHz, $CDCl_3$): δ 7.61 (m, 2H), 7.28 (m, 2H), 6.84 (m, 3H), 6.70 (m, 2H), 3.83 (s, 3H), 3.70 (m, 2H), 3.55 (m, 2H), 3.30 (m, 1H), 3.11 (s, 9H), 2.79 (m, 5H), 2.41 (m, 1H), 2.33 (m, 3H), 2.05 (m, 8H), 1.67 (m, 4H), 1.27 (m, 7H), 0.94 (m, 3H), 0.85 (m, 2H).

Route 43

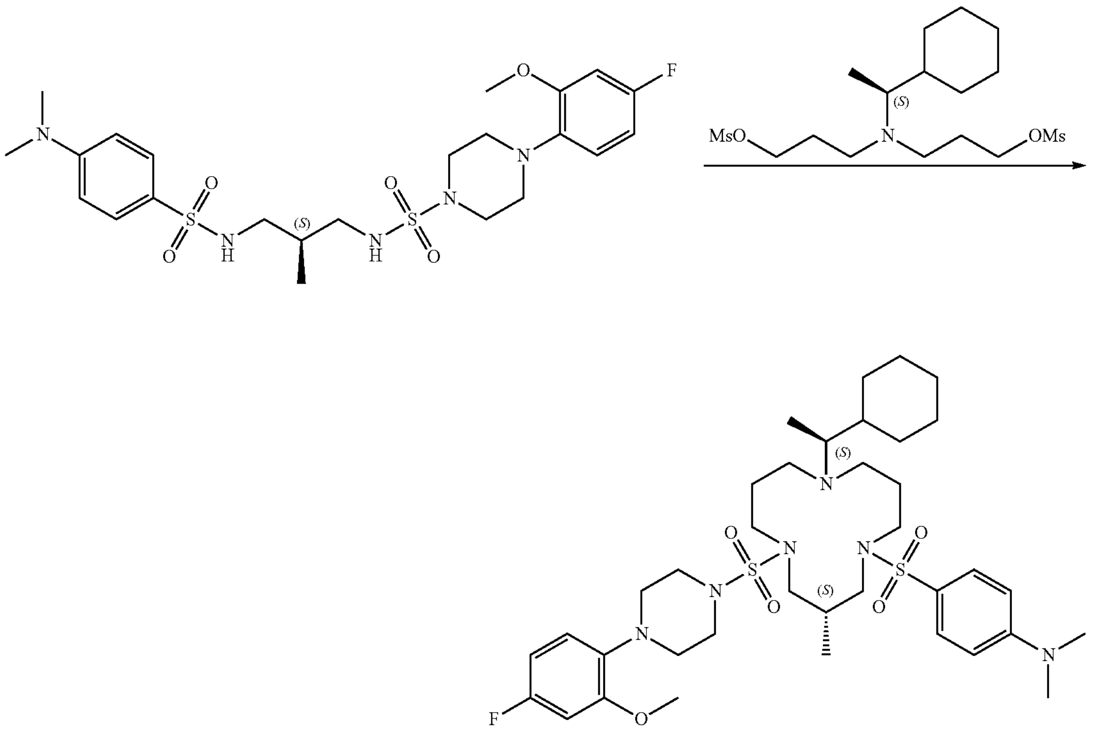

To a solution of (S)-1-(3-(3-methoxyphenyl)piperidin-1-ylsulfonyl)-2,3-dimethyl-1H-imidazol-3-ium trifluoromethanesulfonate (1.1 g, 2.2 mmol) in $CH_3CN$ (11 mL) was added (R)—N-(3-amino-2-methylpropyl)-4-(dimethylamino)benzenesulfonamide (896 mg, 33 mmol). The mixture was stirred at ambient temperature overnight. The solvent was removed. The residue was purified by column chromatography to provide (S)—N—((S)-3-(4-(dimethylamino)phenylsulfonamido)-2-methylpropyl)-3-(3-methoxyphenyl)piperidine-1-sulfonamide. $^1H$ NMR (400 MHz, $CDCl_3$): δ 7.68 (m, 2H), 7.28 (m, 1H), 6.85 (m, 1H), 6.80 (m, 2H), 6.68 (m, 2H), 4.81 (m, 2H), 3.82 (s, 3H), 3.76 (m, 2H), 3.12 (m, 1H), 3.07 (s, 6H), 2.82 (m, 4H), 2.11 (m, 1H), 1.93 (m, 2H), 1.77 (m, 1H), 1.29 (m, 3H), 0.91 (m, 3H).

To a solution of (S)—N—((S)-3-(4-(dimethylamino)phenylsulfonamido)-2-methylpropyl)-3-(3-methoxyphenyl)piperidine-1-sulfonamide (550 mg, 1.05 mmol) in NMP (6 mL) was added sodium hydride (75.6 mg, 3.15 mmol). The To a solution of (S)—N-(3-((4-(dimethylamino)phenyl) sulfonamido)-2-methylpropyl)-4-(4-fluoro-2-methoxyphenyl)piperazine-1-sulfonamide (900 mg, 1.65 mmol) in NMP (5 mL) was added NaH (198 mg, 4.92 mmol, 60%). The mixture was stirred for 0.5 h at 80° C. The mixture was cooled to 70° C. and (S)-3,3'-(1-cyclohexylethylazanediyl) bis(propane-3,1-diyl) dimethanesulfonate (844 mg, 2.49 mmol) was added. The reaction mixture was stirred for 2 h at 70° C. then cooled to 0-5° C. and poured into water. The resulting mixture was extracted with ethyl acetate. The extract was concentrated. The residue was purified by column chromatography (petroleum ether/EtOAc=15:1) to provide compound A203. LC-MS (ESI): m/z 751.33 $[M+H]^+$. $^1H$ NMR (400 MHz, $CDCl_3$): δ 7.68 (m, 2H), 6.92 (m, 1H), 6.78 (m, 4H), 3.92 (s, 4H), 3.86 (m, 1H), 3.62 (m, 1H), 3.40 (m, 2H), 3.19 (m, 3H), 3.04 (s, 9H), 2.87 (m 2H), 2.26 (m, 3H), 1.92 (m, 3H), 1.79 (m, 4H), 1.66 (m, 2H), 1.54 (m, 2H), 1.38 (m, 4H), 1.26 (m, 5H), 0.98 (m, 3H), 0.83 (m, 4H).

The following compounds were synthesized in a similar manner:

| No. | IUPAC | [M + H]+ |
|---|---|---|
| B22 | 4-{[(1S,12R)-10-[(6-chloro-1,2,3,4-tetrahydroisoquinolin-2-yl)sulfonyl]-6-(cyclohexylmethyl)-2,6,10-triazabicyclo[10.2.0]tetradecan-2-yl]sulfonyl}-N,N-dimethylaniline | 706 |

-continued

| No. | IUPAC | [M + H]+ |
|---|---|---|
| A160 | 4-{[(3S,7S,11S)-5-[(6-chloro-1,2,3,4-tetrahydroisoquinolin-2-yl)sulfonyl]-9-(cyclohexylmethyl)-3,7,11-trimethyl-1,5,9-triazacyclododecan-1-yl]sulfonyl}-N,N-dimethylaniline | 722 |
| B16 | 4-{[(3S,7RJ 1 S)-5-[(6-chloro-1,2,3,4-tetrahydroisoquinolin-2-yl)sulfonyl]-9-(cyclohexylmethyl)-3,7,11-trimethyl-1,5,9-triazacyclododecan-1-yl]sulfonyl}-N,N-dimethylaniline | 722 |

Route 44

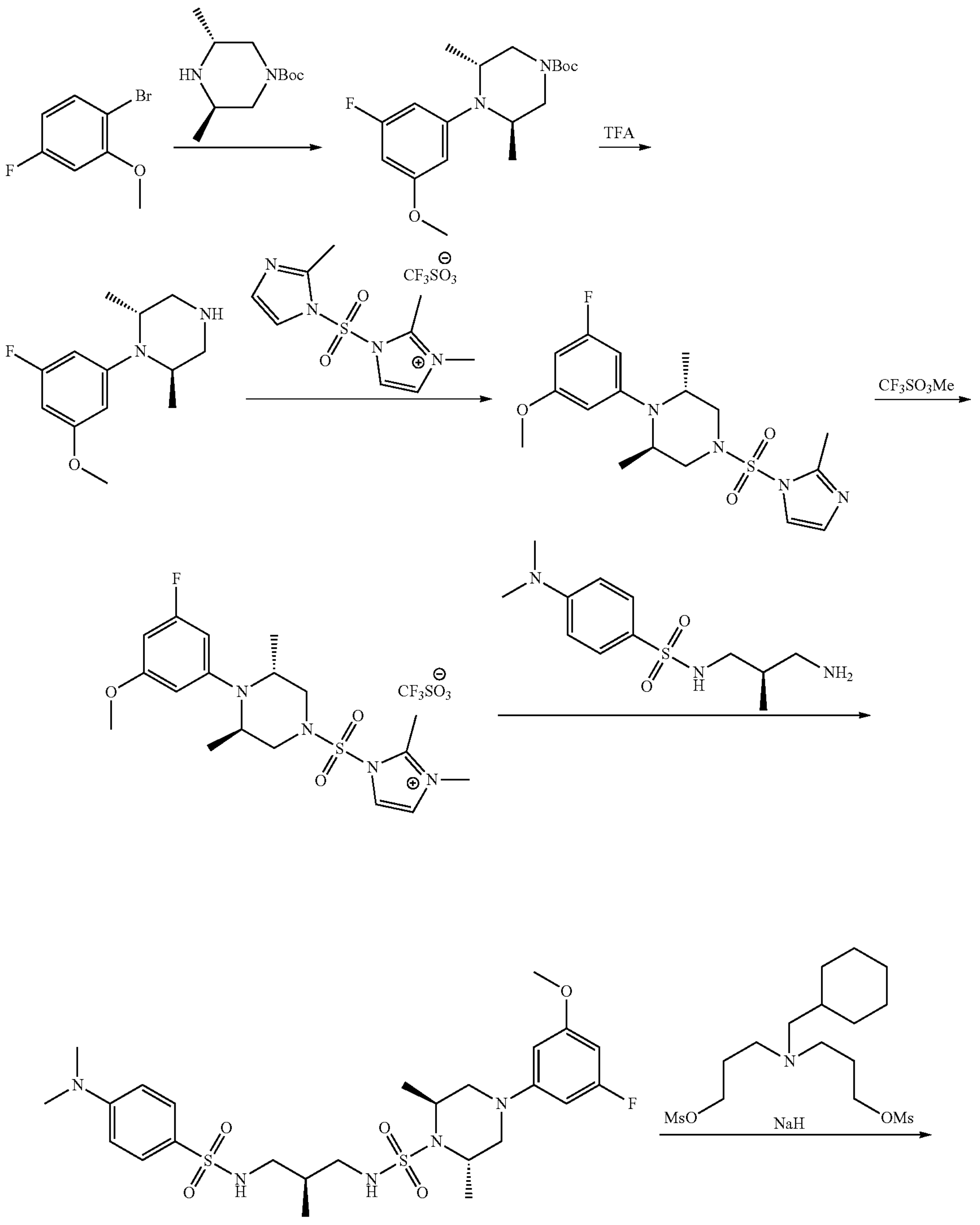

-continued

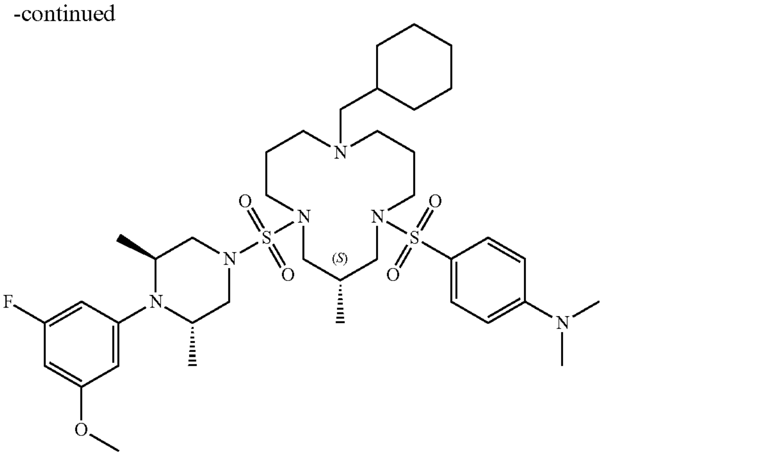

To a solution of 1-bromo-4-fluoro-2-methoxybenzene (910 mg, 4.4 mmol) and 1M KHMDS (18 mL, 18 mmol) in 1,4-dioxane (9 mL) was added tert-butyl (3R,5R)-3,5-dimethylpiperazine-1-carboxylate (950 mg, 4.4 mmol). The reaction mixture was stirred at 100° C. for 3 h. The solvent was removed and the residue was purified by column chromatography (petroleum ether/EtOAc=20:1) to provide tert-butyl (3R,5R)-4-(3-fluoro-5-methoxyphenyl)-3,5-dimethylpiperazine-1-carboxylate. LC-MS (ESI): m/z 339.0 $[M+H]^+$.

To a solution of tert-butyl (3R,5R)-4-(3-fluoro-5-methoxyphenyl)-3,5-dimethylpiperazine-1-carboxylate (800 mg, 2.4 mmol) in DCM (4 mL) was added TFA (4 mL). The mixture was stirred at ambient temperature for 1 h. The solvent was removed. The residue was dissolved in DCM (50 mL) and then washed with saturated aqueous $K_2CO_3$. The organic layer was dried over anhydrous sodium sulfate and concentrated to provide (2R,6R)-1-(3-methoxy-6-methylphenyl)-2,6-dimethylpiperazine.

To a solution of (2R,6R)-1-(3-methoxy-5-methylphenyl)-2,6-dimethylpiperazine (500 mg, 2.1 mmol) in MeCN (5 mL) was added 2,3-dimethyl-1-((2-methyl-1H-imidazol-1-yl)sulfonyl)-1H-imidazol-3-ium trifluoromethanesulfonate (825 mg, 2.1 mmol). The reaction mixture was stirred overnight at ambient temperature. The solvent was removed. The residue was purified by column chromatography (petroleum ether/EtOAc=20:1) to provide (2R,6R)-1-(3-fluoro-5-methoxyphenyl)-2,6-dimethyl-4-((2-methyl-1H-imidazol-1-yl)sulfonyl)piperazine. LC-MS (ESI): m/z 383.53 $[M+H]^+$.

To a solution of (2R,6R)-1-(3-methoxy-5-methylphenyl)-2,6-dimethylpiperazine (450 mg, 1.2 mmol) in DCM (5 mL) was added $CF_3SO_3Me$ (193 mg, 1.2 mmol). The reaction mixture was stirred for 2 h at ambient temperature. The solvent was removed and the residue was washed with ether to provide 1-(((3R,5R)-4-(3-fluoro-5-methoxyphenyl)-3,5-dimethylpiperazin-1-yl)sulfonyl)-2,3-dimethyl-1H-imidazol-3-ium trifluoromethanesulfonate.

To a solution of 1-(((3R,5R)-4-(3-fluoro-5-methoxyphenyl)-3,5-dimethylpiperazin-1-yl)sulfonyl)-2,3-dimethyl-1H-imidazol-3-ium trifluoromethanesulfonate (500 mg, 0.91 mmol) in $CH_3CN$ (5 mL) was added (R)—N-(3-amino-2-methylpropyl)-4-(dimethylamino)benzenesulfonamide (248 mg, 0.91 mmol). The reaction mixture was stirred overnight at ambient temperature. The mixture was concentrated. The residue was purified by column chromatography (petroleum ether/EtOAc=8:1 to 2:1) to provide (2S,6S)—N—((S)-3-((4-(dimethylamino)phenyl)sulfonamido)-2-methylpropyl)-4-(3-fluoro-5-methoxyphenyl)-2,6-dimethylpiperazine-1-sulfonamide. LC-MS (ESI): m/z 572.4 $[M+H]^+$.

To a solution of (2S,6S)—N—((S)-3-((4-(dimethylamino)phenyl)sulfonamido)-2-methylpropyl)-4-(3-fluoro-5-methoxyphenyl)-2,6-dimethylpiperazine-1-sulfonamide (430 mg, 0.75 mmol) in NMP (4 mL) was added NaH (91 mg, 2.3 mmol, 60%). The mixture was stirred for 0.5 h at 80° C. The mixture was cooled to 70° C. and ((cyclohexylmethyl)azanediyl)bis(propane-3,1-diyl) dimethanesulfonate (435 mg, 1.1 mmol) was added. The reaction mixture was stirred for 2 h at 70° C. The solvent was removed and the residue was purified by column chromatography (petroleum ether/EtOAc=15:1) to provide compound A200. LC-MS (ESI): m/z 764.3 $[M+H]^+$. $^1H$ NMR (400 MHz, $CDCl_3$): 7.60 (d, 2H), 6.69 (d, 2H), 6.32 (d, 3H), 3.78 (s, 3H), 3.06 (q, 2H), 3.04 (s, 8H), 3.00 (s, 2H), 2.87 (d, 2H), 2.76 (s, 2H), 2.34 (br s, 4H), 2.09 (br s, 2H), 1.33 (s, 17H), 1.04 (d, 7H), 0.93 (d, 3H).

(S)-3,3'-(1-Cyclohexylethylazanediyl)dipropan-1-ol (Intermediate for Compounds A203, A190, A207)

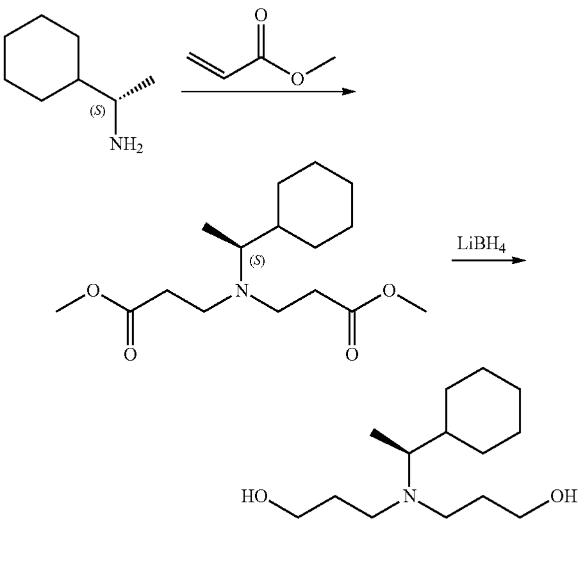

To a solution of (S)-1-cyclohexylethanamine (4.0 g, 31.46 mmol) in methanol (50 mL) was added methyl acrylate (8.1 g, 94.38 mmol). The reaction mixture was stirred for 72 h at 45° C. The mixture was concentrated and the residue was purified by column chromatography (EtOAc/petroleum ether=30:1) to provide (S)-dimethyl 3,3'-(1-cyclohexylethylazanediyl)dipropanoate.

To a solution of (S)-dimethyl 3,3'-(1-cyclohexylethylazanediyl)dipropanoate (4.0 g, 13.37 mmol) in THF (50 mL) was added $LiBH_4$ (1.45 g, 66.84 mmol). The reaction mixture was stirred at 60° C. for 2 h. The mixture was cooled to 0-5° C. and quenched with water (30 mL). The mixture was adjusted to pH=3 with 1 N aqueous hydrochloric acid and stirred for 30 minutes. The resulting mixture was washed with dichloromethane. The aqueous layer was adjusted to pH=9-10 with saturated aqueous sodium carbonate and then extracted with DCM (3×). The combined organic layers were dried over anhydrous sodium sulfate and concentrated to provide (S)-3,3'-(1-cyclohexylethylazanediyl)dipropan-1-ol. $^1H$ NMR (400 MHz, $CDCl_3$): δ 3.66 (s, 1H), 2.82 (m, 2H), 2.42 (m, 2H), 2.21 (m, 1H), 1.96 (m, 2H), 1.67 (m, 4H), 1.22 (m, 4H), 0.91 (m, 3H), 0.81 (m, 1H), 0.72 (m, 1H).

The following compounds were synthesized in a similar manner: (R)-3,3'-(1-Cyclohexylethylazanediyl)dipropan-1-ol (Intermediate for compound A191) and (S)-3,3'-((l-phenylethyl)azanediyl)bis(propan-1-ol) (Intermediate for compound A205)

6-Chloro-N-(((1R,2S)-2-(4-(dimethylamino)phenylsulfonamido)cyclobutyl) methyl)-3,4-dihydroisoquinoline-2(1H)-sulfonamide (Intermediate for compound B22)

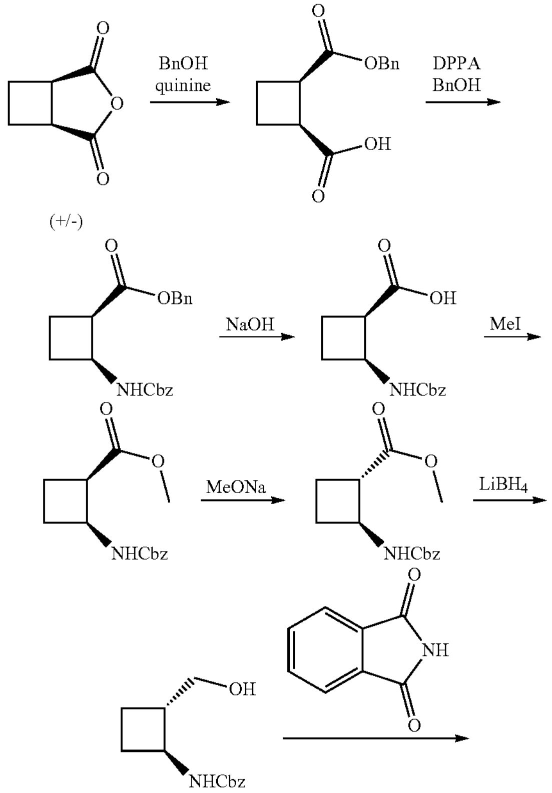

-continued

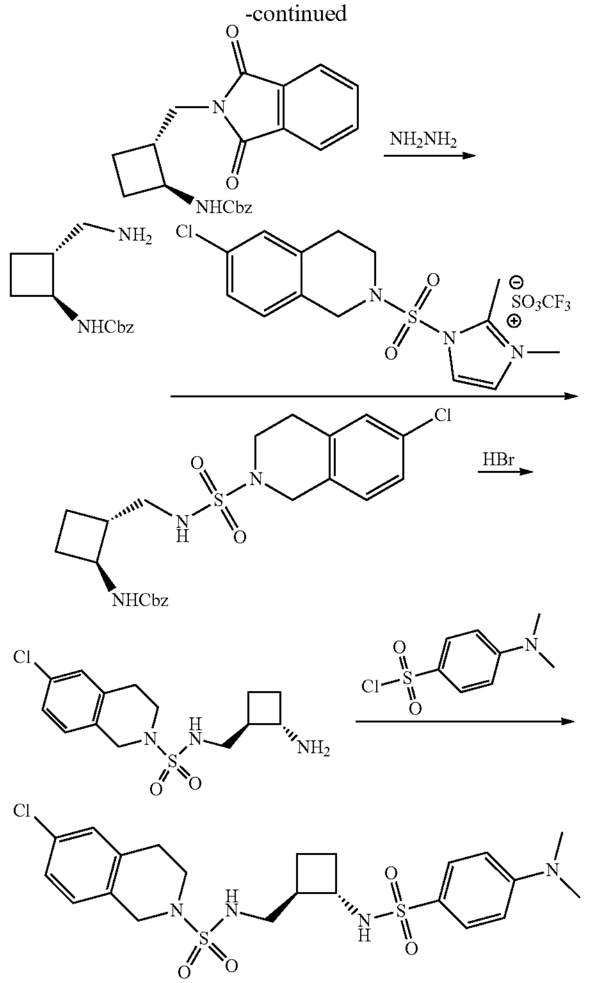

To a suspension of cis-3-oxabicyclo[3.2.0]heptane-2,4-dione (32.8 g, 200 mmol) and quinine (71.4 g, 220 mmol) in toluene (1 L) was added benzyl alcohol (64.9 g, 600 mmol) dropwise over a period of 0.5 h at −55° C. The reaction mixture was stirred at −55° C. for 96 h. The resulting clear solution was concentrated to dryness and the residue was dissolved in diethyl ether (1.2 L). The solution was washed with 2N aqueous HCl (1 L), the organic layer was extracted with saturated aqueous sodium bicarbonate (500×5 mL), and the resulting combined aqueous phases were washed with diethyl ether (500 mL) to remove the traces of benzyl alcohol. The aqueous phase was acidified with 8N aqueous HCl then extracted with DCM (1.0 L×2). The combined organic layers were dried over anhydrous sodium sulfate and concentrated to provide (1S,2R)-2 (benzyloxycarbonyl)cyclobutanecarboxylic acid.

To a solution of (1S,2R)-2-(benzyloxycarbonyl)cyclobutanecarboxylic acid (40.1 g, 171.4 mmol) and triethylamine (26.0 g, 257 mmol) in dichloroethane (400 mL) was added dropwise DPPA (51.8 g, 188.5 mmol) at 0° C. The mixture was stirred for 2 h at ambient temperature then washed with water and dried over anhydrous $NaSO_4$. To the organic solution was added BnOH (18.5 g, 171 mmol) and triethylamine (34.6 g, 342 mmol). The reaction mixture was refluxed overnight and then diluted with DCM (500 mL). The mixture was washed with 1N aqueous HCl (1 L) and saturated aqueous $NaHCO_3$. The organic phase was dried over anhydrous sodium sulfate, concentrated, and purified by column chromatography to provide (1R,2S)-benzyl 2-(benzyloxycarbonylamino) cyclobutanecarboxylate.

To a solution of (1R,2S)-benzyl 2-(benzyloxycarbonylamino)cyclobutanecarboxylate (20 g, 59 mmol) in THF (100 mL) was added 4N aqueous NaOH (50 mL) at 0° C. The reaction mixture was stirred overnight at ambient temperature. The mixture was diluted with water (30 mL) then washed with ether (50 mL×2). The aqueous layer was acidified with 3N aqueous HCl and extracted with ethyl acetate. The extracts were dried over anhydrous sodium sulfate and concentrated to provide (1R,2S)-2-(benzyloxycarbonylamino)cyclobutanecarboxylic acid. $^1$H NMR (400 MHz, $CDCl_3$): δ 7.34 (m, 5H), 5.12 (m, 2H), 4.62 (m, 1H), 3.58 (m, 1H), 2.28 (m, 2H), 1.89 (m, 2H).

To a solution of (1R,2S)-2-(benzyloxycarbonylamino) cyclobutanecarboxylic acid (4.0 g, 16.1 mmol) and $K_2CO_3$ (4.4 g, 32 mmol) in DMF (40 mL) was added MeI (2.96 g, 20.8 mmol). The reaction mixture was stirred at ambient temperature overnight. The mixture was poured into water (150 mL) then extracted with ether (200 mL). The organic phase was dried over anhydrous sodium sulfate and concentrated. The residue was purified by column chromatography to provide (1R,2S)-methyl 2-(benzyloxycarbonylamino)cyclobutanecarboxylate. $^1$H NMR (400 MHz, $CDCl_3$): δ 7.34 (m, 5H), 5.69 (m, 1H), 5.08 (s, 2H), 4.62 (m, 1H), 3.66 (s, 3H), 3.38 (m, 1H), 2.32 (m, 2H), 1.99 (m, 2H).

To a solution of (1R,2S)-methyl 2-(benzyloxycarbonylamino) cyclobutanecarboxylate (8.9 g, 33.8 mmol) in MeOH (250 mL) was added NaOMe (9.1 g, 169 mmol). The mixture was heated at 45° C. for 4 h then cooled to 0° C. and HOAc (10.2 g, 169 mmol) was added dropwise. The mixture was then poured into water (500 mL) and extracted with ethyl acetate (300 mL). The extract was washed with saturated aqueous $NaHCO_3$ and dried over anhydrous sodium sulfate. The organic solution was concentrated and the residue was purified by column chromatography to provide (1S,2S)-methyl 2-(benzyloxycarbonylamino)cyclobutanecarboxylate. NMR (400 MHz, $CDCl_3$): δ 7.34 (m, 5H), 5.08 (m, 3H), 4.38 (m, 1H), 3.72 (s, 3H), 3.38 (m, 1H), 2.32 (m, 2H), 1.89 (m, 2H).

To a solution of (1S,2S)-methyl 2-(benzyloxycarbonylamino) cyclobutanecarboxylate (1.3 g, 4.9 mmol) in THF (10 mL) was added $LiBH_4$ (0.38 g, 9.8 mmol). The reaction mixture was stirred for 3 h at ambient temperature then poured into water (15 mL) and extracted with ethyl acetate. The organic phase was dried over anhydrous sodium sulfate and concentrated to provide benzyl (1S,2S)-2-(hydroxymethyl)cyclobutylcarbamate. $^1$H NMR (400 MHz, $CDCl_3$): δ 7.34 (m, 5H), 5.08 (m, 3H), 3.72 (m, 1H), 3.57 (m, 2H), 2.32 (m, 2H), 1.89 (m, 2H), 1.45 (m, 1H).

To a solution of benzyl (1S,2S)-2-(hydroxymethyl)cyclobutylcarbamate (1.1 g, 4.94 mmol), $PPh_3$ (1.5 g, 5.9 mmol) and isoindoline-1,3-dione (1.0 g, 6.9 mmol) in toluene (10 mL) was added DIAD (1.2 g, 5.9 mmol) at 0° C. The reaction mixture was stirred for 3 h. The precipitate was filtered off and the filtrate was concentrated and purified by column chromatography to provide benzyl (1S,2R)-2-((1,3-dioxoisoindolin-2-yl)methyl)cyclobutylcarbamate.

To a solution of benzyl (1S,2R)-2-((1,3-dioxoisoindolin-2-yl)methyl) cyclobutylcarbamate (2.0 g, 5.5 mmol) in EtOH (40 mL) was added hydrazine hydrate (0.64 g). The reaction mixture was refluxed for 3 h. The mixture was cooled, filtered, and the filtrate was concentrated. The residue was dissolved in 1 N aqueous HCl (30 mL) and then washed with ether (20 mL). The aqueous layer was adjusted to pH=10. The resulting mixture was extracted with DCM (50 mL×2). The combined organics were dried over anhydrous sodium sulfate and concentrated to provide benzyl (1S,2R)-2-(aminomethyl)cyclobutylcarbamate.

To a solution of benzyl (1S,2R)-2-(aminomethyl)cyclobutylcarbamate (0.8 g, 3.4 mmol) in $CH_3CN$ (10 mL) was added 1-((6-chloro-3,4-dihydroisoquinolin-2(1H)-yl)sulfonyl)-2,3-dimethyl-1H-imidazol-3-ium trifluoromethanesulfonate (2.4 g, 5.12 mmol). The reaction mixture was stirred at ambient temperature overnight. The mixture was concentrated and the residue was purified by column chromatography to provide benzyl (1S,2R)-2-((6-chloro-1,2,3,4-tetrahydroisoquinoline-2-sulfonamido)methyl) cyclobutylcarbamate.

To 40% HBr solution in HOAc (10 mL) was added benzyl (1S,2R)-2-((6-chloro-1,2,3,4-tetrahydroisoquinoline-2-sulfonamido)methyl) cyclobutylcarbamate (1.2 g, 2.6 mmol). The mixture was stirred for 3 h then poured into water (50 mL) and washed with ether. The aqueous layer was adjusted to pH=10 with 8N aqueous NaOH. The mixture was extracted with DCM (50 mL). The organic phase was dried over anhydrous sodium sulfate and concentrated to provide N-(((1R,2S)-2-aminocyclobutyl)methyl)-6-chloro-3,4-dihydroisoquinoline-2(1H)-sulfonamide.

To a solution of N-(((1R,2S)-2-aminocyclobutyl)methyl)-6-chloro-3,4-dihydroisoquinoline-2(1H)-sulfonamide (0.66 g, 2.0 mmol) and $NEt_3$ (350 mg, 3.5 mmol) in DCM (5 mL) was added 4-(dimethylamino)benzenesulfonyl chloride (426 mg, 2.0 mmol) at 0° C. The reaction mixture was stirred at ambient temperature for 2 h then concentrated. The residue was dissolved in DCM and washed with water. The organic phase was dried over anhydrous sodium sulfate and concentrated to provide 6-chloro-N-(((1R,2S)-2-(4-(dimethylamino)phenylsulfonamido)cyclobutyl) methyl)-3,4-dihydroisoquinoline-2(1H)-sulfonamide. $^1$H NMR (400 MHz, $CDCl_3$): δ 7.77 (m, 2H), 7.18 (m, 2H), 7.05 (m, 1H), 6.75 (m, 2H), 5.28 (m, 1H), 5.05 (m, 1H), 4.36 (s, 2H), 3.50 (m, 2H), 3.35 (m, 1H), 3.15 (m, 1H), 3.09 (s, 6H), 2.92 (m, 3H), 2.42 (m, 1H), 2.03 (m, 1H), 1.65 (m, 2H), 1.25 (m, 1H).

(S)-3-((Cyclohexylmethyl)((R)-2-methyl-3-(methylsulfonyloxy)propyl)amino)-2-methylpropyl methanesulfonate (Intermediate for compound A178)

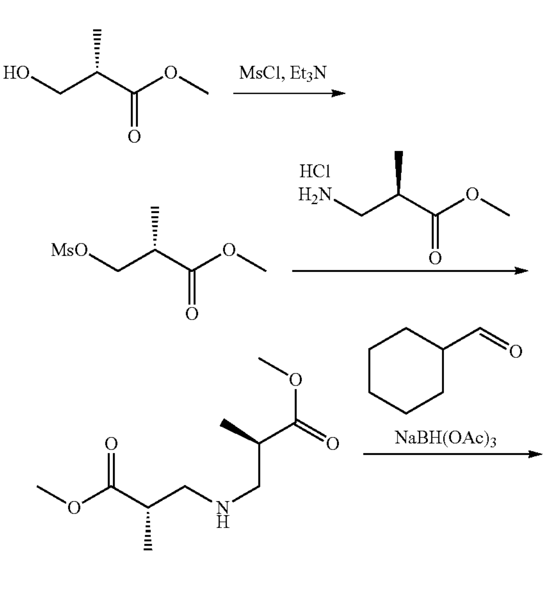

-continued

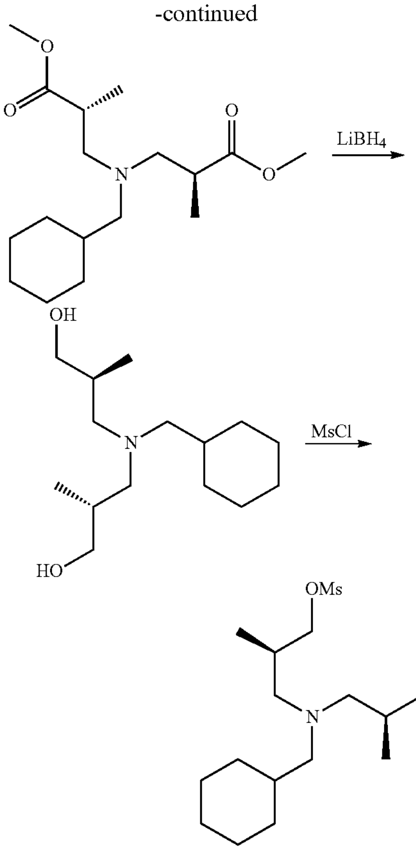

To a solution of (S)-methyl 3-hydroxy-2-methylpropanoate (4.0 g, 25.42 mmol) and triethylamine (5.3 g, 50.84 mmol) in DCM (60 mL) was added slowly methanesulfonyl chloride (5.6 g, 10.20 mmol) at 0-5° C. The reaction mixture was stirred for 1 h at ambient temperature. The mixture was then diluted with DCM (100 mL) and washed with water (50 mL). The organic layer was dried over anhydrous sodium sulfate and concentrated to provide (S)-methyl 2-methyl-3-(methylsulfonyloxy)propanoate.

To a solution of (R)-methyl 2-aminopropanoate hydrochloride (1.60 g, 10.20 mmol) in acetonitrile (200 mL) was added (S)-methyl 2-methyl-3-(methylsulfonyloxy)propanoate (4.2 g, 21.43 mmol) and potassium carbonate (4.20 g, 30.60 mmol). The reaction mixture was refluxed for 16 h then filtered and the filtrate was concentrated to provide (2R,2'S)-dimethyl 2,2'-azanediylbis(methylene)dipropanoate.

To a solution of (2R,2'S)-dimethyl 2,2'-azanediylbis (methylene)dipropanoate (650 mg, 3.0 mmol) in DCM (10 mL) was added cyclohexanecarbaldehyde (336 mg, 3.0 mmol) and sodium triacetoxyborohydride (954 mg, 4.50 mmol). The reaction mixture was stirred overnight at ambient temperature. The mixture was quenched with water and adjusted to pH=10. The resulting mixture was extracted with DCM. The extract was concentrated and the residue was purified by column chromatography to provide (2R,2'S)-dimethyl 2,2'-(cyclohexylmethylazanediyl)bis(methylene) dipropanoate.

To a solution of (2R,2'S)-dimethyl 2,2'-(cyclohexylmethylazanediyl)bis(methylene) dipropanoate (350 mg, 1.28 mmol) in THF (10 mL) was added $LiBH_4$ (486 mg, 12.80 mmol). The reaction mixture was stirred at 80° C. overnight. The mixture was cooled and quenched with water. The resulting mixture was adjusted to pH=5 with 1 N aqueous hydrochloric acid and stirred for 0.5 h then adjusted to pH=10 and extracted with ethyl acetate three times. The combined organics were dried over anhydrous sodium sulfate and concentrated to provide (2R,2'S)-2,2'-(cyclohexylmethylazanediyl)bis(methylene)dipropan-1-ol.

To a solution of (2R,2'S)-2,2'-(cyclohexylmethylazanediyl)bis(methylene) dipropan-1-ol (153 mg, 0.59 mmol) and triethylamine (0.12 g, 1.2 mmol) in DCM (5 mL) was added MsCl (135 mg, 1.18 mmol) at 0° C. The reaction mixture was stirred for 3 h at ambient temperature. The mixture was diluted with DCM (15 mL) and then washed with water (20 mL×2). The organics were dried over anhydrous sodium sulfate and concentrated to provide (S)-3-((cyclohexylmethyl)((R)-2-methyl-3-(methylsulfonyloxy) propyl)amino)-2-methylpropyl methanesulfonate. MS (EI) $C_{17}H_{35}NO_6S_2$, found 414 $[M+H]^+$.

The following compound was synthesized in a similar manner: (2S,2'S)-((cyclohexylmethyl)azanediyl)bis(2-methylpropane-3,1-diyl) dimethanesulfonate (Intermediate for compound A160)

(R)-6-Chloro-N-(4-(4-(dimethylamino)phenylsulfonamido)butan-2-yl)-3,4-dihydroisoquinoline-2(1H)-sulfonamide (Intermediate for compound A148)

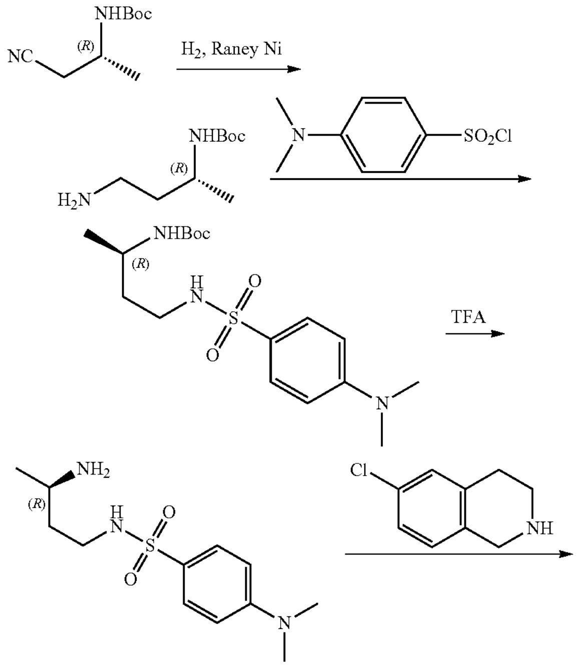

-continued

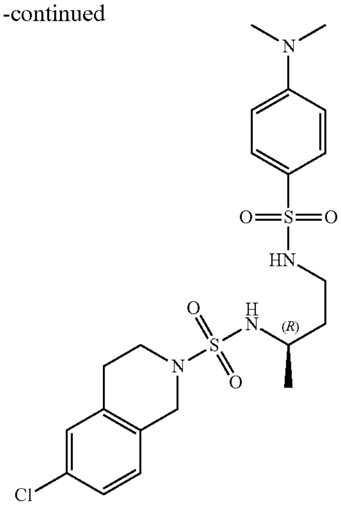

A solution of (R)-tert-butyl 1-cyanopropan-2-ylcarbamate (13.0 g, 71 mmol) in ethanol (250 mL) saturated with anhydrous ammonia was treated with Raney-Ni (24 g) under 55 psi of $H_2$ overnight. The mixture was filtered through a pad of celite and the filtrate was concentrated. The residue was purified by column chromatography to provide (R)-tert-Butyl 4-aminobutan-2-ylcarbamate.

To a solution of (R)-tert-butyl 4-aminobutan-2-ylcarbamate (2.5 g, 13.3 mmol) and triethylamine (1.33 g, 13.3 mmol) in DCM (25 mL) was added slowly a solution of 4-(dimethylamino)benzene-1-sulfonyl chloride (2.93 g, 13.3 mmol) in DCM (15 mL) at 0-5° C. The reaction mixture was stirred for 1 h at ambient temperature. The mixture was diluted with DCM (50 mL) and washed with water (30 mL). The organic layer was dried over anhydrous sodium sulfate and concentrated. The residue was purified by column chromatography to provide (R)-tert-butyl 4-(4-(dimethylamino)phenylsulfonamido)butan-2-ylcarbamate.

To a solution of (R)-tert-butyl 4-(4-(dimethylamino)phenylsulfonamido)butan-2-ylcarbamate (1.2 g, 3.2 mmol) in DCM (15 mL) was added TFA (7 mL). The mixture was stirred for 2 h and the solvent was removed. The residue was dissolved in DCM (30 mL) and then washed with saturated aqueous $NaHCO_3$. The organic phase was dried over anhydrous sodium sulfate and concentrated to provide (R)—N-(3-aminobutyl)-4-(dimethylamino)benzenesulfonamide (0.88 g, quantitative).

To a solution of (R)—N-(3-aminobutyl)-4-(dimethylamino)benzenesulfonamide (0.88 g, 4.0 mmol) in $CH_3CN$ (10 mL) was added 6-chloro-1,2,3,4-tetrahydroisoquinoline (1.98 g, 4.0 mmol). The reaction mixture was stirred at ambient temperature overnight. The mixture was concentrated and the residue was purified by column chromatography to provide (R)-6-chloro-N-(4-(4-(dimethylamino)phenylsulfonamido)butan-2-yl)-3,4-dihydroisoquinoline-2(1H)-sulfonamide.

The following compounds were synthesized in a similar manner: (S)-6-chloro-N-(4-((4-(dimethylamino)phenyl)sulfonamido)butan-2-yl)-3,4-dihydroisoquinoline-2(1H)-sulfonamide (Intermediate for compound A147); (S)-6-chloro-N-(3-((4-(dimethylamino)phenyl)sulfonamido)butyl)-3,4-dihydroisoquinoline-2(1H)-sulfonamide (Intermediate for compound A150); and (R)-6-chloro-N-(3-((4-(dimethylamino)phenyl)sulfonamido)butyl)-3,4-dihydroisoquinoline-2(1H)-sulfonamide (Intermediate for compound A149)

(R)-1-(4-fluoro-2-methoxyphenyl)-2-methylpiperazine (Intermediate for compound A177)

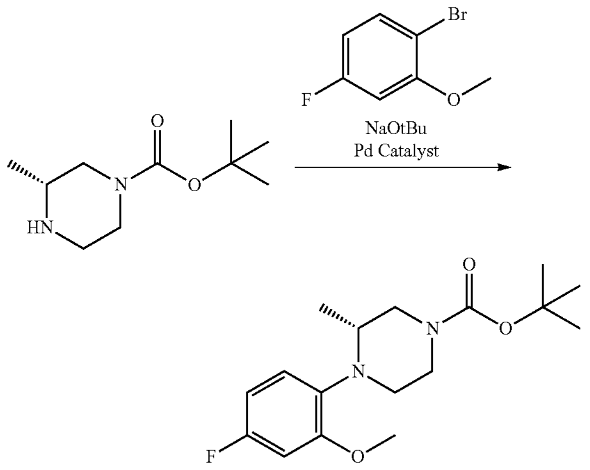

To tert-butyl (R)-3-methylpiperazine-1-carboxylate (5.37 g, 26.8 mmol) and 1-bromo-4-fluoro-2-methoxybenzene (5.00 g, 24.4 mmol) in toluene (50 mL) was added sodium tert-butoxide (4.69 g, 48.8 mmol) followed by BrettPhos palladacycle G3 (66.4 mg, 0.0732 mmol). The mixture was sealed under nitrogen and stirred at 100° C. and after 1 h the mixture was cooled to ambient temp, diluted with ethyl acetate and water. The organic layer was dried with sodium sulfate, filtered, and concentrated. Crude product was purified by column chromatography (0-40%, ethyl acetate/hexanes) to provide the product. MS(EI) for $C_{17}H_{25}FN_2O_3$, found 325 $[M+H]^+$.

To tert-butyl (R)-4-(4-fluoro-2-methoxyphenyl)-3-methylpiperazine-1-carboxylate (0.51 g, 1.6 mmol) was added HCl (1.6 mL, 4 N in dioxane) and the mixture was allowed to stand at ambient temp for 16 h then diluted with water (5 mL) and ethyl acetate (5 mL). The organic layer was removed and washed with water (1×5 mL). The combined aqueous layers were washed with ethyl acetate (1×5 mL), basified with NaOH (5 N to pH ~12), extracted with DCM (3×5 mL), dried with sodium sulfate, filtered, and concentrated to provide (R)-1-(4-fluoro-2-methoxyphenyl)-2-methylpiperazine which was carried forward without further purification. MS(EI) for $C_{12}H_{17}FN_2O$, found 225 $[M+H]^+$.

The following compounds were synthesized in a similar manner:

1-(4-fluoro-2-methoxyphenyl)piperazine (Intermediate for A137)
1-(2-methoxyphenyl)piperazine (Intermediate A154)
2-(piperazin-1-yl)benzonitrile (Intermediate for A118)
1-(2,6-dimethylphenyl)piperazine (Intermediate for A119)
2-(4-fluoro-2-methyl)-2,6-diazaspiro[3.3]heptane (Intermediate for A161)
(S)-1-(4-fluoro-2-methylphenyl)-3-methylpiperazine (Intermediate for A162)
(R)-1-(4-fluoro-2-methylphenyl)-3-methylpiperazine (Intermediate for A163)
1-(2-(trifluoromethoxy)phenyl)piperazine (Intermediate for A173)
1-(3,4-difluoro-2-methoxyphenyl)piperazine (Intermediate for A174)
1-(3-fluoro-2-methoxyphenyl)piperazine (Intermediate for A175)

1-(5-fluoro-2-methoxyphenyl)piperazine (Intermediate for A176)
1-(2-chlorophenyl)piperazine (Intermediate for A198)
1-(4-methoxyphenyl)piperazine (Intermediate for A199)
1-(3-methoxyphenyl)piperazine (Intermediate for A201)
1-(3-fluoro-4-methoxyphenyl)piperazine (Intermediate for A202)
1-(2-chloro-4-fluorophenyl)piperazine (Intermediate for A206)
(S)-1-(3-fluoro-5-methoxyphenyl)-2-methylpiperazine (Intermediate for A194)
(R)-1-(3-fluoro-5-methoxyphenyl)-2-methylpiperazine (Intermediate for A195)
(2S,6R)-1-(3-fluoro-5-methoxyphenyl)-2,6-dimethylpiperazine (Intermediate for A197)
(2R,6R)-1-(3-fluoro-5-methoxyphenyl)-2,6-dimethylpiperazine (Intermediate for A200)

Assays

Dox Induced PD1-ss-Gluc Assay

Flp-In 293 T-REx™ cells were transfected with pcDNA™5/FRT/TO plasmid inserted with cDNA encoding *Gaussia* Luciferase fused to the 3' end of cDNA encoding PD1 signal sequence plus 10 amino acids (N-MQIPQAPWPVVWAVLQLGWRPGWFLDSPDR-C) (SEQ ID NO: 1). Transfected cells were selected for resistance to the selectable markers Hygromycin and Blasticidin to create a stable cell line that contained the PD1-ss+10aa/*Gaussia* Luciferase cDNA insert whose expression was regulated under the T-REx™ system. The day before assay, cells were trypsinized and plated in 384-well tissue culture plates. The next day, compound dilutions in DMSO/media containing doxycycline were added to the wells and incubated at 37° C., 5% $CO_2$. 24 hours later, coelenterazine substrate was added to each well and luciferase signal was quantified using Tecan Infinite M1000 Pro for potency determination.

Results for select compounds provided herein are shown in Table 1, below. For chemical structures that include one or more stereoisomers, but are illustrated without indicating stereochemistry, the assay data refers to a mixture of stereoisomers.

Dox Induced PD1-FL-Gluc Assay

Flp-In 293 T-REx™ cells were transfected with pcDNA™5/FRT/TO plasmid inserted with cDNA encoding Firefly Luciferase fused to the 3' end of cDNA encoding full length PD1 (amino acids 1-288). Transfected cells were selected for resistance to the selectable markers Hygromycin and Blasticidin to create a stable cell line that contained the PD1-FL/Firefly Luciferase cDNA insert whose expression was regulated under the T-REx™ system. The day before assay, cells were trypsinized and plated in 384-well tissue culture plates. The next day, compound dilutions in DMSO/media containing doxycycline were added to the wells and incubated at 37° C., 5% $CO_2$. 24 hours later, coelenterazine substrate was added to each well and luciferase signal was quantified using Tecan Infinite M1000 Pro for potency determination.

Results for select compounds provided herein are shown in Table 1, below. For chemical structures that include one or more stereoisomers, but are illustrated without indicating stereochemistry, the assay data refers to a mixture of stereoisomers.

Dox Induced TNFα-FL-Gluc Assay

Flp-In 293 T-REx™ cells were transfected with pcDNA™5/FRT/TO plasmid inserted with cDNA encoding *Gaussia* Luciferase fused to the 3' end of cDNA encoding full length TNFα (amino acids 1-233). Transfected cells were selected for resistance to the selectable markers Hygromycin and Blasticidin to create a stable cell line that contained the TNFα-FL/*Gaussia* Luciferase cDNA insert whose expression was regulated under the T-REx™ system. The day before assay, cells were trypsinized and plated in 384-well tissue culture plates. The next day, compound dilutions in DMSO/media containing doxycycline were added to the wells and incubated at 37° C., 5% $CO_2$. 24 hours later, coelenterazine substrate was added to each well and luciferase signal was quantified using Tecan Infinite M1000 Pro for potency determination.

Results for select compounds provided herein are shown in Table 1, below. For chemical structures that include one or more stereoisomers, but are illustrated without indicating stereochemistry, the assay data refers to a mixture of stereoisomers.

Dox Induced IL2-FL-Gluc Assay

Flp-In 293 T-REx™ cells were transfected with pcDNA™5/FRT/TO plasmid inserted with cDNA encoding *Gaussia* Luciferase fused to the 3' end of cDNA encoding full length IL-2 (amino acids 1-153). Transfected cells were selected for resistance to the selectable markers Hygromycin and Blasticidin to create a stable cell line that contained the IL-2-FL/*Gaussia* Luciferase cDNA insert whose expression was regulated under the T-REx™ system. The day before assay, cells were trypsinized and plated in 384-well tissue culture plates. The next day, compound dilutions in DMSO/media containing doxycycline were added to the wells and incubated at 37° C., 5% $CO_2$. 24 hours later, coelenterazine substrate was added to each well and luciferase signal was quantified using Tecan Infinite M1000 Pro for potency determination.

Results for select compounds provided herein are shown in Table 1, below. For chemical structures that include one or more stereoisomers, but are illustrated without indicating stereochemistry, the assay data refers to a mixture of stereoisomers.

Dox Induced HER3-ss-Gluc Assay

Flp-In 293 T-REx™ cells were transfected with pcDNA™5/FRT/TO plasmid inserted with cDNA encoding *Gaussia* Luciferase fused to the 3' end of cDNA encoding HER3 signal sequence plus 4 amino acids (N-MRANDALQVLGLLFSLARGSEVG-C) (SEQ ID NO: 2). Transfected cells were selected for resistance to the selectable markers Hygromycin and Blasticidin to create a stable cell line that contained the HER3-ss+4aa/*Gaussia* Luciferase cDNA insert whose expression was regulated under the T-REx™ system. The day before assay, cells were trypsinized and plated in 384-well tissue culture plates. The next day, compound dilutions in DMSO/media containing doxycycline were added to the wells and incubated at 37° C., 5% $CO_2$. 24 hours later, coelenterazine substrate was added to each well and luciferase signal was quantified using Tecan Infinite M1000 Pro for potency determination.

Results for select compounds provided herein are shown in the below table. For chemical structures that include one or more stereoisomers, but are illustrated without indicating stereochemistry, the assay data refers to a mixture of stereoisomers.

TABLE

| for HER3 activity | |
|---|---|
| No. | 24 hr Dox Inducible Her3(ss + 4) Gluc 293FRT/TO: Mean IC50 (nM) |
| A122 | 110.63 |
| A120 | 31.42 |
| A137 | 10.85 |
| A151 | 276.03 |
| A177 | 10.86 |
| A179 | 399.69 |
| A124 | 912.67 |
| A182 | 203.11 |
| A183 | 2145.26 |
| A184 | 155.56 |
| A185 | 85.5 |
| A107 | 44.21 |
| A187 | 802.1 |
| A188 | 88.04 |
| A189 | 959.52 |
| A190 | 35.6 |
| A191 | 116.79 |
| A192 | 1709.12 |
| A193 | 50.85 |
| A194 | 303.25 |
| A195 | 381.8 |
| A196 | 78.19 |
| A197 | 77.48 |
| A198 | 44.08 |
| A199 | 131.52 |
| A200 | 29.08 |
| A201 | 211.04 |
| A202 | 129.54 |
| A203 | 34.13 |
| A204 | 134.41 |
| A205 | 230.38 |
| A206 | 38.19 |
| A207 | 17.98 |
| A208 | 427.53 |
| A209 | 497.91 |
| A210 | 342.58 |
| B22 | 57.77 |

H929 Cell Viability Assay

The human multiple myeloma cell line NCI-H929 was cultured in Advanced RPMI 1640 media (Gibco®) supplemented with 6% fetal bovine serum, 2 mM Glutamine, and 1× Penicillin/Streptomycin. On the day of assay, cells were resuspended in RPMI 1640 media supplemented with 10% fetal bovine serum, 2 mM Glutamine, and 1× Penicillin/Streptomycin and plated in 384-well tissue culture plates and treated with compound dilutions in DMSO/media. Plates were incubated at 37° C., 5% $CO_2$ for 48 hours. After 48 hours, Celltiter-Glo® (Promega) was added to each well and luciferase signal was quantified using Tecan Infinite M1000 Pro for cell viability determination.

Results for select compounds provided herein are shown in Table 1, below. For chemical structures that include one or more stereoisomers, but are illustrated without indicating stereochemistry, the assay data refers to a mixture of stereoisomers.

U266 Cell Viability Assay

The human multiple myeloma cell line U266B1 was cultured in RPMI 1640 media supplemented with 10% fetal bovine serum, 2 mM Glutamine, and 1× Penicillin/Streptomycin. Cells were plated in 384-well tissue culture plates and treated with compound dilutions in DMSO/media. Plates were incubated at 37° C., 5% $CO_2$ for 48 hours. After 48 hours, Celltiter-Glo® (Promega) was added to each well and luciferase signal was quantified using Tecan Infinite M1000 Pro for cell viability determination.

Results for select compounds provided herein are shown in Table 1, below. For chemical structures that include one or more stereoisomers, but are illustrated without indicating stereochemistry, the assay data refers to a mixture of stereoisomers In Vitro Microsome Stability Assays Potassium phosphate (4234 of a 0.1 M solution) was added to 8-strip deep well tubes followed by human, mouse, rat, or monkey microsomes (25 µL of a 20 mg/mL solution). The tubes were then placed on ice and the test article (2 µL of a 0.25 mM solution in DMSO) was added. The mixture was preincubated at 37° C. for 3 to 5 minutes (shaking at 150 rpm) then the reaction was initiated by adding 50 µL NADPH. An aliquot of samples (100 µL) were collected at 0 and 30 min and 200 µL of an acetonitrile mixture containing IS (compound 914) was added to quench the reaction. After centrifuging for 10 min at 4000 rpm, a mixed solution of the 20 µL of the supernatant (20 µL) plus 100 µL ACN/$H_2O$ (1:1) were injected for LC-MS/MS analysis. Liver microsome stability is assessed by the % remaining of compound at 30 min which is calculated using the following equation:

$$[(AUCanalyteT=30/AUCIS)/(AUCanalyteT=0/AUCIS)]*100$$

Results for select compounds provided herein are shown in Table 1, below. For chemical structures that include one or more stereoisomers, but are illustrated without indicating stereochemistry, the assay data refers to a mixture of stereoisomers.

Transiently Expressed Dox Induced Signal Sequence-Gluc Assay

Flp-In 293 T-REx™ cells were transfected with 500 ng pcDNA™5/FRT/TO plasmids inserted with cDNA encoding *Gaussia* Luciferase fused to the 3' end of cDNA encoding target signal sequences plus 10 amino acids. Transfected cells were incubated overnight then cells were trypsinized and plated in 384-well tissue culture plates. The next day, compound dilutions in DMSO/media containing doxycycline were added to the wells and incubated at 37° C., 5% $CO_2$. 24 hours later, coelenterazine substrate was added to each well and luciferase signal was quantified using Tecan Infinite M1000 Pro for potency determination.

| Target | Signal Peptide Sequence | +10 Amino Acids | A87 | A137 | A151 |
|---|---|---|---|---|---|
| TNFR1 | MGLSTVPDLLLPLVLLELLVGIYPS GVIG (SEQ ID NO: 3) | LVPHLGDREK (SEQ ID NO: 4) | 307 | 152 | 1625 |

-continued

| Target | Signal Peptide Sequence | +10 Amino Acids | A87 | A137 | A151 |
|---|---|---|---|---|---|
| TNFR2 | MAPVAVWAALAVGLELWAAAHA (SEQ ID NO: 5) | LPAQVAFTPY (SEQ ID NO: 6) | 564 | 186 | 2114 |
| IL-17a | MTPGKTSLVSLLLLLSLEAIVKA (SEQ ID NO: 7) | GITIPRNPGC (SEQ ID NO: 8) | 447 | 216 | 1816 |
| IL-17Ra | MGAARSPPSAVPGPLLGLLLLLLGVLAPGGAS (SEQ ID NO: 9) | LRLLDHRALV (SEQ ID NO: 10) | 424 | 176 | 1862 |
| IL-23a | MLGSRAVMLLLLLPWTAQG (SEQ ID NO: 11) | RAVPGGSSPA (SEQ ID NO: 12) | 567 | 223 | 1924 |
| IL-12b (p40) | MCHQQLVISWFSLVFLASPLVA (SEQ ID NO: 13) | IWELKKDVYV (SEQ ID NO: 14) | 155 | 74 | 913 |
| IL-23R | MNQVTIQWDAVIALYILFSWCHG (SEQ ID NO: 15) | GITNINCSGH (SEQ ID NO: 16) | 111 | 47 | 666 |
| IL-6 | MNSFSTSAFGPVAFSLGLLLVLPAAFPAP (SEQ ID NO: 17) | VPPGEDSKDV (SEQ ID NO: 18) | 66 | 38 | 437 |
| IL-6R | MLAVGCALLAALLAAPGAA (SEQ ID NO: 19) | LAPRRCPAQE (SEQ ID NO: 20) | 78 | 48 | 445 |
| GP130 | MLTLQTWLVQALFIFLTTESTG (SEQ ID NO: 21) | ELLDPCGYIS (SEQ ID NO: 22) | 201 | 161 | 969 |
| IL-1R1 | MKVLLRLICFIALLISS (SEQ ID NO: 23) | LEADKCKERE (SEQ ID NO: 24) | 374 | 282 | 1474 |
| IL-1R2 | MLRLYVLVMGVSA (SEQ ID NO: 25) | FTLQPAAHTG (SEQ ID NO: 26) | 23 | 17 | 168 |
| IL-IRa (isoform 1) | MEICRGLRSHLITLLLFLFHSETIC (SEQ ID NO: 27) | RPSGRKSSKM (SEQ ID NO: 28) | 111 | 47 | 666 |
| IL-2Ra (CD25) | MDSYLLMWGLLTFIMVPGCQA (SEQ ID NO: 29) | ELCDDDPPEI (SEQ ID NO: 30) | 159 | 55 | 876 |
| IFN-a1 | MASPFALLMVLVVLSCKSSCSLG (SEQ ID NO: 31) | CDLPETHSLD (SEQ ID NO: 32) | 128 | 57 | 820 |
| IFN-a2 | MALTFALLVALLVLSCKSSCSVG (SEQ ID NO: 33) | CDLPQTHSLG (SEQ ID NO: 34) | 51 | 44 | 404 |
| IFN-a4 | MALSFSLLMAVLVLSYKSICSLG (SEQ ID NO: 35) | CDLPQTHSLG (SEQ ID NO: 36) | 221 | 89 | 1129 |
| IFN-b | MTNKCLLQIALLLCFSTTALS (SEQ ID NO: 37) | MSYNLLGFLQ (SEQ ID NO: 38) | 818 | 288 | 4305 |
| IFNAR1 | MMVVLLGATTLVLVAVAPWVLSAAAGG (SEQ ID NO: 39) | KNLKSPQKVE (SEQ ID NO: 40) | 14 | 6 | 145 |
| IFNAR2 | MLLSQNAFIFRSLNLVLMVYISLVFG (SEQ ID NO: 41) | ISYDSPDYTD (SEQ ID NO: 42) | 133 | 42 | 778 |
| CTLA-4 | MACLGFQRHKAQLNLATRTWPGTLLFFLLFIPVFC (SEQ ID NO: 43) | KAMHVAQPAV (SEQ ID NO: 44) | 259 | 112 | 1145 |
| PD-L1 | MRIFAVFIFMTYWHLLNA (SEQ ID NO: 45) | FTVTVPKDLY (SEQ ID NO: 46) | 56 | 19 | 366 |
| LAG3 | MWEAQFLGLLFLQPLWVAPVKPLQPGAE (SEQ ID NO: 47) | VPVVWAQEGA (SEQ ID NO: 48) | 75 | 48 | 464 |
| TIM3 | MFSHLPFDCVLLLLLLLLTRS (SEQ ID NO: 49) | SEVEYRAEVG (SEQ ID NO: 50) | 282 | 132 | 1354 |

-continued

| Target | Signal Peptide Sequence | +10 Amino Acids | A87 | A137 | A151 |
|---|---|---|---|---|---|
| TIGIT | MRWCLLLIWAQGLRQAPLASG (SEQ ID NO: 51) | MMTGTIETTG (SEQ ID NO: 52) | 162 | 79 | 737 |
| CD96 | MEKKWKYCAVYYIIQIHFVKG (SEQ ID NO: 53) | VWEKTVNTEE (SEQ ID NO: 54) | 12 | 7 | 107 |
| VISTA | MGVPTALEAGSWRWGSLLFALF LAASLGPVAA (SEQ ID NO: 55) | FKVATPYSLY (SEQ ID NO: 56) | 211 | 150 | 911 |
| B7H3 | MLRRRGSPGMGVHVGAALGAL WFCLTGA (SEQ ID NO: 57) | LEVQVPEDPV (SEQ ID NO: 58) | 27 | 9 | 201 |
| CD73 | MCPRAARAPATLLLALGAVLWP AAGA (SEQ ID NO: 59) | WELTILHTND (SEQ ID NO: 60) | 58 | 44 | 375 |
| PDGFRa | MGTSHPAFLVLGCLLTGLSLILC (SEQ ID NO: 61) | QLSLPSILPN (SEQ ID NO: 62) | 90 | 37 | 565 |
| VGFR2 | MQSKVLLAVALWLCVETRA (SEQ ID NO: 63) | ASVGLPSVSL (SEQ ID NO: 64) | 684 | 213 | 2591 |
| IL-7R | MTILGTTFGMVFSLLQVVSG (SEQ ID NO: 65) | ESGYAQNGDL (SEQ ID NO: 66) | 58 | 16 | 392 |
| EGFR | MRPSGTAGAALLALLAALCPA SRA (SEQ ID NO: 67) | LEEKKVCQGT (SEQ ID NO: 68) | 60 | 47 | 412 |
| HER3 | MRANDALQVLGLLFSLARG (SEQ ID NO: 69) | SEVGNSQAVC (SEQ ID NO: 70) | 89 | 57 | 522 |
| VEGF | MNFLLSWVHWSLALLLYLHHAK WSQA (SEQ ID NO: 71) | APMAEGGGQN (SEQ ID NO: 72) | 111 | 51 | 645 |
| TACE (ADAM17) | MRQSLLFLTSVVPFVLA (SEQ ID NO: 73) | PRPPDDPGFG (SEQ ID NO: 74) | 66 | 40 | 391 |
| ADAM10 | MVLLRVLILLLSWAAGMGG (SEQ ID NO: 75) | QYGNPLNKYI (SEQ ID NO: 76) | 231 | 127 | 849 |

Human Peripheral Blood Mononuclear Cell (PBMC) Cytokine Assay

Human PBMC were freshly isolated from whole blood collections of 3 normal donors utilizing density gradient centrifugation followed by red blood cell lysis. PBMC from each donor were assayed separately. Cells were suspended in RPMI 1640 media supplemented with 5% fetal bovine serum, 2 mM L-glutamine, 10 mM HEPES, and 1× penicillin/streptomycin. PBMC were seeded at 200,000 cells/well in 96-well round-bottom plates either without stimulation or with stimulation by lipopolysaccharide (LPS, 1 μg/mL) or antibodies against human CD3 (plate-bound, 2 μg/mL) and human CD28 (soluble, 2 μg/mL). Serial dilutions of compound in DMSO/media were simultaneously added and PBMC were incubated at 37° C., 5% $CO_2$ for 24 hours. After 24 hours, plates were centrifuged and half of the supernatant volume removed for cytokine analysis by electrochemiluminescent immunoassay (U-PLEX® Biomarker Multiplex, Meso Scale Discovery). For viability analysis, CellTiter-Glo® (Promega) was added to the remaining material in each well and quantified via luminescent plate reader.

| Mean IC50 (nM) [Stimulation Condition] | A87 | A137 | A133 | A177 |
|---|---|---|---|---|
| GM-CSF [Anti-CD3/CD28] | 165 | 25 | 404 | 19 |
| IFNγ [Anti-CD3/CD28] | 152 | 21 | 234 | 19 |
| IL-1β [LPS] | >25000 | >25000 | >25000 | >25000 |
| IL-2 [Anti-CD3/CD28] | 31 | 8 | 197 | 10 |
| IL-6 [LPS] | 61 | 12 | 193 | 24 |
| IL-23 [LPS] | 200 | 79 | 1054 | 54 |
| TNFα [Anti-CD3/CD28] | 82 | 17 | 216 | 13 |
| CellTiter-Glo Viability [No Stimulation] | >25000 | >25000 | >25000 | >25000 |

Efficacy Study: Effect of Compound A87 on Tumor Growth and Body Weight in a B16F10 Model Comparted to Anti-PD-1 Therapy Female C57BL/6 mice (7-8 week old) were injected in the flank subcutaneously with $5\times10^6$ B16F10 cells in 0.1 ml on Day 0. On Day 3, compound A87 formulated in 10% ETOH/10% Kolliphor EL was administered IV 30 mg/kg QW, IV 10 mg/kg D1D2, or IP 15 mg/kg QOD. Anti-PD1 antibody treatment (RMP1-14 from Bioxcell, 200 μg) was administered i.p. on a QOD×3 dose schedule. Tumor size was monitored with a digital caliper (Fowler) every 2-3 d until reaching a size of 1.5-2.0 cm and expressed as volume (length×width×height). B16F10, a melanoma line, was obtained from ATCC. C57/BL6 mice were purchased from Charles rivers laboratories.

TABLE 1

Activities of Compounds

| No. | 24 hr Dox Inducible PD1ssGluc 293FRT/TO: Mean IC50 (nM) | 24 hr Dox Inducible PD1FLFluc 293FRT/TO: Mean IC50 (nM) | 24 hr Dox Inducible TNFaFLGluc 293FRT/TO: Mean IC50 (nM) | 24 hr Dox Inducible IL2FLGluc 293FRT/TO: Mean IC50 (nM) | 48 hr H929 Viability Celltiter-Glo: Mean EC50 (nM) | 48 hr U266 Viability Celltiter-Glo: Mean EC50 (nM) | Liver Microsome Stability- % Left after 30 min w/NADPH (%) Mouse Rat Monkey Human |
|---|---|---|---|---|---|---|---|
| A1 | 1026.3 | 1396.1 | I.A. | 1170.58 | I.A. | I.A. | 0.21<br>0.12<br>0.18<br>0.18 |
| A2 | 344.75 | 807.39 | I.A. | | 10141 | I.A. | 0.09<br>0.59<br>0.09<br>0.04 |
| A3 | 241.49 | 637.58 | 11412 | | 5080.51 | I.A. | 0.09<br>0.37<br>0.83<br>0.25 |
| A4 | 93.87 | 310.79 | 3763.69 | | 1220.45 | I.A. | 0.56<br>1.17<br>1.17<br>0.25 |
| A5 | 651.38 | | I.A. | | 8429.37 | I.A. | 0.27<br>0.24<br>0.31<br>0.24 |
| A6 | 4747.33 | | I.A. | | 24073.2 | I.A. | 0.12<br>0.17<br>0.44<br>0.53 |
| A7 | 2314.7 | | I.A. | | 22428.6 | I.A. | 0.17<br>0.23<br>0.99<br>0.29 |
| A8 | 2681.93 | | I.A. | | I.A. | I.A. | 0.17<br>0.61<br>0.19<br>0.09 |
| A9 | 1106.83 | | I.A. | | I.A. | I.A. | 0.34<br>0.14<br>0.66<br>0.09 |
| A10 | 123.42 | | 4687.09 | | 2863.07 | I.A. | 0.2<br>8.85<br>0.14<br>0.77 |
| A11 | 365.31 | 865.78 | I.A. | 623.7 | I.A. | I.A. | 0.18<br>0.17<br>0.08<br>0.21 |
| A12 | 857.59 | | I.A. | | I.A. | I.A. | 0.1<br>0.07<br>0.22<br>0.11 |
| A13 | 25.01 | | 1471.73 | | 987.14 | I.A. | 0.04<br>0.1<br>0.1<br>0.65 |
| A14 | 640.11 | 1234.03 | I.A. | 1163.27 | I.A. | I.A. | 5.39<br>1.13<br>1.4<br>0.08 |
| A15 | 95.1 | | 3063.1 | | 2955.87 | 14604.7 | 0.29<br>0.061<br>0.13<br>0.07 |
| A16 | 108.07 | | 6341.65 | | 4977.83 | I.A. | 2.09<br>2.62<br>41.1<br>0.11 |

TABLE 1-continued

Activities of Compounds

| No. | 24 hr Dox Inducible PD1ssGluc 293FRT/TO: Mean IC50 (nM) | 24 hr Dox Inducible PD1FLFluc 293FRT/TO: Mean IC50 (nM) | 24 hr Dox Inducible TNFaFLGluc 293FRT/TO: Mean IC50 (nM) | 24 hr Dox Inducible IL2FLGluc 293FRT/TO: Mean IC50 (nM) | 48 hr H929 Viability Celltiter-Glo: Mean EC50 (nM) | 48 hr U266 Viability Celltiter-Glo: Mean EC50 (nM) | Liver Microsome Stability- % Left after 30 min w/NADPH (%) Mouse Rat Monkey Human |
|---|---|---|---|---|---|---|---|
| A17 | 942.97 | | I.A. | | I.A. | I.A. | 0.41<br>1.06<br>0.36<br>0.49 |
| A18 | I.A. | | I.A. | | I.A. | 15473.2 | 0.05<br>0.11<br>0.05<br>0.04 |
| A19 | 325.83 | | I.A. | | I.A. | 21895.5 | 0.24<br>0.1<br>0.08<br>0.05 |
| A20 | 206.77 | | I.A. | | 12798.2 | I.A. | 0.07<br>0.19<br>0.06<br>0.05 |
| A21 | 184.02 | | 10002.6 | | 8288.81 | I.A. | 1.77<br>0.62<br>0.11<br>0.14 |
| A22 | 155.66 | 404.42 | 6377.93 | 370.18 | 6673.8 | I.A. | 0.12<br>0.4<br>0.11<br>0.16 |
| A23 | 758.88 | | I.A. | | I.A. | I.A. | 0.17<br>0.13<br>0.03<br>0.04 |
| A24 | I.A. | | I.A. | | I.A. | I.A. | 0.13<br>0.04<br>0.03<br>0.03 |
| A25 | 435.17 | | I.A. | | I.A. | I.A. | 0.32<br>4.16<br>0.2<br>0.12 |
| A26 | 224.49 | | I.A. | | 16068.5 | I.A. | 3.4<br>1.84<br>0.13<br>6.65 |
| A27 | 492.55 | | I.A. | | I.A. | I.A. | 2.15<br>0.98<br>2.07<br>2.52 |
| A28 | 5251.11 | | I.A. | | 10426 | I.A. | 0.06<br>0.14<br>0.06<br>— |
| A29 | 241.1 | 591.29 | I.A. | 446.59 | I.A. | I.A. | 32.4<br>43.3<br>19.5<br>39.6 |
| A30 | 792.84 | | I.A. | | I.A. | I.A. | 0.35<br>0.28<br>0.03<br>0.12 |
| A31 | 619.25 | | I.A. | | I.A. | I.A. | 0.25<br>0.09<br>0.03<br>0.05 |
| A32 | I.A. | | I.A. | | I.A. | I.A. | 0.51<br>0.27<br>0.09<br>0.06 |
| A33 | I.A. | | I.A. | | I.A. | I.A. | 0.08<br>0.13<br>0.07<br>0.05 |

TABLE 1-continued

Activities of Compounds

| No. | 24 hr Dox Inducible PD1ssGluc 293FRT/TO: Mean IC50 (nM) | 24 hr Dox Inducible PD1FLFluc 293FRT/TO: Mean IC50 (nM) | 24 hr Dox Inducible TNFaFLGluc 293FRT/TO: Mean IC50 (nM) | 24 hr Dox Inducible IL2FLGluc 293FRT/TO: Mean IC50 (nM) | 48 hr H929 Viability Celltiter-Glo: Mean EC50 (nM) | 48 hr U266 Viability Celltiter-Glo: Mean EC50 (nM) | Liver Microsome Stability- % Left after 30 min w/NADPH (%) Mouse Rat Monkey Human |
|---|---|---|---|---|---|---|---|
| A34 | I.A. | | I.A. | | I.A. | I.A. | 0.24<br>0.12<br>0.09<br>0.03 |
| A35 | 83.03 | 243.99 | >11897.98 | | I.A. | I.A. | 20.9<br>30<br>13.6<br>24.8 |
| A36 | 118.49 | 319.35 | >21809.41 | 300.59 | >15385.93 | I.A. | 1.85<br>0.94<br>1.54<br>6.69 |
| A37 | 202.16 | | I.A. | | I.A. | I.A. | 6.03<br>13.5<br>5.69<br>8.26 |
| A38 | 75.12 | | 5490.99 | | >11844.59 | I.A. | 12.6<br>24.2<br>9.04<br>11.4 |
| A39 | 761.18 | | I.A. | | I.A. | 10421.2 | 0.26<br>6<br>0.11<br>0.05 |
| A40 | 308.26 | | >15070.18 | | I.A. | I.A. | 0.19<br>0.12<br>0.04<br>0.04 |
| A41 | 17532.8 | | I.A. | | I.A. | I.A. | 0.2<br>0.14<br>0.1<br>0.08 |
| A42 | 696.43 | | I.A. | | I.A. | I.A. | 0.79<br>7.69<br>0.81<br>2.65 |
| A43 | 46.87 | 160.55 | 1208.05 | 132.63 | 2974.53 | I.A. | 20.1<br>22.3<br>12<br>15.4 |
| A44 | 132.1 | | 12652.5 | | I.A. | I.A. | 43.8<br>54<br>38<br>47.6 |
| A46 | 50.13 | | 1758.33 | | 3336.62 | I.A. | 3.63<br>4.46<br>1.44<br>6.12 |
| A47 | 258.84 | | I.A. | | I.A. | I.A. | 5.68<br>10.7<br>1.68<br>12.6 |
| A48 | 991.35 | | I.A. | | I.A. | I.A. | 0.07<br>0.4<br>0.1<br>0.19 |
| A49 | 407.05 | | I.A. | | I.A. | I.A. | 11.8<br>16.4<br>9.36<br>3.5 |
| A50 | 22.21 | 74.12 | 660.73 | 56.97 | 1007.74 | 6536.29 | 70.1<br>3.6<br>0.79<br>1.32 |
| A51 | 61.36 | | 3068.97 | | 6153.41 | I.A. | 28<br>34.7<br>23.6<br>26.7 |

TABLE 1-continued

Activities of Compounds

| No. | 24 hr Dox Inducible PD1ssGluc 293FRT/TO: Mean IC50 (nM) | 24 hr Dox Inducible PD1FLFluc 293FRT/TO: Mean IC50 (nM) | 24 hr Dox Inducible TNFaFLGluc 293FRT/TO: Mean IC50 (nM) | 24 hr Dox Inducible IL2FLGluc 293FRT/TO: Mean IC50 (nM) | 48 hr H929 Viability Celltiter-Glo: Mean EC50 (nM) | 48 hr U266 Viability Celltiter-Glo: Mean EC50 (nM) | Liver Microsome Stability- % Left after 30 min w/NADPH (%) Mouse Rat Monkey Human |
|---|---|---|---|---|---|---|---|
| A52 | 45.56 | | 1035.16 | | 2105.88 | I.A. | 29.3 |
| | | | | | | | 40.1 |
| | | | | | | | 38.3 |
| | | | | | | | 31 |
| A53 | 35.33 | | 1014.07 | | 1717.71 | >10260.36 | 39.2 |
| | | | | | | | 50.5 |
| | | | | | | | 39 |
| | | | | | | | 38 |
| A54 | 26.51 | | 952.37 | | 1907.23 | I.A. | 34.6 |
| | | | | | | | 42.4 |
| | | | | | | | 30.5 |
| | | | | | | | 33.8 |
| A55 | 1540.39 | | I.A. | | I.A. | I.A. | 1.18 |
| | | | | | | | 0.97 |
| | | | | | | | 0.34 |
| | | | | | | | 4.87 |
| A56 | 32.76 | | 1255.87 | | 1634.05 | I.A. | 53.2 |
| | | | | | | | 57.3 |
| | | | | | | | 42.6 |
| | | | | | | | 44.5 |
| A57 | 73.41 | | 7807.65 | | I.A. | I.A. | 60.2 |
| | | | | | | | 84 |
| | | | | | | | 28.5 |
| | | | | | | | 31.9 |
| A58 | 72.14 | | 8500.05 | | I.A. | I.A. | 72.8 |
| | | | | | | | 66.7 |
| | | | | | | | 53.1 |
| | | | | | | | 31.6 |
| A59 | 24.23 | | 615.54 | | 1442.63 | I.A. | 3.73 |
| | | | | | | | 3.9 |
| | | | | | | | 1.94 |
| | | | | | | | 1.89 |
| A60 | 18.54 | | 886.17 | | 1483.8 | I.A. | 60.8 |
| | | | | | | | 50.3 |
| | | | | | | | 38.7 |
| | | | | | | | 46.7 |
| A61 | 955.94 | | I.A. | | I.A. | I.A. | 17.9 |
| | | | | | | | 19.6 |
| | | | | | | | 8.96 |
| | | | | | | | 13.3 |
| A63 | 43.65 | | 1873.85 | | 7433.97 | I.A. | 85.2 |
| | | | | | | | 88.2 |
| | | | | | | | 84.4 |
| | | | | | | | 76.4 |
| A64 | 74.98 | | 3293.48 | | 6402.59 | I.A. | 53.1 |
| | | | | | | | 63.1 |
| | | | | | | | 48 |
| | | | | | | | 53.3 |
| A65 | 153.77 | | 8715.63 | | I.A. | I.A. | 73.4 |
| | | | | | | | 78 |
| | | | | | | | 57.8 |
| | | | | | | | 53.1 |
| A66 | 187.59 | | 3495.74 | | 9211 | I.A. | 0.02 |
| | | | | | | | 0.39 |
| | | | | | | | 0.35 |
| | | | | | | | 0.13 |
| A67 | 40.77 | | 937.29 | | 2398.75 | I.A. | 28 |
| | | | | | | | 45.4 |
| | | | | | | | 27.6 |
| | | | | | | | 33.2 |
| A68 | 156.12 | | 6440.61 | | I.A. | I.A. | 55.1 |
| | | | | | | | 57.1 |
| | | | | | | | 57.1 |
| | | | | | | | 50.5 |
| A69 | 136.39 | | I.A. | | I.A. | I.A. | 64.6 |
| | | | | | | | 74.3 |
| | | | | | | | 58.2 |
| | | | | | | | 63 |

TABLE 1-continued

Activities of Compounds

| No. | 24 hr Dox Inducible PD1ssGluc 293FRT/TO: Mean IC50 (nM) | 24 hr Dox Inducible PD1FLFluc 293FRT/TO: Mean IC50 (nM) | 24 hr Dox Inducible TNFaFLGluc 293FRT/TO: Mean IC50 (nM) | 24 hr Dox Inducible IL2FLGluc 293FRT/TO: Mean IC50 (nM) | 48 hr H929 Viability Celltiter-Glo: Mean EC50 (nM) | 48 hr U266 Viability Celltiter-Glo: Mean EC50 (nM) | Liver Microsome Stability- % Left after 30 min w/NADPH (%) Mouse Rat Monkey Human |
|---|---|---|---|---|---|---|---|
| A70 | 46.08 | | 1301.94 | | 3023.7 | I.A. | 3.14<br>6.75<br>3.26<br>1.36 |
| A71 | 63.32 | | 2014.74 | | 7724.78 | I.A. | 11.5<br>17.2<br>6.75<br>5.55 |
| A72 | 96.18 | | 6972.14 | | 10286.3 | I.A. | 43.3<br>54.6<br>53.2<br>62.5 |
| A73 | 37.27 | | 1861.53 | | 3471.61 | I.A. | 16.3<br>71.5<br>25.4<br>18.2 |
| A74 | 77.38 | 257.97 | I.A. | 248.26 | I.A. | I.A. | 53.7<br>55.7<br>60.6<br>56.3 |
| A75 | 104.41 | 255.94 | 3782.3 | 233.05 | 3029.96 | I.A. | 2.75<br>7.54<br>0.28<br>3.08 |
| A76 | I.A. | I.A. | I.A. | I.A. | I.A. | I.A. | 28.6<br>33.9<br>35.7<br>53.1 |
| A77 | 95.05 | 338 | 5544.21 | 359.68 | 4012.61 | I.A. | 37.3<br>32.5<br>20.8<br>30.1 |
| A78 | 359.83 | | I.A. | | I.A. | I.A. | 0.15<br>0.25<br>0.11<br>0.2 |
| A79 | 408.23 | | I.A. | | I.A. | I.A. | 10.6<br>0.1<br>0.06<br>0.16 |
| A80 | 272.95 | | I.A. | | I.A. | I.A. | 13.4<br>14.1<br>2.56<br>10.8 |
| A81 | 476.93 | | I.A. | | I.A. | I.A. | 0.12<br>0.12<br>0.03<br>0.2 |
| A82 | 30.52 | | 1547.55 | | 2298.14 | I.A. | 0.08<br>0.16<br>0.23<br>0.3 |
| A83 | 28.17 | | 961.05 | | 959.61 | I.A. | 23.4<br>47.6<br>34.9<br>39.3 |
| A84 | 175.94 | | I.A. | | I.A. | I.A. | 68.3<br>67.3<br>65.8<br>60.6 |
| A85 | 87.46 | | I.A. | | I.A. | I.A. | 52.2<br>64.9<br>42.9<br>25.6 |
| A86 | | 428.72 | I.A. | 394.88 | 5625.91 | I.A. | 34.1<br>39.9<br>29.2<br>41.3 |

TABLE 1-continued

Activities of Compounds

| No. | 24 hr Dox Inducible PD1ssGluc 293FRT/TO: Mean IC50 (nM) | 24 hr Dox Inducible PD1FLFluc 293FRT/TO: Mean IC50 (nM) | 24 hr Dox Inducible TNFaFLGluc 293FRT/TO: Mean IC50 (nM) | 24 hr Dox Inducible IL2FLGluc 293FRT/TO: Mean IC50 (nM) | 48 hr H929 Viability Celltiter-Glo: Mean EC50 (nM) | 48 hr U266 Viability Celltiter-Glo: Mean EC50 (nM) | Liver Microsome Stability- % Left after 30 min w/NADPH (%) Mouse Rat Monkey Human |
|---|---|---|---|---|---|---|---|
| A87 | 19.15 | | 492.19 | 50.23 | 223.57 | I.A. | 49.6<br>43.6<br>32.7<br>39.7 |
| A88 | 4330.54 | | I.A. | I.A. | I.A. | I.A. | 15.9<br>15.2<br>1.33<br>11.7 |
| A89 | 82.05 | | 1208.13 | 186.53 | 1751.25 | I.A. | 17.1<br>22.2<br>13.5<br>18.5 |
| A90 | 207.02 | | 2413.57 | 493.18 | 3786.86 | I.A. | 28.2<br>20.2<br>14.1<br>20.1 |
| A91 | 193.42 | | 2459.27 | 376.81 | 3011.92 | 14653.1 | 25.4<br>21.6<br>21.8<br>23.7 |
| A92 | 304.02 | | I.A. | 518.65 | I.A. | I.A. | 40.8<br>51.8<br>40.4<br>44.3 |
| A93 | 670.27 | | I.A. | 911.37 | 10427.9 | I.A. | 0.4<br>0.51<br>0.18<br>0.84 |
| A94 | 36.37 | | 550.17 | 78.29 | 800.16 | I.A. | 45.7<br>45.5<br>30.3<br>42.1 |
| A95 | 198.02 | | 4897.04 | 390.92 | 6711.7 | I.A. | 54.2<br>43.1<br>46.1<br>43.9 |
| A96 | 121.85 | | 1847.65 | 231.78 | 5104.13 | I.A. | 37.6<br>41.9<br>32.8<br>40.5 |
| A97 | 41.78 | | 565.68 | 87.04 | 725.76 | I.A. | 77.7<br>71.4<br>66.1<br>71.1 |
| A98 | 201.79 | | 7335.28 | 351.2 | I.A. | I.A. | 55.2<br>32.8<br>26.9<br>57.5 |
| A99 | 115.58 | | 3535.19 | 349.8 | I.A. | I.A. | 60.8<br>50.8<br>37<br>41.9 |
| A100 | 1150.93 | | I.A. | 1560.04 | I.A. | I.A. | 0.1<br>2.18<br>0.04<br>0.22 |
| A101 | 220.23 | | 3425.89 | 564.3 | I.A. | I.A. | 20.8<br>25.4<br>18.8<br>30.2 |
| A102 | 33.39 | | 477.31 | 90.53 | 558.29 | I.A. | 86.6<br>101.9<br>70<br>62.3 |
| A103 | 445.68 | | I.A. | 698.23 | I.A. | I.A. | 42.2<br>36.5<br>38.5<br>31.6 |

TABLE 1-continued

Activities of Compounds

| No. | 24 hr Dox Inducible PD1ssGluc 293FRT/TO: Mean IC50 (nM) | 24 hr Dox Inducible PD1FLFluc 293FRT/TO: Mean IC50 (nM) | 24 hr Dox Inducible TNFaFLGluc 293FRT/TO: Mean IC50 (nM) | 24 hr Dox Inducible IL2FLGluc 293FRT/TO: Mean IC50 (nM) | 48 hr H929 Viability Celltiter-Glo: Mean EC50 (nM) | 48 hr U266 Viability Celltiter-Glo: Mean EC50 (nM) | Liver Microsome Stability- % Left after 30 min w/NADPH (%) Mouse Rat Monkey Human |
|---|---|---|---|---|---|---|---|
| A106 | 52.35 | | 1118.61 | 126.18 | 902.63 | I.A. | 8.81<br>18.9<br>30.7<br>7.18 |
| A107 | 26.11 | | 609.25 | 72.97 | 1176.64 | I.A. | 16.1<br>19.3<br>25.0<br>83.9 |
| A108 | 29.58 | | 546.31 | 68.29 | 420.52 | I.A. | 0.62<br>2.05<br>0.88<br>1.06 |
| A118 | 67.79 | | 2093.86 | 172.7 | 5345.11 | I.A. | 22.1<br>18.3<br>14.7<br>14.2 |
| A119 | 52.34 | | 1077.79 | 170.3 | 7675.81 | I.A. | 50.8<br>66.1<br>53.9<br>71.7 |
| A120 | 15.58 | | 238.67 | 27.34 | 672.16 | I.A. | 19.2<br>28.5<br>16.3<br>4.78 |
| A122 | 51.93 | | 885.26 | 134.57 | 2420.21 | I.A. | 36.4<br>0.17<br>0.15<br>0.38 |
| A123 | 13.98 | | 424.92 | 45.93 | 834.51 | I.A. | 6.13<br>7.41<br>3.47<br>5.02 |
| A124 | 606.76 | | I.A. | 802.05 | I.A. | I.A. | 1.01<br>1.25<br>1.91<br>18.9 |
| A125 | 829.42 | | 11524.98 | 1090.55 | I.A. | I.A. | 0.14<br>0.37<br>8.67<br>0.2 |
| A131 | 145.44 | | 2403.07 | 426.19 | 4744.68 | I.A. | 101<br>73.9<br>70.2<br>84.5 |
| A133 | 36.84 | | 748.55 | 134.51 | 5121.95 | I.A. | 82.2<br>87.3<br>67.3<br>71.3 |
| A134 | 11.04 | | 309.22 | 27.28 | 540.66 | I.A. | 27.9<br>41.3<br>9.76<br>31.9 |
| A135 | 21.58 | | 625.08 | 48.58 | 1239.26 | I.A. | 26.1<br>56.3<br>39.2<br>9.36 |
| A136 | 26.46 | | 543.65 | 101.39 | 1726.93 | I.A. | 14.3<br>26.6<br>23.2<br>65.3 |
| A137 | 8.30 | | 191.24 | 21.45 | 281.93 | I.A. | 28<br>31.6<br>14.2<br>48.8 |
| A138 | 73.91 | | 947.28 | 156.27 | 2396.92 | I.A. | 13.2<br>17.1<br>12.5<br>8.84 |

TABLE 1-continued

Activities of Compounds

| No. | 24 hr Dox Inducible PD1ssGluc 293FRT/TO: Mean IC50 (nM) | 24 hr Dox Inducible PD1FLFluc 293FRT/TO: Mean IC50 (nM) | 24 hr Dox Inducible TNFaFLGluc 293FRT/TO: Mean IC50 (nM) | 24 hr Dox Inducible IL2FLGluc 293FRT/TO: Mean IC50 (nM) | 48 hr H929 Viability Celltiter-Glo: Mean EC50 (nM) | 48 hr U266 Viability Celltiter-Glo: Mean EC50 (nM) | Liver Microsome Stability- % Left after 30 min w/NADPH (%) Mouse Rat Monkey Human |
|---|---|---|---|---|---|---|---|
| A140 | 491.56 | | 3009.42 | 808.08 | I.A. | I.A. | 3.68<br>0.56<br>1.56<br>0.41 |
| A141 | 431.02 | | 4235.2 | 862.9 | 9106.16 | I.A. | 0.48<br>1.14<br>0.66<br>0.26 |
| A142 | 38.25 | | 741.05 | 67.02 | 1446.85 | I.A. | 16<br>22.6<br>3.89<br>11.8 |
| A147 | 4122.89 | | I.A. | I.A. | I.A. | I.A. | 0.74<br>1.16<br>0.99<br>2.76 |
| A148 | 925.61 | | I.A. | 1117.32 | I.A. | I.A. | 1.59<br>1.29<br>0.67<br>0.52 |
| A149 | I.A. | | I.A. | I.A. | I.A. | I.A. | 0.83<br>0.47<br>0.96<br>0.44 |
| A150 | 30.29 | | 467.79 | 41.34 | 2000.66 | I.A. | 1.38<br>2.02<br>2.2<br>4.6 |
| A151 | 152.57 | | 1216.54 | 305.64 | 2711.98 | I.A. | 4.55<br>4.2<br>3.98<br>4.28 |
| A152 | 81.5 | | 1028.9 | 173.82 | 2171.97 | I.A. | 5.06<br>3.6<br>3.22<br>3.69 |
| A153 | 1293.98 | | I.A. | 1255.35 | I.A. | I.A. | 0.87<br>6.23<br>1.26<br>2.57 |
| A154 | 14.94 | | 504.45 | 58.66 | 749.43 | I.A. | 17.5<br>12.3<br>10.2<br>7.33 |
| A155 | 1350.05 | | | 3484.03 | 7795.99 | I.A. | 16.8<br>38.8<br>4.86<br>17.8 |
| A156 | 92.46 | | 1825.18 | 206.72 | 3707.48 | I.A. | 75.6<br>82.1<br>80.6<br>81.3 |
| A157 | 23.33 | | 584.47 | 77.41 | 858.16 | I.A. | 23.3<br>32.2<br>27.3<br>21.1 |
| A160 | 152.83 | | 10687.02 | 452.72 | I.A. | I.A. | 61.3<br>51.1<br>46.1<br>71.8 |
| A161 | 577.46 | | I.A. | 725.52 | I.A. | I.A. | 26.5<br>27.3<br>16.7<br>20.2 |
| A162 | 101.25 | | 6263.53 | 200.98 | I.A. | I.A. | 62.5<br>69.6<br>60.3<br>70.5 |

TABLE 1-continued

Activities of Compounds

| No. | 24 hr Dox Inducible PD1ssGluc 293FRT/TO: Mean IC50 (nM) | 24 hr Dox Inducible PD1FLFluc 293FRT/TO: Mean IC50 (nM) | 24 hr Dox Inducible TNFaFLGluc 293FRT/TO: Mean IC50 (nM) | 24 hr Dox Inducible IL2FLGluc 293FRT/TO: Mean IC50 (nM) | 48 hr H929 Viability Celltiter-Glo: Mean EC50 (nM) | 48 hr U266 Viability Celltiter-Glo: Mean EC50 (nM) | Liver Microsome Stability- % Left after 30 min w/NADPH (%) Mouse Rat Monkey Human |
|---|---|---|---|---|---|---|---|
| A163 | 55.56 | | 1928.36 | 81.21 | 13622.1 | I.A. | 72.8<br>54.9<br>57.5<br>64.2 |
| A164 | 454.69 | | I.A. | 974.47 | I.A. | I.A. | 69.0<br>57.9<br>40.9<br>64.8 |
| A165 | 131.14 | | 1857.05 | 293.51 | 4086.76 | I.A. | 14.9<br>11.9<br>12.8<br>2.23 |
| A166 | 16.68 | | 278.28 | 30.25 | 547.83 | I.A. | 26.4<br>31.3<br>18.7<br>14.0 |
| A167 | 200.61 | | 2656.44 | 412.45 | 6495.51 | I.A. | 18.3<br>9.19<br>73<br>5.68 |
| A168 | 1491.98 | | I.A. | 1144.17 | I.A. | I.A. | 42<br>42.1<br>73<br>25.7 |
| A169 | 81.52 | | 1048.04 | 192.27 | 3272.71 | I.A. | 22.5<br>13.1<br>4.23<br>34.7 |
| A170 | 56.13 | | 797.63 | 133.66 | 1775.44 | I.A. | 3.65<br>10.8<br>1.37<br>7.2 |
| A171 | I.A. | | I.A. | I.A. | I.A. | I.A. | 0.91<br>0.90<br>0.26<br>0.60 |
| A172 | 29.18 | | 436.2 | 66.4 | 1750.08 | I.A. | 3.65<br>2.23<br>2.63<br>3.46 |
| A173 | 78.83 | | 5638.24 | 248.3 | I.A. | I.A. | 49.2<br>53.8<br>55.9<br>56.1 |
| A174 | 15.79 | | 565.56 | 53.31 | 1861.24 | I.A. | 36.9<br>44.4<br>28.4<br>41.7 |
| A175 | 9.35 | | 393.21 | 40.35 | 1436.98 | I.A. | 6.73<br>6.28<br>2.27<br>4.26 |
| A176 | 17.11 | | 631.2 | 62.1 | 3109.99 | I.A. | 32.4<br>23.0<br>15.2<br>31.9 |
| A177 | 4.95 | | 154.54 | 12.57 | 179.88 | I.A. | 11.6<br>14.5<br>2.8<br>13.7 |
| A178 | 134.76 | | 4820.51 | 255.26 | I.A. | I.A. | 22.8<br>29.2<br>25.8<br>24.0 |
| A179 | 269.79 | | 3249.91 | 72.57 | 11347.74 | I.A. | 0.5<br>0.18<br>0.26<br>0.04 |

TABLE 1-continued

| Activities of Compounds | | | | | | | |
|---|---|---|---|---|---|---|---|
| No. | 24 hr Dox Inducible PD1ssGluc 293FRT/TO: Mean IC50 (nM) | 24 hr Dox Inducible PD1FLFluc 293FRT/TO: Mean IC50 (nM) | 24 hr Dox Inducible TNFaFLGluc 293FRT/TO: Mean IC50 (nM) | 24 hr Dox Inducible IL2FLGluc 293FRT/TO: Mean IC50 (nM) | 48 hr H929 Viability Celltiter-Glo: Mean EC50 (nM) | 48 hr U266 Viability Celltiter-Glo: Mean EC50 (nM) | Liver Microsome Stability- % Left after 30 min w/NADPH (%) Mouse Rat Monkey Human |
| A180 | 2742.03 | | I.A. | 13843.24 | 20179.62 | I.A. | 0.44<br>1.97<br>0.08<br>0.80 |
| A181 | 38.69 | | 983.85 | 122.41 | 1479.93 | I.A. | 17.1<br>22.0<br>27.9<br>23.3 |
| A182 | 78.84 | | 1957.98 | 255.55 | I.A. | I.A. | 61.7<br>41.9<br>41.5<br>53.7 |
| A183 | 1443.55 | | | 2524.48 | 6116.1 | I.A. | 7.39<br>3.17<br>0.75<br>10.1 |
| A184 | 100.13 | | 1079.53 | 232.68 | 6916.08 | I.A. | 5.64<br>7.47<br>1.23<br>2.56 |
| A185 | 43.18 | | 573.1 | 85.38 | 1468.19 | I.A. | 30.1<br>37.8<br>10.0<br>21.8 |
| A187 | 427.09 | | 6171.01 | 1087.5 | 3866.88 | I.A. | 0.03<br>0.07<br>0.15<br>0.05 |
| A188 | 38.94 | | 714.46 | 99.28 | 1555.52 | I.A. | 4.48<br>27.8<br>12.4<br>27 |
| A189 | 512.4 | | 8138.23 | 1358.47 | 10609.19 | I.A. | 0.14<br>0.07<br>0.01<br>0.06 |
| A190 | 16.23 | | 294.54 | 45.7 | 867.11 | I.A. | 69.3<br>85.3<br>71.6<br>74.1 |
| A191 | 57.62 | | 1095.62 | 144.64 | 6734.93 | I.A. | 55.3<br>65.0<br>68.3<br>48.6 |
| A192 | 1153.54 | | I.A. | 2332.92 | 9362.89 | I.A. | 0.18<br>0.08<br>0.10<br>0.02 |
| A193 | 23.8 | | 748.16 | 81.77 | 6806.9 | I.A. | 10.1<br>11.3<br>7.72<br>34.2 |
| A194 | 261.32 | | I.A. | 401.51 | I.A. | I.A. | 68.5<br>59.2<br>65.0<br>63.6 |
| A195 | 210.96 | | 11201.43 | 668.05 | I.A. | I.A. | 58.5<br>63.3<br>32.8<br>53.6 |
| A196 | 30.96 | | 1474.7 | 104.78 | I.A. | I.A. | |
| A197 | 34.25 | | 666.07 | 95.53 | 4125.97 | I.A. | 65.4<br>76.6<br>92.8<br>70.7 |
| A198 | 18.54 | | 372.95 | 53.28 | 1170.31 | I.A. | 68.2<br>61.4<br>65.1<br>39.2 |

TABLE 1-continued

Activities of Compounds

| No. | 24 hr Dox Inducible PD1ssGluc 293FRT/TO: Mean IC50 (nM) | 24 hr Dox Inducible PD1FLFluc 293FRT/TO: Mean IC50 (nM) | 24 hr Dox Inducible TNFaFLGluc 293FRT/TO: Mean IC50 (nM) | 24 hr Dox Inducible IL2FLGluc 293FRT/TO: Mean IC50 (nM) | 48 hr H929 Viability Celltiter-Glo: Mean EC50 (nM) | 48 hr U266 Viability Celltiter-Glo: Mean EC50 (nM) | Liver Microsome Stability- % Left after 30 min w/NADPH (%) Mouse Rat Monkey Human |
|---|---|---|---|---|---|---|---|
| A199 | 80.8 | | 1420.53 | 162.14 | I.A. | I.A. | 23.7<br>28.3<br>25.5<br>8.0 |
| A200 | 11.23 | | 284.85 | 27.87 | 435.72 | I.A. | 71.9<br>83.1<br>73.9<br>78.1 |
| A201 | 117.7 | | 7086.36 | 282.88 | I.A. | I.A. | 39.1<br>35.4<br>26.5<br>32.8 |
| A202 | 56.59 | | 2052.14 | 175.52 | 2914.63 | I.A. | 55.0<br>50.8<br>38.3<br>13.3 |
| A203 | 14.76 | | 434.38 | 30.44 | 396.26 | I.A. | 80.3<br>78.7<br>77.9<br>83.4 |
| A204 | 58.42 | | 981.88 | 157.89 | 1487.11 | I.A. | 62.6<br>58.3<br>49.7<br>48.4 |
| A205 | 128.76 | | 1806.9 | 305.32 | 2362.23 | I.A. | 38.9<br>38.7<br>31.7<br>37.2 |
| A206 | 17.37 | | 395.41 | 38.95 | 657.05 | I.A. | 84.3<br>80.5<br>65<br>54.7 |
| A207 | 7.93 | | 221.47 | 10.6 | 105.74 | I.A. | 84.3<br>98.8<br>63.0<br>62.7 |
| A208 | 343 | | I.A. | 615.95 | I.A. | I.A. | 51.8<br>68.9<br>37.5<br>23.3 |
| A209 | 326.73 | | I.A. | 672.98 | I.A. | I.A. | 31.8<br>44.7<br>45.7<br>22.6 |
| A210 | 202.76 | | I.A. | 446.86 | I.A. | I.A. | 76.0<br>54.6<br>55.4<br>47.4 |
| B1 | 423.7 | | I.A. | | I.A. | I.A. | 0.02<br>0.01<br>0.02<br>0.04 |
| B2 | 1721.99 | | I.A. | | I.A. | I.A. | 0.55<br>1.46<br>0.23<br>0.35 |
| B3 | 7382.27 | | I.A. | | 9441.64 | 12597.4 | 0.15<br>0.1<br>0.08<br>0.26 |
| B4 | I.A. | | I.A. | | I.A. | 16627.8 | 2.21<br>2.79<br>1.7<br>12.1 |
| B5 | 1497.99 | | I.A. | | I.A. | I.A. | 0.24<br>7.08<br>0.21<br>0.54 |

TABLE 1-continued

Activities of Compounds

| No. | 24 hr Dox Inducible PD1ssGluc 293FRT/TO: Mean IC50 (nM) | 24 hr Dox Inducible PD1FLFluc 293FRT/TO: Mean IC50 (nM) | 24 hr Dox Inducible TNFaFLGluc 293FRT/TO: Mean IC50 (nM) | 24 hr Dox Inducible IL2FLGluc 293FRT/TO: Mean IC50 (nM) | 48 hr H929 Viability Celltiter-Glo: Mean EC50 (nM) | 48 hr U266 Viability Celltiter-Glo: Mean EC50 (nM) | Liver Microsome Stability- % Left after 30 min w/NADPH (%) Mouse Rat Monkey Human |
|---|---|---|---|---|---|---|---|
| B6 | 416.05 | | I.A. | | I.A. | I.A. | 81.8<br>13.2<br>4.57<br>7.66 |
| B7 | 6900.19 | | 24323 | | 6858.59 | 7481.69 | 1.47<br>0.58<br>0.04<br>0.03 |
| B8 | I.A. | | I.A. | | I.A. | I.A. | 17.1<br>23.8<br>15.5<br>22.1 |
| B9 | 3642.93 | | I.A. | | I.A. | I.A. | 0.36<br>3.74<br>0.26<br>0.49 |
| B10 | 16476.4 | | I.A. | 6923.68 | I.A. | I.A. | |
| B11 | I.A. | | I.A. | I.A. | I.A. | I.A. | |
| B12 | 5655.74 | | I.A. | I.A. | I.A. | I.A. | |
| B16 | 449.25 | | 13885 | 825.91 | I.A. | I.A. | 58.4<br>72.3<br>44.7<br>55.2 |
| B19 | 220.99 | | 15364.2 | | I.A. | I.A. | 13.5<br>15.7<br>0.98<br>9.46 |
| B20 | 794.07 | | I.A. | | I.A. | I.A. | 3.41<br>11.1<br>1.73<br>5.43 |
| B21 | 3951.77 | | I.A. | I.A. | I.A. | I.A. | 0.16<br>0.06<br>0.03<br>0.17 |
| B22 | 31.31 | | 519.36 | 80.48 | 1648.2 | I.A. | 8.31<br>10.1<br>1.77<br>1.77 |

*I.A. means and IC50 or EC50 of greater than 25 μM

I claim:
1. A method of inhibiting protein secretion from a cell via inhibition of Sec61, wherein the protein is not CD4, comprising contacting the cell with a compound is selected from the group consisting of:
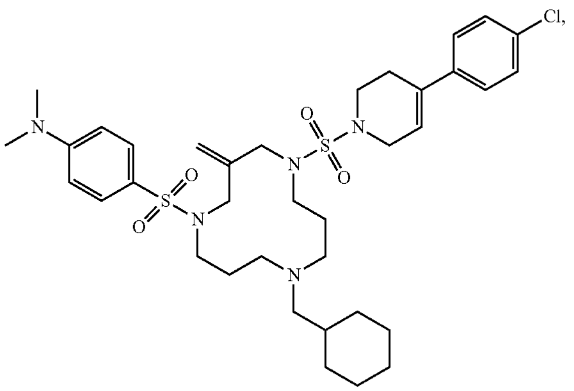
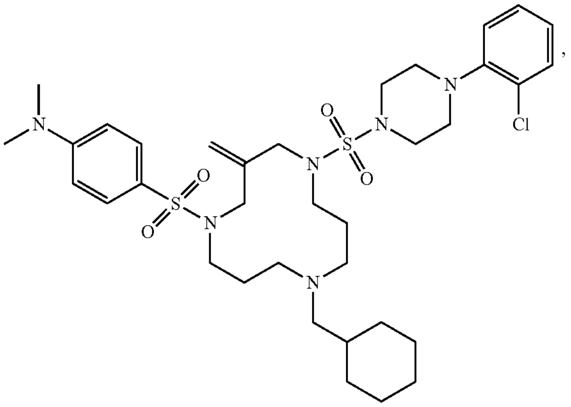
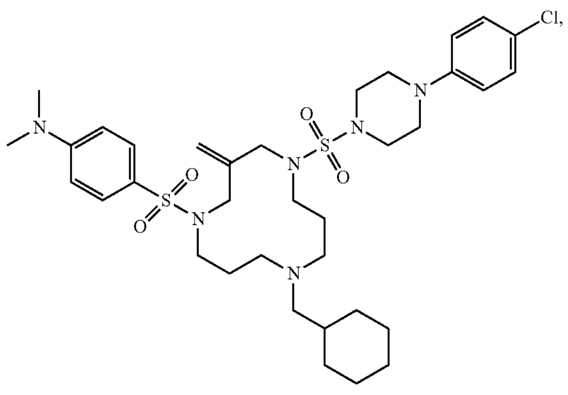
-continued
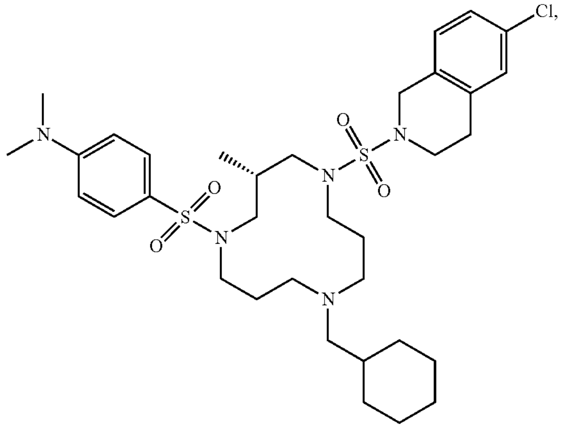
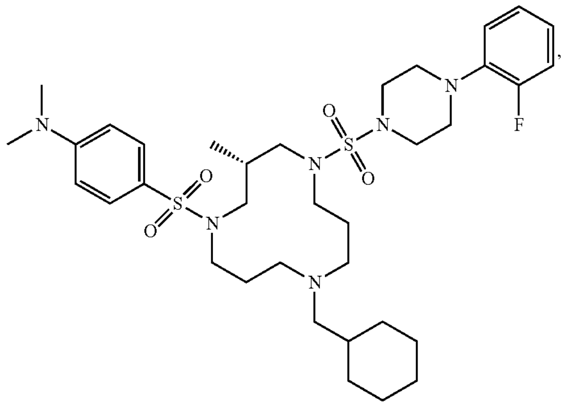
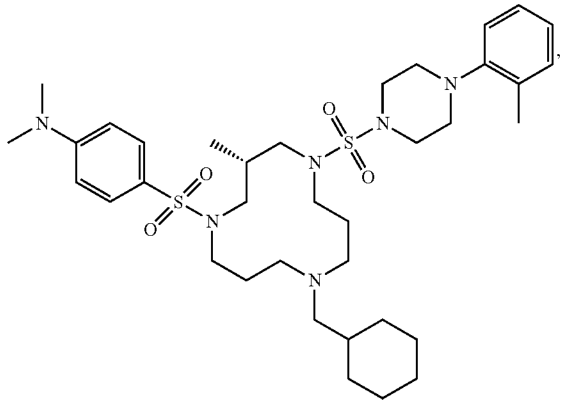
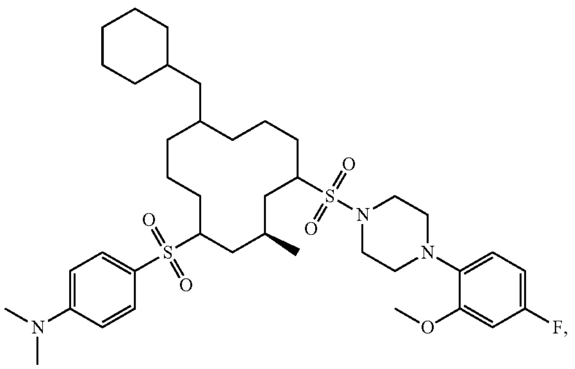

-continued

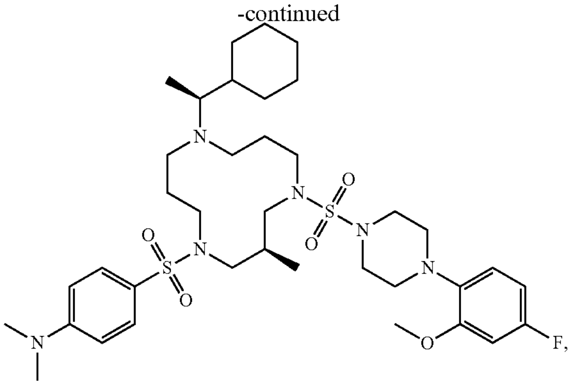

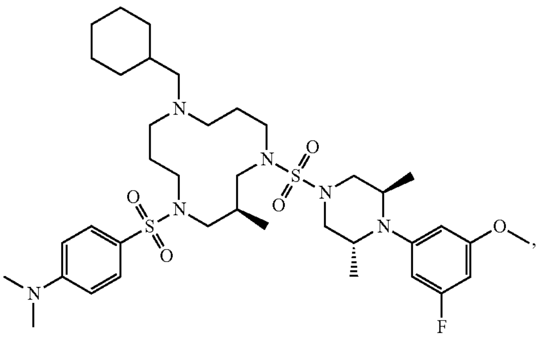

, and

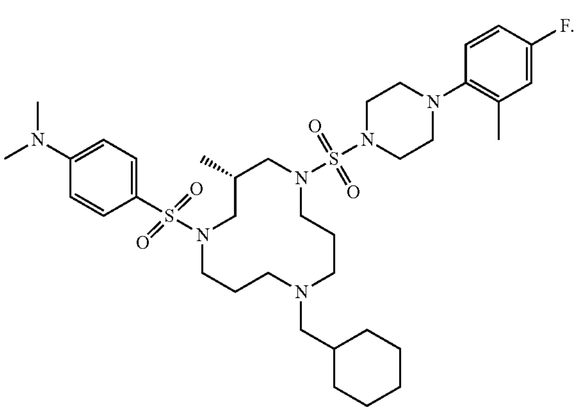

2. The method of claim 1, wherein the protein is at least one of PD-1, PD-L1, TIM-1, LAG-3, CTLA4, BTLA, OX-40, B7H1, B7H4, CD137, CD47, CD96, CD73, CD40, VISTA, TIGIT, LAIR1, CD160, 2B4, TGFRβ and combinations thereof, or TNFα, VCAM, PRL, IL-2, INFg, or insulin.

3. The method of claim 1, wherein the contacting comprises administering the compound to a subject.

4. The method of claim 3, wherein the subject suffers from inflammation.

5. The method of claim 3, wherein the subject suffers from cancer.

6. The method of claim 3, wherein the subject suffers from an autoimmune disease.

7. The method of claim 3, wherein the subject suffers from a neurodegenerative disease.

8. The method of claim 3, wherein the subject suffers from an inflammatory disease.

9. The method of claim 1, wherein the compound is

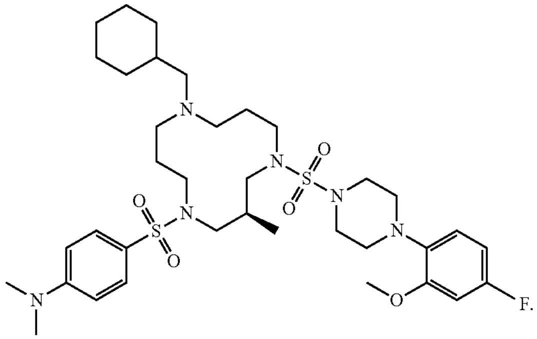 [SMILES: COc1cc(F)ccc1N1CCN(S(=O)(=O)N2CCCN(CC3CCCCC3)CCCN(S(=O)(=O)c3ccc(N(C)C)cc3)C[C@H](C)C2)CC1]

10. The method of claim 1, wherein the compound is

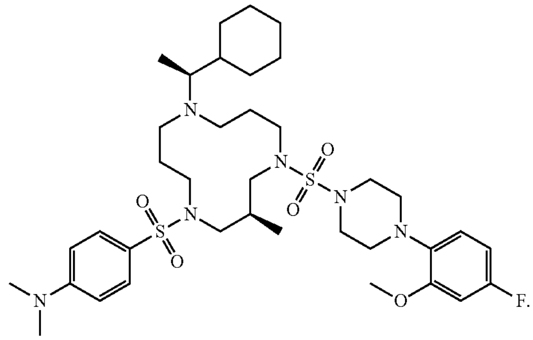 [SMILES: COc1cc(F)ccc1N1CCN(S(=O)(=O)N2CCCN([C@@H](C)C3CCCCC3)CCCN(S(=O)(=O)c3ccc(N(C)C)cc3)C[C@H](C)C2)CC1]

11. The method of claim 1, wherein the compound is

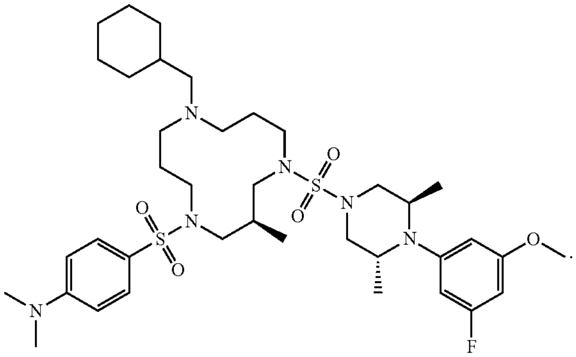

12. The method of claim 1, wherein the compound is
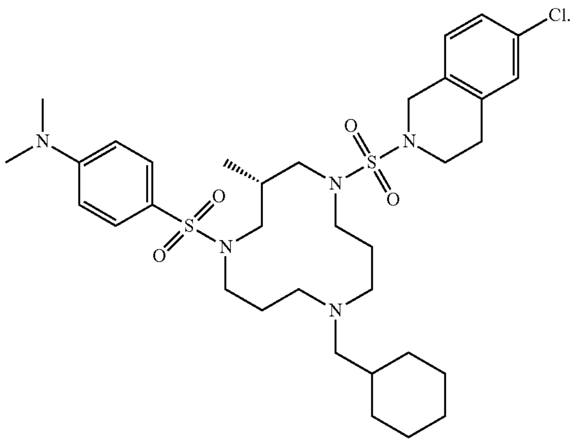 [SMILES: C[C@H]1CN(S(=O)(=O)c2ccc(N(C)C)cc2)CCCN(CC2CCCCC2)CCCN(S(=O)(=O)N2CCc3cc(Cl)ccc3C2)C1]
* * * * *

SEQUENCE LISTING

<160> NUMBER OF SEQ ID NOS: 76

<210> SEQ ID NO 1
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg
            20                  25                  30

<210> SEQ ID NO 2
<211> LENGTH: 23
<212> TYPE: PRT

<213> ORGANISM: Artificial Sequence
<220> FEATURE:
<223> OTHER INFORMATION: Synthetic Polypeptide

<400> SEQUENCE: 2

Met Arg Ala Asn Asp Ala Leu Gln Val Leu Gly Leu Leu Phe Ser Leu
1 5 10 15

Ala Arg Gly Ser Glu Val Gly
20

<210> SEQ ID NO 3
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 3

Met Gly Leu Ser Thr Val Pro Asp Leu Leu Leu Pro Leu Val Leu Leu
1 5 10 15

Glu Leu Leu Val Gly Ile Tyr Pro Ser Gly Val Ile Gly
20 25

<210> SEQ ID NO 4
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 4

Leu Val Pro His Leu Gly Asp Arg Glu Lys
1 5 10

<210> SEQ ID NO 5
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 5

Met Ala Pro Val Ala Val Trp Ala Ala Leu Ala Val Gly Leu Glu Leu
1 5 10 15

Trp Ala Ala Ala His Ala
20

<210> SEQ ID NO 6
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 6

Leu Pro Ala Gln Val Ala Phe Thr Pro Tyr
1 5 10

<210> SEQ ID NO 7
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 7

-continued

Met Thr Pro Gly Lys Thr Ser Leu Val Ser Leu Leu Leu Leu Leu Ser
1 5 10 15

Leu Glu Ala Ile Val Lys Ala
20

<210> SEQ ID NO 8
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 8

Gly Ile Thr Ile Pro Arg Asn Pro Gly Cys
1 5 10

<210> SEQ ID NO 9
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 9

Met Gly Ala Ala Arg Ser Pro Pro Ser Ala Val Pro Gly Pro Leu Leu
1 5 10 15

Gly Leu Leu Leu Leu Leu Leu Gly Val Leu Ala Pro Gly Gly Ala Ser
20 25 30

<210> SEQ ID NO 10
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 10

Leu Arg Leu Leu Asp His Arg Ala Leu Val
1 5 10

<210> SEQ ID NO 11
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 11

Met Leu Gly Ser Arg Ala Val Met Leu Leu Leu Leu Leu Pro Trp Thr
1 5 10 15

Ala Gln Gly

<210> SEQ ID NO 12
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 12

Arg Ala Val Pro Gly Gly Ser Ser Pro Ala
1 5 10

<210> SEQ ID NO 13

<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 13

```
Met Cys His Gln Gln Leu Val Ile Ser Trp Phe Ser Leu Val Phe Leu
1               5                   10                  15

Ala Ser Pro Leu Val Ala
            20
```

<210> SEQ ID NO 14
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 14

```
Ile Trp Glu Leu Lys Lys Asp Val Tyr Val
1               5                   10
```

<210> SEQ ID NO 15
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 15

```
Met Asn Gln Val Thr Ile Gln Trp Asp Ala Val Ile Ala Leu Tyr Ile
1               5                   10                  15

Leu Phe Ser Trp Cys His Gly
            20
```

<210> SEQ ID NO 16
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 16

```
Gly Ile Thr Asn Ile Asn Cys Ser Gly His
1               5                   10
```

<210> SEQ ID NO 17
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 17

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro
            20                  25
```

<210> SEQ ID NO 18
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 18

Val Pro Pro Gly Glu Asp Ser Lys Asp Val
1 5 10

<210> SEQ ID NO 19
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 19

Met Leu Ala Val Gly Cys Ala Leu Leu Ala Ala Leu Leu Ala Ala Pro
1 5 10 15

Gly Ala Ala

<210> SEQ ID NO 20
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 20

Leu Ala Pro Arg Arg Cys Pro Ala Gln Glu
1 5 10

<210> SEQ ID NO 21
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 21

Met Leu Thr Leu Gln Thr Trp Leu Val Gln Ala Leu Phe Ile Phe Leu
1 5 10 15

Thr Thr Glu Ser Thr Gly
20

<210> SEQ ID NO 22
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 22

Glu Leu Leu Asp Pro Cys Gly Tyr Ile Ser
1 5 10

<210> SEQ ID NO 23
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 23

Met Lys Val Leu Leu Arg Leu Ile Cys Phe Ile Ala Leu Leu Ile Ser
1 5 10 15

Ser

<210> SEQ ID NO 24
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 24

Leu Glu Ala Asp Lys Cys Lys Glu Arg Glu
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 25

Met Leu Arg Leu Tyr Val Leu Val Met Gly Val Ser Ala
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 26

Phe Thr Leu Gln Pro Ala Ala His Thr Gly
1               5                   10

<210> SEQ ID NO 27
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 27

Met Glu Ile Cys Arg Gly Leu Arg Ser His Leu Ile Thr Leu Leu Leu
1               5                   10                  15

Phe Leu Phe His Ser Glu Thr Ile Cys
            20                  25

<210> SEQ ID NO 28
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 28

Arg Pro Ser Gly Arg Lys Ser Ser Lys Met
1               5                   10

<210> SEQ ID NO 29
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 29

Met Asp Ser Tyr Leu Leu Met Trp Gly Leu Leu Thr Phe Ile Met Val
1               5                   10                  15

-continued

```
Pro Gly Cys Gln Ala
            20


<210> SEQ ID NO 30
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 30

Glu Leu Cys Asp Asp Asp Pro Pro Glu Ile
1               5                   10


<210> SEQ ID NO 31
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 31

Met Ala Ser Pro Phe Ala Leu Leu Met Val Leu Val Val Leu Ser Cys
1               5                   10                  15

Lys Ser Ser Cys Ser Leu Gly
            20


<210> SEQ ID NO 32
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 32

Cys Asp Leu Pro Glu Thr His Ser Leu Asp
1               5                   10


<210> SEQ ID NO 33
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 33

Met Ala Leu Thr Phe Ala Leu Leu Val Ala Leu Leu Val Leu Ser Cys
1               5                   10                  15

Lys Ser Ser Cys Ser Val Gly
            20


<210> SEQ ID NO 34
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 34

Cys Asp Leu Pro Gln Thr His Ser Leu Gly
1               5                   10


<210> SEQ ID NO 35
<211> LENGTH: 23
<212> TYPE: PRT
```

-continued

<213> ORGANISM: Artificial Sequence
<220> FEATURE:
<223> OTHER INFORMATION: Synthetic Polypeptide

<400> SEQUENCE: 35

Met Ala Leu Ser Phe Ser Leu Leu Met Ala Val Leu Val Leu Ser Tyr
1 5 10 15

Lys Ser Ile Cys Ser Leu Gly
20

<210> SEQ ID NO 36
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 36

Cys Asp Leu Pro Gln Thr His Ser Leu Gly
1 5 10

<210> SEQ ID NO 37
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 37

Met Thr Asn Lys Cys Leu Leu Gln Ile Ala Leu Leu Leu Cys Phe Ser
1 5 10 15

Thr Thr Ala Leu Ser
20

<210> SEQ ID NO 38
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 38

Met Ser Tyr Asn Leu Leu Gly Phe Leu Gln
1 5 10

<210> SEQ ID NO 39
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 39

Met Met Val Val Leu Leu Gly Ala Thr Thr Leu Val Leu Val Ala Val
1 5 10 15

Ala Pro Trp Val Leu Ser Ala Ala Ala Gly Gly
20 25

<210> SEQ ID NO 40
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 40

Lys Asn Leu Lys Ser Pro Gln Lys Val Glu
1 5 10

<210> SEQ ID NO 41
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 41

Met Leu Leu Ser Gln Asn Ala Phe Ile Phe Arg Ser Leu Asn Leu Val
1 5 10 15

Leu Met Val Tyr Ile Ser Leu Val Phe Gly
20 25

<210> SEQ ID NO 42
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 42

Ile Ser Tyr Asp Ser Pro Asp Tyr Thr Asp
1 5 10

<210> SEQ ID NO 43
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 43

Met Ala Cys Leu Gly Phe Gln Arg His Lys Ala Gln Leu Asn Leu Ala
1 5 10 15

Thr Arg Thr Trp Pro Cys Thr Leu Leu Phe Phe Leu Leu Phe Ile Pro
20 25 30

Val Phe Cys
35

<210> SEQ ID NO 44
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 44

Lys Ala Met His Val Ala Gln Pro Ala Val
1 5 10

<210> SEQ ID NO 45
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 45

Met Arg Ile Phe Ala Val Phe Ile Phe Met Thr Tyr Trp His Leu Leu
1 5 10 15

Asn Ala

<210> SEQ ID NO 46
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 46

Phe Thr Val Thr Val Pro Lys Asp Leu Tyr
1               5                   10

<210> SEQ ID NO 47
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 47

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu
            20                  25

<210> SEQ ID NO 48
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 48

Val Pro Val Val Trp Ala Gln Glu Gly Ala
1               5                   10

<210> SEQ ID NO 49
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 49

Met Phe Ser His Leu Pro Phe Asp Cys Val Leu Leu Leu Leu Leu Leu
1               5                   10                  15

Leu Leu Thr Arg Ser
            20

<210> SEQ ID NO 50
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 50

Ser Glu Val Glu Tyr Arg Ala Glu Val Gly
1               5                   10

<210> SEQ ID NO 51
<211> LENGTH: 21
<212> TYPE: PRT
<213> ORGANISM: Artificial Sequence
<220> FEATURE:
<223> OTHER INFORMATION: Synthetic Polypeptide -continued

<400> SEQUENCE: 51

```
Met Arg Trp Cys Leu Leu Leu Ile Trp Ala Gln Gly Leu Arg Gln Ala
1               5                   10                  15

Pro Leu Ala Ser Gly
            20
```

<210> SEQ ID NO 52
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 52

```
Met Met Thr Gly Thr Ile Glu Thr Thr Gly
1               5                   10
```

<210> SEQ ID NO 53
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 53

```
Met Glu Lys Lys Trp Lys Tyr Cys Ala Val Tyr Tyr Ile Ile Gln Ile
1               5                   10                  15

His Phe Val Lys Gly
            20
```

<210> SEQ ID NO 54
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 54

```
Val Trp Glu Lys Thr Val Asn Thr Glu Glu
1               5                   10
```

<210> SEQ ID NO 55
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 55

```
Met Gly Val Pro Thr Ala Leu Glu Ala Gly Ser Trp Arg Trp Gly Ser
1               5                   10                  15

Leu Leu Phe Ala Leu Phe Leu Ala Ala Ser Leu Gly Pro Val Ala Ala
            20                  25                  30
```

<210> SEQ ID NO 56
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 56

```
Phe Lys Val Ala Thr Pro Tyr Ser Leu Tyr
1               5                   10
```

<210> SEQ ID NO 57
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 57

Met Leu Arg Arg Arg Gly Ser Pro Gly Met Gly Val His Val Gly Ala
1 5 10 15

Ala Leu Gly Ala Leu Trp Phe Cys Leu Thr Gly Ala
20 25

<210> SEQ ID NO 58
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 58

Leu Glu Val Gln Val Pro Glu Asp Pro Val
1 5 10

<210> SEQ ID NO 59
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 59

Met Cys Pro Arg Ala Ala Arg Ala Pro Ala Thr Leu Leu Leu Ala Leu
1 5 10 15

Gly Ala Val Leu Trp Pro Ala Ala Gly Ala
20 25

<210> SEQ ID NO 60
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 60

Trp Glu Leu Thr Ile Leu His Thr Asn Asp
1 5 10

<210> SEQ ID NO 61
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 61

Met Gly Thr Ser His Pro Ala Phe Leu Val Leu Gly Cys Leu Leu Thr
1 5 10 15

Gly Leu Ser Leu Ile Leu Cys
20

<210> SEQ ID NO 62
<211> LENGTH: 10
<212> TYPE: PRT

<213> ORGANISM: Artificial Sequence
<220> FEATURE:
<223> OTHER INFORMATION: Synthetic Polypeptide

<400> SEQUENCE: 62

Gln Leu Ser Leu Pro Ser Ile Leu Pro Asn
1               5                   10

<210> SEQ ID NO 63
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 63

Met Gln Ser Lys Val Leu Leu Ala Val Ala Leu Trp Leu Cys Val Glu
1               5                   10                  15

Thr Arg Ala

<210> SEQ ID NO 64
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 64

Ala Ser Val Gly Leu Pro Ser Val Ser Leu
1               5                   10

<210> SEQ ID NO 65
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 65

Met Thr Ile Leu Gly Thr Thr Phe Gly Met Val Phe Ser Leu Leu Gln
1               5                   10                  15

Val Val Ser Gly
            20

<210> SEQ ID NO 66
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 66

Glu Ser Gly Tyr Ala Gln Asn Gly Asp Leu
1               5                   10

<210> SEQ ID NO 67
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 67

Met Arg Pro Ser Gly Thr Ala Gly Ala Ala Leu Leu Ala Leu Leu Ala
1               5                   10                  15

Ala Leu Cys Pro Ala Ser Arg Ala
20

<210> SEQ ID NO 68
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 68

Leu Glu Glu Lys Lys Val Cys Gln Gly Thr
1 5 10

<210> SEQ ID NO 69
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 69

Met Arg Ala Asn Asp Ala Leu Gln Val Leu Gly Leu Leu Phe Ser Leu
1 5 10 15

Ala Arg Gly

<210> SEQ ID NO 70
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 70

Ser Glu Val Gly Asn Ser Gln Ala Val Cys
1 5 10

<210> SEQ ID NO 71
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 71

Met Asn Phe Leu Leu Ser Trp Val His Trp Ser Leu Ala Leu Leu Leu
1 5 10 15

Tyr Leu His His Ala Lys Trp Ser Gln Ala
20 25

<210> SEQ ID NO 72
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 72

Ala Pro Met Ala Glu Gly Gly Gly Gln Asn
1 5 10

<210> SEQ ID NO 73
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 73

Met Arg Gln Ser Leu Leu Phe Leu Thr Ser Val Val Pro Phe Val Leu
1 5 10 15

Ala

<210> SEQ ID NO 74
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 74

Pro Arg Pro Pro Asp Asp Pro Gly Phe Gly
1 5 10

<210> SEQ ID NO 75
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 75

Met Val Leu Leu Arg Val Leu Ile Leu Leu Leu Ser Trp Ala Ala Gly
1 5 10 15

Met Gly Gly

<210> SEQ ID NO 76
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 76

Gln Tyr Gly Asn Pro Leu Asn Lys Tyr Ile
1 5 10